US009562053B2

(12) United States Patent
Sui et al.

(10) Patent No.: US 9,562,053 B2
(45) Date of Patent: Feb. 7, 2017

(54) BENZO-FUSED HETEROCYCLIC DERIVATIVES USEFUL AS AGONISTS OF GPR120

(71) Applicant: Janssen Pharmaceutica NV, Beerse (BE)

(72) Inventors: Zhihua Sui, Norristown, PA (US); Nalin Subasinghe, Exton, PA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 14/200,093

(22) Filed: Mar. 7, 2014

(65) Prior Publication Data
US 2014/0275172 A1    Sep. 18, 2014

Related U.S. Application Data

(60) Provisional application No. 61/783,118, filed on Mar. 14, 2013.

(51) Int. Cl.
C07D 493/04 (2006.01)
C07D 307/80 (2006.01)
C07D 333/56 (2006.01)
C07D 307/81 (2006.01)
C07D 405/12 (2006.01)
C07D 277/64 (2006.01)
C07D 263/56 (2006.01)
C07D 231/56 (2006.01)
C07D 333/54 (2006.01)
C07D 401/12 (2006.01)
C07D 493/02 (2006.01)
C07D 307/79 (2006.01)
C07D 307/82 (2006.01)
C07D 307/84 (2006.01)

(52) U.S. Cl.
CPC ........... C07D 493/04 (2013.01); C07D 231/56 (2013.01); C07D 263/56 (2013.01); C07D 277/64 (2013.01); C07D 307/79 (2013.01); C07D 307/80 (2013.01); C07D 307/81 (2013.01); C07D 307/82 (2013.01); C07D 307/84 (2013.01); C07D 333/54 (2013.01); C07D 333/56 (2013.01); C07D 401/12 (2013.01); C07D 405/12 (2013.01); C07D 493/02 (2013.01)

(58) Field of Classification Search
None
See application file for complete search history.

(56) References Cited

U.S. PATENT DOCUMENTS

2011/0313003 A1* 12/2011 Shi et al. ............... 514/345

FOREIGN PATENT DOCUMENTS

| EP | 1559422 A1 | 8/2005 |
|---|---|---|
| EP | 1731505 A1 | 12/2006 |
| EP | 2151236 A1 | 2/2010 |
| WO | WO 2004/063155 A1 | 7/2004 |
| WO | WO 2005/063729 A1 | 7/2005 |
| WO | WO 2005/066136 A1 | 7/2005 |
| WO | WO 2008/030520 A1 | 3/2008 |
| WO | WO 2008/038251 A2 | 4/2008 |
| WO | WO 2008/030618 A1 | 8/2008 |
| WO | WO 2008/103501 A1 | 8/2008 |
| WO | WO 2009/117421 A2 | 9/2009 |
| WO | WO 2010/048207 A2 | 4/2010 |
| WO | WO 2010/080537 A1 | 7/2010 |
| WO | WO 2010/104195 A1 | 9/2010 |
| WO | WO 2011/094890 A1 | 8/2011 |
| WO | WO 2011/159297 A1 | 12/2011 |

OTHER PUBLICATIONS

Shimpukade et al., Discovery of a Potent and Selective GPR120 Agonist. Journal of Medicinal Chemistry, 2012, 55, 4511-4515.*
Oh et al., A Gpr120-selective agonist improves insulin resistance and chronic inflammation in obese mice. Nature Medicine, 2014, 20, 942-949.*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
International Search Report and Written Opinion of the International Searching Authority relating to International Patent Application No. PCT/US2014/021762, which corresponds to U.S. Appl. No. 14/200,114. Date of Mailing: May 21, 2014.
International Search Report and Written Opinion of the International Searching Authority relating to International Patent Application No. PCT/US2014/021775, which corresponds to U.S. Appl. No. 14/200,127. Date of Mailing: May 15, 2014.
International Search Report and Written Opinion of the International Searching Authority relating to International Patent Application No. PCT/US2014/021740, which corresponds to U.S. Appl. No. 14/200,097. Date of Mailing: May 23, 2014.
International Search Report and Written Opinion of the International Searching Authority relating to International Patent Application No. PCT/US2014/021732, which corresponds to U.S. Appl. No. 14/200,108. Date of Mailing: May 20, 2014.
Partial International Search Report relating to International Patent Application No. PCT/2014/021790. Date of Mailing: Jun. 24, 2014.
Sun et al., "Structure-Activity Relationships of GPR120 Agonists Based on a Docking Simulation.", Molecular Pharmaceology, Nov. 1, 2010, pp. 804-810, vol. 78(5), XP0055122562.
Adachi et al., "Free fatty acids administered into the colon promote the secretion of glucagon-like peptide-1 and insulin.", Biochem. Biophys. Res. Commun., 2006, pp. 332-337, vol. 340.
American Diabetes Association, "Economic Costs of Diabetes in the U.S. in 2007", Diabetes Care, 2008, pp. 1-20, vol. 31.
American Diabetes Association. DiabetesPro: Health Professional Resources and Statistics. Fact Sheet. 2014.
Bell, G.I. and Polonsky, K.S., "Diabetes mellitus and genetically programmed defects in β cell function", Nature, Dec. 13, 2001, pp. 788-791, vol. 414.

(Continued)

Primary Examiner — Rebecca Anderson
Assistant Examiner — Po-Chih Chen

(57) ABSTRACT

The present invention is directed to benzo-fused heterocyclic derivatives, pharmaceutical compositions containing them and their use in the treatment of disorders and conditions modulated by GPR120. More particularly, the compounds of the present invention are agonists of GPR120, useful in the treatment of, such as for example, Type II diabetes mellitus.

3 Claims, No Drawings

(56) References Cited

OTHER PUBLICATIONS

Fukuda et al., "Directed Lithiation of N-Benzenesulfonyl-3-bromopyrrole. Electrophile-Controlled Regioselective Functionalization via Dynamic Equilibrium between C-2 and C-5 Lithio Species.", Organic Letters, 2010, pp. 2734-2737, vol. 12(12).
Gotoh et al., "The regulation of adipogenesis through GPR120.", Biochem. Biophys. Res. Commun., 2007, pp. 591-597, vol. 354.
Hara et al., "Novel selective ligands for free fatty acid receptors GPR120 and GPR40.", Naunyn-Schmied Arc. Pharmacol., 2009, pp. 247-255, vol. 380.
Hirasawa et al., "Free fatty acids regulate gut incretin glucagon-like peptide-1 secretion through GPR120", Nature Med, 2005, pp. 90-94, vol. 11(1).
Ishikawa et al., "Cesium Fluroide-Mediated Claisen Rearrangements Of Phenyl Propargyl Esters: Effect Of A Substituent On The Phenyl Ring On The Rearrangement[1].", Heterocycles, 1994, pp. 371-380, vol. 39(1).
Itoh et al., "Free fatty acids regulate insulin secretion from pancreatic β cells through GPR40", Nature, Mar. 13, 2003, pp. 173-176, vol. 422.
Knop et al., "Incretin-Based Therapy of Type 2 Diabetes Mellitus.", Curr.Protein Pept. Sci., 2009, pp. 46-55, vol. 10.
Moller, D.E., "New Drug Targets for type 2 diabetes and the metabolic syndrome.", Nature, Dec. 13, 2001, pp. 821-827, vol. 414.
Nathan, D.M., "Initial Management of Glycemia in Type 2 Diabetes Mellitus", N. Engl. J. Med., Oct. 24, 2002, pp. 1342-1349, vol. 347(17).
Steneberg et al., "The FFA receptor GPR40 links hyperinsulinemia, hepatic steatosis and impaired glucose homeostasis in mouse"., Cell Metab, Apr. 2005, pp. 245-258, vol. 1.
Turner et al., "Glycemic Control With Diet, Sulfonylurea, Metformin or Insulin in Patients With Type 2 Diabetes Mellitus.", JAMA, Jun. 2, 1999, pp. 2005-2012, vol. 281(21).
Wild et al., "Global Prevalence of Diabetes", Diabetes Care, May 2004, pp. 1047-1053, vol. 27(5).

\* cited by examiner

BENZO-FUSED HETEROCYCLIC DERIVATIVES USEFUL AS AGONISTS OF GPR120

CROSS REFERENCE TO RELATED APPLICATIONS

This application claims the benefit of U.S. Provisional Application 61/783,118, filed on Mar. 14, 2013, which is incorporated by reference herein in its entirety.

FIELD OF THE INVENTION

The present invention is directed to benzo-fused heterocyclic derivatives, pharmaceutical compositions containing them and their use in the treatment of disorders and conditions modulated by GPR120. More particularly, the compounds of the present invention are agonists of GPR120, useful in the treatment of related diseases and disorders, such as for example, Type II diabetes mellitus.

BACKGROUND OF THE INVENTION

A diabetes mellitus epidemic is unfolding across the globe with the World Health Organization (WHO) reporting a worldwide prevalence of 177 million patients with diabetes. It is estimated that the incidence of all forms of diabetes totals approximately 2.8% of the world population. The number of newly diagnosed diabetic patients is increasing by 4-5% per year. The total number of people with diabetes worldwide is projected to rise to 366 million (4.4% prevalence) in 2030. Type 2 diabetes accounts for approximately 95% of all diabetes cases. Long-term complications of type 2 diabetes include atherosclerosis, heart disease, stroke, end-stage renal disease, retinopathy leading to blindness, nerve damage, sexual dysfunction, frequent infections, and difficult-to-treat foot ulcers, sometimes resulting in lower limb amputation. Diabetics are twice as likely to develop cardiovascular disease or have a stroke, 2 to 6 times more likely to have transient ischemic attacks, and 15 to 40 times more likely to require lower-limb amputation compared with the general population. The total estimated cost of diabetes in 2007 in the US was $174 billion, including $116 billion in medical expenditures. The largest components of medical expenditures attributed to diabetes are hospital inpatient care (50% of total cost), diabetes medication and supplies (12%), retail prescriptions to treat complications of diabetes (11%), and physician office visits (9%). This may be related to the lack of durable efficacy of current drug therapies for Type 2 diabetes (>50% Type 2 patients are not reaching the targeted blood glucose control with current oral medications after 5 years of treatment). There is a general consensus that a considerable need exists for improved awareness, diagnosis and new, more effective, drug therapies for diabetes.

GLP-1 is secreted from specific cells in the colon following a meal and is a key regulator of glucose homeostasis, linking the gut, brain and pancreas. GLP-1 potentiates insulin secretion, reduces glucagon secretion and preserves β-cell function whilst also improving satiety. Levels of post-prandial GLP-1 are reduced in type 2 diabetics and dramatically elevated following gastric by-pass surgery, contributing to the amelioration of type 2 diabetes in these patients. Approaches that prolong the half-life of GLP-1 (JANUVIA (Merck), GALVUS (Novartis)) or activate the GLP-1 receptor (BYETTA (Amylin)) have been recently approved for use in type 2 diabetes.

Hyperinsulinemia in patients with type 2 diabetes mellitus results from peripheral insulin resistance, coupled with inadequate pancreatic insulin secretion and elevated glucagon levels. There is a strong correlation between obesity and peripheral insulin resistance and hyperinsulinemia. Accumulation of free fatty acids in insulin responsive tissues other than fat (i.e. muscle and liver) results in tissue insulin resistance. Additionally, free fatty acids have a direct effect on the pancreas and in the colon and further stimulate glucose-dependent insulin secretion and GLP-1 release with acute exposure whereas chronic exposure of free fatty acids impairs insulin secretion and becomes toxic to the β-cell. In the liver, hyperinsulinemia per se has been linked to exacerbating insulin resistance by increasing liver fatty acid accumulation and hepatic glucose output creating a vicious cycle of disease progression. Current therapeutic strategies only partially address the complex pathology of free fatty acids in the exacerbation of diabetes. Agents that target both liver and pancreas function, directly or indirectly via GLP-1 release, either individually or in combination with current treatment, could significantly improve blood glucose control while maintaining β-cell function. Agents that potentiate GLP-1 release also have the ability to reduce weight, providing additional benefits.

GPR120 is a seven transmembrane g-protein coupled receptor (GPCR) that is predominantly expressed in the intestine and adipose. GPR120 functions as a receptor for long chain free fatty acids (FFAs). Acute FFA stimulation of GPR120 in GLP-1 expressing cell-lines amplifies GLP-1 release. Administration of α-linolenic acid into the colon of mice increases GLP-1 and potentiates insulin release following a glucose challenge. In contrast to agonists of GPR40, the existing literature suggests that a GPR120 agonist would potentiate insulin secretion and reduce glucagon indirectly via GLP-1 release. GPR120 is also expressed in adipose, with expression induced during differentiation. Inhibition of GPR120 expression in 3T3-L1 adipocytes has been shown to reduce adipocyte differentiation. The role of the receptor in the adipose or in the taste cells of the tongue where it has also been found remains unclear.

GPR120 is a Gq coupled GPCR that acts a receptor for long chain fatty acids. It belongs to a family of lipid binding GPCRs that include GPR 40, 41, 43. Functionally, GPR120s closest homolog is GPR40. The cloned rat and mouse GPR120 receptors have been cloned and have >85% homology with the human receptor. GPR120 signals through Gq to elevate intracellular Ca+2 levels as well as activate MAP kinase signal transduction cascades. GPR120's activation of calcium flux and PKC activation is most likely how FFAs contribute to the release GLP-1 in the L-cell.

Although relatively little is known about GPR120 due to lack of potent, selective pharmacological tools or a documented metabolic phenotype of GPR120 knockout mice, the potential to elevate GLP-1 from a small-molecule perspective is attractive as a novel approach to unmet medical need in the treatment of type 2 diabetes mellitus and related disorders. The beneficial effects of elevating GLP-1 are already well validated in the clinic and in addition to improved glucose homeostasis, offer the potential of weight loss. Thus it is theorized that GPR120 agonists may be complementary to existing diabetes therapies that affect liver insulin sensitivity and those that preserve β-cell function.

There remains a need for GPR120 agonists for the treatment of disorders including, but not limited to obesity, Type II diabetes mellitus, dyslipidemia, and the like.

SUMMARY OF THE INVENTION

The present invention is directed to compounds of formula (I)

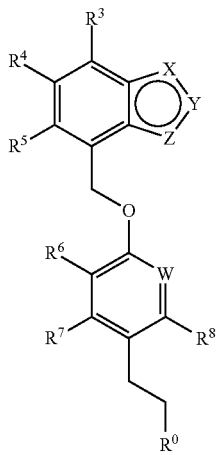
(I)

wherein

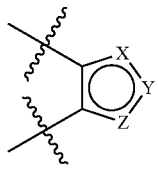

is selected from the group consisting of

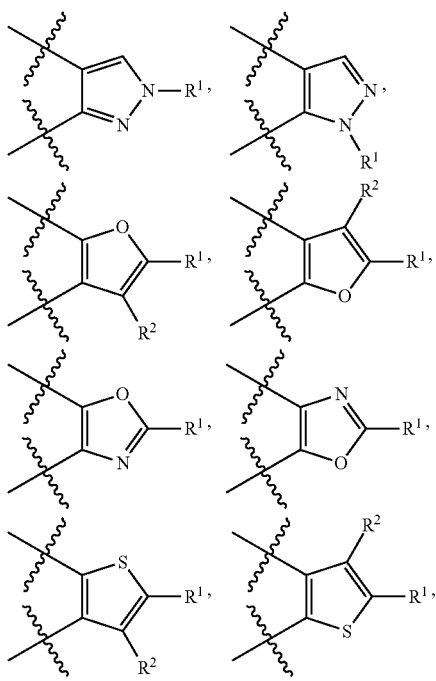

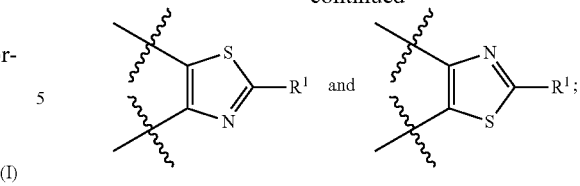

$R^1$ is selected from the group consisting of cyano, $C_{1-6}$alkyl, -(hydroxy substituted $C_{1-4}$alkyl), chloro substituted $C_{1-4}$alkyl, fluoro substituted $C_{1-4}$alkyl, $C_{2-4}$alkenyl, chloro substituted $C_{2-4}$alkenyl, fluoro substituted $C_{2-4}$alkenyl, $C_{2-4}$alkynyl, —($C_{1-4}$alkyl)-O—($C_{1-4}$alkyl), —($C_{1-4}$alkyl)-SO—($C_{1-4}$alkyl), —($C_{1-4}$alkyl)-SO$_2$—($C_{1-4}$alkyl), —($C_{1-4}$alkyl)-NR$^A$R$^B$, —($C_{1-4}$alkyl)-NR$^A$—C(O)—($C_{1-4}$alkyl), —($C_{1-4}$alkyl)-NR$^A$—SO$_2$—($C_{1-4}$alkyl), —C(O)OH, —C(O)O—($C_{1-4}$alkyl), —C(O)—($C_{1-4}$alkyl), —C(O)—NR$^A$R$^B$, $C_{3-8}$cycloalkyl, —($C_{1-4}$alkyl)-($C_{3-8}$cycloalkyl), aryl and —($C_{1-2}$alkyl)-(aryl);

wherein $R^A$ and $R^B$ are each independently selected from the group consisting of hydrogen and $C_{1-4}$alkyl;

$R^2$ is selected from the group consisting of hydrogen, halogen and $C_{1-4}$alkyl;

$R^3$ is selected from the group consisting of hydrogen, chloro and fluoro;

$R^4$ and $R^5$ are each independently selected from the group consisting of hydrogen, halogen, cyano, $C_{1-4}$alkyl, chloro substituted $C_{1-4}$alkyl, fluoro substituted $C_{1-4}$alkyl, $C_{2-4}$alkenyl, chloro substituted $C_{2-4}$alkenyl, fluoro substituted $C_{2-4}$alkenyl, $C_{2-4}$alkynyl, chloro substituted $C_{2-4}$alkynyl, fluoro substituted $C_{2-4}$alkynyl, $C_{1-4}$alkoxy, fluoro substituted $C_{1-4}$alkoxy, —O—($C_{1-4}$alkyl)-O—($C_{1-4}$alkyl), —($C_{1-4}$ alkyl)-O—($C_{1-4}$alkyl), —($C_{1-4}$alkyl)-SO$_2$—($C_{1-4}$ alkyl), —($C_{2-4}$alkenyl)-SO$_2$—($C_{1-4}$alkyl), —C(O)—NR$^C$R$^D$, —O-(aryl) and —O—($C_{1-2}$alkyl)-aryl;

wherein $R^C$ and $R^D$ are each independently selected from the group consisting of hydrogen and $C_{1-4}$alkyl;

provided that at least one of $R^4$ or $R^5$ is selected from the group consisting of hydrogen, chloro and fluoro;

alternatively, wherein

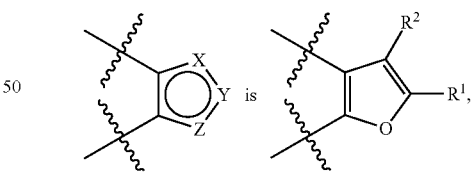

$R^4$ and $R^5$ may be taken together with the carbon atoms to which they are bound to form a ring structure selected from the group consisting of

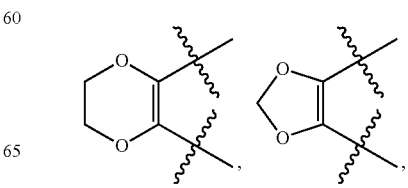

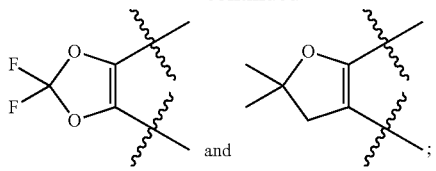

W is selected from the group consisting of C(R⁹); wherein R⁹ is selected from the group consisting of hydrogen, fluoro and bromo;

alternatively, wherein

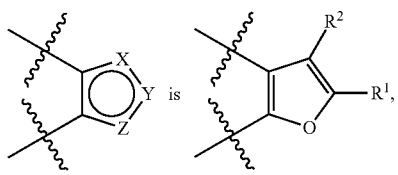

W may be N;

R⁶ and R⁷ are each independently selected from the group consisting of hydrogen, halogen, cyano, $C_{1-6}$alkyl, chloro substituted $C_{1-4}$alkyl, fluoro substituted $C_{1-4}$alkyl, bromo substituted $C_{1-4}$alkyl, $C_{1-4}$alkoxy and fluoro substituted $C_{1-4}$alkoxy;

alternatively, wherein

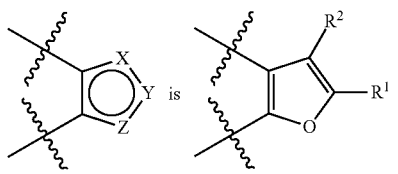

and W is C(R⁹), R⁶ and R⁷ may be taken together with the carbon atoms to which they are bound to form

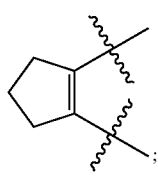 [SMILES: *C1=C(*)CCC1 ; ";"]

R⁸ is selected from the group consisting of hydrogen, halogen, cyano, $C_{1-6}$alkyl, chloro substituted $C_{1-4}$alkyl, fluoro substituted $C_{1-4}$alkyl, bromo substituted $C_{1-4}$alkyl, $C_{1-4}$alkoxy, fluoro substituted $C_{1-4}$alkoxy and —($C_{1-4}$alkyl)-C(O)OH;

R⁰ is selected from the group consisting of —CH₂OH and —C(O)OH;

and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder modulated by GPR120 (selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders) comprising administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder modulated by GPR120 (selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders). In another embodiment, the present invention is directed to a composition comprising a compound of formula (I) for the treatment of a disorder modulated by GPR120 (selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders).

Another example of the invention is the use of any of the compounds described herein in the preparation of a medicament for treating: (a) obesity, (b) obesity related disorders, (c) impaired oral glucose tolerance, (d) insulin resistance, (e) Type II diabetes mellitus, (f) metabolic syndrome, (g) metabolic syndrome X, (h) dyslipidemia, (i) elevated LDL, (j) elevated triglycerides, (k) obesity induced inflammation, (l) osteoporosis and (m) obesity related cardiovascular disorders, in a subject in need thereof. In another example, the present invention is directed to a compound as described herein for use in a methods for treating a disorder selected from the group consisting of obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders, in a subject in need thereof.

DETAILED DESCRIPTION OF THE INVENTION

The present invention is directed to compounds of formula (I)

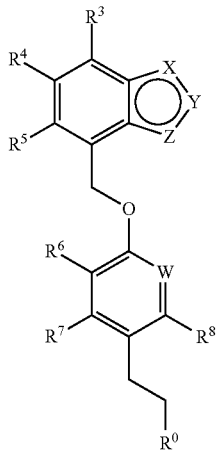

(I)

wherein

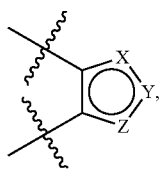

$R^3$, $R^4$, $R^5$, $R^6$, $R^7$, $R^8$, W and $R^0$ are as herein defined. The compounds of the present invention are GPR120 agonists useful in the treatment of related disorders and diseases, including, obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus or dyslipidemia.

The compounds of formula (I) of the present invention have been unexpectedly found not to induce P450 activity. More particularly, it was unexpectedly found that substitution at the $R^4$ and/or $R^5$ positions, preferably at the $R^4$ position, was most effective in achieving this desired effect.

In an embodiment, the present invention is directed to compounds of formula (I) wherein

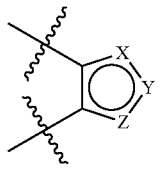

is selected from the group consisting of

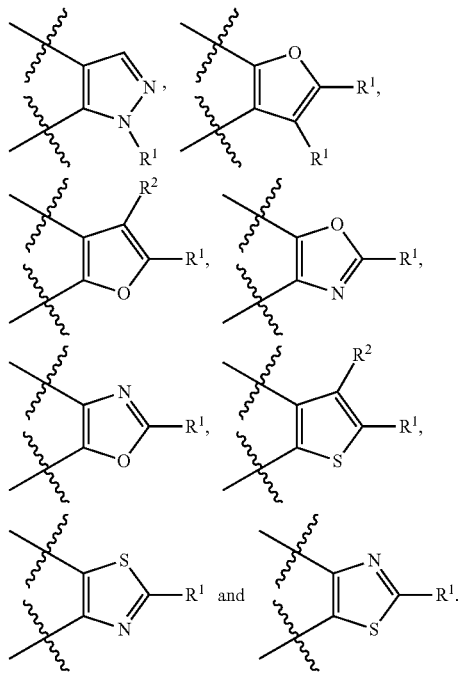

In another embodiment, the present invention is directed to compounds of formula (I) wherein

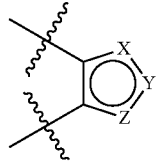

is selected from the group consisting of

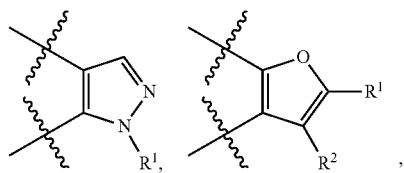

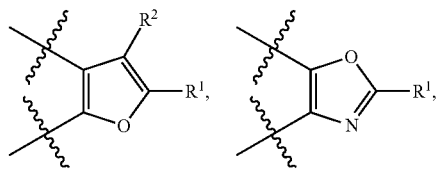

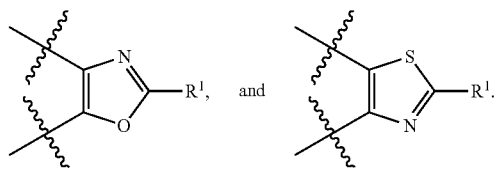

In another embodiment, the present invention is directed to compounds of formula (I) wherein

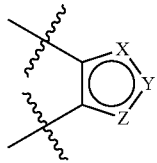

is selected from the group consisting of

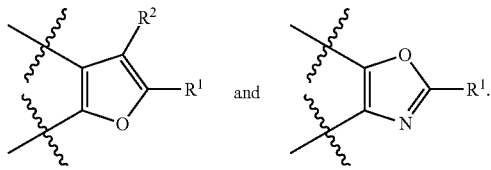

In another embodiment, the present invention is directed to compounds of formula (I) wherein

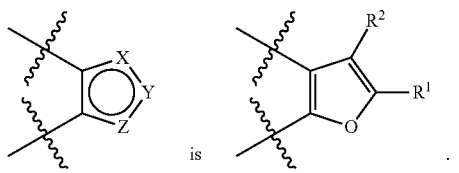

In another embodiment, the present invention is directed to compounds of formula (I) wherein

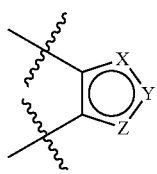

is selected from the group consisting of

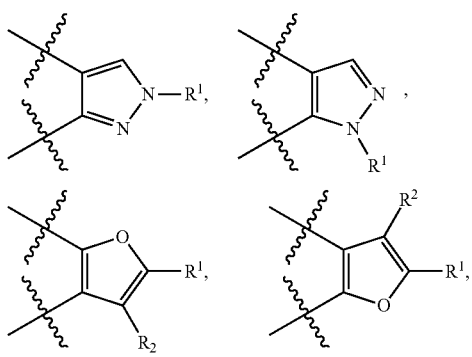

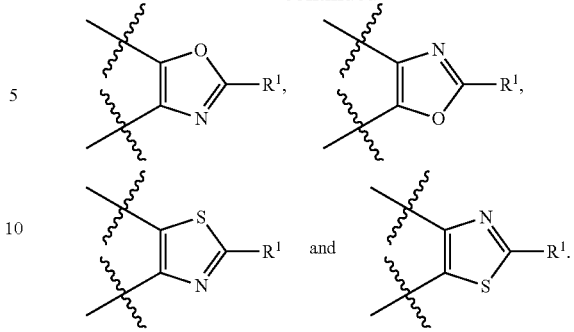

In an embodiment, the present invention is directed to compounds of formula (I) wherein $R^1$ is selected from the group consisting of cyano, $C_{1-6}$alkyl, -(hydroxy substituted $C_{1-4}$alkyl), fluoro substituted $C_{1-4}$alkyl, $C_{2-4}$alkenyl, fluoro substituted $C_{2-4}$alkenyl, $C_{2-4}$alkynyl, —($C_{1-4}$alkyl)-O—($C_{1-4}$ alkyl), —($C_{1-4}$alkyl)-$NR^A R^B$, —($C_{1-4}$alkyl)-$NR^A$—C(O)—($C_{1-4}$alkyl), —($C_{1-4}$alkyl)-$NR^A$—$SO_2$—($C_{1-4}$alkyl), —C(O)OH, —C(O)O—($C_{1-4}$alkyl), —C(O)—($C_{1-4}$alkyl), —C(O)—$NR^A R^B$, $C_{3-6}$cycloalkyl, —($C_{1-4}$alkyl)-($C_{3-6}$cycloalkyl), phenyl and —($C_{1-2}$alkyl)-(phenyl); wherein $R^A$ and $R^B$ are each independently selected from the group consisting of hydrogen and $C_{1-4}$alkyl. In another embodiment, the present invention is directed to compounds of formula (I) wherein $R^1$ is selected from the group consisting of cyano, $C_{1-4}$alkyl, -(hydroxy substituted $C_{1-2}$alkyl), fluoro substituted $C_{1-2}$alkyl, fluoro substituted $C_{2-4}$alkenyl, —($C_{1-2}$alkyl)-O—($C_{1-2}$alkyl), —($C_{1-2}$alkyl)-$NR^A R^B$, —($C_{1-2}$alkyl)-$NR^A$—C(O)—($C_{1-2}$alkyl), —($C_{1-2}$alkyl)-$NR^A$—$SO_2$—($C_{1-2}$alkyl), —C(O)OH, —C(O)—($C_{1-2}$alkyl), —C(O)—$NR^A R^B$, $C_{5-6}$cycloalkyl, —($C_{1-2}$alkyl)-($C_{5-6}$cycloalkyl), phenyl and —($C_{1-2}$alkyl)-(phenyl); wherein $R^A$ and $R^B$ are each independently selected from the group consisting of hydrogen and methyl.

In another embodiment, the present invention is directed to compounds of formula (I) wherein $R^1$ is selected from the group consisting of cyano, methyl, ethyl, n-propyl, isopropyl, isopentyl, isobutyl, t-butyl, difluoromethyl, trifluoromethyl, 2,2-difluoroethyl, 2-fluoro-ethen-1-yl, hydroxyl-methyl-, hydroxyl-ethyl-, methoxy-methyl-, methoxy-ethyl-, carboxy-, methyl-carbonyl-, aminocarbonyl-, dimethylamino-ethyl-, methyl-carbonyl-amino-ethyl-, methyl-sulfonyl-amino-ethyl-, cyclopentyl, cyclopentyl-methyl- and benzyl.

In another embodiment, the present invention is directed to compounds of formula (I) wherein $R^1$ is selected from the group consisting of cyano, methyl, ethyl, n-propyl, isopropyl, isobutyl, difluoromethyl, trifluoromethyl, 2,2-difluoroethyl, 2-fluoro-ethen-1-yl, hydroxyl-ethyl-, methoxy-methyl- and methoxy-ethyl-. In another embodiment, the present invention is directed to compounds of formula (I) wherein $R^1$ is selected from the group consisting of methyl, ethyl, n-propyl, isopropyl, 2,2-difluoroethyl, 2-fluoro-ethen-1-yl, and methoxy-methyl-. In another embodiment, the present invention is directed to compounds of formula (I) wherein $R^1$ is selected from the group consisting of methyl, ethyl, n-propyl, 2,2-difluoroethyl and 2-fluoro-ethen-1-yl. In another embodiment, the present invention is directed to compounds of formula (I) wherein $R^1$ is selected from the group consisting of methyl, ethyl, n-propyl, 2,2-difluoroethyl and 2-fluoro-ethen-1-yl.

In an embodiment, the present invention is directed to compounds of formula (I) wherein $R^2$ is selected from the group consisting of hydrogen, halogen and $C_{1-4}$alkyl. In another embodiment, the present invention is directed to compounds of formula (I) wherein $R^2$ is selected from the group consisting of hydrogen, halogen and $C_{1-2}$alkyl.

In another embodiment, the present invention is directed to compounds of formula (I) wherein $R^2$ is selected from the group consisting of hydrogen, fluoro, bromo and methyl. In another embodiment, the present invention is directed to compounds of formula (I) wherein $R^2$ is selected from the group consisting of hydrogen and methyl. In another embodiment, the present invention is directed to compounds of formula (I) wherein $R^2$ is hydrogen.

In an embodiment, the present invention is directed to compounds of formula (I) wherein $R^3$ is selected from the group consisting of hydrogen, chloro and fluoro. In another embodiment, the present invention is directed to compounds of formula (I) wherein $R^3$ is selected from the group consisting of hydrogen and fluoro. In another embodiment, the present invention is directed to compounds of formula (I) wherein $R^3$ is hydrogen.

In an embodiment, the present invention is directed to compounds of formula (I) wherein $R^4$ and $R^5$ are each independently selected from the group consisting of hydrogen, halogen, cyano, $C_{1-4}$alkyl, fluoro substituted $C_{1-4}$alkyl, $C_{2-4}$alkenyl, fluoro substituted $C_{2-4}$alkenyl, $C_{2-4}$alkynyl, fluoro substituted $C_{2-4}$alkynyl, $C_{1-4}$alkoxy, fluoro substituted $C_{1-4}$alkoxy, —O—($C_{1-4}$alkyl)-O—($C_{1-4}$alkyl), —($C_{1-4}$alkyl)-O—($C_{1-4}$alkyl), —($C_{1-4}$alkyl)-SO$_2$—($C_{1-4}$alkyl), —($C_{2-4}$alkenyl)-SO$_2$—($C_{1-4}$alkyl), —C(O)—NR$^C$R$^D$, —O-(phenyl) and —O—($C_{1-2}$alkyl)-(phenyl); wherein R$^C$ and R$^D$ are each independently selected from the group consisting of hydrogen and $C_{1-4}$alkyl; provided that at least one of $R^4$ or $R^5$ is selected from the group consisting of hydrogen, chloro and fluoro. In another embodiment, the present invention is directed to compounds of formula (I) wherein $R^4$ and $R^5$ are each independently selected from the group consisting of hydrogen, halogen, cyano, $C_{1-4}$alkyl, fluoro substituted $C_{1-4}$alkyl, $C_{2-4}$alkynyl, fluoro substituted $C_{2-4}$alkynyl, $C_{1-4}$alkoxy, fluoro substituted $C_{1-4}$alkoxy, —O—($C_{1-2}$alkyl)-O—($C_{1-2}$alkyl), —($C_{1-4}$alkyl)-SO$_2$—($C_{1-2}$alkyl), —($C_{2-4}$alkenyl)-SO$_2$—($C_{1-2}$alkyl), —C(O)—NR$^C$R$^D$, —O-(phenyl) and —O—($C_{1-2}$alkyl)-(phenyl); wherein R$^C$ and R$^D$ are each independently selected from the group consisting of hydrogen and $C_{1-2}$alkyl; provided that at least one of $R^4$ or $R^5$ is selected from the group consisting of hydrogen, chloro and fluoro.

In another embodiment, the present invention is directed to compounds of formula (I) wherein $R^4$ and $R^5$ are each independently selected from the group consisting of hydrogen, halogen, cyano, $C_{1-4}$alkyl, chloro substituted $C_{1-4}$alkyl, fluoro substituted $C_{1-4}$alkyl, $C_{2-4}$alkenyl, chloro substituted $C_{2-4}$alkenyl, fluoro substituted $C_{2-4}$alkenyl, $C_{2-4}$alkynyl, chloro substituted $C_{2-4}$alkynyl, fluoro substituted $C_{2-4}$alkynyl, $C_{1-4}$alkoxy, fluoro substituted $C_{1-4}$alkoxy, —O—($C_{1-4}$alkyl)-O—($C_{1-4}$alkyl), —($C_{1-4}$alkyl)-O—($C_{1-4}$alkyl), —($C_{1-4}$alkyl)-SO$_2$—($C_{1-4}$alkyl), —C(O)—NR$^C$R$^D$, —O-(aryl) and —O—($C_{1-2}$alkyl)-aryl; wherein R$^C$ and R$^D$ are each independently selected from the group consisting of hydrogen and $C_{1-4}$alkyl; provided that at least one of $R^4$ or $R^5$ is selected from the group consisting of hydrogen, chloro and fluoro.

In another embodiment, the present invention is directed to compounds of formula (I) wherein $R^4$ and $R^5$ are each independently selected from the group consisting of hydrogen, chloro, fluoro, bromo, iodo, methyl, ethyl, trifluoromethyl, ethyl, 1,1-difluoroethyl, ethynyl, prop-1-yn-1-yl, 3,3,3-trifluoroprop-1-yn-1-yl, methoxy, ethoxy, isopropyloxy, isobutyloxy, difluoromethoxy, trifluoromethoxy, 2,2,2-trifluoroethoxy, phenyloxy, benzyloxy, cyano, dimethylaminocarbonyl-, methoxy-ethoxy-, 3-(methylsulfonyl)-prop-1-yl and 3-(methylsulfonyl)-prop-1-yn-1-yl; provided that at least one of $R^4$ or $R^5$ is selected from the group consisting of hydrogen, chloro and fluoro.

In another embodiment, the present invention is directed to compounds of formula (I) wherein $R^4$ is selected from the group consisting of hydrogen, chloro, fluoro, bromo, iodo, trifluoromethyl, 1,1,-difluoroethyl, ethynyl, prop-1-yn-1-yl, 3,3,3-trifluoroprop-1-yn-1-yl, ethoxy, difluoromethoxy, trifluoromethoxy, cyano, dimethylaminocarbonyl-, 3-(methylsulfonyl)-prop-1-yl and 3-(methylsulfonyl)-prop-1-yn-1-yl.

In another embodiment, the present invention is directed to compounds of formula (I) wherein $R^4$ is selected from group consisting of hydrogen, chloro, fluoro, bromo, iodo, ethynyl, trifluoromethyl, ethoxy, difluoromethoxy, trifluoromethoxy, prop-1-yn-1-yl and cyano. In another embodiment, the present invention is directed to compounds of formula (I) wherein $R^4$ is selected from group consisting of hydrogen, chloro, fluoro, bromo, iodo, ethynyl, trifluoromethyl, difluoromethoxy, trifluoromethoxy, prop-1-yn-1-yl and cyano. In another embodiment, the present invention is directed to compounds of formula (I) wherein $R^4$ is selected from group consisting of chloro, bromo, iodo, ethynyl, trifluoromethyl, difluoromethoxy, trifluoromethoxy and cyano.

In another embodiment, the present invention is directed to compounds of formula (I) wherein $R^5$ is selected from the group consisting of hydrogen, fluoro, methyl, ethyl, methoxy, ethoxy, isopropyloxy, isobutyloxy, 2,2,2-trifluoroethoxy, difluoromethoxy, phenyloxy, benzyloxy, methoxy-ethoxy- and 3-(methylsulfonyl)-prop-1-yl.

In another embodiment, the present invention is directed to compounds of formula (I) wherein $R^5$ is selected from the group consisting of hydrogen, fluoro, methyl, ethyl, methoxy, ethoxy, isopropyloxy, isobutyloxy, 2,2,2-trifluoroethoxy, difluoromethoxy and methoxy-ethoxy-. In another embodiment, the present invention is directed to compounds of formula (I) wherein $R^5$ is selected from the group consisting of hydrogen, methyl, ethyl, methoxy and difluoromethoxy.

In an embodiment, the present invention is directed to compounds of formula (I) wherein

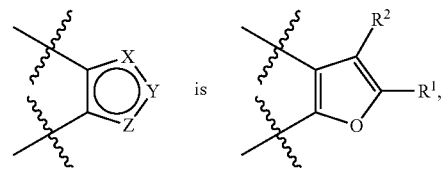

and wherein $R^4$ and $R^5$ may be taken together with the carbon atoms to which they are bound to form a ring structure selected from the group consisting of

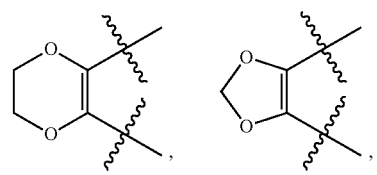

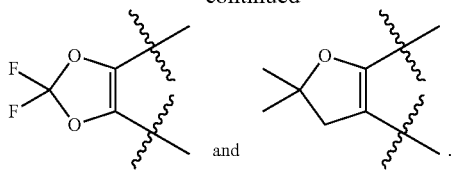

and

In another embodiment, the present invention is directed to compounds of formula (I) wherein

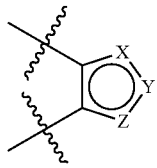

is selected from the group consisting of

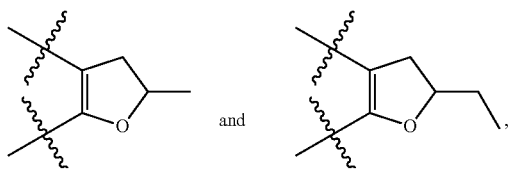

and wherein $R^4$ and $R^5$ may be taken together with the carbon atoms to which they are bound to form a ring structure selected from the group consisting of

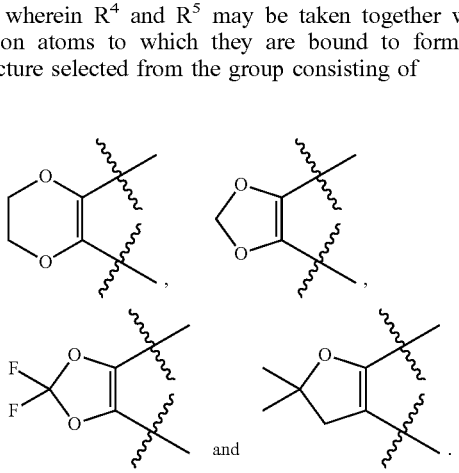

In another embodiment, the present invention is directed to compounds of formula (I) wherein alternatively, wherein

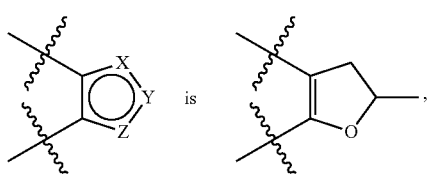

$R^4$ and $R^5$ may be taken together with the carbon atoms to which they are bound to form a ring structure selected from the group consisting of

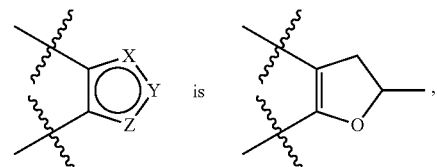

In another embodiment, the present invention is directed to compounds of formula (I) wherein alternatively, wherein

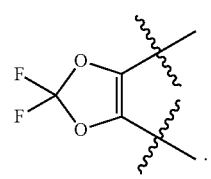

is $R^4$ and $R^5$ may be taken together with the carbon atoms to which they are bound to form

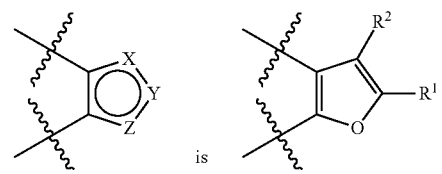

In an embodiment the present invention is directed to compounds of formula (I) wherein W is selected from the group consisting of CH, C(F) and C(Br). In another embodiment, the present invention is directed to compounds of formula (I) wherein W is selected from the group consisting of CH and C(F). In another embodiment, the present invention is directed to compounds of formula (I) wherein W is CH. In another embodiment, the present invention is directed to compounds of formula (I) wherein W is N.

In an embodiment, the present invention is directed to compounds of formula (I) wherein and wherein W may be N. In another embodiment, the present invention is directed to compounds of formula (I) wherein

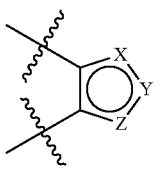

is selected from the group consisting of

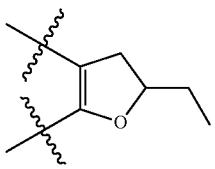 and 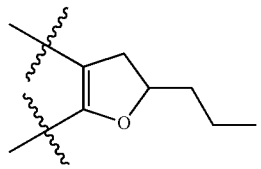

and wherein W may be N.

In an embodiment, the present invention is directed to compounds of formula (I) wherein $R^6$ and $R^7$ are each independently selected from the group consisting of hydrogen, halogen, cyano, $C_{1-6}$alkyl, fluoro substituted $C_{1-4}$alkyl, $C_{1-4}$alkoxy and fluoro substituted $C_{1-4}$alkoxy. In another embodiment, the present invention is directed to compounds of formula (I) wherein $R^6$ and $R^7$ are each independently selected from the group consisting of hydrogen, halogen, $C_{1-6}$alkyl, fluoro substituted $C_{1-2}$alkyl and cyano.

In another embodiment, the present invention is directed to compounds of formula (I) wherein $R^6$ and $R^7$ are each independently selected from the group consisting of hydrogen, fluoro, methyl, n-propyl, isobutyl, isopentyl, trifluoromethyl and cyano.

In another embodiment, the present invention is directed to compounds of formula (I) wherein $R^6$ is selected from the group consisting of hydrogen, fluoro, methyl and cyano. In another embodiment, the present invention is directed to compounds of formula (I) wherein $R^6$ is selected from the group consisting of hydrogen, fluoro and methyl. In another embodiment, the present invention is directed to compounds of formula (I) wherein $R^6$ is methyl.

In another embodiment, the present invention is directed to compounds of formula (I) wherein $R^7$ is selected from the group consisting of hydrogen, fluoro, methyl, n-propyl, isobutyl, isopentyl and trifluoromethyl. In another embodiment, the present invention is directed to compounds of formula (I) wherein $R^7$ is selected from the group consisting of hydrogen, fluoro, methyl, n-propyl, isopentyl and trifluoromethyl. In another embodiment, the present invention is directed to compounds of formula (I) wherein $R^7$ is selected from the group consisting of fluoro, methyl, n-propyl and trifluoromethyl. In another embodiment, the present invention is directed to compounds of formula (I) wherein $R^7$ is selected from the group consisting of fluoro, methyl and n-propyl. In another embodiment, the present invention is directed to compounds of formula (I) wherein $R^7$ is methyl.

In an embodiment, the present invention is directed to compounds of formula (I) wherein

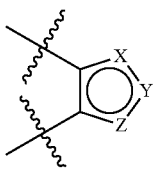 is 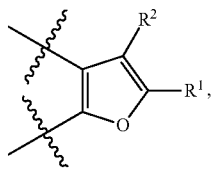, wherein W is $C(R^9)$ and wherein $R^6$ and $R^7$ may be taken together with the carbon atoms to which they are bound to form

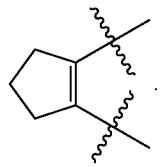

In another embodiment, the present invention is directed to compounds of formula (I) wherein

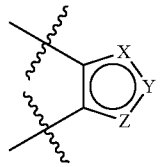

is selected from the group consisting of

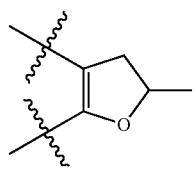 and 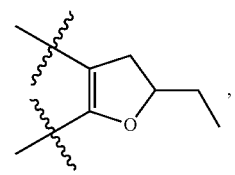, wherein W is CH and wherein $R^6$ and $R^7$ may be taken together with the carbon atoms to which they are bound to form

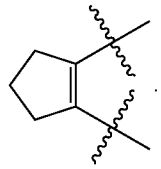 [SMILES: *C1=C(*)CCC1]

In an embodiment, the present invention is directed to compounds of formula (I) wherein $R^8$ is selected from the group consisting of hydrogen, halogen, cyano, $C_{1-4}$alkyl, fluoro substituted $C_{1-4}$alkyl, $C_{1-4}$alkoxy, fluoro substituted $C_{1-4}$alkoxy and —$(C_{1-4}$alkyl)-C(O)OH. In another embodiment, the present invention is directed to compounds of formula (I) wherein $R^8$ is selected from the group consisting of hydrogen, $C_{1-2}$alkyl and fluoro substituted $C_{1-2}$alkyl.

In another embodiment, the present invention is directed to compounds of formula (I) wherein $R^8$ is selected from the group consisting of hydrogen, methyl and trifluoromethyl. In another embodiment, the present invention is directed to compounds of formula (I) wherein $R^8$ is selected from the group consisting of hydrogen and trifluoromethyl. In another embodiment, the present invention is directed to compounds of formula (I) wherein $R^8$ is hydrogen.

In an embodiment, the present invention is directed to compounds of formula (I) wherein $R^0$ is —$CH_2OH$. In another embodiment, the present invention is directed to compounds of formula (I) wherein $R^0$ is —C(O)OH.

Additional embodiments of the present invention, include those wherein the substituents selected for one or more of the variables defined herein (i.e.

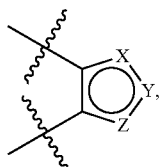

$R^0$, $R^1$, $R^2$, $R^3$, $R^4$, $R^5$, $R^6$, $R^7$, $R^8$, $R^9$, $R^{10}$, $R^{11}$, W, etc.) are independently selected to be any individual substituent or any subset of substituents selected from the complete list as defined herein.

In another embodiment of the present invention is any single compound or subset of compounds selected from the representative compounds listed in Tables 1-4 below. Representative compounds of the present invention are as listed in Table 1 to 4 below. Unless otherwise noted, wherein a stereogenic center is present in the listed compound, the compound was prepared as a mixture of stereo-isomers.

TABLE 1

Representative Compounds of Formula (I)

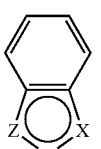

| ID No | Y | $R^3$ | $R^4$ | $R^5$ | $R^6$ | $R^7$ | $R^8$ |
|---|---|---|---|---|---|---|---|
| 1 | 4-(2,3-dimethyl-benzofuryl) | H | H | H | F | F | H |
| 2 | 7-(2-methyl-benzofuryl) | H | F | H | CH$_3$ | CH$_3$ | H |
| 3 | 7-(2-ethyl-benzofuryl) | H | F | H | CH$_3$ | CH$_3$ | H |
| 4 | 7-(2-trifluoro-methyl-benzofuryl) | H | F | H | CH$_3$ | CH$_3$ | H |
| 5 | 7-(2-methyl-3-fluoro-benzofuryl) | H | F | H | CH$_3$ | CH$_3$ | H |
| 6 | 4-(2-methyl-benzofuryl) | H | H | H | F | F | H |
| 7 | 7-(1-methyl-indazolyl) | H | Cl | H | CH$_3$ | CH$_3$ | H |
| 8 | 7-(2-methyl-indazolyl) | H | Cl | H | CH$_3$ | CH$_3$ | H |
| 9 | 7-(2-isopentyl-benzofuryl) | H | F | H | CH$_3$ | CH$_3$ | H |
| 10 | 7-(2-methoxy-ethyl-benzofuryl) | H | F | H | CH$_3$ | CH$_3$ | H |
| 11 | 7-(2-ethyl-benzofuryl) | H | Cl | H | CH$_3$ | CH$_3$ | H |
| 12 | 7-(2-ethyl-benzofuryl) | H | OCF$_3$ | H | CH$_3$ | CH$_3$ | H |
| 13 | 7-(2-n-propyl-benzofuryl) | H | F | H | CH$_3$ | CH$_3$ | H |
| 14 | 7-(2-hydroxy-methyl-benzofuryl) | H | F | H | CH$_3$ | CH$_3$ | H |
| 15 | 7-(2-hydroxy-ethyl-benzofuryl) | H | F | H | CH$_3$ | CH$_3$ | H |
| 16 | 7-(2-ethyl-benzofuryl) | H | F | H | F | F | H |
| 18 | 7-(2-cyclo-pentyl-benzofuryl) | H | F | H | CH$_3$ | CH$_3$ | H |
| 19 | 7-(2-cyclo-pentyl-methyl-benzofuryl) | H | F | H | CH$_3$ | CH$_3$ | H |
| 20 | 7-(2-benzyl-benzofuryl) | H | F | H | CH$_3$ | CH$_3$ | H |
| 21 | 7-(2-methoxy-methyl-benzofuryl) | H | F | H | CH$_3$ | CH$_3$ | H |
| 22 | 7-(2-isopropyl-benzofuryl) | H | F | H | CH$_3$ | CH$_3$ | H |
| 23 | 7-(2-isobutyl-benzofuryl) | H | F | H | CH$_3$ | CH$_3$ | H |
| 24 | 7-(2-methyl-carbonyl-amino-ethyl-benzofuryl) | H | F | H | CH$_3$ | CH$_3$ | H |
| 25 | 7-(2-methyl-sulfonyl-amino-ethyl-benzofuryl) | H | F | H | CH$_3$ | CH$_3$ | H |

TABLE 1-continued

Representative Compounds of Formula (I)

| ID No | Y | R³ | R⁴ | R⁵ | R⁶ | R⁷ | R⁸ |
|---|---|---|---|---|---|---|---|
| 26 | 7-(2-dimethyl-amino-ethyl-benzofuryl) | H | F | H | CH₃ | CH₃ | H |
| 27 | 7-(2-t-butyl-benzofuryl) | H | F | H | CH₃ | CH₃ | H |
| 29 | 7-(2-ethyl-benzofuryl) | H | —O-ethyl | H | CH₃ | CH₃ | H |
| 31 | 7-(2-n-propyl-benzofuryl) | H | Cl | H | CH₃ | CH₃ | H |
| 32 | 7-(2-difluoro-methyl-benzofuryl) | H | F | H | CH₃ | CH₃ | H |
| 35 | 7-(2-n-propyl-benzofuryl) | H | OCF₃ | H | CH₃ | CH₃ | H |
| 36 | 7-(2-methyl-benzofuryl) | H | OCF₃ | H | CH₃ | CH₃ | H |
| 37 | 7-(2-n-propyl-benzofuryl) | H | CF₃ | H | CH₃ | CH₃ | H |
| 38 | 7-(2-n-propyl-benzofuryl) | H | ethynyl | H | CH₃ | CH₃ | H |
| 40 | 7-(2-ethyl-benzofuryl) | H | Cl | CH₃ | CH₃ | CH₃ | H |
| 41 | 7-(2-n-propyl-benzofuryl) | H | Cl | H | cyano | CH₃ | H |
| 42 | 7-(2-amino-carbonyl-benzofuryl) | H | F | H | CH₃ | CH₃ | H |
| 43 | 7-(2-carboxy-benzofuryl) | H | F | H | CH₃ | CH₃ | H |
| 44 | 7-(2-ethyl-benzofuryl) | H | Cl | OCH₃ | CH₃ | CH₃ | H |
| 45 | 7-(2-ethyl-benzofuryl) | H | Br | H | CH₃ | CH₃ | H |
| 46 | 7-(2-n-propyl-benzofuryl) | H | —C(O)—N(CH₃)₂ | H | CH₃ | CH₃ | H |
| 47 | 7-(2-n-propyl-benzofuryl) | H | I | H | CH₃ | CH₃ | H |
| 48 | 7-(2,3-dimethyl-benzofuryl) | H | F | H | CH₃ | CH₃ | H |
| 49 | 7-(2-cyano-benzofuryl) | H | F | H | CH₃ | CH₃ | H |
| 56 | 7-(2-methyl-carbonyl-benzofuryl) | H | F | H | CH₃ | CH₃ | H |
| 57 | 7-(2-ethyl-benzofuryl) | H | difluoro-methoxy | H | CH₃ | CH₃ | H |
| 58 | 7-(2-n-propyl-benzofuryl) | H | prop-1-yn-1-yl | H | CH₃ | CH₃ | H |
| 59 | 7-(2-n-propyl-benzofuryl) | H | Cl | H | F | F | H |
| 60 | 4-(2,3-dimethyl-benzofuryl) | H | H | H | CH₃ | CH₃ | H |
| 61 | 7-(2-ethyl-benzofuryl) | H | Cl | ethyl | CH₃ | CH₃ | H |
| 62 | 7-(2-ethyl-benzofuryl) | H | Cl | ethoxy | CH₃ | CH₃ | H |
| 63 | 7-(2-ethyl-benzofuryl) | H | Cl | methoxy-ethoxy- | CH₃ | CH₃ | H |
| 64 | 7-(2-ethyl-benzofuryl) | H | Cl | 2,2,2-trifluoro-ethoxy | CH₃ | CH₃ | H |
| 65 | 7-(2-ethyl-benzofuryl) | H | Cl | iso-propyl-oxy- | CH₃ | CH₃ | H |
| 66 | 7-(2-ethyl-benzofuryl) | H | H | ethoxy | CH₃ | CH₃ | H |
| 67 | 7-(2-ethyl-benzofuryl) | H | Cl | isobutyl-oxy | CH₃ | CH₃ | H |
| 68 | 7-(2-ethyl-benzofuryl) | H | Cl | benzyl-oxy- | CH₃ | CH₃ | H |
| 69 | 7-(2-ethyl-benzofuryl) | H | Cl | difluoro-methoxy | CH₃ | CH₃ | H |
| 70 | 7-(2-ethyl-benzofuryl) | H | H | difluoro-methoxy | CH₃ | CH₃ | H |
| 71 | 7-(2-methyl-benzofuryl) | F | OCF₃ | F | CH₃ | CH₃ | H |
| 72 | 7-(2-n-propyl-benzofuryl) | H | 3,3,3-trifluoro-prop-1-yn-1-yl | H | CH₃ | CH₃ | H |
| 73 | 7-(2-ethyl-benzofuryl) | H | Cl | phenyl-oxy- | CH₃ | CH₃ | H |
| 74 | 7-(2-methyl-benzofuryl) | OCH₃ | OCF₃ | F | F | F | H |
| 75 | 7-(2-methyl-benzofuryl) | F | OCF₃ | F | F | F | H |
| 76 | 7-(2-methyl-benzofuryl) | H | difluoro-methoxy | H | CH₃ | CH₃ | H |
| 77 | 7-(2-n-propyl-benzofuryl) | H | difluoro-methoxy | H | CH₃ | CH₃ | H |
| 78 | 7-(2-methyl-benzofuryl) | H | Cl | H | CH₃ | CH₃ | H |
| 79 | 7-(2-n-propyl-benzofuryl) | H | 1,1-difluoro-ethyl- | H | CH₃ | CH₃ | H |

TABLE 1-continued

Representative Compounds of Formula (I)

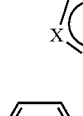

| ID No | | R³ | R⁴ | R⁵ | R⁶ | R⁷ | R⁸ |
|---|---|---|---|---|---|---|---|
| 80 | 4-(2,3-dimethyl-benzofuryl) | H | Cl | H | CH₃ | CH₃ | H |
| 81 | 4-(2-methyl-benzofuryl) | H | Cl | H | CH₃ | CH₃ | H |
| 83 | 7-(2-methyl-benzofuryl) | H | prop-1-yn-1-yl | H | CH₃ | CH₃ | H |
| 84 | 7-(2-methyl-benzoxazolyl) | H | Cl | H | CH₃ | CH₃ | H |
| 85 | 7-(2-methyl-benzofuryl) | H | Cl | CH₃ | CH₃ | CH₃ | H |
| 87 | 7-(2-(2,2-difluoro-ethyl)-benzofuryl) | H | Cl | H | CH₃ | CH₃ | H |
| 88 | 7-(2-(2-fluoro-ethen-1-yl)-benzofuryl) | H | Cl | H | CH₃ | CH₃ | H |
| 91 | 7-(2-methyl-benzothienyl) | H | Cl | H | CH₃ | CH₃ | H |
| 94 | 7-(2-hydroxy-ethyl-benzofuryl) | H | OCF₃ | H | CH₃ | CH₃ | H |
| 95 | 4-(2-methyl-benzoxazolyl) | H | Cl | H | CH₃ | CH₃ | H |
| 96 | 7-(2-(2,2-difluoro-ethyl)-benzofuryl) | H | OCF₃ | H | CH₃ | CH₃ | H |
| 97 | 7-(2-(2-fluoro-ethen-1-yl)-benzofuryl) | H | OCF₃ | H | CH₃ | CH₃ | H |
| 98 | 4-(2-methyl-benzothiazolyl) | H | Cl | H | CH₃ | CH₃ | H |
| 99 | 7-(2-methyl-benzofuryl) | H | 3-(methylsulfonyl)-prop-1-yn-1-yl | H | CH₃ | CH₃ | H |
| 100 | 7-(2-methyl-benzofuryl) | H | 3-(methylsulfonyl)-prop-1-yl | H | CH₃ | CH₃ | H |
| 101 | 4-(2-methyl-benzothienyl) | H | Cl | H | CH₃ | CH₃ | H |
| 104 | 4-(2-t-butyl-benzothiazolyl) | H | Cl | H | CH₃ | CH₃ | H |
| 105 | 4-(2-ethyl-benzothiazolyl) | H | F | H | CH₃ | CH₃ | H |
| 106 | 4-(2-isopropyl-benzothiazolyl) | H | Cl | H | CH₃ | CH₃ | H |
| 107 | 4-(2-t-butyl-benzothiazolyl) | H | F | H | CH₃ | CH₃ | H |
| 108 | 7-(2-methyl-benzofuryl) | H | Cl | 3-(methylsulfonyl)prop-1-yl | CH₃ | CH₃ | H |
| 109 | 4-(2-ethyl-benzothiazolyl) | H | Cl | H | CH₃ | CH₃ | H |
| 110 | 4-(2-isobutyl-benzothiazolyl) | H | Cl | H | CH₃ | CH₃ | H |
| 111 | 4-(2-isopropyl-benzothiazolyl) | H | F | H | CH₃ | CH₃ | H |
| 112 | 7-(2-methyl-benzofuryl) | H | OCF₃ | H | H | CF₃ | H |
| 115 | 4-(2-isobutyl-benzothiazolyl) | H | F | H | CH₃ | CH₃ | H |
| 117 | 4-(2-trifluoro-methyl-benzothiazolyl) | H | F | H | CH₃ | CH₃ | H |
| 118 | 4-(2-methyl-benzothiazolyl) | H | OCF₃ | H | CH₃ | CH₃ | H |
| 119 | 4-(2-trifluoro-methyl-benzothiazolyl) | H | Cl | H | CH₃ | CH₃ | H |
| 121 | 7-(2-methyl-benzothiazolyl) | H | Cl | H | CH₃ | CH₃ | H |
| 122 | 7-(2-ethyl-benzofuryl) | H | cyano | H | CH₃ | CH₃ | H |

In Table 2 which follows herein, the ring structures shown in the columns headed "R⁶ and R⁷ taken together" and "R⁴ and R⁵ taken together" are incorporated into the structure drawn at the head of the table, in the orientation as drawn.

TABLE 2

Representative Compounds of Formula (I)

| ID No | (ring) | R⁴ | R⁵ | R⁶ and R⁷ taken together |
|---|---|---|---|---|
| 52 | 7-(2-ethyl-benzofuryl) | OCF₃ | H | cyclopentene |
| 54 | 7-(2-ethyl-benzofuryl) | Cl | H | cyclopentene |
| 55 | 7-(2-methyl-benzofuryl) | OCF₃ | H | cyclopentene |

| ID No | (ring) | R⁴ and R⁵ taken together | R⁶ | R⁷ |
|---|---|---|---|---|
| 30 | 7-(2-ethyl-benzofuryl) | dimethyl-dihydrofuran | CH₃ | CH₃ |
| 82 | 7-(2-methyl-benzofuryl) | dioxole | CH₃ | CH₃ |

TABLE 2-continued

Representative Compounds of Formula (I)

| ID No | (ring) | R⁴ and R⁵ taken together | R⁶ | R⁷ |
|---|---|---|---|---|
| 89 | 7-(2-methyl-benzofuryl) | difluoro-dioxole | CH₃ | CH₃ |
| 90 | 7-(2-methyl-benzofuryl) | dioxine | CH₃ | CH₃ |

TABLE 3

Representative Compounds of Formula (I)

| ID No | (ring) | R⁴ | R⁵ | R⁶ | R⁷ | R⁹ | R⁰ |
|---|---|---|---|---|---|---|---|
| 17 | 7-(2-ethyl-benzofuryl) | F | H | F | H | F | C(O)OH |
| 50 | 7-(2-ethyl-benzofuryl) | OCF₃ | H | H | n-propyl | F | C(O)OH |
| 51 | 7-(2-ethyl-benzofuryl) | OCF₃ | H | H | isopentyl | F | C(O)OH |
| 53 | 7-(2-ethyl-benzofuryl) | OCF₃ | H | H | isobutyl | F | C(O)OH |
| 86 | 7-(2-methyl-benzofuryl) | Cl | CH₃ | F | H | F | C(O)OH |
| 92 | 7-(2-methyl-benzothienyl) | Cl | H | F | H | F | C(O)OH |
| 93 | 7-(2-methyl-benzothienyl) | Cl | H | F | H | F | CH₂OH |
| 102 | 4-(2-methyl-benzothienyl) | Cl | H | F | H | F | C(O)OH |
| 103 | 4-(2-methyl-benzothienyl) | Cl | H | F | H | F | CH₂OH |
| 120 | 4-(2-methyl-3-bromo-benzofuryl) | OCF₃ | H | CH₃ | CH₃ | Br | C(O)OH |

TABLE 4

Representative Compounds of Formula (I)

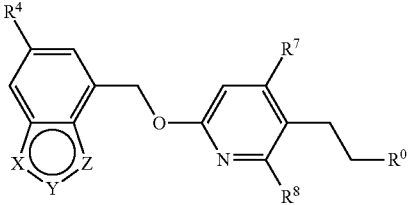

| ID No | Z–X–Y | R⁴ | R⁷ | R⁸ | R⁹ |
|---|---|---|---|---|---|
| 28 | 7-(2-ethyl-benzofuryl) | F | H | CF₃ | C(O)OH |
| 33 | 7-(2-ethyl-benzofuryl) | F | CH₃ | H | C(O)OH |
| 34 | 7-(2-n-propyl-benzofuryl) | Cl | CH₃ | H | C(O)OH |
| 123 | 7-(2-ethyl-benzofuryl) | F | H | CH₃ | C(O)OH |

In another embodiment, the present invention is directed to one or more compounds independently selected from the compounds listed in Table 5, below.

TABLE 5

Representative Compounds of the Present Invention

| ID No. | Compound name | Synthesis Example No. |
|---|---|---|
| 1 | 3-{4-[(2,3-Dimethyl-1-benzofuran-4-yl)methoxy]-2,3-difluorophenyl}propanoic acid | 86 |
| 2 | 3-{4-[(5-Fluoro-2-methyl-1-benzofuran-7-yl)methoxy]-2,3-dimethylphenyl}propanoic acid | 1 |
| 3 | 3-{4-[(2-Ethyl-5-fluoro-1-benzofuran-7-yl)methoxy]-2,3-dimethylphenyl}propanoic acid | 83 |
| 4 | 3-(4-{[5-Fluoro-2-(trifluoromethyl)-1-benzofuran-7-yl]methoxy}-2,3-dimethylphenyl)propanoic acid | 84 |
| 5 | 3-{4-[(3,5-Difluoro-2-methyl-1-benzofuran-7-yl)methoxy]-2,3-dimethylphenyl}propanoic acid | 85 |
| 6 | 3-{2,3-Difluoro-4-[(2-methyl-1-benzofuran-4-yl)methoxy]phenyl}propanoic acid | 87 |
| 7 | 3-{4-[(5-Chloro-1-methyl-1H-indazol-7-yl)methoxy]-2,3-dimethylphenyl}propanoic acid | 81 |
| 8 | 3-{4-[(5-Chloro-2-methyl-2H-indazol-7-yl)methoxy]-2,3-dimethylphenyl}propanoic acid | 82 |
| 9 | 3-(4-{[5-Fluoro-2-(3-methylbutyl)-1-benzofuran-7-yl]methoxy}-2,3-dimethylphenyl)propanoic acid | 2 |
| 10 | 3-(4-{[5-Fluoro-2-(2-methoxyethyl)-1-benzofuran-7-yl]methoxy}-2,3-dimethylphenyl)propanoic acid | 3 |
| 11 | 3-{4-[(5-Chloro-2-ethyl-1-benzofuran-7-yl)methoxy]-2,3-dimethylphenyl}propanoic acid | 88 |
| 12 | 3-(4-{[2-Ethyl-5-(trifluoromethoxy)-1-benzofuran-7-yl]methoxy}-2,3-dimethylphenyl)propanoic acid | 89 |
| 13 | 3-{4-[(5-Fluoro-2-propyl-1-benzofuran-7-yl)methoxy]-2,3-dimethylphenyl}propanoic acid | 4 |
| 14 | 3-(4-{[5-Fluoro-2-(hydroxymethyl)-1-benzofuran-7-yl]methoxy}-2,3-dimethylphenyl)propanoic acid | 5 |
| 15 | 3-(4-{[5-Fluoro-2-(2-hydroxyethyl)-1-benzofuran-7-yl]methoxy}-2,3-dimethylphenyl)propanoic acid | 6 |
| 16 | 3-{4-[(2-Ethyl-5-fluoro-1-benzofuran-7-yl)methoxy]-2,3-difluorophenyl}propanoic acid | 90 |
| 17 | 3-{4-[(2-Ethyl-5-fluoro-1-benzofuran-7-yl)methoxy]-3,5-difluorophenyl}propanoic acid | 91 |
| 18 | 3-{4-[(2-Cyclopentyl-5-fluoro-1-benzofuran-7-yl)methoxy]-2,3-dimethylphenyl}propanoic acid | 7 |
| 19 | 3-(4-{[2-(Cyclopentylmethyl)-5-fluoro-1-benzofuran-7-yl]methoxy}-2,3-dimethylphenyl)propanoic acid | 8 |
| 20 | 3-{4-[(2-Benzyl-5-fluoro-1-benzofuran-7-yl)methoxy]-2,3-dimethylphenyl}propanoic acid | 9 |
| 21 | 3-(4-{[5-Fluoro-2-(methoxymethyl)-1-benzofuran-7-yl]methoxy}-2,3-dimethylphenyl)propanoic acid | 10 |
| 22 | 3-(4-{[5-Fluoro-2-(1-methylethyl)-1-benzofuran-7-yl]methoxy}-2,3-dimethylphenyl)propanoic acid | 11 |
| 23 | 3-(4-{[5-Fluoro-2-(2-methylpropyl)-1-benzofuran-7-yl]methoxy}-2,3-dimethylphenyl)propanoic acid | 12 |
| 24 | 3-[4-({2-[2-(Acetylamino)ethyl]-5-fluoro-1-benzofuran-7-yl}methoxy)-2,3-dimethylphenyl]propanoic acid | 13 |
| 25 | 3-{4-[(5-Fluoro-2-{2-[(methylsulfonyl)amino]ethyl}-1-benzofuran-7-yl)methoxy]-2,3-dimethylphenyl}propanoic acid | 14 |
| 26 | 3-[4-({2-[2-(Dimethylamino)ethyl]-5-fluoro-1-benzofuran-7-yl}methoxy)-2,3-dimethylphenyl]propanoic acid | 15 |
| 27 | 3-{4-[(2-tert-Butyl-5-fluoro-1-benzofuran-7-yl)methoxy]-2,3-dimethylphenyl}propanoic acid | 16 |
| 28 | 3-{6-[(2-Ethyl-5-fluoro-1-benzofuran-7-yl)methoxy]-2-(trifluoromethyl)pyridin-3-yl}propanoic acid | 92 |
| 29 | 3-{4-[(5-Ethoxy-2-ethyl-1-benzofuran-7-yl)methoxy]-2,3-dimethylphenyl}propanoic acid | 17 |
| 30 | 3-{4-[(6-Ethyl-2,2-dimethyl-2,3-dihydrobenzo[1,2-b:4,5-b']difuran-4-yl)methoxy]-2,3-dimethylphenyl}propanoic acid | 93 |
| 31 | 3-{4-[(5-Chloro-2-propyl-1-benzofuran-7-yl)methoxy]-2,3-dimethylphenyl}propanoic acid | 94 |
| 32 | 3-(4-{[2-(Difluoromethyl)-5-fluoro-1-benzofuran-7-yl]methoxy}-2,3-dimethylphenyl)propanoic acid | 95 |
| 33 | 3-{6-[(2-Ethyl-5-fluoro-1-benzofuran-7-yl)methoxy]-4-methylpyridin-3-yl}propanoic acid | 96 |
| 34 | 3-{6-[(5-Chloro-2-propyl-1-benzofuran-7-yl)methoxy]-4-methylpyridin-3-yl}propanoic acid | 97 |
| 35 | 3-(2,3-Dimethyl-4-{[2-propyl-5-(trifluoromethoxy)-1-benzofuran-7-yl]methoxy}phenyl)propanoic acid | 98 |
| 36 | 3-(2,3-Dimethyl-4-{[2-methyl-5-(trifluoromethoxy)-1-benzofuran-7-yl]methoxy}phenyl)propanoic acid | 99 |
| 37 | 3-(2,3-Dimethyl-4-{[2-propyl-5-(trifluoromethyl)-1-benzofuran-7-yl]methoxy}phenyl)propanoic acid | 18 |
| 38 | 3-{4-[(5-Ethynyl-2-propyl-1-benzofuran-7-yl)methoxy]-2,3-dimethylphenyl}propanoic acid | 19 |
| 40 | 3-{4-[(5-Chloro-2-ethyl-6-methyl-1-benzofuran-7-yl)methoxy]-2,3-dimethylphenyl}propanoic acid | 20 |
| 41 | 3-{4-[(5-Chloro-2-propyl-1-benzofuran-7-yl)methoxy]-3-cyano-2-methylphenyl}propanoic acid | 100 |
| 42 | 3-{4-[(2-Carbamoyl-5-fluoro-1-benzofuran-7-yl)methoxy]-2,3-dimethylphenyl}propanoic acid | 21 |
| 43 | 7-{[4-(2-Carboxyethyl)-2,3-dimethylphenoxy]methyl}-5-fluoro-1-benzofuran-2-carboxylic acid | 22 |
| 44 | 3-{4-[(5-Chloro-2-ethyl-6-methoxy-1-benzofuran-7-yl)methoxy]-2,3-dimethylphenyl}propanoic acid | 23 |
| 45 | 3-{4-[(5-Bromo-2-ethyl-1-benzofuran-7-yl)methoxy]-2,3-dimethylphenyl}propanoic acid | 101 |
| 46 | 3-(4-{[5-(Dimethylcarbamoyl)-2-propyl-1-benzofuran-7-yl]methoxy}-2,3-dimethylphenyl)propanoic acid | 24 |
| 47 | 3-{4-[(5-Iodo-2-propyl-1-benzofuran-7-yl)methoxy]-2,3-dimethylphenyl}propanoic acid | 25 |
| 48 | 3-{4-[(5-Fluoro-2,3-dimethyl-1-benzofuran-7-yl)methoxy]-2,3-dimethylphenyl}propanoic acid | 102 |
| 49 | 3-{4-[(2-Cyano-5-fluoro-1-benzofuran-7-yl)methoxy]-2,3-dimethylphenyl}propanoic acid | 26 |
| 50 | 3-(4-{[2-Ethyl-5-(trifluoromethoxy)-1-benzofuran-7-yl]methoxy}-5-fluoro-2-propylphenyl)propanoic acid | 27 |
| 51 | 3-[4-{[2-Ethyl-5-(trifluoromethoxy)-1-benzofuran-7-yl]methoxy}-5-fluoro-2-(3-methylbutyl)phenyl]propanoic acid | 28 |
| 52 | 3-(7-{[2-Ethyl-5-(trifluoromethoxy)-1-benzofuran-7-yl]methoxy}-2,3-dihydro-1H-inden-4-yl)propanoic acid | 29 |

TABLE 5-continued

Representative Compounds of the Present Invention

| ID No. | Compound name | Synthesis Example No. |
|---|---|---|
| 53 | 3-[4-{[2-Ethyl-5-(trifluoromethoxy)-1-benzofuran-7-yl]methoxy}-5-fluoro-2-(2-methylpropyl)phenyl] propanoic acid | 30 |
| 54 | 3-{7-[(5-Chloro-2-ethyl-1-benzofuran-7-yl)methoxy]-2,3-dihydro-1H-inden-4-yl}propanoic acid | 31 |
| 55 | 3-(7-{[2-Methyl-5-(trifluoromethoxy)-1-benzofuran-7-yl]methoxy}-2,3-dihydro-1H-inden-4-yl)propanoic acid | 103 |
| 56 | 3-{4-(2-Acetyl-5-fluoro-1-benzofuran-7-yl) methoxy]-2,3-dimethylphenyl}propanoic acid | 32 |
| 57 | 3-(4-{[5-(Difluoromethoxy)-2-ethyl-1-benzofuran-7-yl]methoxy}-2,3-dimethylphenyl)propanoic acid | 33 |
| 58 | 3-{2,3-Dimethyl-4-[(2-propyl-5-prop-1-yn-1-yl-1-benzofuran-7-yl)methoxy]phenyl}propanoic acid | 34 |
| 59 | 3-{4-[(5-Chloro-2-propyl-1-benzofuran-7-yl)methoxy]-2,3-difluorophenyl}propanoic acid | 104 |
| 60 | 3-{4-[(2,3-Dimethyl-1-benzofuran-4-yl)methoxy]-2,3-dimethylphenyl}propanoic acid | 105 |
| 61 | 3-{4-[(5-Chloro-2,6-diethyl-1-benzofuran-7-yl)methoxy]-2,3-dimethylphenyl}propanoic acid | 35 |
| 62 | 3-{4-[(5-Chloro-6-ethoxy-2-ethyl-1-benzofuran-7-yl)methoxy]-2,3-dimethylphenyl}propanoic acid | 36 |
| 63 | 3-(4-{[5-Chloro-2-ethyl-6-(2-methoxyethoxy)-1-benzofuran-7-yl]methoxy}-2,3-dimethylphenyl) propanoic acid | 37 |
| 64 | 3-(4-{[5-Chloro-2-ethyl-6-(2,2,2-trifluoroethoxy)-1-benzofuran-7-yl]methoxy}-2,3-dimethylphenyl) propanoic acid | 38 |
| 65 | 3-(4-{[5-Chloro-2-ethyl-6-(1-methylethoxy)-1-benzofuran-7-yl]methoxy}-2,3-dimethylphenyl) propanoic acid | 39 |
| 66 | 3-{4-[(6-Ethoxy-2-ethyl-1-benzofuran-7-yl) methoxy]-2,3-dimethylphenyl}propanoic acid | 40 |
| 67 | 3-(4-{[5-Chloro-2-ethyl-6-(2-methylpropoxy)-1-benzofuran-7-yl]methoxy}-2,3-dimethylphenyl) propanoic acid | 41 |
| 68 | 3-(4-{[6-(Benzyloxy)-5-chloro-2-ethyl-1-benzofuran-7-yl]methoxy}-2,3-dimethylphenyl)propanoic acid | 42 |
| 69 | 3-(4-{[5-Chloro-6-(difluoromethoxy)-2-ethyl-1-benzofuran-7-yl]methoxy}-2,3-dimethylphenyl) propanoic acid | 43 |
| 70 | 3-(4-{[6-(Difluoromethoxy)-2-ethyl-1-benzofuran-7-yl]methoxy}-2,3-dimethylphenyl)propanoic acid | 44 |
| 71 | 3-(4-{[4,6-Difluoro-2-methyl-5-(trifluoromethoxy)-1-benzofuran-7-yl]methoxy}-2,3-dimethylphenyl) propanoic acid | 106 |
| 72 | 3-(2,3-Dimethyl-4-{[2-propyl-5-(3,3,3-trifluoroprop-1-yn-1-yl)-1-benzofuran-7-yl]methoxy}phenyl) propanoic acid | 45 |
| 73 | 3-{4-[(5-Chloro-2-ethyl-6-phenoxy-1-benzofuran-7-yl)methoxy]-2,3-dimethylphenyl}propanoic acid | 46 |
| 74 | 3-(2,3-Difluoro-4-{[6-fluoro-4-methoxy-2-methyl-5-(trifluoromethoxy)-1-benzofuran-7-yl]methoxy} phenyl)propanoic acid | 107 |
| 75 | 3-(4-{[4,6-Difluoro-2-methyl-5-(trifluoromethoxy)-1-benzofuran-7-yl]methoxy}-2,3-difluorophenyl) propanoic acid | 108 |
| 76 | 3-(4-{[5-(Difluoromethoxy)-2-methyl-1-benzofuran-7-yl]methoxy}-2,3-dimethylphenyl)propanoic acid | 47 |
| 77 | 3-(4-{[5-(Difluoromethoxy)-2-propyl-1-benzofuran-7-yl]methoxy}-2,3-dimethylphenyl)propanoic acid | 48 |
| 78 | 3-{4-[(5-Chloro-2-methyl-1-benzofuran-7-yl) methoxy]-2,3-dimethylphenyl}propanoic acid | 49 |
| 79 | 3-(4-{[5-(1,1-Difluoroethyl)-2-propyl-1-benzofuran-7-yl]methoxy}-2,3-dimethylphenyl)propanoic acid | 50 |
| 80 | 3-{4-[(6-Chloro-2,3-dimethyl-1-benzofuran-4-yl) methoxy]-2,3-dimethylphenyl}propanoic acid | 109 |
| 81 | 3-{4-[(6-Chloro-2-methyl-1-benzofuran-4-yl) methoxy]-2,3-dimethylphenyl}propanoic acid | 110 |
| 82 | 3-{2,3-Dimethyl-4-[(6-methylfuro[2,3-f][1,3] benzodioxol-4-yl)methoxy]phenyl}propanoic acid | 51 |
| 83 | 3-{2,3-Dimethyl-4-[(2-methyl-5-prop-1-yn-1-yl-1-benzofuran-7-yl)methoxy]phenyl}propanoic acid | 52 |
| 84 | 3-{4-[(5-Chloro-2-methyl-1,3-benzoxazol-7-yl) methoxy]-2,3-dimethylphenyl}propanoic acid | 111 |
| 85 | 3-{4-[(5-Chloro-2,6-dimethyl-1-benzofuran-7-yl) methoxy]-2,3-dimethylphenyl}propanoic acid | 53 |
| 86 | 3-{4-[(5-Chloro-2,6-dimethyl-1-benzofuran-7-yl) methoxy]-3,5-difluorophenyl}propanoic acid | 54 |
| 87 | 3-(4-{[5-Chloro-2-(2,2-difluoroethyl)-1-benzofuran-7-yl]methoxy}-2,3-dimethylphenyl)propanoic acid | 112 |
| 88 | 3-(4-((5-Chloro-2-(2-fluorovinyl)benzofuran-7-yl) methoxy)-2,3-dimethylphenyl)propanoic acid | 77 |
| 89 | 3-{4-[(2,2-Difluoro-6-methylfuro[2,3-f][1,3] benzodioxol-4-yl)methoxy]-2,3-dimethylphenyl} propanoic acid | 55 |
| 90 | 3-{2,3-Dimethyl-4-[(7-methyl-2,3-dihydrofuro[2,3-g] [1,4]benzodioxin-5-yl)methoxy]phenyl}propanoic acid | 56 |
| 91 | 3-{4-[(5-Chloro-2-methyl-1-benzothiophen-7-yl) methoxy]-2,3-dimethylphenyl}propanoic acid | 57 |
| 92 | 3-{4-[(5-Chloro-2-methyl-1-benzothiophen-7-yl) methoxy]-3,5-difluorophenyl}propanoic acid | 58 |
| 93 | 3-{4-[(5-Chloro-2-methyl-1-benzothiophen-7-yl) methoxy]-3,5-difluorophenyl}propan-1-ol | 59 |
| 94 | 3-(4-{[2-(2-Hydroxyethyl)-5-(trifluoromethoxy)-1-benzofuran-7-yl]methoxy}-2,3-dimethylphenyl) propanoic acid | 113 |
| 95 | 3-{4-[(6-Chloro-2-methyl-1,3-benzoxazol-4-yl) methoxy]-2,3-dimethylphenyl}propanoic acid | 114 |
| 96 | 3-(4-{[2-(2,2-Difluoroethyl)-5-(trifluoromethoxy)-1-benzofuran-7-yl]methoxy}-2,3-dimethylphenyl) propanoic acid | 115 |
| 97 | 3-(4-{[2-(2-Fluoroethenyl)-5-(trifluoromethoxy)-1-benzofuran-7-yl]methoxy}-2,3-dimethylphenyl) propanoic acid | 116 |
| 98 | 3-{4-[(6-Chloro-2-methyl-1,3-benzothiazol-4-yl) methoxy]-2,3-dimethylphenyl}propanoic acid | 117 |
| 99 | 3-[2,3-Dimethyl-4-({2-methyl-5-[3-(methylsulfonyl) prop-1-yn-1-yl]-1-benzofuran-7-yl}methoxy)phenyl] propanoic acid | 60 |
| 100 | 3-[2,3-Dimethyl-4-({2-methyl-5-[3-(methylsulfonyl) propyl]-1-benzofuran-7-yl}methoxy)phenyl] propanoic acid | 61 |
| 101 | 3-{4-[(6-Chloro-2-methyl-1-benzothiophen-4-yl) methoxy]-2,3-dimethylphenyl}propanoic acid | 62 |
| 102 | 3-{4-[(6-Chloro-2-methyl-1-benzothiophen-4-yl) methoxyl-3,5-difluorophenyl}propanoic acid | 63 |
| 103 | 3-{4-[(6-Chloro-2-methyl-1-benzothiophen-4-yl) methoxy]-3,5-difluorophenyl}propan-1-ol | 64 |
| 104 | 3-{4-[(2-tert-Butyl-6-chloro-1,3-benzothiazol-4-yl) methoxy]-2,3-dimethylphenyl}propanoic acid | 65 |
| 105 | 3-{4-[(2-Ethyl-6-fluoro-1,3-benzothiazol-4-yl) methoxy]-2,3-dimethylphenyl}propanoic acid | 66 |
| 106 | 3-(4-{[6-Fluoro-2-(1-methylethyl)-1,3-benzothiazol-4-yl]methoxy}-2,3-dimethylphenyl)propanoic acid | 67 |
| 107 | 3-{4-[(2-tert-butyl-6-fluoro-1,3-benzothiazol-4-yl) methoxy]-2,3-dimethylphenyl}propanoic acid | 68 |
| 108 | 3-[4-({5-Chloro-2-methyl-6-[3-(methylsulfonyl) propyl]-1-benzofuran-7-yl}methoxy)-2,3-dimethylphenyl]propanoic acid | 69 |
| 109 | 3-{4-[(6-Chloro-2-ethyl-1,3-benzothiazol-4-yl) methoxy]-2,3-dimethylphenyl}propanoic acid | 70 |
| 110 | 3-(4-{[6-Chloro-2-(2-methylpropyl)-1,3-benzothiazol-4-yl]methoxy}-2,3-dimethylphenyl)propanoic acid | 71 |
| 111 | 3-(4-{[6-Fluoro-2-(1-methylethyl)-1,3-benzothiazol-4-yl]methoxy}-2,3-dimethylphenyl)propanoic acid | 72 |
| 112 | 3-(4-{[2-Methyl-5-(trifluoromethoxy)-1-benzofuran-7-yl]methoxy}-2-(trifluoromethyl)phenyl]propanoic acid | 73 |
| 115 | 3-(4-{[6-Fluoro-2-(2-methylpropyl)-1,3-benzothiazol-4-yl]methoxy}-2,3-dimethylphenyl)propanoic acid | 76 |
| 117 | 3-(4-{[6-Fluoro-2-(trifluoromethyl)-1,3-benzothiazol-4-yl]methoxy}-2,3-dimethylphenyl)propanoic acid | 78 |
| 118 | 3-(2,3-Dimethyl-4-{[2-methyl-6-(trifluoromethoxy)-1,3-benzothiazol-4-yl]methoxy}phenyl)propanoic acid | 118 |

TABLE 5-continued

Representative Compounds of the Present Invention

| ID No. | Compound name | Synthesis Example No. |
|---|---|---|
| 119 | 3-(4-{[6-Chloro-2-(trifluoromethyl)-1,3-benzothiazol-4-yl]methoxy}-2,3-dimethylphenyl)propanoic acid | 79 |
| 120 | 3-(5-Bromo-4-{[3-bromo-2-methyl-5-(trifluoromethoxy)-1-benzofuran-7-yl]methoxy}-2,3-dimethylphenyl)propanoic acid | 119 |
| 121 | 3-{4-[(5-Chloro-2-methyl-1,3-benzothiazol-7-yl)methoxy]-2,3-dimethylphenyl}propanoic acid | 80 |
| 122 | 3-(6-((2-ethyl-5-fluorobenzofuran-7-yl)methoxy)-2-methylpyridin-3-yl)propanoic acid | 75 |
| 123 | 3-(4-((5-cyano-2-ethylbenzofuran-7-yl)methoxy)-2,3-dimethylphenyl)propanoic acid | 74 |

In an embodiment, the present invention is directed to compounds of formula (I) selected from the group consisting of 3-{4-[(5-Chloro-2-ethyl-1-benzofuran-7-yl)methoxy]-2,3-dimethylphenyl}propanoic acid; 3-(2,3-Dimethyl-4-{[2-methyl-5-(trifluoromethoxy)-1-benzofuran-7-yl]methoxy}phenyl)propanoic acid; 3-(7-{[2-Methyl-5-(trifluoromethoxy)-1-benzofuran-7-yl]methoxy}-2,3-dihydro-1H-inden-4-yl)propanoic acid; 3-{4-[(5-Chloro-2-methyl-1-benzofuran-7-yl)methoxy]-2,3-dimethylphenyl}propanoic acid; 3-{4-[(5-Chloro-2,6-dimethyl-1-benzofuran-7-yl)methoxy]-2,3-dimethylphenyl}propanoic acid; 3-(4-{[2-(2-Fluoroethenyl)-5-(trifluoromethoxy)-1-benzofuran-7-yl]methoxy}-2,3-dimethylphenyl)propanoic acid; 3-{4-[(6-Chloro-2-methyl-1,3-benzothiazol-4-yl)methoxy]-2,3-dimethylphenyl}propanoic acid; and pharmaceutically acceptable salts thereof.

In an embodiment, the present invention is directed to a compound of formula (I); wherein the compound of formula has a measured $EC_{50}$ according to the β-arrestin A procedure taught in Biological Example 1, which follows herein or less than about 1.0 mM, preferably less than about 0.500 mM, more preferably less than about 0.200 mM, more preferably less than about 0.100 mM, more preferably less than about 0.050 mM.

In an embodiment, the present invention is directed to a compound of formula (I); wherein the compound of formula has a measured $EC_{50}$ according to the Calcium A procedure taught in Biological Example 2, which follows herein or less than about 1.0 mM, preferably less than about 0.500 mM, more preferably less than about 0.200 mM, more preferably less than about 0.100 mM, more preferably less than about 0.050 mM.

Definitions

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, n-pentyl and the like. Unless otherwise noted, the term "$C_{X-Y}$alkyl" wherein X and Y are integers shall include straight and branched chain composition of between X and Y carbon atoms. For example, "$C_{1-4}$alkyl" shall include straight and branched chain composition of between 1 and 4 carbon atoms, including methyl, ethyl, n-propyl, isopropyl, n-butyl, isobutyl and t-butyl.

One skilled in the art will recognize that the term "—($C_{1-4}$alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, unless otherwise noted, the term "fluoro substituted $C_{1-4}$alkyl" shall mean any $C_{1-4}$alkyl group as defined above substituted with at least one fluoro atom, preferably substituted with one to three fluoro atoms. Suitable examples include but are not limited to —$CF_3$, —$CH_2$—$CF_3$, —$CF_2$—$CF_2$—$CF_2$—$CF_3$, —$CF_2$—$CF_3$, and the like.

As used herein, unless otherwise noted, the term "chloro substituted $C_{1-4}$alkyl" shall mean any $C_{1-4}$alkyl group as defined above substituted with at least one chloro atom, preferably substituted with one to three chloro atoms. Suitable examples include but are not limited to —$CCl_3$, —$CH_2$—$CCl_3$, —$CCl_2$—$CCl_2$—$CCl_2$—$CCl_3$, —$CCl_2$—$CCl_3$, and the like.

As used herein, unless otherwise noted, the term "bromo substituted $C_{1-4}$alkyl" shall mean any $C_{1-4}$alkyl group as defined above substituted with at least one bromo atom, preferably substituted with one to three bromo atoms. Suitable examples include but are not limited to —$CH_2Br$, —$CH_2$—$CBr_3$, —$CH_2$—$CH_2$—$CH_2$—$CH_2Br$, —$CH(Br)$—$CH_3$, and the like.

As used herein, unless otherwise noted, the term "hydroxy substituted $C_{1-4}$alkyl" shall mean $C_{1-4}$alkyl group as defined above substituted with at least one hydroxy group. In an embodiment, the $C_{1-4}$alkyl group is substituted with one hydroxy group. In another embodiment, the $C_{1-4}$alkyl group is substituted with a hydroxy group at the terminal carbon. Suitable examples include, but are not limited to, —$CH_2$(OH), —$CH_2$—$CH_2$—OH, —$CH_2$—$CH(OH)$—$CH_3$, —$CH_2$—$CH_2$—$CH_2$—OH, and the like.

As used herein, the term "alkenyl" whether used alone or as part of a substituent group, include straight and branched carbon chains containing at least one double bond, preferably one double bond. Unless otherwise noted, the term "$C_{X-Y}$alkenyl" wherein X and Y are integers shall include straight and branched chain composition containing at least one double bond of between X and Y carbon atoms. For example, "$C_{2-4}$alkenyl" shall include straight and branched chain composition of between 2 and 4 carbon atoms containing at least one double bong, including for example, —CH═$CH_2$, —$CH_2$—CH═$CH_2$, —CH═CH—$CH_3$, —$CH_2$—$CH_2$—CH═$CH_2$, —$CH_2$—CH═CH—$CH_3$, —CH═CH—$CH_2$—$CH_3$, and the like.

As used herein, unless otherwise noted, the term "fluoro substituted $C_{2-4}$alkenyl" shall mean any $C_{2-4}$alkenyl group as defined above substituted with at least one fluoro atom, preferably substituted with one to three fluoro atoms. Suitable examples include but are not limited to 2-fluoroethenyl, and the like.

As used herein, unless otherwise noted, the term "chloro substituted $C_{2-4}$alkenyl" shall mean any $C_{2-4}$alkenyl group as defined above substituted with at least one chloro atom, preferably substituted with one to three chloro atoms. Suitable examples include but are not limited to 2-chloroethenyl, and the like.

As used herein, the term "alkynyl" whether used alone or as part of a substituent group, include straight and branched carbon chains containing at least one triple bond, preferably one triple bond. Unless otherwise noted, the term "$C_{X-Y}$alkynyl" wherein X and Y are integers shall include straight and branched chain composition containing at least one triple bond of between X and Y carbon atoms. For example, "$C_{2-4}$alkynyl" shall include straight and branched chain composition of between 2 and 4 carbon atoms containing at least one double bond, including for example, —CCH$_2$, —CH$_2$—CCH$_2$, —CC—CH$_3$, —CH$_2$—CH$_2$—CCH, —CH$_2$—CC—CH$_3$, —CC—CH$_2$—CH$_3$, and the like.

As used herein, unless otherwise noted, the term "fluoro substituted $C_{2-4}$alkynyl" shall mean any $C_{2-4}$alkynyl group as defined above substituted with at least one fluoro atom, preferably substituted with one to three fluoro atoms. Suitable examples include but are not limited to 3-fluoro-prop-1-yn-1-yl, and the like.

As used herein, unless otherwise noted, the term "chloro substituted $C_{2-4}$alkynyl" shall mean any $C_{2-4}$alkynyl group as defined above substituted with at least one chloro atom, preferably substituted with one to three chloro atoms. Suitable examples include but are not limited to 3-chloro-prop-1-yn-1-yl, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, the term "$C_{X-Y}$alkoxy" wherein X and Y are integers shall include an oxygen ether radical as described above of between X and Y carbon atoms. For example, "$C_{1-4}$allkoxy" shall include oxygen ether radicals of between 1 and 4 carbon atoms, including methoxy, ethoxy, n-propoxy, isopropoxy, n-butoxy, isobutoxy and t-butoxy.

One skilled in the art will recognize that the term "—($C_{1-4}$ alkoxy)-" shall denote any oxygen ether radicals of between 1 and 4 carbon atoms as herein defined, wherein said $C_{1-4}$alkoxy is divalent and is further bound through two points of attachment, preferably through two terminal carbon atoms.

As used herein, unless otherwise noted, the term "fluoro substituted $C_{1-4}$alkoxy" shall mean any $C_{1-4}$alkoxy group as defined above substituted with at least one fluoro atom, preferably substituted with one to three fluoro atoms. Suitable examples include but are not limited to —O—CF$_3$, —O—CH$_2$—CF$_3$, —O—CF$_2$—CF$_2$—CF$_2$—CF$_3$, —O—CF$_2$—CF$_3$, and the like.

As used herein, unless otherwise noted, the term "$C_{3-8}$cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, "aryl" shall refer to unsubstituted carbocylic aromatic groups such as phenyl, naphthyl, fluorenyl, and the like. In an embodiment, the aryl group is phenyl or naphthyl, preferably phenyl.

When a particular group is "substituted" (e.g., $C_{1-4}$alkyl, $C_{2-4}$alkenyl, $C_{2-4}$alkynyl, $C_{5-6}$cycloalkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers.

It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

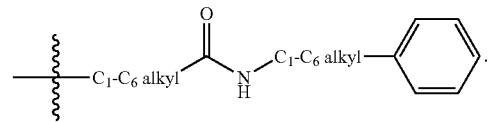

Abbreviations used in the specification, particularly the Schemes and Examples, are as follows:
AcOH=Acetic acid
ADDP=1,1'-(azodicarbonyl)dipiperidine
AlBN=Azobisisobutyronitrile
BrettPhos=palladium 2-(dicyclohexylphosphino)3,6-[(COD)Pd(CH$_2$TMS)$_2$]dimethoxy-2',4',6'-triisopropyl-1,1'-biphenyl
Bu$_3$P=Tributylphosphine
BuLi=Butyl lithium
n-BuLi=n-Butyl lithium Sec-BuLi=sec-Butyl lithium
t-BuLi=tert-butyl lithium
Cu(OAc)$_2$=Copper Acetate
DAST in [C$_{8min}$][PF$_6$]=Diethylaminosulfur trifluoride in 1-methyl-3-octylimidazolium hexafluorophosphate
DCE=Dichloroethane
DCE=Dichloroethane
DCM=Dichloromethane
DEA=diethylamine
DEAD=Diethylazodicarboxylate
DIBAL or DIBAL-H=Diisobutylaluminium hydride
DIAD=Diisopropylazodicarboxylate
DIBAL or DIBAL-H=Diisobutylaiuminium hydride
DIPEA or DIEA=Diisopropylethylamine
DMA=Dimethyl adipate
DMAP=4-N,N-Dimethylaminopyridine
DME=Dimethylether
DMF=N,N-Dimethylformamide
DMP=Dess-Martin periodinane
DMSO=Dimethylsulfoxide
dppf=1,1'-Bis(diphenylphosphino)ferrocene
Et$_2$NH=Diethylamine
Et$_2$O=Diethyl ether
Et$_3$N or TEA=Triethylamine
EtOAc=Ethyl acetate
EtOH=Ethanol
EtOMesylate or =Ethyl methanesulonate
EtOMs EtOTriflate or EtOTf=Ethyl trifluoromethanesulfonate
hep=heptane
HPLC=High Pressure Liquid Chromatography
LAH=Lithium aluminum hydride
LDA=Lithium diisopropylamide
LDL=Low density Lipoprotein
Li(Bu$^t$O)$_3$AlH=Lithium tri-tert-butoxyaluminum hydride
mCPBA or m-CPBA=meta-Chloroperoxybenzoic acid
Me=Methyl (i.e. —CH$_3$)
MeOH=Methanol
Mesyl=Methylsulfonyl
MOM=Methoxy methyl ether
MsCl=Mesyl chloride
MsOH=Methanse sulfonic acid
MTBE=Methyl t-butyl ether
NAHMDS=Sodium bis(trimethylsilyl)amide
NBS=N-Bromosuccinimide
n-BuLi=n-Butyl Lithium
NCS=N-Chlorosuccinimide
NMP=N-methyl-2-pyrrolidinone
Pd/C=Palladium on Carbon Catalyst
Pd$_2$(dba)$_3$=Tris(dibenzylidene acetone)dipalladium(0)
Pd(dppe)Cl$_2$=Palladium 1,2-Bis(diphenylphosphino)ethane dichloride
Pd(dppf)Cl$_2$=[1,1'-Bis(diphenylphosphino) ferrocene]dichloropalladium(II)
Pd$_2$(OAc)$_2$=Palladium(II)acetate
Pd(PPh$_3$)$_2$Cl$_2$ or =Bis(triphenylphosphine)palladium (II) PdCl$_2$(Ph$_3$P)$_2$ chloride
Pd(PPh$_3$)$_4$=Tetrakistriphenylphosphine palladium (0)
PE=Petroleum ether
PPA=Phenylpropanolamie
PPh$_3$=Triphenylphosphine
P(o-tol)$_3$ or P(o-tolyl)$_3$=Tri(o-tolyl)phosphine
Rochelle's Salt=Potassium sodium tartrate
sec-BuLi=Sec-Butyl Lithium
TBAF=Tetra-n-butylammonium fluoride
TBDMS=Tert-Butyldimethylsilyl
TBDMSCl=Tert-Butyldimethylsilyl chloride
t-BuNO$_2$=Tert-Butylnitrate
TEA=Triethylamine
TF$_2$O=Triflic anhydride
TFA=Trifluoroacetic acid
THF=Tetrahydrofuran
THP=Tetrahydropyranyl
TLC=Thin Layer Chromatography
TMEDA=Tetramethylethylenediamine
TMS=Trimethylsilyl
Tosyl=p-Toluenesulfonyl
TsOH or p-TsOH=Toluene sulfonic acid For purposes of the present invention, the term "modulated by the GPR120 receptor" is used to refer to the condition of being affected by the modulation of the GPR120 receptor, including but not limited to, the state of being mediated by the GPR120 receptor.

As used herein, unless otherwise noted, the term "disorder modulated by the GPR120 receptor" shall mean any disease, disorder or condition characterized in that at least one of its characteristic symptoms is alleviated or eliminated upon treatment with a GPR120 receptor agonist. Suitably examples include, but are not limited to obesity, obesity related disorders, impaired oral glucose tolerance, insulin resistance, Type II diabetes mellitus, metabolic syndrome, metabolic syndrome X, dyslipidemia, elevated LDL, elevated triglycerides, obesity induced inflammation, osteoporosis and obesity related cardiovascular disorders; preferably, obesity, insulin resistance, Type II diabetes mellitus, dyslipidemia or metabolic syndrome X; more preferably, Type II diabetes mellitus or dyslipidemia.

As used herein unless otherwise noted, the term "obesity related cardiovascular disorders" shall mean any cardiovascular disease, disorder or condition in which obesity or diabetes (preferably, Type II Diabetes) has a role in the initiation or exacerbation of said disorder or condition. Suitable examples include but are not limited to hypertension, atherosclerosis and cardiac fibrosis.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications (including, to reduce the frequency or severity of one or more symptoms), or eliminate the disease, condition, or disorder.

As used herein, unless otherwise noted, the term "prevention" shall include (a) the delay or avoidance of the development of additional symptoms; and/or (b) delay or avoidance of the development of the disorder or condition along a known development pathway.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. A subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

To provide a more concise description, some of the quantitative expressions yieldn herein are not qualified with the term "about". It is understood that whether the term "about" is used explicitly or not, every quantity yieldn herein is meant to refer to the actual yieldn value, and it is also meant to refer to the approximation to such yieldn value that would reasonably be inferred based on the ordinary skill in the art, including approximations due to the experimental and/or measurement conditions for such yieldn value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter. One skilled in the art will further recognize that wherein a reaction step of the present invention may be carried out in a variety of solvents or solvent systems, said reaction step may also be carried out in a mixture of the suitable solvents or solvent systems.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention yield rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-}obs]/[\alpha\text{-}\max])\times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts in vivo to the specified compound after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthetic Methods

Compounds of formula (I) may be prepared according to the process outlined in Scheme 1, below.

Scheme 1

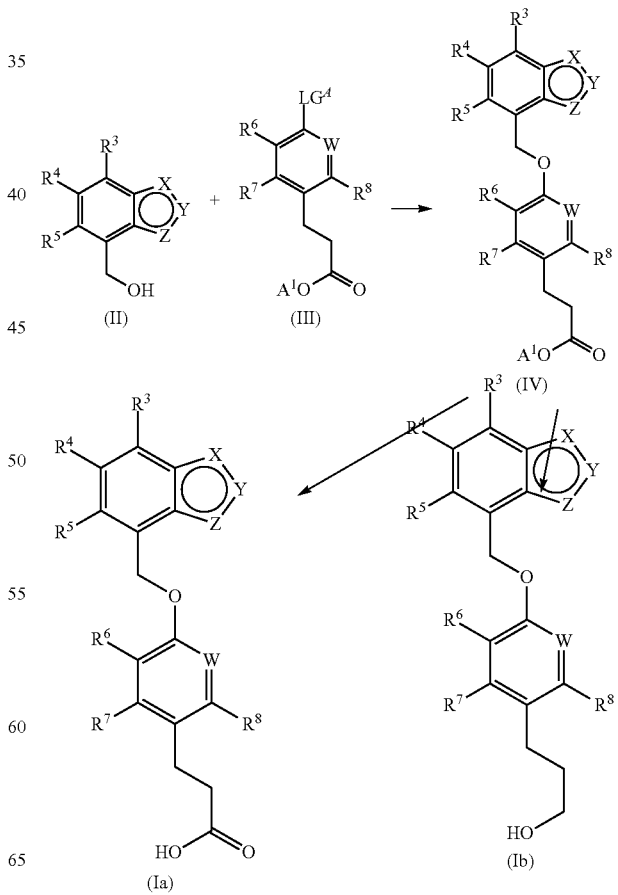

Accordingly, a suitably substituted compound of formula (II), a compound prepared by known methods or prepared as described hereinafter, is reacted with a suitably substituted compound of formula (III), wherein $LG^A$ is a suitably selected leaving group such as OH, and the like, and wherein $A^1$ is a suitably selected $C_{1-4}$alkyl, such as methyl, ethyl, t-butyl, and the like, a known compound or compound prepared by known methods, in the presence of a suitably selected coupling system such as DEAD/PPh$_3$, ADDP/Bu$_3$P, DIAD/PPh$_3$, and the like; in a suitably selected organic solvent such as THF, 1,4-dioxane, CH$_2$Cl$_2$, toluene and the like; to yield the corresponding compound of formula (IV).

Alternatively, a suitably substituted compound of formula (II), a compound prepared by known methods or prepared as described hereinafter, is reacted with compounds off formula (III), wherein $LG^A$ is a suitably selected leaving group such as F, Cl, Br, mesyl, and the like, a known compound or compound prepared by known methods; in the presence of a suitably selected base such as NaH, and the like; in a suitably selected solvent such as DMF, DMSO, NMP, and the like; to yield the corresponding compound of formula (IV).

One skilled in the art will recognize that compounds of formula (IV) may alternatively be prepared by reacting a suitably substituted compound of formula (V)

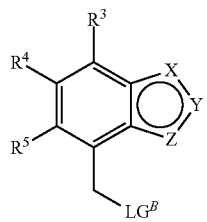

(V)

wherein $LG^B$ is a suitably selected leaving group such as Cl, Br, I, mesyl, tosyl, and the like, a known compound or compound prepared by known methods, with a suitably substituted compound of formula (III), wherein $LG^A$ is a suitably selected leaving group such as OH, and the like, a known compound or compound prepared by known methods; in the presence of a suitably selected base such as potassium carbonate, cesium carbonate, TEA, DIEA, and the like; in a suitably selected solvent such as DMF, THF, DCM, and the like; to yield the corresponding compound of formula (IV).

The compound of formula (IV) is reacted with a suitably selected base such as NaOH, LiOH, KOH, and the like; or when $A^1$ is t-butyl with a suitably selected acid such TFA, and the like; to yield the corresponding compound of formula (Ia), a compound of formula (I) wherein $R^0$ is C(O)OH.

Alternatively, the compound of formula (IV) is reacted with a suitably selected reducing agent such as LAH, DIBAL, and the like; to yield the corresponding compound of formula (Ib), a compound of formula (I) wherein $R^0$ is CH$_2$OH.

Compounds of formula (II) wherein

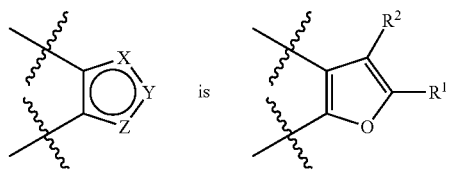

and wherein $R^2$ is hydrogen, may be prepared according to the process outlined in Scheme 2, below.

Scheme 2

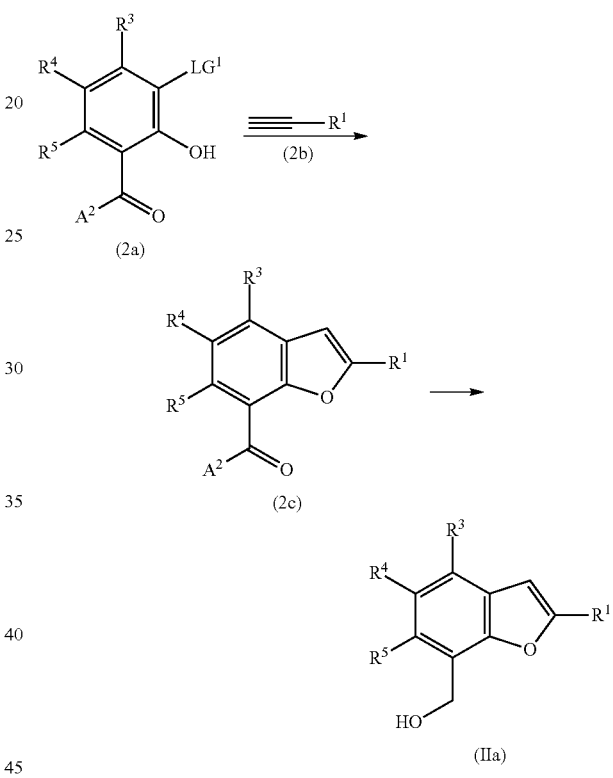

(IIa)

Accordingly, a suitably substituted compound of formula (2a), wherein $LG^1$ is a suitably selected leaving group such as Br, I, —OSO$_2$CF$_3$, and the like, and wherein $A^2$ is hydrogen or a suitably selected $C_{1-4}$alkoxy such as methoxy, ethoxy and the like, a known compound or compound prepared by known methods, is reacted with a suitably substituted compound of formula (2b), a known compound or compound prepared by known methods; in the presence of a suitably selected coupling agent such as Pd(PPh$_3$)$_2$Cl$_2$, Pd(PPh$_3$)$_4$, Pd(dppe)Cl$_2$ and the like; in the presence of CuI; in the presence of a suitably selected organic base such as TEA, Et$_2$NH, and the like; in a suitably selected organic solvent such as DMF, TEA, Et$_2$NH, and the like; to yield the corresponding compound of formula (2c).

One skilled in the art will further recognize in the preparation of the compounds of formula (2c), the desired $R^4$ and/or $R^5$ substituent group(s) may alternatively by reacting a suitably substitituted compound of formula (2c) wherein $R^4$ and/or $R^5$ is CH$_3$O, with a suitably selected de-methylating agent such as BBr$_3$, and the like; and the resulting compound alkylated with for example, chlorodifluoromethane; to yield the corresponding compound of formula (2c)

wherein R⁴ and/or R⁵ is —OCF₂H; or reacting a suitably substituted compound of formula (2c) wherein R⁴ and/or R⁵ is CH₃O—, with bromoethane; to yield the corresponding compound of formula (2c) wherein R⁴ and/or R⁵ is —OCH₂CH₃; or reacting a suitably substitituted compound of formula (2c) wherein R⁴ and/or R⁵ is CH₃O, with for example, 1-bromo-2-methoxyethane; to yield the corresponding compound of formula (2c) wherein R⁴ and/or R⁵ is —OCH₂CH₂OCH₃; or by reacting a suitably substitituted compound of formula (2c) wherein R⁴ and/or R⁵ is CH₃O, with for example, trifluoromethyl trifluoromethanesulfonate; to yield the corresponding compound of formula (2c) wherein R⁴ and/or R⁵ is —OCH₂CF₃; or reacting a suitably substitituted compound of formula (2c) wherein R⁴ and/or R⁵ is CH₃O, with for example, 2-bromopropane; to yield the corresponding compound of formula (2c) wherein R⁴ and/or R⁵ is —OCH(CH₃)₂; or reacting a suitably substitituted compound of formula (2c) wherein R⁴ and/or R⁵ is CH₃O, with for example, 1-bromo-2-methylpropane; to yield the corresponding compound of formula (2c) wherein R⁴ and/or R⁵ is —OCH₂CH(CH₃)₂; or by reacting a suitably substitituted compound of formula (2c) wherein R⁴ and/or R⁵ is CH₃O, with for example, 2-(trimethysilyl)phenyl triflate; to yield the corresponding compound of formula (2c) wherein R⁴ and/or R⁵ is —O-phenyl.

Alternatively, a suitably substituted compound of formula (2c) wherein R⁴ and/or R⁵ is CH₃O is reacted with a suitably selected demethylated agent such as for example BBr₃ and the resulting product reacted with for example, triflic anhydride; and the resulting product reacted with a suitably substituted boronic acid, under Suzuki coupling conditions (e.g. in the presence of a suitably selected catalyst such as Pd(Ph₃)₄, and the like; in the presence of a suitably selected base such as K₃PO₄, and the like; in a suitably selected solvent such as THF, and the like; to yield the corresponding compound of formula (2c) wherein R⁴ and/or R⁵ is CH₃.

Alternatively, a suitably substituted compound of formula (2c) wherein R⁴ and/or R⁵ is CH₃O s reacted with a suitably selected demethylated agent such as for example BBr₃; and the resulting product reacted with for example, triflic anhydride; and the resulting product reacted with for example diethylzinc, in the presence of a suitably selected catalyst such as Pd(dppf)Cl₂, and the like; in a suitably selected solvent such as THF, and the like; to yield the corresponding compound of formula (2c) wherein R⁴ and/or R⁵ is CH₂CH₃;

Alternatively, a suitably substituted compound of formula (2c) wherein R⁴ and/or R⁵ is Cl may be reacted with for example, LiAlH₄, and the like; in a suitably selected solvent such as THF, and the like; to yield the corresponding compound of formula (2c) wherein R⁴ and/or R⁵ is H.

Alternatively, a suitably substituted compound of formula (2c) wherein R⁴ and/or R⁵ is iodo may be reacted with for example a suitably substituted propy-1-nyl such as 3-(methylsulfanyl)prop-1-yne, in the presence of CuI, in the presence of a suitably selected catalyst such as Pd(PPh₃)₂Cl₂, and the like; in the presence of a suitably selected base such as TEA, and the like; in a suitably selected solvent such as acetonitrile, DMF, and the like; at a temperature in the range of from about 70° C. to about 90° C.; to yield the corresponding compound of formula (2c) wherein R⁴ and/or R⁵ is CH₃SCH₂CC—.

The compound of formula (2c) is reacted to yield the corresponding compound of formula (IIa). More particularly, wherein A² is hydrogen, the compound of formula (2c) is reacted with a suitably selected reducing agent such as NaBH₄, LAH, and the like; in a suitably selected organic solvent such as THF, MeOH, toluene, and the like; to yield the corresponding compound of formula (IIa). Alternatively, wherein A² is a suitably selected C₁₋₄alkoxy, the compound of formula (2c) is reacted with a suitably selected reducing agent such as DIBAL, LAH, LiBH₄, and the like; in a suitably selected organic solvent such as THF, toluene, CH₂Cl₂, and the like; at a suitable temperature (as determined by the choice of reducing agent and readily determined by one skilled in the art); to yield the corresponding compound of formula (IIa).

Compounds of formula (II) wherein

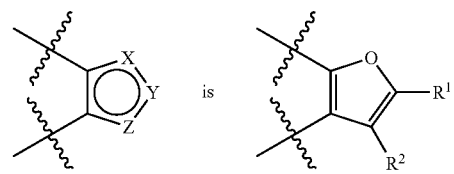

and wherein for example, R¹ is methyl and R² is hydrogen, may be prepared according to the process outlined in Scheme 3, below.

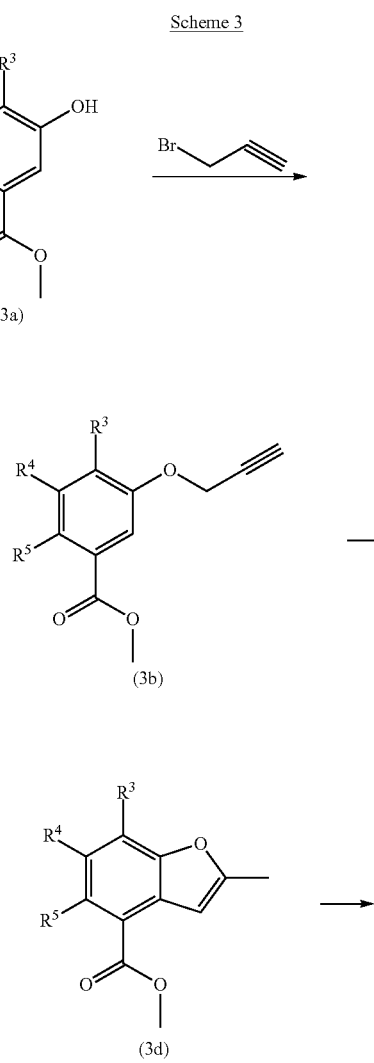

Scheme 3

Scheme 4

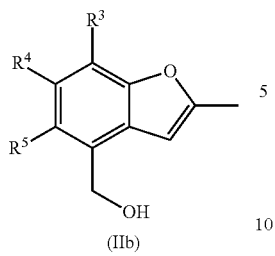
(IIb)

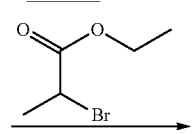

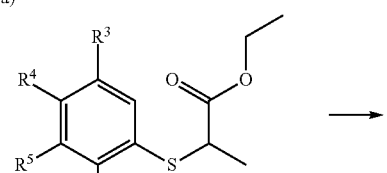
(4a)

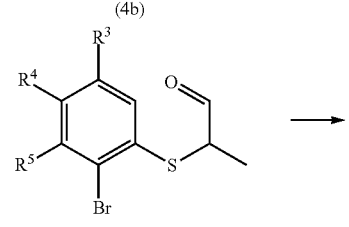
(4b)

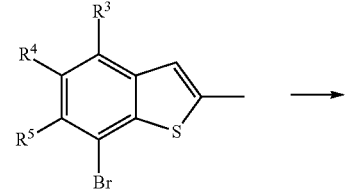
(4c)

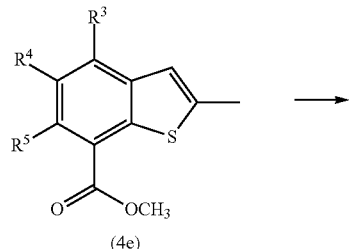
(4d)

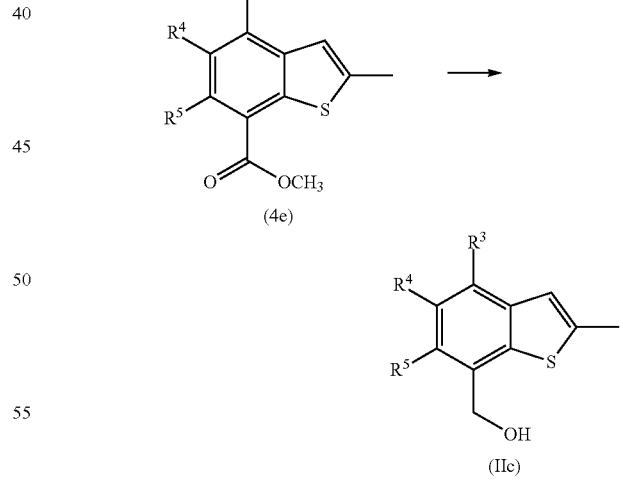
(4e)

Accordingly, a suitably substituted compound of formula (3a), a known compound or compound prepared by known methods, is reacted with alkynylbromide, a known compound; in the presence of a suitably selected inorganic base such as $K_2CO_3$, $Cs_2CO_3$, NaH, and the like; in a suitably selected organic solvent such as DMF, THF, $CH_3CN$, and the like; to yield the corresponding compound of formula (3b).

The compound of formula (3b) is refluxed (at about 217° C.) in N,N-diethylaniline, in the presence of catalytic amounts of CsF to yield the corresponding compound of formula (3c).

The compound of formula (3c) is reacted with a suitably selected reducing agent such as DIBAL, LAH, $LiBH_4$ and the like; in a suitably selected organic solvent such as THF, toluene, $CH_2Cl_2$, and the like; to yield the corresponding compound of formula (IIb).

One skilled in the art will recognize that compounds of formula (I) wherein

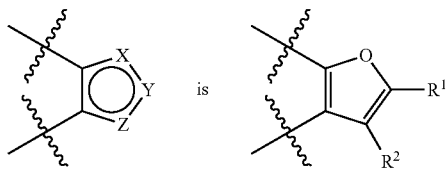

and wherein $R^1$ is other than methyl and/or wherein $R^2$ is other than hydrogen, may be similarly prepared according to the process outlined in Scheme 3 above by substituting a suitably substituted compound of formula Br—CC($R^2$) for the alkynyl bromide.

Compounds of formula (II) wherein

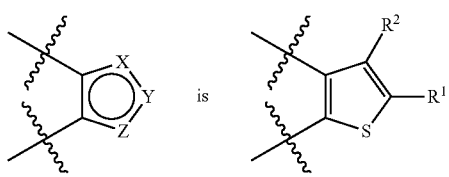

and wherein $R^1$ is methyl and wherein $R^2$ is hydrogen, may be prepared according to the process outlined in Scheme 4, below.

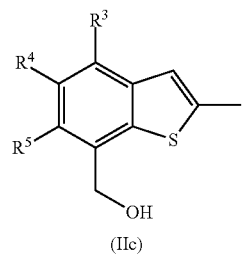
(IIc)

Accordingly, a suitably substituted compound of formula (4a), a known compound or compound prepared by known methods, is reacted with ethyl 2-bromopropanoate, a known compound; in the presence of a suitably selected base such as $K_2CO_3$, $Cs_2CO_3$, NaH, DIPEA and the like; in a suitably selected organic solvent such as THF, DMF, acetone, $CH_3CN$, and the like; to yield the corresponding compound of formula (4b).

The compound of formula (4b) is reacted with a suitably selected reducing agent such as DIBAL, LAH, LiBH$_4$ and the like; in a suitably selected organic solvent such as THF, Et$_2$O, CH$_2$Cl$_2$ and the like; to yield the corresponding compound of formula (4c).

The compound of formula (4c) is mixed with PPA, and heated at 150° C. to yield the corresponding compound of formula (4d).

The compound of formula (4d) is reacted with carbon monoxide; in the presence of a suitably selected catalyst such as Pd(dppf)Cl$_2$, Pd(OAc)$_2$/1,1'-bis(diphenylphosphino)ferrocene, and the like; in methanol at 60° C. for 18 h to yield the corresponding compound of formula (4e).

The compound of formula (4e) is reacted with a suitably selected reducing agent such as LAH, LiBH$_4$, DIBAL, and the like; in a suitably selected organic solvent such as THF, CH$_2$Cl$_2$, toluene and the like; to yield the corresponding compound of formula (IIc).

Compounds of formula (II) wherein

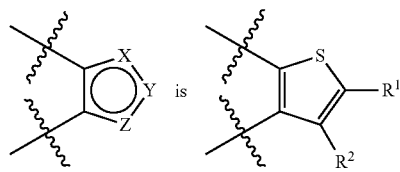

and wherein R$^1$ is methyl and R$^2$ is hydrogen may be prepared according to the process outlined in Scheme 5, below.

Scheme 5

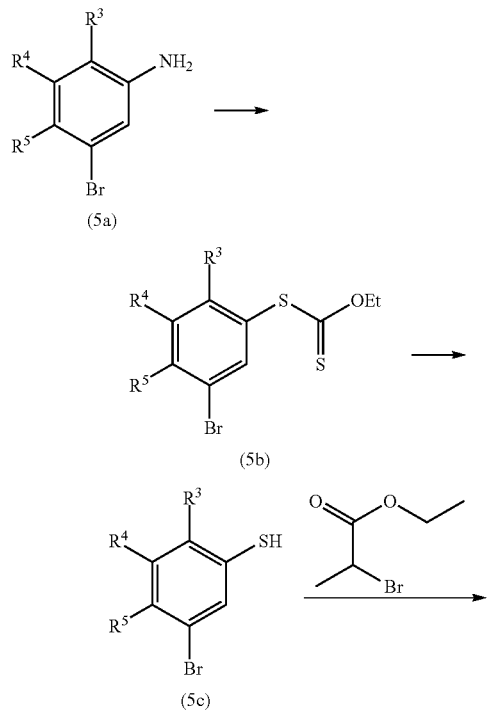

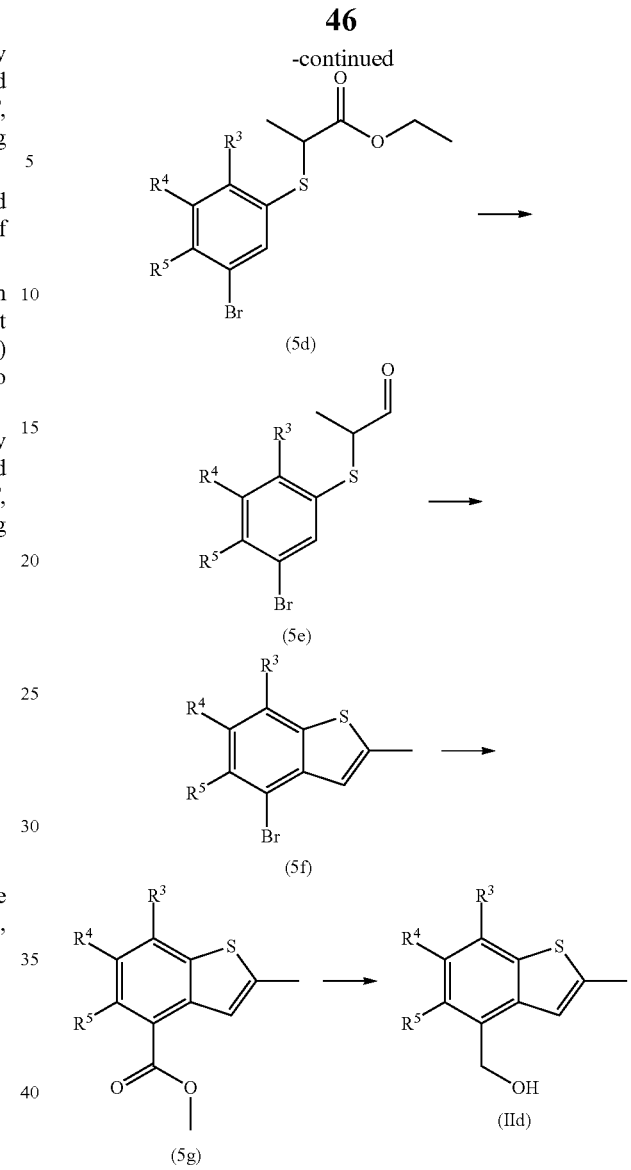

Accordingly, a suitably substituted compound of formula (5a), a known compound or compound prepared by known methods, is reacted with NaNO$_2$ and HCl$_{(aq)}$ to form the diazonium salt which is then reacted with KSC(=S)OCH$_2$CH$_3$, a known compound; neat; to yield the corresponding compound of formula (5b); which is then reacted with a suitably selected base such as KOH, NaOH, and the like; to yield the corresponding compound of formula (5c).

The compound of formula (5c) is reacted with ethyl 2-bromopropanoate, a known compound; in the presence of a suitably selected base such as K$_2$CO$_3$, Cs$_2$CO$_3$, NaH, DIPEA, and the like; in a suitably selected organic solvent such as THF, DMF, acetone, CH$_3$CN and the like; to yield the corresponding compound of formula (5d).

The compound of formula (5d) is reacted with a suitably selected reducing agent such as DIBAL, LiBH$_4$, LAH, and the like; in a suitably selected organic solvent such as THF, CH$_2$Cl$_2$, toluene, and the like; preferably at a temperature in the range of form about −78° C. to about 20° C., for example, at about −78° C. ((as determined by the choice of reducing agent and readily determined by one skilled in the art); to yield the corresponding compound of formula (5e).

The compound of formula (5e) is mixed with PPA, a known compound, and heated to about 150° C.; to yield the corresponding compound of formula (5f).

The compound of formula (5f) is reacted with carbon monoxide in the presence of a suitably selected catalyst such as Pd(dppf)Cl$_2$, Pd(OAc)$_2$/1,1'-bis(diphenylphosphino)ferrocene, and the like; in the presence of a suitably selected organic base such as TEA, in a organic solvent such as methanol at 60° C. for 18 h; to yield the corresponding compound of formula (5g).

The compound of formula (5g) is reacted with a suitably selected reducing agent such as DIBAL, LAH, LiBH$_4$, and the like; in a suitably selected organic solvent such as THF, CH$_2$Cl$_2$, toluene, and the like; preferably at a temperature in the range of from about −78° C. to about 30° C., for example, at about −78° C.; to yield the corresponding compound of formula (IId).

One skilled in the art will recognize that compounds of formula (I) wherein

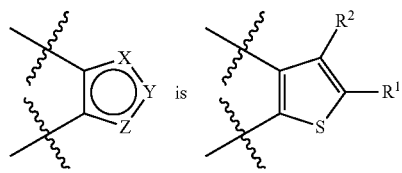

and wherein R$^2$ is hydrogen and wherein R$^1$ is other than methyl may be similarly prepared according to the process outlined in Scheme 4 or Scheme 5 above by substituting a suitably substituted compound of the formula Br—CH(R$^1$)—CO$_2$CH$_2$CH$_3$ for the ethyl 2-bromopropanoate.

Compounds of formula (I) wherein

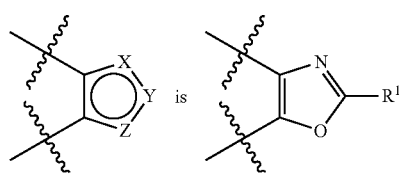

and wherein R$^1$ is for example, alkyl, halogen substituted alkyl, alkyl ester, phenyl or benzyl, may be prepared according to the process outlined in Scheme 6, below.

Scheme 6

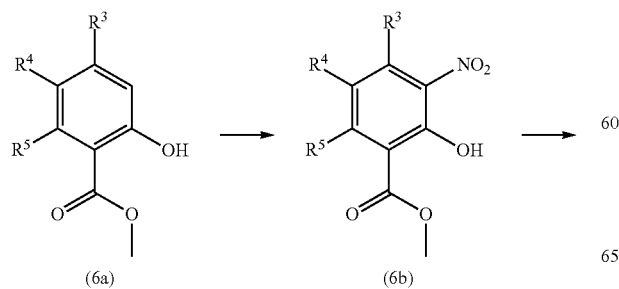

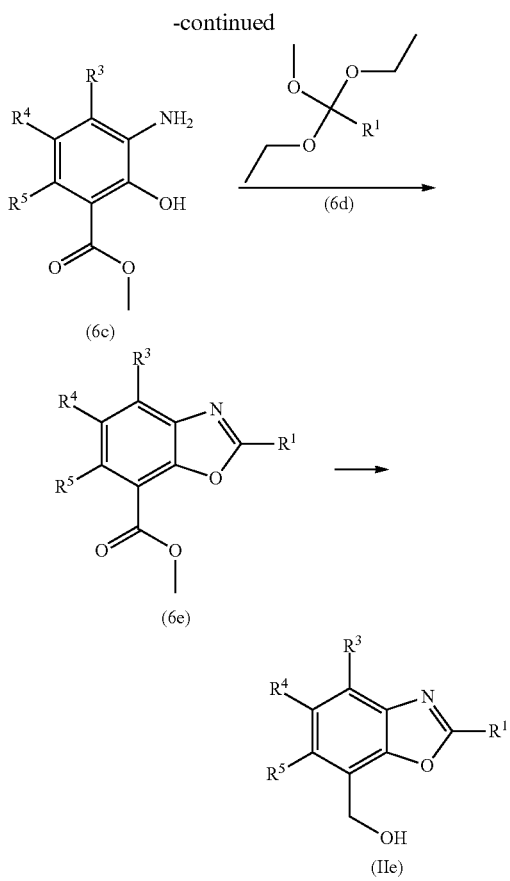

Accordingly, a suitably substituted compound of formula (6a), a known compound or compound prepared by known methods, is reacted with a suitably selected nitrating agent such as HNO$_3$/H$_2$SO$_4$, KNO$_3$/H$_2$SO$_4$, to yield the corresponding compound of formula (6b).

The compound of formula (6b) is reacted with a suitably selected reducing agent such as Fe, SnCl$_2$, TiCl$_3$; in a suitably selected organic solvent such as AcOH, EtOAc, THF, and the like; to yield the corresponding compound of formula (6c).

The compound of formula (6c) is reacted with a suitably substituted compound of formula (6d), a known compound or compound prepared by known methods; in the presence of a suitably selected acid such as pTsOH, and the like; preferably at a temperature in the range of from about 100° C. to about 120° C., for example at about 100° C.; to yield the corresponding compound of formula (6e).

The compound of formula (6e) is reacted with a suitably selected reducing agent such as DIBAL, LAH, LiBH$_4$, and the like; in a suitably selected organic solvent such as THF, toluene, CH$_2$Cl$_2$, and the like; preferably at a temperature in the range of from about −78° C. to about 30° C., for example, at about −78° C.; to yield the corresponding compound of formula (IIe).

Compounds of formula (I) wherein

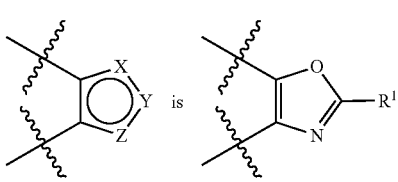

may be prepared according to the process outlined in Scheme 7, below.

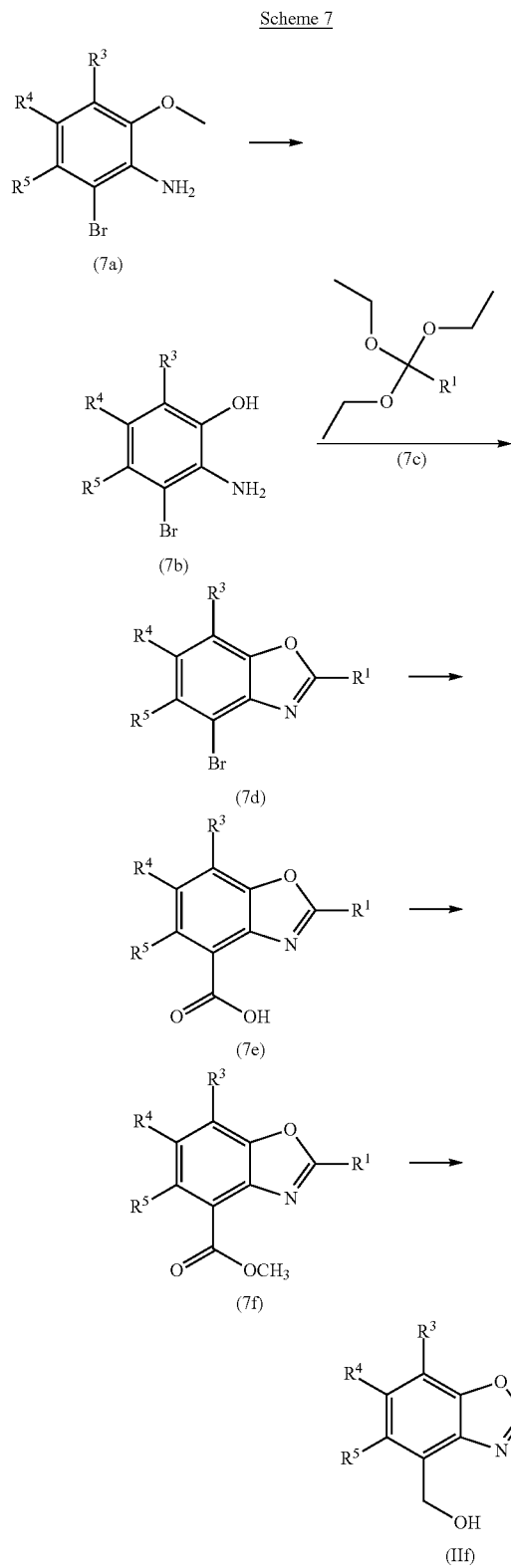

Accordingly, a suitably substituted compound of formula (7a), a known compound or compound prepared by known methods, is reacted with for example, BBr$_3$, in a suitably selected organic solvent such as CH$_2$Cl$_2$, and the like, at about room temperature; to yield the corresponding compound of formula (7b).

The compound of formula (7b) is reacted with a suitably substituted compound of formula (7c), a known compound or compound prepared by known methods; in the presence of a suitably selected acid such as pTsOH, sulfuric acid, MsOH, and the like; preferably at a temperature in the range of from about 80° C. to about 120° C., for example at about 100° C.; to yield the corresponding compound of formula (7d).

The compound of formula (7d) is reacted with carbon monoxide in the presence of a suitably selected catalyst such as Pd(dppf)Cl$_2$, Pd(OAc)$_2$/1,1'-bis(diphenylphosphino)ferrocene, and the like; in the presence of suitably selected inorganic base such as K$_2$CO$_3$ in DMF at 80° C. for 18 h to yield the corresponding compound of formula (7e).

The compound of formula (7e) is reacted with for example, TMS-diazomethane, a known compound; in a suitably selected solvent such as methanol, ethanol, and the like; to yield the corresponding compound of formula (7f).

The compound of formula (7f) is reacted a suitably selected reducing agent such as DIBAL, LAH, LiBH$_4$, and the like; in a suitably selected organic solvent such as THF, CH$_2$Cl$_2$, toluene, and the like; preferably at a temperature in the range of from about −78° C. to about 30° C., for example, at about −78° C.; to yield the corresponding compound of formula (IIf).

Compounds of formula (I) wherein

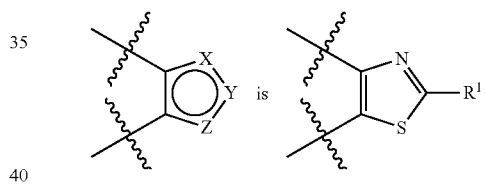

may be prepared according to the process outlined in Scheme 8, below.

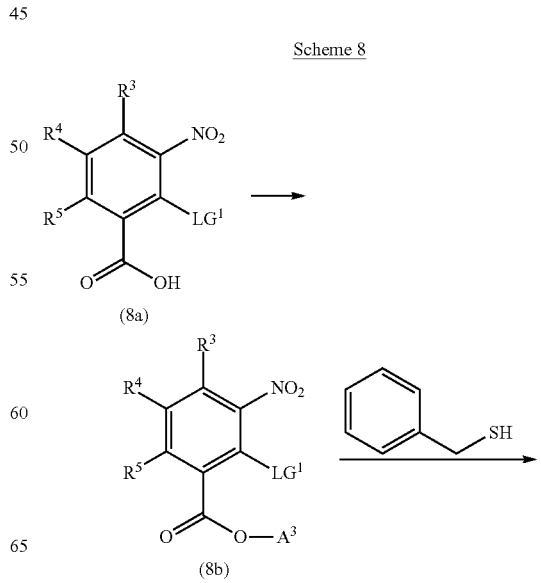

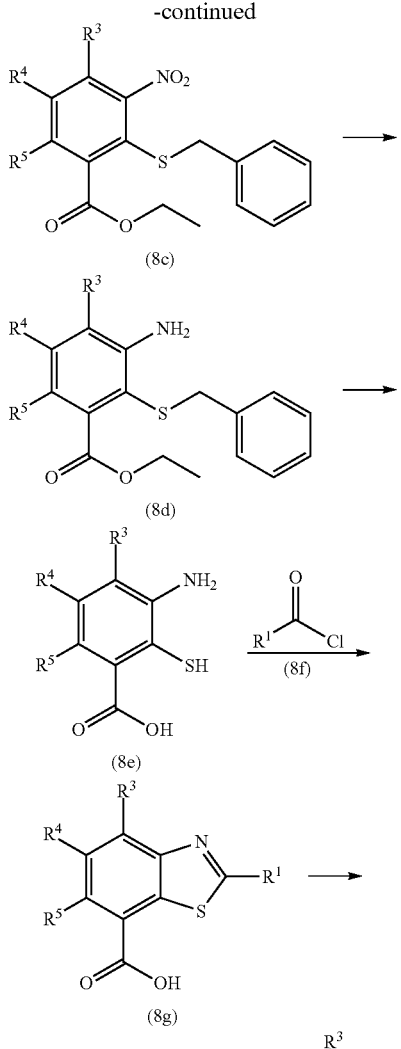

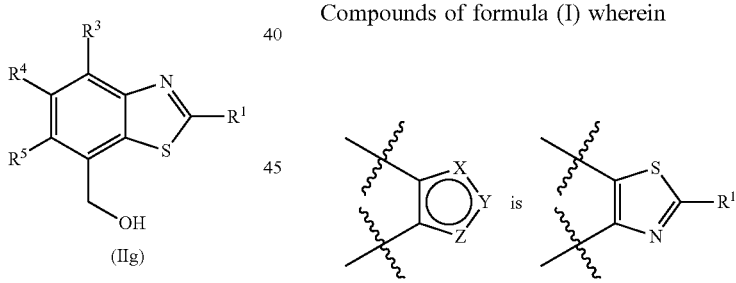

Accordingly, a suitably substituted compound of formula (8a), a known compound or compound prepared by known methods, is reacted (to yield the corresponding ester) with a suitably selected alkylating agent such as diethyl sulfate, dimethyl sulfate, and the like; in the presence of suitably selected inorganic base such as $K_2CO_3$, $Na_2CO_3$, $Cs_2CO_3$, and the like; in a suitably selected organic solvent such as acetone, $CH_3CN$, and the like; preferably at a temperature in the range of from about 20° C. to about 80° C., for example at about 55° C.; to yield the corresponding compound of formula (8b) wherein $A^3$ is a suitably selected alkyl, preferably $C_{1-4}$alkyl, such as methyl, ethyl, t-butyl, and the like. Alternatively the compound of formula (8a) is reacted with for example, diazomethane in methanol or reacted with HCl in a suitably selected alcohol of the formula $A^3OH$, wherein $A^3$ is methyl or ethyl; to yield the corresponding compound of formula (8b), wherein $A^3$ is the corresponding alkyl.

The compound of formula (8b) is reacted with phenylmethanethiol, a known compound or compound prepared by known methods; in the presence of suitably selected inorganic base such as $K_2CO_3$, $Cs_2CO_3$, and the like; in a suitably selected organic solvent such as DMF, NMP, DMA, and the like; preferably at a temperature of about 90° C.; to yield the corresponding compound of formula (8c).

The compound of formula (8c) is reacted with a suitably selected reducing agent such as Fe, $SnCl_2$, $TiCl_2$, and the like; in the presence of a suitably selected solvent such as ethanol, THF, AcOH, and the like; preferably at a temperature in the range of from about 20° C. to about 80° C., for example at about 60° C.; to yield the corresponding compound of formula (8d).

The compound of formula (8d) is reacted with for example, $AlCl_3$, in a suitably selected solvent such as toluene, benzene, and the like; preferably at an elevated temperature in the range of from about 30° C. to about 80° C., for example at a temperature of about 30° C.; to yield the corresponding compound of formula (8e).

The compound of formula (8e) is reacted with a suitably substituted compound of formula (8f), a known compound or compound prepared by known methods; in a suitably selected solvent such as NMP, DMF, and the like; preferably at an elevated temperature in the range of from about 150° C. to about 170° C., for example at a temperature of about 160° C.; to yield the corresponding compound of formula (8g).

The compound of formula (8g) is reacted with a suitably selected reducing agent such as $LiAlH_4$, $BH_3.THF$ and the like; in a suitably selected organic solvent such as diethyl ether, THF and the like; preferably at a temperature in the range of form about 0° C. to about 22° C., for example, at about 0° C.; to yield the corresponding compound of formula (IIg).

Compounds of formula (I) wherein

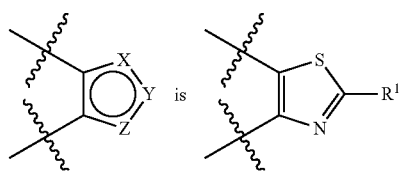

may be prepared according to the process outlined in Scheme 9, below.

Scheme 9

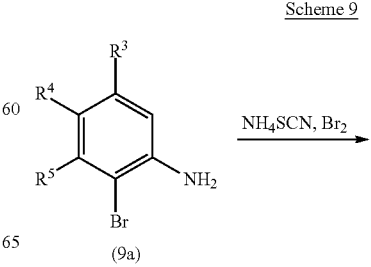

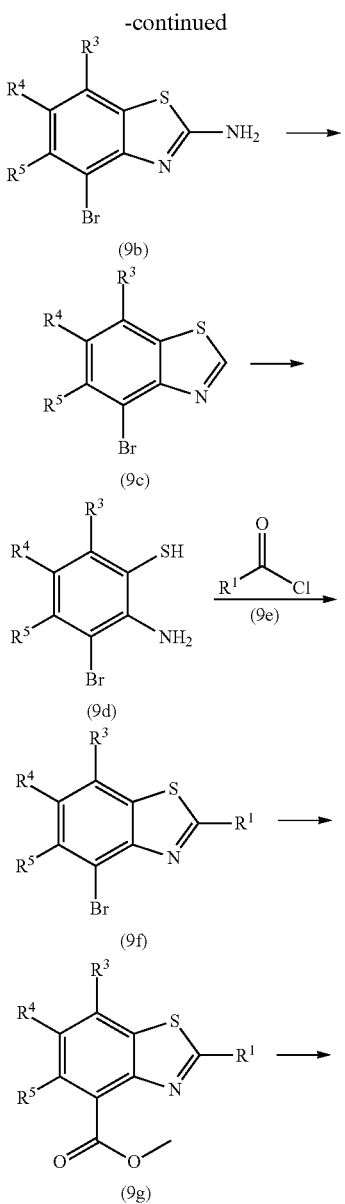

ture in the range of from about 50° C. to about 80° C., for example, at about 60° C.; to yield the corresponding compound of formula (9c).

The compound of formula (9c) is reacted with for example, N₂H₄; in a suitably selected solvent such as ethanol, and the like; preferably at a temperature in the range of from about 70° C. to about 100° C., for example at about 80° C.; to yield the corresponding compound of formula (9d).

The compound of formula (9d) is reacted with a suitably substituted compound of formula (9e), a known compound or compound prepared by known methods; in a suitably selected solvent such as NMP, and the like; preferably at a temperature in the range of from about 120° C. to about 140° C., for example at about 130° C.; to yield the corresponding compound of formula (9f).

The compound of formula (9f) is reacted with carbon monoxide in the presence of a suitably selected catalyst such as Pd(dppf)Cl₂, Pd(OAc)₂/1,1'-bis(diphenylphosphino)ferrocene, and the like; in the presence of a suitably selected inorganic base such as K₂CO₃, Cs₂CO₃, and the like; in a suitably selected solvent such as DMF, DMSO, and the like; preferably at a temperature in the range of from about room temperature to about 100° C., for example at about 80° C.; to yield the corresponding compound of formula (9g).

The compound of formula (9g) is reacted with a suitably selected reducing agent such as LAH, DIBAL, and the like; in a suitably selected organic solvent such as THF, DCM, toluene, and the like; preferably at a temperature in the range of from about 0° C. to about 22° C., for example at about 0° C.; to yield the corresponding compound of formula (IIh).

Compounds of formula (I) wherein

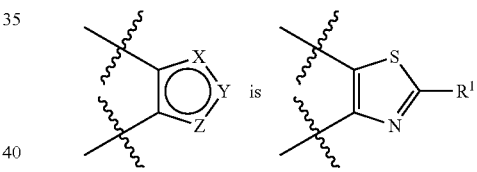

and wherein R¹ is for example, methyl, may alternatively be prepared according to the process outlined in Scheme 10, below.

Accordingly, a suitably substituted compound of formula (9a), a known compound or compound prepared by known methods, is reacted with NH₄SCN and Br₂, known compounds; in a suitably selected solvent such as acetic acid, and the like; preferably at a temperature in the range of from about 0° C. to about room temperature, for example at about 0° C.; to yield the corresponding compound of formula (9b).

The compound of formula (9b) is reacted with a suitably selected nitrite such as t-BuNO₂, isoamyl nitrite, and the like; in a suitably selected organic solvent such as 1,4-dioxane, THF, DMF, and the like; preferably at a tempera- Scheme 10

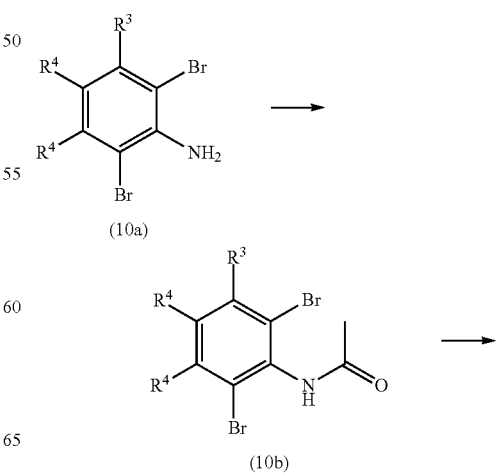

-continued

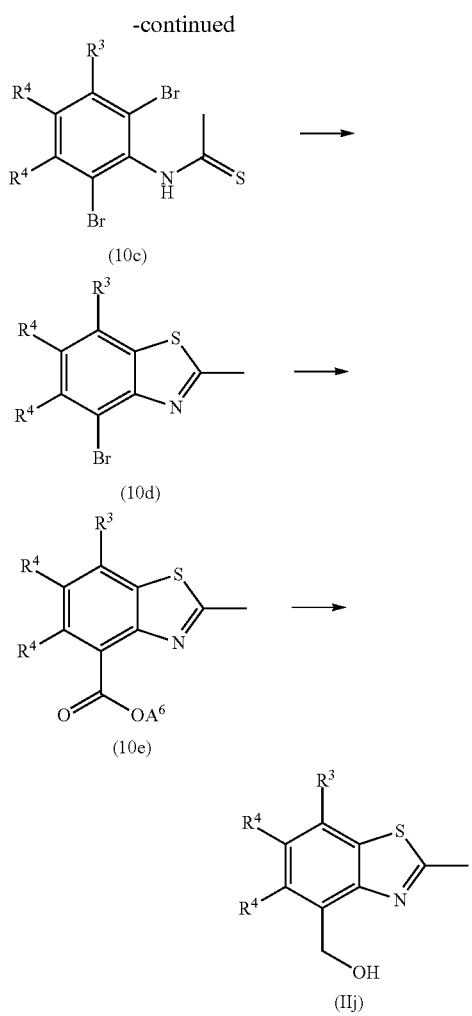

(10c)

(10d)

(10e)

(IIj)

Accordingly, a suitably substituted compound of formula (10a), a known compound or compound prepared by known methods, is reacted with acetic anhydride in acetic acid at a temperature in the range of from about 80° C. to about 100° C., for example at about 90° C.; to yield the corresponding compound of formula (10b).

The compound of formula (10b) is reacted with 2,4-bis (4-methoxyphenyl)-1,3,2,4-dithiadiphosphetane 2,4-disulfide, a known compound; in a suitably selected organic solvent such as toluene, benzene, and the like; preferably at a temperature in the range of from about 80° C. to about 120° C., for example at about 111° C.; to yield the corresponding compound of formula (10c).

The compound of formula (10c) is reacted with 3,4,7,8-tetramethyl-1,10-phenanthroline, a known compound; in the presence of CuI; in the presence of $Cs_2CO_3$; in a suitably selected organic solvent such as DME, 1,4-dioxane, and the like; preferably at a temperature in the range of from about 70° C. to about 100° C., for example at about 81° C.; to yield the corresponding compound of formula (10d).

The compound of formula (10d) is reacted with carbon monoxide in the presence of a suitably selected catalyst such as $Pd(dppf)Cl_2$, and the like; in the presence of a suitably selected base such as TEA, DIPEA, and the like; in a suitably selected alcohol of the formula $A^6OH$, wherein $A^6$ is $C_{1-4}$alkyl, preferably methyl or ethyl (i.e. a $C_{1-4}$alkyl alcohol, preferably methanol or ethanol), and the like; preferably at a temperature of about 60° C.; to yield the corresponding compound of formula (10e).

Alternatively, the compound of formula (10d) is reacted with carbon monoxide in the presence of a suitably selected catalyst such as $Pd(dppf)Cl_2$, $Pd(OAc)_2$/1,1'-bis(diphenylphosphino)ferrocene, and the like; in the presence of suitably selected inorganic base such as $K_2CO_3$, and the like; in a suitably selected solvent such as DMF, and the like; at a temperature of for example, 80° C.; to yield the corresponding carboxylic acid, a compound of formula (10f)

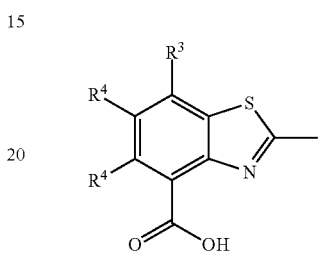

which compound of formula (10f) is esterified by reacting with for example, TMS-diazomethane, a known compound; in a suitably selected solvent such as methanol, ethanol, and the like; to yield the corresponding compound of formula (10e) wherein $A^6$ is methyl.

The compound of formula (10e) is reacted with a suitably selected reducing agent such as DIBAL, LAH, $LiBH_4$, and the like; in a suitably selected organic solvent such as $CH_2Cl_2$, THF, toluene, and the like; preferably at a temperature in the range of form about −78° C. to about 22° C., for example, at about −78° C.; to yield the corresponding compound of formula (IIj).

Compounds of formula (I) wherein

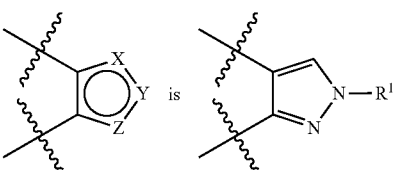

and/or

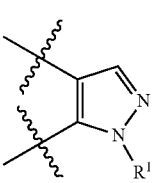

may be prepared as outlined in Scheme 11, below.

Scheme 11

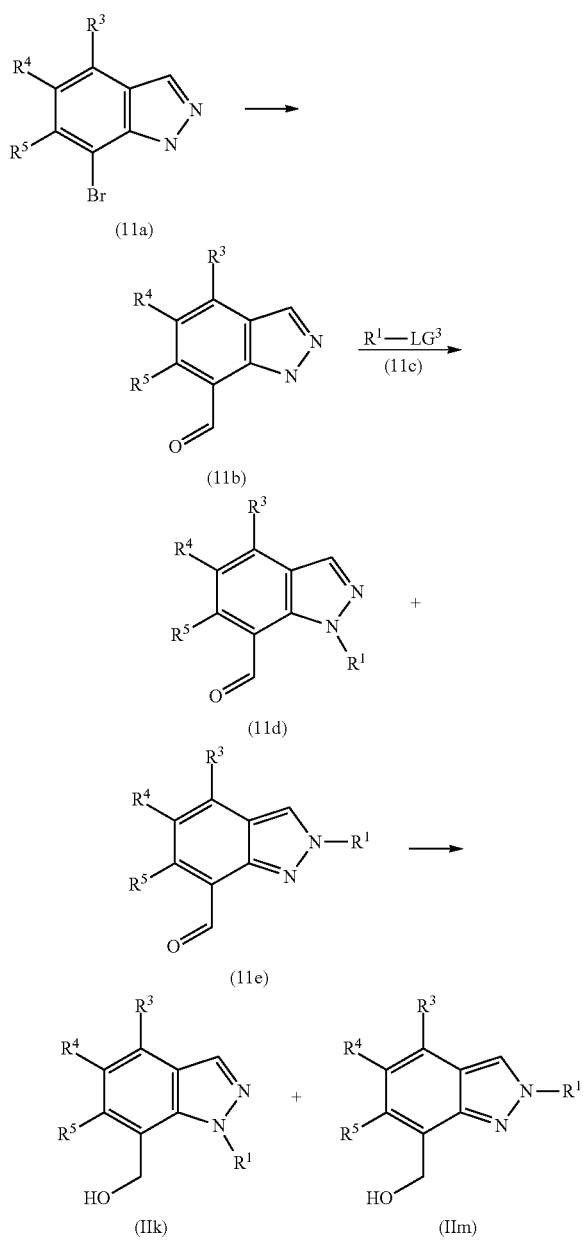

Accordingly, a suitably substituted compound of formula (11a), a known compound or compound prepared by known methods, is reacted with a suitably selected base such as NaH, phenyl lithium, and the like; in a suitably selected organic solvent such as THF, diethyl ether, and the like; and then reacted with a suitably selected base such as t-BuLi, n-BuLi, sec-BuLi and the like, and then with DMF; in a suitably selected organic solvent such as THF, 1,4-dioxane, and the like; to yield the corresponding compound of formula (11b). Alternatively, the compound of formula (11a) is reacted with two or more equivalents of for example, n-BuLi, and DMF in, for example THF, to yield the corresponding compound (11b).

The compound of formula (11b) is reacted with a suitably selected compound of formula (11c), wherein $LG^3$ is a suitably selected leaving group such as Br, I, and the like, a known compound or compound prepared by known methods, according to known methods, to yield a mixture of the corresponding compound of formula (11d) and the compound of formula (11e). For example, wherein $R^1$ is alkyl, the compound of formula (11b) is reacted with a suitably selected alkylating agent such as $CH_3I$, EtOtriflate, EtOmesylate, and the like.

The mixture of the compound of formula (11d) and the compound of formula (11e) is reacted with a suitably selected reducing such as $Li(Bu^tO)_3AlH$, $NaBH_4$, and the like; in a suitably selected organic solvent such as THF, methanol, and the like; to yield a mixture of the corresponding compound of formula (IIk) and the compound of formula (IIm).

The mixture of the compound of formula (IIk) and the compound of formula (IIk) is optionally separated according to known methods, for example by reverse phase HPLC.

Compounds of formula (II) wherein

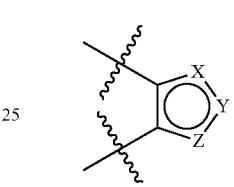

is selected from the group consisting of

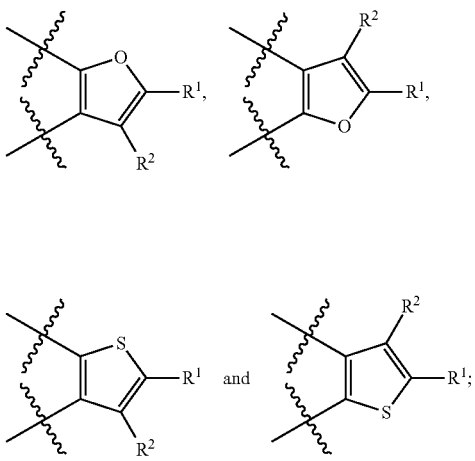

and wherein $R^2$ is other than hydrogen, may be prepared as described in Scheme 12, below.

Scheme 12

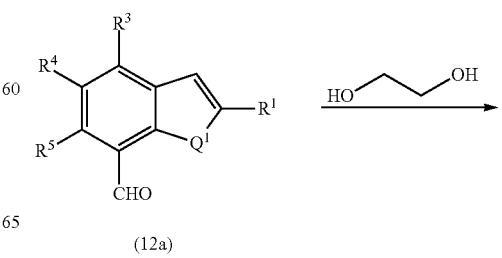

(12a)

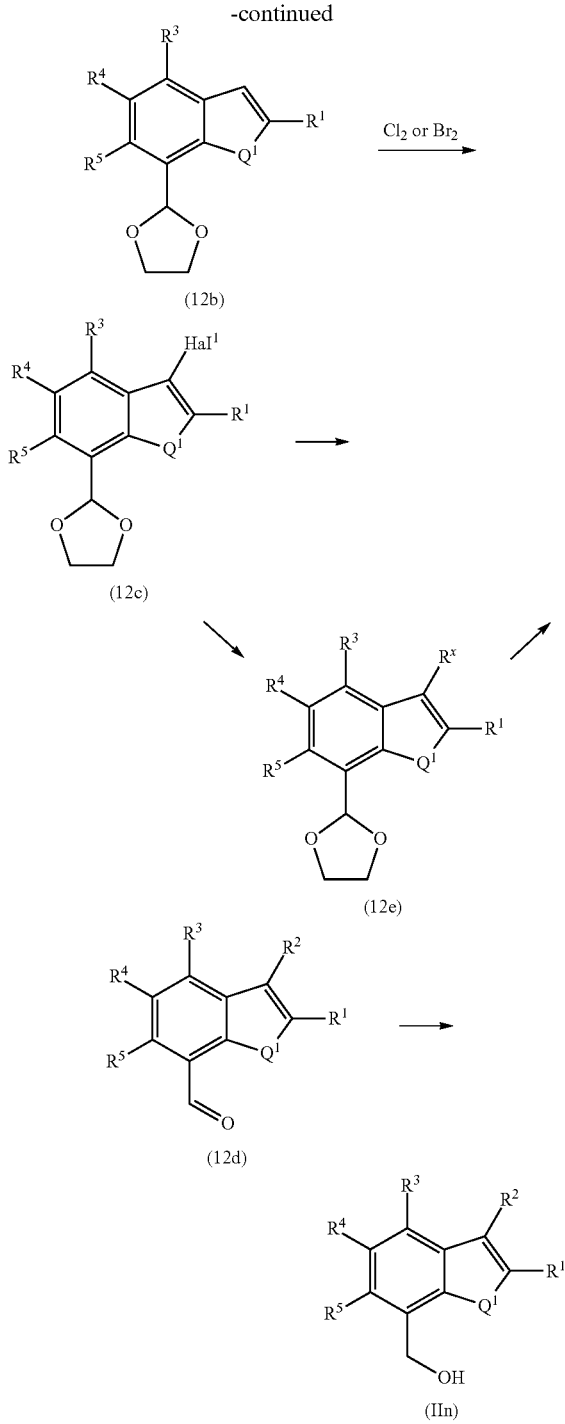

example, wherein Hal¹ is chloro, the compound of formula (12b) may be reacted with $Cl_2$, in the presence of acetic acid. Alternatively, wherein Hal¹ is bromo, the compound of formula (12b) may be reacted with $Br_2$, in the presence of sodium acetate, and the like; in a solvent such as chloroform, acetic acid, and the like; preferably at temperature in the range of from about 0° C. to about room temperature.

The compound of formula (12c) is reacted with for example HCl in water at room temperature to yield the corresponding compound of formula (12d).

Alternatively, the compound of formula (12c) is then further optionally reacted (through one or more steps), according to known methods, to yield the corresponding compound of formula (12e) wherein $R^X$ is selected from the group consisting of halogen, $C_{1-4}$alkyl, $C_{2-4}$alkenyl and $C_{2-4}$alkynyl. For example, the compound of formula (12c) may be reacted with a suitably selected fluorinated agent, such as CsF, in the presence of, for example, a palladium 2-(dicyclohexylphosphino)3,6-dimethoxy-2',4',6'-triisopropyl-1,1'-biphenyl catalyst (BrettPhos [(COD)Pd(CH₂TMS)₂]), in a solvent such as toluene, to yield the corresponding compound of formula (12e) wherein $R^2$ is fluoro. Alternatively, the compound of formula (12c) may be reacted with a suitably selected alkyl iodide such as $CH_3I$ according to known methods, to yield the corresponding compound of formula (12e) wherein $R^2$ is $C_{1-4}$alkyl. Alternatively still, the compound of formula (12c) may be reacted with a suitably selected alkenyl-zinc bromide such as $CH_2=CH$—ZnBr, and the like in the presence of $CH_3MgBr$, Ni acetylacetonate, 4,5-bis(diphenylphoshino)-9,9-dimethylxanthene, in THF at about 50° C. or with a suitably selected alkynyl such as CCH—$CH_3$, and the like, in the presence of TEA, C:CuI, C:$PdCl_2(PPh_3)_2$, in DMF at about 80° C.; to yield the corresponding compound of formula (12e) wherein $R^X$ is the corresponding $C_{2-4}$alkenyl or $C_{2-4}$alkynyl.

The compound of formula of formula (12e) is reacted to yield the corresponding compound of formula (12d). For example, the compound of formula (12e) is reacted with $H^+$ in water at room temperature; to yield the corresponding compound of formula (12d). One skilled in the art will recognize that wherein the compound of formula (12e) $R^X$ is $C_{2-4}$alkenyl or $C_{2-4}$alkynyl, reacting the compound of formula (12e) with $H_2(g)$ in the presence of a suitably selected catalyst such as Pd/C, and the like; to yield conversion of the 1,3-dioxolan-2-yl to hydroxymethyl (remove prot by open ring) and reduction of the $C_{2-4}$alkenyl or $C_{2-4}$alkynyl to the corresponding $C_{2-4}$alkyl.

The compound of formula (12d) is reacted with a suitably selected reducing agent such as Li(Bu$^t$O)₃AlH, NaBH₄, and the like; in a suitably selected solvent such as methanol, THF, and the like; to yield the corresponding compound of formula (IIn).

Compounds of formula (II) wherein

Accordingly, a suitably substituted compound of formula (12a), wherein Q¹ is selected from the group consisting of O and S, a known compound or compound prepared by known methods, is reacted with ethane-1,2-diol, a known compound; in the presence of p-TsOH, MsOH, and the like; in a the presence of triethyl orthoformate, a known compound; in a suitably selected solvent such as toluene, triethyl orthoformate, and the like; to yield the corresponding compound of formula (12b).

The compound of formula (12b) is reacted, according to known methods, to yield the corresponding compound of formula (12c) wherein Hal¹ is chloro or bromo. For

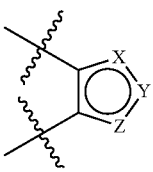

is selected from the group consisting of

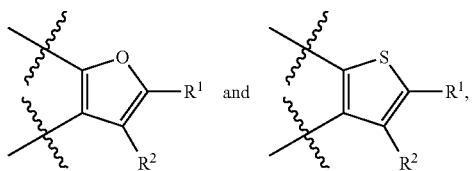

and wherein R² is other than hydrogen, may be similarly prepared according to the procedures as described in Scheme 12 above, by selecting and substituting a suitably substituted compound of formula (12e)

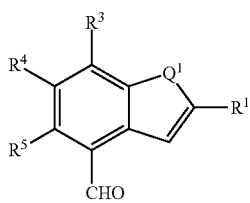

(12e)

wherein Q¹ is selected from the group consisting of O and S for the compound of formula (12a) and reacting as described therein.

Compounds of formula (II) wherein

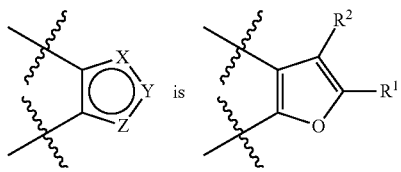

and wherein R² is other than hydrogen may alternatively be prepared according to the procedure as described in Scheme 13, below.

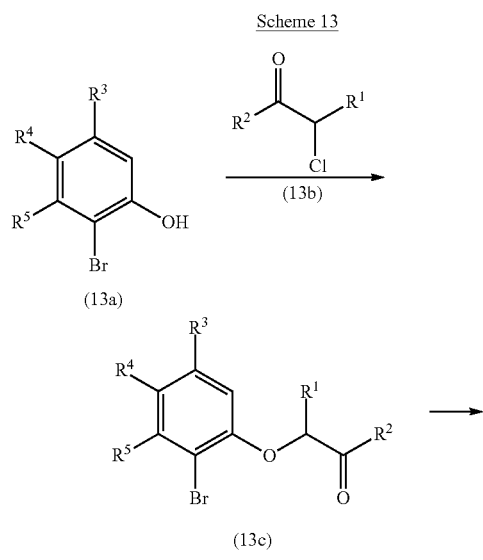

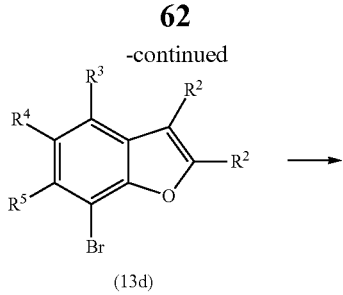

(13d)

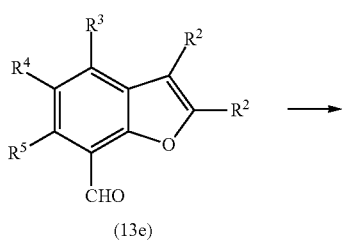

(13e)

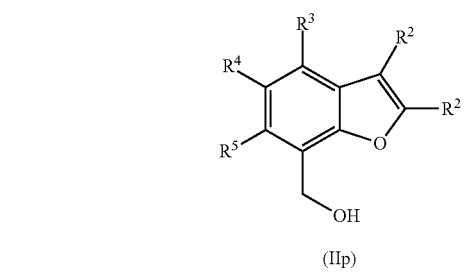

(IIp)

Accordingly, a suitably substituted compound of formula (13a), a known compound or compound prepared by known methods, is reacted with a suitably substituted compound of formula (13b), a known compound or compound prepared by known methods; in the presence of a suitably selected inorganic base such as $K_2CO_3$, $Cs_2CO_3$, and the like; in the presence of a suitably selected catalyst such as KI, and the like; in a suitably selected solvent such as acetone, DMF, acetonitrile, and the like; preferably at a temperature in the range of from about 60° C. to about 120° C., for example at about reflux temperature (about 70° C.); to yield the corresponding compound of formula (13c).

The compound of formula (13c) is reacted with a suitably selected acid such as $H_2SO_4$, TFA, camphosulfonic, and the like; neat; preferably at a temperature in the range of from about 22° C. to about 40° C. (for example at about 30° C.); to yield the corresponding compound of formula (13d).

The compound of formula (13d) is reacted with a suitably selected base such as n-BuLi, isopropyl magnesium chloride, and the like; in the presence of for example, DMF, and the like; in a suitably selected solvent such as THF, diethyl ether, and the like; to yield the corresponding compound of formula (13e).

The compound of formula (13e) is reacted with a suitably selected reducing agent such as $NaBH_4$, DIBAL, and the like; in a suitably selected solvent such as methanol, THF, DCM, and the like; to yield the corresponding compound of formula (IIp).

Compounds of formula (II) wherein

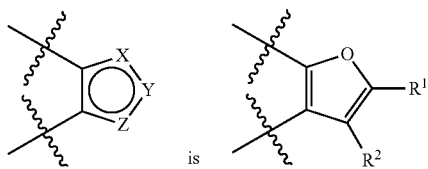

is and wherein $R^2$ is other than hydrogen may alternatively be prepared according to the procedure as described in Scheme 14, below.

Scheme 14

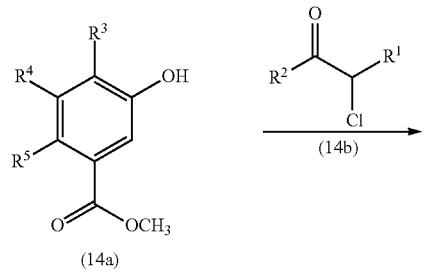

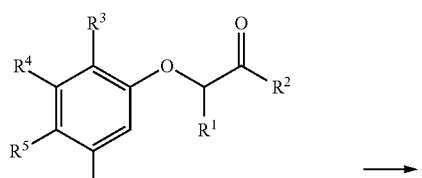
(14c)

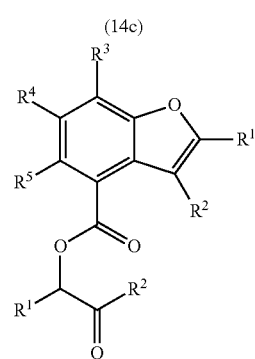
(14d)

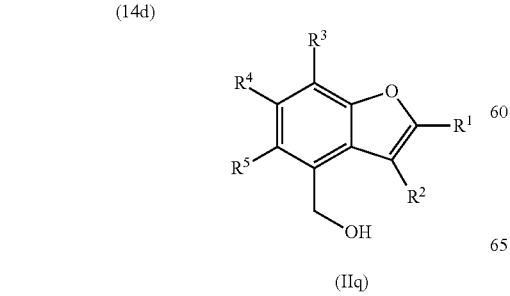
(IIq)

Accordingly, a suitably substituted compound of formula (14a), a known compound or compound prepared by known methods, is reacted with a suitably substituted compound of formula (14b), a known compound or compound prepared by known methods, in the presence of a suitably selected inorganic base such as $K_2CO_3$, $Cs_2CO_3$, and the like; in the presence of a suitably selected catalyst such as KI, and the like; in a suitably selected solvent such as acetone, DMF, acetonitrile, and the like; preferably at a temperature in the range of from about 60° C. to about 120° C., for example at about reflux temperature (about 70° C.); to yield the corresponding compound of formula (14c).

The compound of formula (14c) is reacted with a suitably selected acid such as $H_2SO_4$, TFA, camphosulfonic, and the like; neat; preferably at a temperature in the range of from about 22° C. to about 40° C. (for example at about 30° C.); to yield the corresponding compound of formula (14d).

The compound of formula (14d) is reacted with a suitably selected reducing agent such as DIBAL, $LiBH_4$, and the like; in a suitably selected solvent such as DCM, methanol, and the like; to yield the corresponding compound of formula (IIq).

One skilled in the art will recognize that compounds of formula (II) wherein

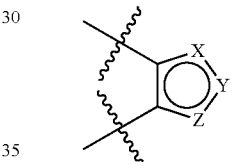

is selected from the group consisting of

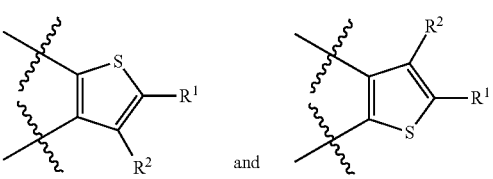
and may be similarly prepared according to the procedures as described in Scheme 13 and 14 above, by selecting and substituting a suitably substituted compound of formula (14e)

(14e)

for the compound of formula (14b), therein.

Compounds of formula (II) wherein $R^4$ and $R^5$ are taken together with the carbon atoms to which they are bound to form

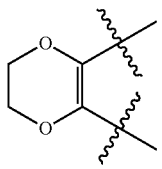

may be prepared according to the procedure as described in Scheme 15, below.

Scheme 15

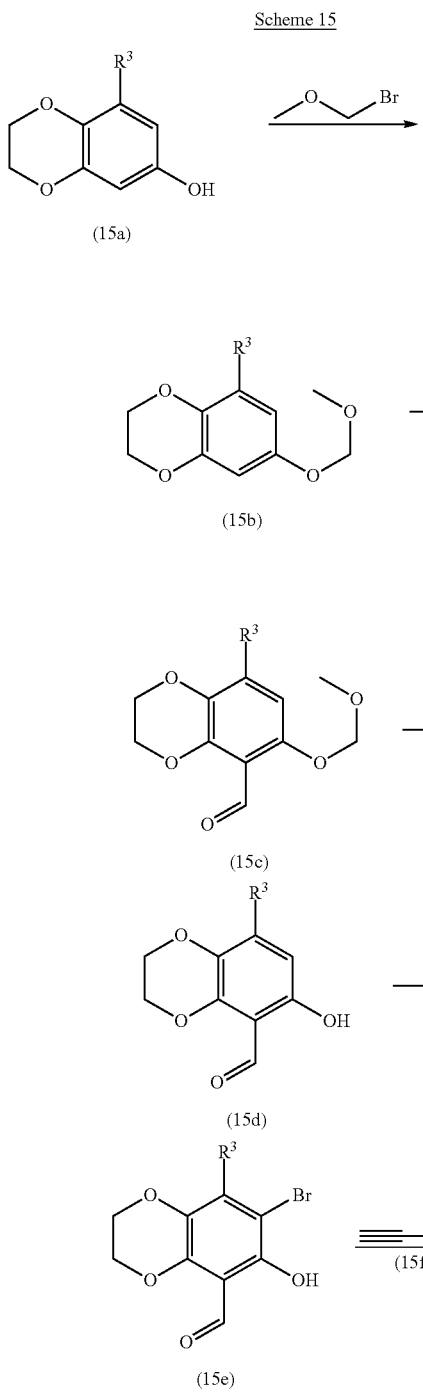

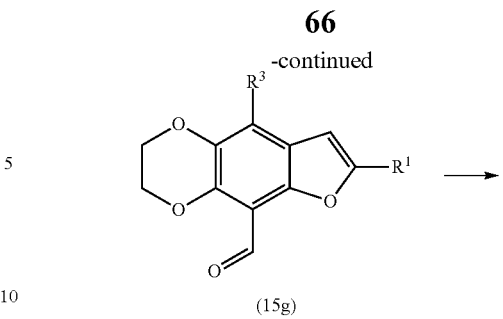

Accordingly, a suitably substituted compound of formula (15a) is reacted with bromo(methoxy)methane, a known compound; in the presence of a suitably selected base such as NaH, $Cs_2CO_3$, and the like; in a suitably selected solvent such as THF, DMF, and the like; to yield the corresponding compound of formula (15b).

The compound of formula (15b) is reacted with a suitably selected base such as n-BuLi, and the like; in the presence of DMF, and the like; in a suitably selected solvent such as THF, diethyl ether, and the like; to yield the corresponding compound of formula (15c).

The compound of formula (15c) is reacted with a suitably selected acid such as TFA, HCl, and the like; in a suitably selected solvent such as DCM, diethyl ether, and the like; to yield the corresponding compound of formula (15d).

The compound of formula (15d) is reacted with a suitably selected brominating agent such as $Br_2$, NBS, and the like; in a suitably selected solvent such as chloroform, DCM, and the like; to yield the corresponding compound of formula (15e).

The compound of formula (15e) is reacted with a suitably substituted compound of formula (15f), a known compound or compound prepared by known methods; in the presence of a suitably selected coupling agent such as $Pd(PPh_3)_2Cl_2$, $Pd(PPh_3)_4$, $Pd(dppe)Cl_2$, and the like; in the presence of CuI; in the presence of a suitably selected organic base such as TEA, DIPEA, and the like; neat or in a suitably selected solvent such as DMF, and the like; to yield the corresponding compound of formula (15g).

The compound of formula (15g) is reacted with a suitably selected reducing agent such as LAH, $NaBH_4$, and the like; in a suitably selected solvent such as THF, methanol, and the like; to yield the corresponding compound of formula (IIr).

Compounds of formula (II) wherein $R^4$ and $R^5$ are taken together with the carbon atoms to which they are bound to form

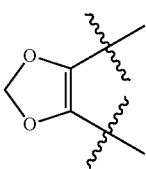 [SMILES: *C1=C(*)OCO1]

may be similarly prepared according to the procedure as described in Scheme 15 above, by selecting and substituting a suitably substituted compound of formula (15h)

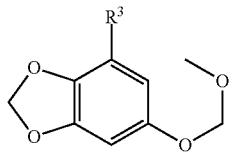
(15h)

for the compound of formula (15b) and reacting as described therein.

Compounds of formula (II) wherein $R^4$ and $R^5$ are taken together with the carbon atoms to which they are bound to form

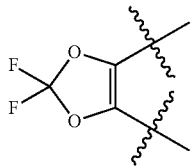 [SMILES: *C1=C(*)OC(F)(F)O1]

may be prepared according to the procedure as described in Scheme 16, below.

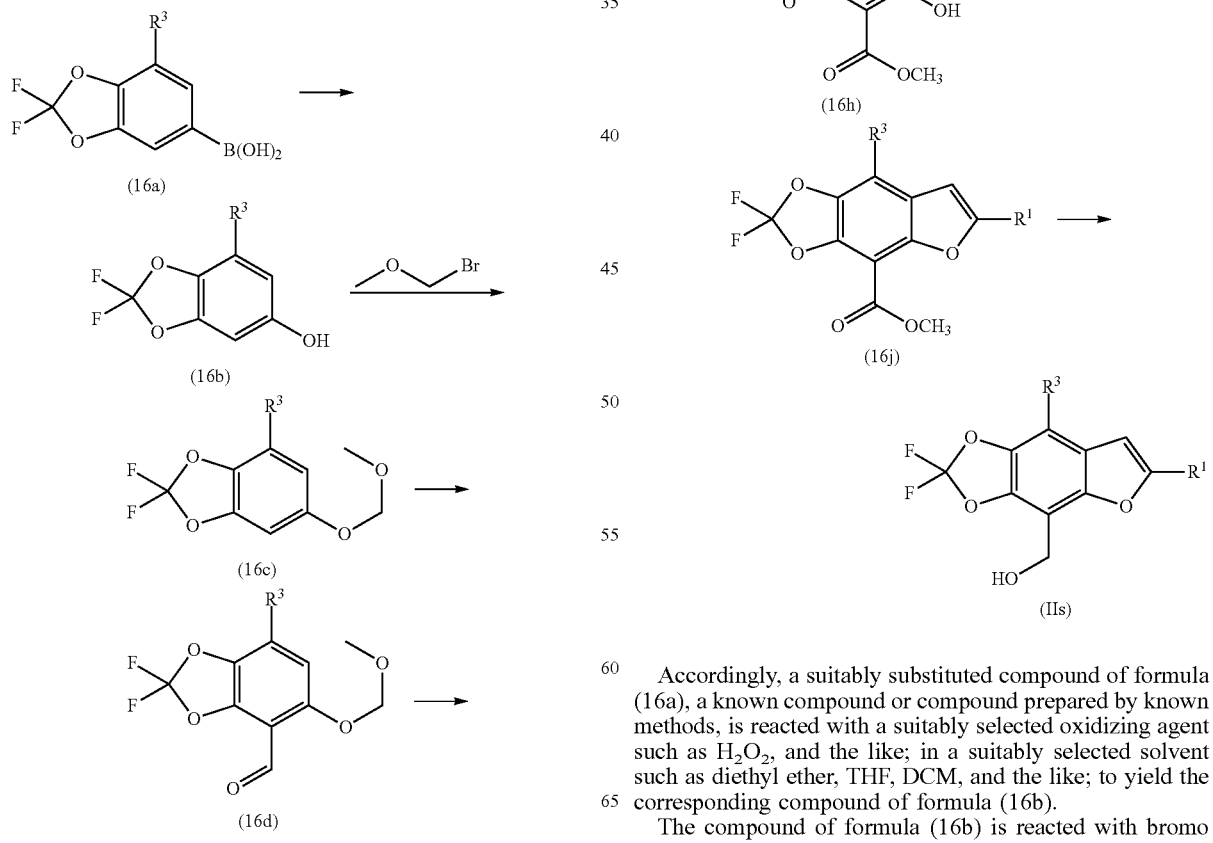

Accordingly, a suitably substituted compound of formula (16a), a known compound or compound prepared by known methods, is reacted with a suitably selected oxidizing agent such as $H_2O_2$, and the like; in a suitably selected solvent such as diethyl ether, THF, DCM, and the like; to yield the corresponding compound of formula (16b).

The compound of formula (16b) is reacted with bromo(methoxy)methane, a known compound; in the presence of a suitably selected base such as NaH, Cs$_2$CO$_3$, and the like; in a suitably selected solvent such as THD, DMF, and the like; to yield the corresponding compound of formula (16c).

The compound of formula (16c) is reacted with a suitably selected base such as n-BuLi, and the like; in the presence of for example, DMF, and the like; in a suitably selected solvent such as THF, diethyl ether, and the like; to yield the corresponding compound of formula (16d).

The compound of formula (16d) is reacted with a suitably selected oxidizing agent such as Ag$_2$O, mCPBA, sodium hypochlorite, and the like; in a suitably selected solvent such as aqueous NaOH, aqueous potassium hydroxide, and the like; to yield the corresponding compound of formula (16e).

The compound of formula (16e) is reacted with TMS diazomethane, a known compound; in a suitably selected solvent such as methanol, ethanol, and the like; to yield the corresponding compound of formula (16f).

The compound of formula (16f) is reacted with a suitably selected acid such as TFA, HCl, and the like; in a suitably selected solvent such as DCM, diethyl ether, THF, and the like; to yield the corresponding compound of formula (16g).

The compound of formula (16g) is reacted with a suitably selected brominating agent such as Br$_2$, NBS, and the like; in a suitably selected solvent such as chloroform, DCM, and the like; to yield the corresponding compound of formula (16h).

The compound of formula (16h) is reacted with a suitably substituted compound of formula (16i), a known compound or compound prepared by known methods; in the presence of a suitably selected coupling agent such as Pd(PPh$_3$)$_2$Cl$_2$, Pd(PPh$_3$)$_4$, Pd(dppe)Cl$_2$, and the like; in the presence of CuI; in the presence of a suitably selected organic base such as DIPEA, TEA, and the like; neat or in a suitably selected solvent such as DMF, and the like; to yield the corresponding compound of formula (16j).

The compound of formula (16j) is reacted with a suitably selected reducing agent such as LAH, NaBH$_4$, and the like; in a suitably selected solvent such as THF, methanol, and the like; to yield the corresponding compound of formula (IIs).

Compounds of formula (II) wherein R$^4$ and R$^5$ are taken together with the carbon atoms to which they are bound to form

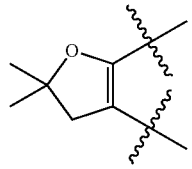 [SMILES: *C1=C(*)OC(C)(C)C1]

may be prepared according to the procedure as described in Scheme 17, below.

Scheme 17

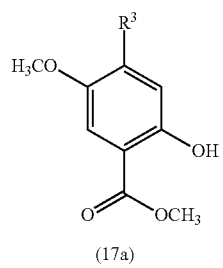
(17a)

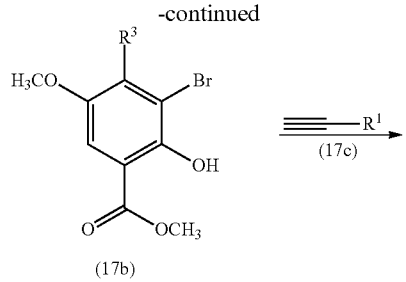
(17b)

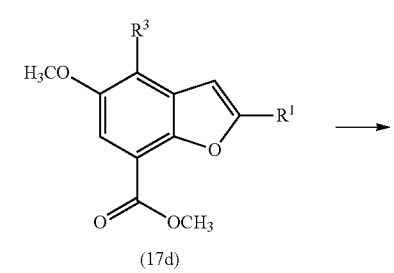
(17d)

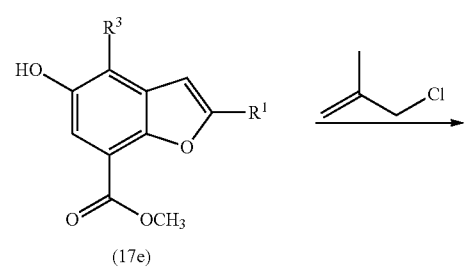
(17e)

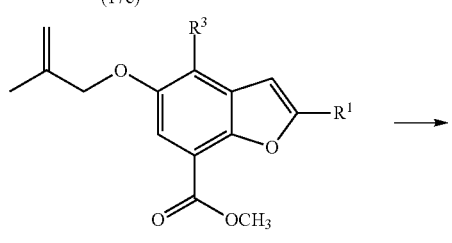
(17f)

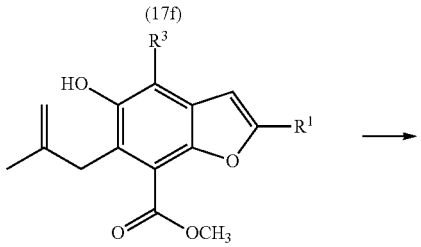
(17g)

(17h)

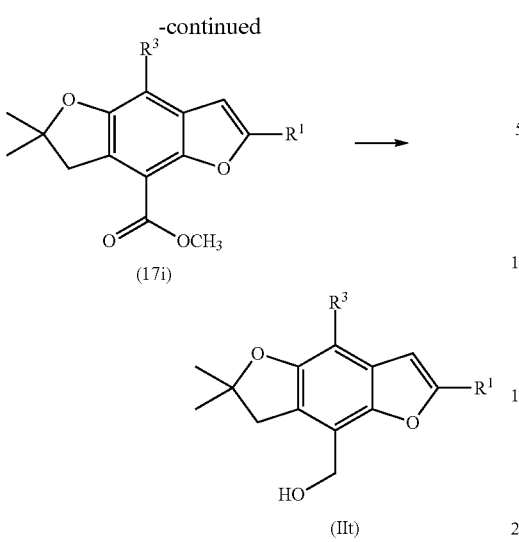

(17i)

(IIt)

Accordingly, a suitably substituted compound of formula (17a), a known compound or compound prepared by known methods is reacted with a suitably selected brominating agent such as $Br_2$, NBS, and the like; in a suitably selected solvent such as chloroform, DCM, and the like; to yield the corresponding compound of formula (17b).

The compound of formula (17b) is reacted with a suitably substituted compound of formula (17c), a known compound or compound prepared by known methods; in the presence of a suitably selected coupling agent such as $Pd(PPh_3)_2Cl_2$, $Pd(PPh_3)_4$, $Pd(dppe)Cl_2$, and the like; in the presence of CuI; in the presence of a suitably selected organic base such as TEA, DIPEA, and the like; neat or in a suitably selected solvent such as DMF, and the like; to yield the corresponding compound of formula (17d).

The compound of formula (17d) is reacted with a suitably selected Lewis acid such as $BBr_3$, and the like; in a suitably selected solvent such as DCM, DCE, and the like; to yield the corresponding compound of formula (17e).

The compound of formula (17e) is reacted with 3-chloro-2-methylprop-1-ene, a known compound; in the presence of a suitably selected base such as $K_2CO_3$, $Cs_2CO_3$, and the like; in a suitably selected solvent such as DMF, acetone, and the like; to yield the corresponding compound of formula (17f).

The compound of formula (17e) is heated to a temperature in the range of from about 180° C. to about 200° C., for example to about 192° C.; and maintained at that temperature to effect a rearrangement; to yield the corresponding compound of formula (17f).

The compound of formula (17f) is reacted with a suitably selected organic acid such as aqueous formic acid, acetic acid, TFA, and the like; neat or in a suitably selected solvent such as DCM, and the like; to yield the corresponding compound of formula (17g).

The compound of formula (17g) is reacted with TMS diazomethane, a known compound; in a suitably selected solvent such as methanol, ethanol, and the like; to yield the corresponding compound of formula (17h).

The compound of formula (17h) is reacted with a suitably selected reducing agent such as DIBAL, LAH, and the like; in a suitably selected solvent such as DCM, THF, and the like; to yield the corresponding compound of formula (IIt).

Compounds of formula (II) wherein

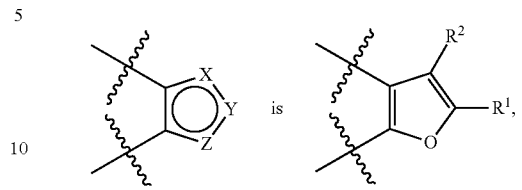

wherein $R^2$ is hydrogen and wherein $R^1$ is selected from the group consisting of —CN, —C(O)O—($C_{1-4}$alkyl) and —C(O)—($C_{1-4}$alkyl) may be prepared according to the process outlined in Scheme 18, below.

Scheme 18

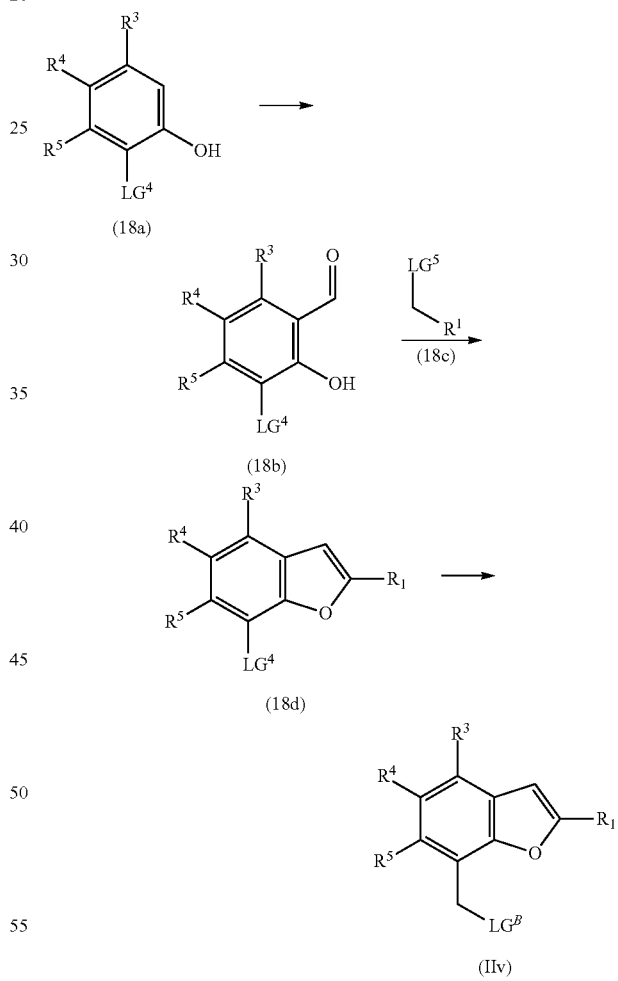

Accordingly, a suitably substituted compound of formula (18a), wherein $LG^4$ is a suitably selected group such as $CH_3$, Br, I, and the like, a known compound or compound prepared by known methods; is reacted with for example, hexamethylenetetramine; in the presence of a suitably selected acid such as TFA, and the like; neat; at a temperature in the range of from about room temperature to about 100° C., for example, at about 80° C.; to yield the corresponding compound of formula (18b).

The compound of formula (18b) is reacted with a suitably substituted compound of formula (18c), wherein $LG^5$ is a suitably selected leaving group such as Cl, Br, I, $OSO_2CF_3$, and the like, and wherein $R^1$ is selected from the group consisting of —CN, —C(O)O—($C_{1-4}$alkyl) and —C(O)—($C_{1-4}$alkyl), a known compound or compound prepared by known methods, in the presence of a suitably selected base such as potassium carbonate, $Cs_2CO_3$ and the like; in a suitably selected organic solvent such as acetonitrile, acetone, DMF, and the like; to yield the corresponding compound of formula (18d).

The compound of formula (18d) is reacted to yield the corresponding compound of formula (IIv), wherein $LG^B$ is a suitably selected leaving group such as Br, OH, and the like. Wherein $LG^4$ is methyl, the compound of formula (18d) is reacted with a suitably selected brominating agent such as NBS, and the like; in the presence of for example AIBN, and the like; in a suitably selected solvent such as DCM, $CCl_4$, and the like; at at temperature in the range of from about 50° C. to about 80° C.; to yield the corresponding compound of formula (IIv), wherein $LG^B$ is Br.

Alternatively, wherein $LG^4$ is bromo or iodo, the compound of formula (18d) is reated with carbon monoxide; in the presence of a suitably selected catalyst such as Pd(dppf)$Cl_2$, and the like; in the presence of a suitably selected base such as TEA, DIPEA, and the like; in a suitably selected alcohol of the formula $A^4OH$, wherein $A^4$ is selected from the group consisting of $C_{1-4}$alkyl, preferably methyl or ethyl; at for example, about 60° C.; to yield the corresponding ester, a compound of formula (18e)

which is then reacted with a suitably selected reducing agent such as DIBAL, LAH, $LiBH_4$, and the like; in a suitably selected organic solvent such as $CH_2Cl_2$, THF, toluene, and the like; preferably at a temperature in the range of form about −78° C. to about 22° C., for example, at about −78° C.; to yield the corresponding compound of formula (IIv) wherein $LG^B$ is OH.

Compounds of formula (I) wherein

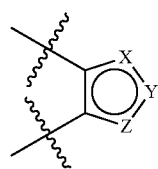 is 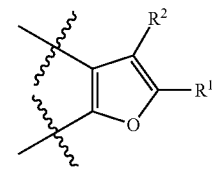

and wherein $R^1$ is selected from the group consisting of —($C_{1-4}$alkyl)-$NR^AR^B$, —($C_{1-4}$alkyl)-$NR^A$—C(O)—($C_{1-4}$alkyl), —($C_{1-4}$alkyl)-$NR^A$—$SO_2$—($C_{1-4}$alkyl) may alternatively be prepared according to the procedure as described in Scheme 19, below.

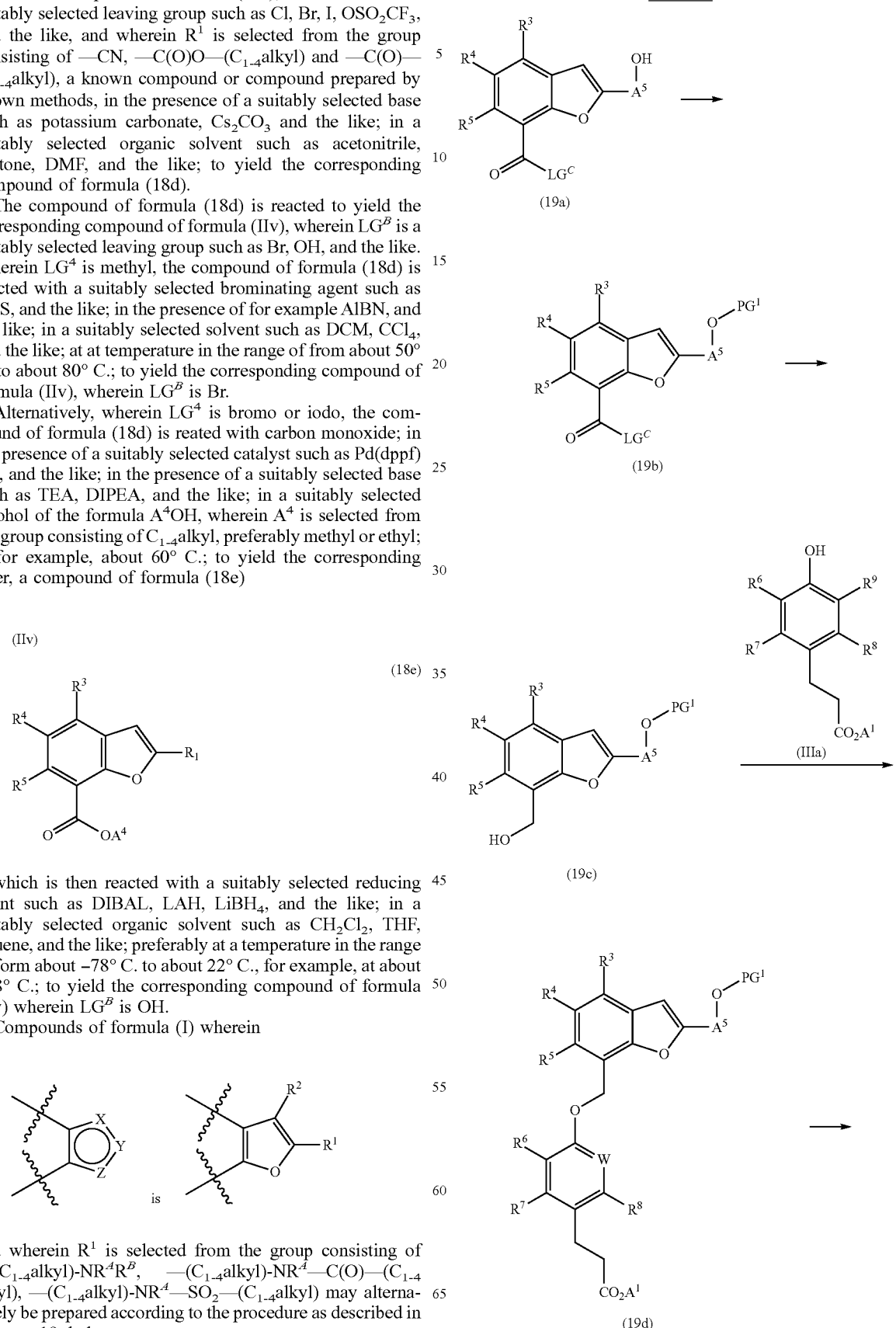

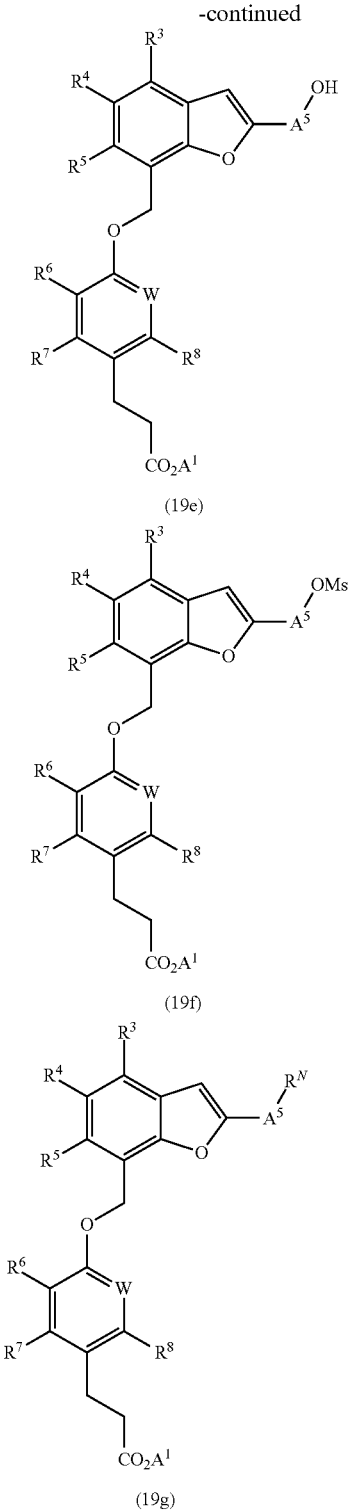

(19e)

(19f)

(19g)

Accordingly, a suitably substituted compound of formula (19a), wherein $A^5$ is a —($C_{1-4}$alkyl)-, and wherein $LG^C$ is OH or a suitably selected $C_{1-4}$alkoxy such as methoxy, ethoxy and the like, prepared for example, as described in Scheme 2 above, is protected according to known methods, to yield the corresponding compound of formula (19b) wherein $PG^1$ is the corresponding oxygen protecting group. For example, the compound of formula (19a) may be reacted with TBDMSCl in THF; to yield the corresponding compound of formula (19b), wherein $PG^1$ is TBDMS.

The compound of formula (19b) is reacted with a suitably selected reducing agent such as LAH, $NaBH_4$, and the like; in a suitably selected solvent such as THF, MeOH, toluene, and the like; to yield the corresponding compound of formula (19c).

The compound of formula (19c) is reacted with a suitably substituted compound of formula (IIIa), as described in Scheme 1 above, for example, in the presence of a suitably selected coupling system such as for example a mixture of $PPh_3$ and DEAD, in a suitably selected solvent such as THF; to yield the corresponding compound of formula (19d).

The compound of formula (19d) is de-protected according to known methods, for example, wherein the protecting group is TBDMS, by reacting with TBAF in THF; to yield the corresponding compound of formula (19e).

The compound of formula (19e) is reacted with for example mesyl chloride, in the presence of a suitably selected organic base such as TEA, and the like, in a suitably selected solvent such as DCM, and the like; to yield the corresponding compound of formula (19f).

The compound of formula (19f) is then reacted in one or more steps, according to known methods, to further functionalize the $R^1$ substituent group. For example, the compound of formula (19f) may be reacted with a suitably substituted amine of the formula $NR^A R^B$, in the presence of a suitably selected base such as $K_2CO$, and the like, in a suitably selected solvent such as DMF, and the like; to yield the corresponding compound of formula (19g) wherein $R^N$ is $NR^A R^B$. Alternatively, the compound of formula (19f) may be reacted with $NaN_3$, in a suitably selected solvent such as DMF, and the like; and then further reacted with a suitably selected reducing agent such as hydrogen in the presence of a suitably selected catalyst such as Pd/C, and the like, in a suitably selected solvent such as methanol, and the like; to yield the corresponding compound of formula (19g) wherein $R^N$ is $NH_2$.

One skilled in the art will recognize that the compound of formula (19g) wherein $R^N$ is $NH_2$ may be further reacted accoridng to known methods to functionalize the terminal amine, for example, by reacting with a suitably substituted acid chloride or a suitably substituted sulfonyl chloride, to yield the corresponding compound of formula (19g) wherein $R^N$ is —NH—C(O)—($C_{1-4}$alkyl) or —NH—$SO_2$—($C_{1-4}$alkyl), respectively.

One skilled in the art will further recognize that the compound of formula (19g) corresponds to the compound of formula (IV) as described in Scheme 1 above, and may be reacted as described in Scheme 1 above, to yield the corresponding compound of formula (Ia) or formula (Ib).

Compounds of formula (I) wherein

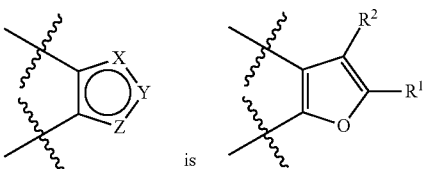

is and wherein $R^1$ is for example, —($C_{1-4}$alkyl)-$CF_2$H or —CHCHF may be prepared according to the procedure as described in Scheme 20, below.

Scheme 20

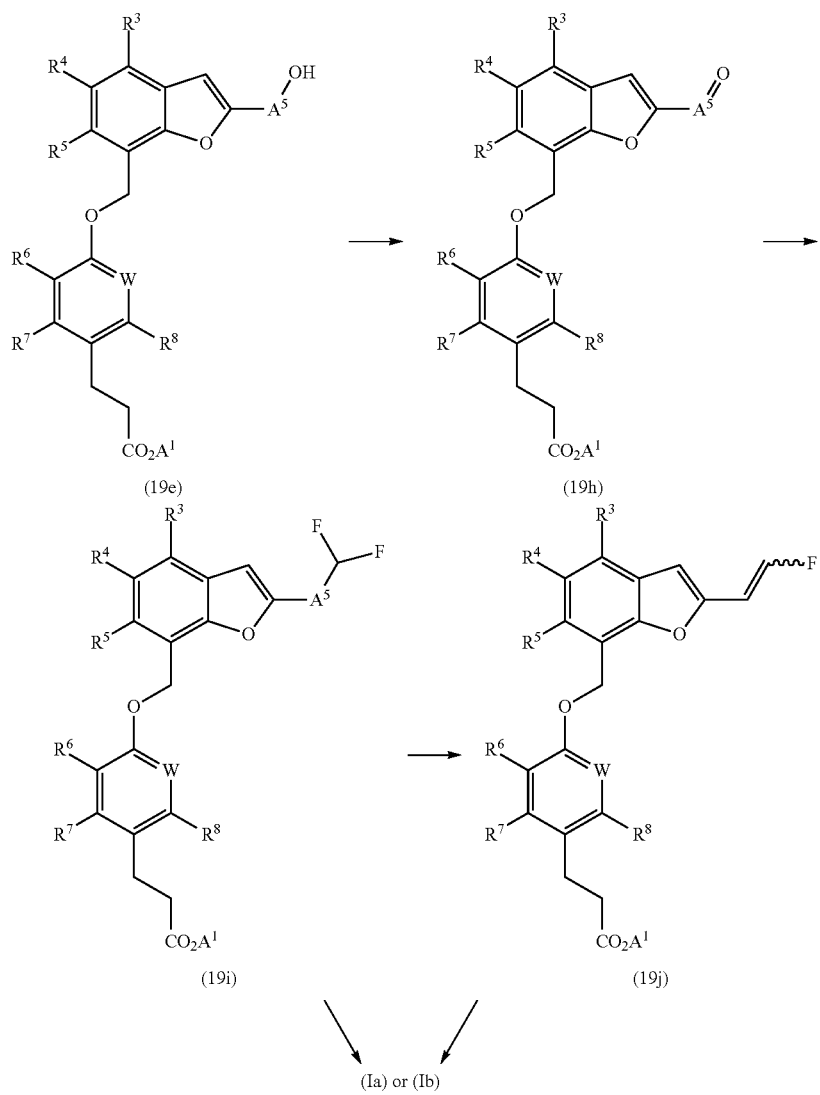

Accordingly, a suitably substituted compound of formula (19e), wherein the hydroxy group is bound to the $A^5$—($C_{1-4}$ alkyl)- at a terminal carbon atom, prepared for example as described in Scheme 19 above, is reacted with a suitably selected oxidized agent such as Dess-Martin periodinane (1,1,1-triacetoxy-1,1-dihydro-1,2-benziodoxol-3(1H)-one), pyridinium chlorochromate, and the like; in a suitably selected solvent such as THF, DCM, and the like; to yield the corresponding compound of formula (19h) (wherein -$A^5$=O represents the corresponding aldehyde).

The compound of formula (19h) is reacted with a suitably selected fluorinating reagent such as diethylaminosulfur trifluoride, bis(2-methoxyethyl)aminosulfur trifluoride, and the like; in a suitably selected solvent such as THF, DCM, and the like; at a tempeature in the range of from about 0° C. to about room temperature; yield the corresponding compound of formula (19i).

One skilled in the art will further recognize that the compound of formula (19i) corresponds to the compound of formula (IV) as described in Scheme 1 above, and may be reacted as described in Scheme 1 above, to yield the corresponding compound of formula (Ia) or formula (Ib).

Alternatively, wherein the compound of formula (19i) $A^2$ is —$CH_2$—, the compound of formula (19i) may be reacted with a suitably selected base such as sodium methoxide, sodium hydroxide, and the like; in a suitably selected solvent such as THF, methanol, and the like; at for example, room temperature; to yield the corresponding compound of formula (19j).

One skilled in the art will further recognize that the compound of formula (19j) corresponds to the compound of formula (IV) as described in Scheme 1 above, and may be reacted as described in Scheme 1 above, to yield the corresponding compound of formula (Ia) or formula (Ib).

Compounds of formula (III) wherein may be prepared according to the procedure as described in Scheme 21.

Scheme 21

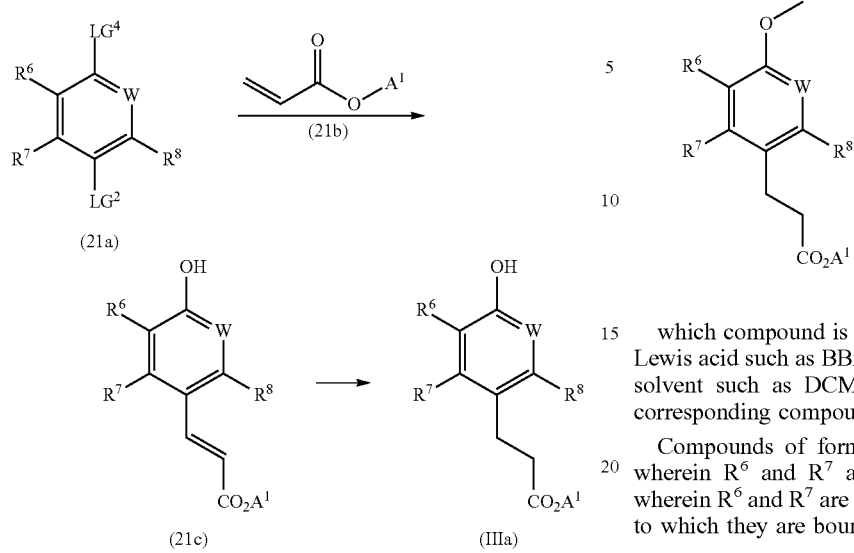

Accordingly, a suitably substituted compound of formula (21a), wherein $LG^2$ is a suitably selected leaving group such as bromo, iodo, triflate and the like, and wherein $LG^4$ is OH (when W is $C(R^9)$) or halogen (when W is N), a known compound or compound prepared by known methods, is reacted with a suitably substituted compound of formula (21b), wherein $A^1$ is a suitably selected $C_{1-4}$alkyl, such as methyl, ethyl, t-butyl, and the like, a known compound or compound prepared by known methods; in the presence of a suitably selected catalyst such as $PdCl_2$, $Pd(OAc)_2$, and the like; in the presence of a suitably selected ligand such as $P(o\text{-tolyl})_3$, $PPh_3$, and the like; in the presence of a suitably selected base such as DIPEA, TEA, and the like; in a suitably selected solvent such as DMF, NMP, and the like; preferably at a temperature in the range of from about 110° C. to about 140° C., for example, at about 120° C.; to yield the corresponding compound of formula (21c).

The compound of formula (21c) is reacted with a suitably selected reducing agent such as $H_2$ gas; in the presence of a suitably selected catalyst such as Pd/C, and the like; in a suitably selected solvent such as methanol, ethyl acetate, and the like; to yield the corresponding compound of formula (IIIa).

One skilled in the art will recognize that compounds of formula (III) may alternatively be prepared according to the procedure as described in Scheme 19 above, by selecting and substituting a suitably substituted compound of formula (21d)

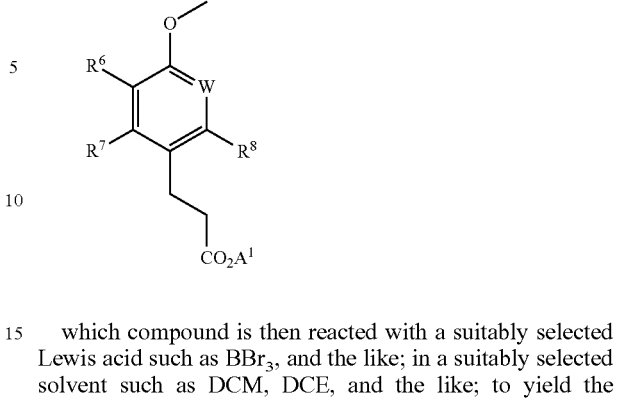

for the compound of formula (21a) and reacting said compound, as described therein; to yield the corresponding compound of formula (21e)

which compound is then reacted with a suitably selected Lewis acid such as $BBr_3$, and the like; in a suitably selected solvent such as DCM, DCE, and the like; to yield the corresponding compound of formula (III).

Compounds of formula (III) wherein W is $C(R^9)$ and wherein $R^6$ and $R^7$ are as herein defined, for example, wherein $R^6$ and $R^7$ are taken together with the carbon atoms to which they are bound to form

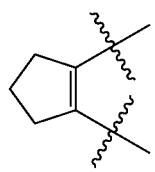 [SMILES: *C1=C(*)CCC1]

may be prepared according to the procedure as described in Scheme 22, below.

Scheme 20

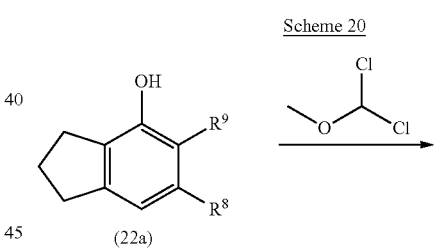

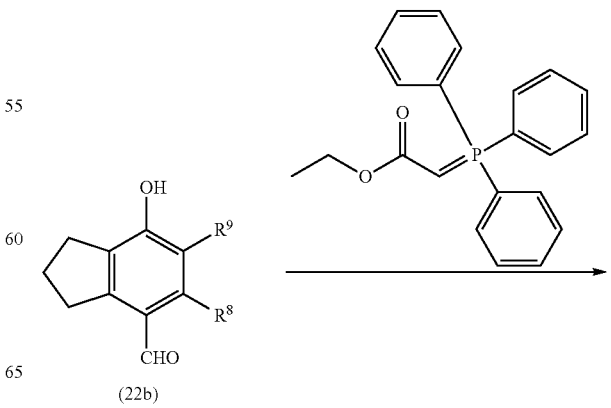

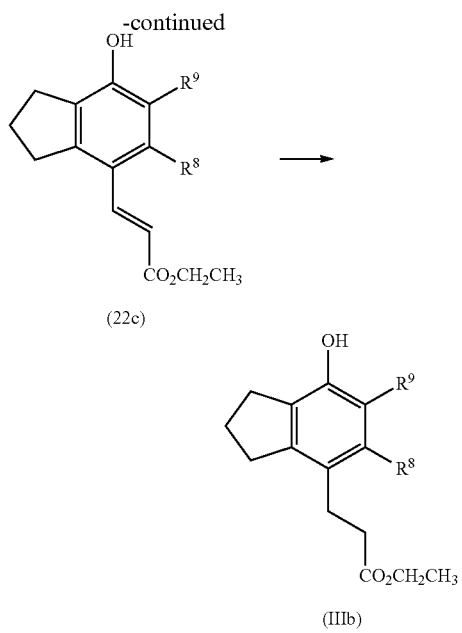

Accordingly, a suitably substituted compound of formula (22a), a known compound or compound prepared by known methods, is reacted with dichloromethylether, a known compound; in the presence of a suitably selected Lewis acid such as TiCl$_4$, and the like; in a suitably selected solvent such as DCM, DCE, and the like; to yield the corresponding compound of formula (22b).

The compound of formula (22b) is reacted with ethyl (triphenylphosphoranylidene)acetate, a known compound; in the presence of a suitably selected base such as NaH, NaHMDS, and the like; in a suitably selected solvent such as THF, DCM, and the like; to yield the corresponding compound of formula (22c).

The compound of formula (22c) is reacted with a suitably selected reducing agent such as H$_2$ gas; in the presence of a suitably selected catalyst such as Pd/C, and the like; in a suitably selected solvent such as methanol, ethyl acetate, and the like; to yield the corresponding compound of formula (IIIb).

One skilled in the art will further recognize that the R$^4$ substituent group may alternatively be incorporated into the compound of formula (I) by reacting a suitably substituted compound of formula (IV) wherein R$^4$ is for example iodo, according to known methods. For example, (a) a suitably substituted compound of formula (IV) wherein R$^4$ is iodo may be reacted with for example methyl 2,2-difluoro-2-(fluorosulfonyl)acetate, in the presence of CuI, NMP/DMP at about 100° C., then reacted with a base for example LiOH, in a mixture of THF and water; to yield the corresponding compound of formula (IV) wherein R$^4$ is CF$_3$; alternatively, (b) a suitably substituted compound of formula (IV) wherein R$^4$ is iodo may be reacted with for example a suitable substituted amine of the formula HNR$^C$R$^D$, a known compound, in the presence of a catalyst such as Pd(PPh$_3$)$_2$Cl$_2$, in the presence of CO(g), in a solvent such as DMF; then reacted with a base for example LiOH, in a mixture of THF and water; to yield the corresponding compound of formula (IV) wherein R$^4$ is the corresponding substituted amide (—C(O)—NR$^C$R$^D$); alternatively, (c) a suitably substituted compound of formula (IV) wherein R$^4$ is iodo may be reacted with for example acetic anhydride, in the presence of Pd$_2$(dba)$_3$, DIPEA and LiCl, in DMF, at about 150° C. under microwave; to yield the corresponding compound of formula (IV) wherein R$^4$ is —C(O)CH$_3$; which may be further optionally reacted with for example, DAST in [C$_{8min}$][PF$_6$], a known compound, overnight at about 55° C.; then reacted with a base for example LiOH, in a mixture of THF and water; to yield the corresponding compound of formula (IV) wherein R$^4$ is —CF$_2$(CH$_3$)$_2$ alternatively (d) a suitably substituted compound of formula (IV) wherein R$^4$ is iodo may be reacted with for example 2-bromo-3,3,3-trifluoroprop-1-ene, a known compound, in the presence of DIPEA, n-BuLi, ZnCl$_2$.TMEDA, Pd(PPh$_3$)$_4$, at about 80° C., overnight, to yield the corresponding compound of formula (IV) wherein R$^4$ is —CC—CF$_3$; alternatively, (e) a suitably substituted compound of formula (IV) wherein R$^4$ is iodo may be reacted with for example a fluoro, chloro or TMS substituted ethyne, in the presence of CuI, Pd(PPh$_3$)$_2$Cl$_2$, TEA, in for example, acetonitrile, overnight at about 70° C. to about 90° C.; then reacted with a base for example LiOH, in a mixture of THF and water; to yield the corresponding compound of formula (IV) wherein R$^4$ is the corresponding fluoro, chloro or TMS substituted ethynyl; which may be further reacted with for example TBAF, in THF at about 30° C., then with a base for example LiOH, in a mixture of THF and water; to yield the corresponding compound of formula (IV) wherein R$^4$ is ethynyl.

One skilled in the art will further recognize that the R$^4$ substituent group may alternatively be incorporated into the compound of formula (I) by reacting a suitably substituted compound of formula (IV) wherein R$^4$ is for example CH$_3$SCH$_2$CC—, according to known methods. For example, (a) a suitably substituted compound of formula (IV) wherein R$^4$ is for CH$_3$SCH$_2$CC— may be reacted with a suitably selected oxidizing agent such as mCPBA, potassium peroxysulfate, hydrogen peroxide, and the like; in a suitably selected solvent such as DCM, water/methanol, and the like; to yield the corresponding compound of formula (IV) wherein R$^4$CH$_3$SO$_2$CH$_2$CC—; alternatively, (b) a suitably substituted compound of formula (IV) wherein R$^4$ is CH$_3$SCH$_2$CC— may be reacted with a suitably selected reducing agent such as hydrogen; in the presence of a suitably selected catalyst such as Pd/C, and the like; to yield the corresponding compound of formula (IV) wherein R$^4$ is CH$_3$SCH$_2$CH$_2$CH$_2$—; which compound is then reacted with a suitably selected oxidizing agent such as mCPBA, potassium peroxysulfate, hydrogen peroxide, and the like; in a suitably selected solvent such as DCM, water/methanol, and the like; to yield the corresponding compound of formula (IV) wherein R$^4$ CH$_3$SO$_2$CH$_2$CH$_2$CH$_2$—.

One skilled in the art will further recognize that the transformations described above may alternatively be applied to compounds of formula (IV) wherein R$^5$ is iodo, to yield the corresponding compounds of formula (IV), wherein the R$^5$ group is functionalized as described.

Pharmaceutical Compositions

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 100 mg/kg/day, or any amount or range therein, preferably from about 0.5 mg/kg/day to about 50 mg/kg/day, preferably from about 1.0 mg/kg/day to about 25 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method(s) of treating disorders as described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders, as described herein, is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.1 to about 100.0 mg/kg of body weight per day, or any amount or range therein. More preferably, from about 0.5 to about 50.0 mg/kg of body weight per day, or any amount or range therein. More preferably, from about 1.0 to about 25.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a yieldn disorder.

One skilled in the art will further recognize that human clinical trials including first-in-human, dose ranging and efficacy trials, in healthy patients and/or those suffering from a yieldn disorder, may be completed according to methods well known in the clinical and medical arts.

SYNTHESIS EXAMPLES

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

3-{4-[(5-Fluoro-2-methyl-1-benzofuran-7-yl)methoxy]-2,3-dimethylphenyl}propanoic acid

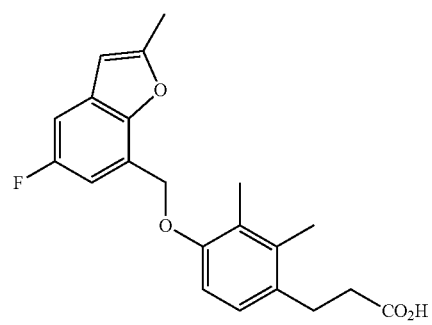 [SMILES: Cc1cc2cc(F)cc(COc3ccc(CCC(=O)O)c(C)c3C)c2o1]

a) Methyl 5-fluoro-2-methylbenzofuran-7-carboxylate

To a mixture of methyl 3-bromo-5-fluoro-2-hydroxybenzoate (6 g, 24.09 mmol, prepared as in Example 5 step (b)), PdCl$_2$(PPh$_3$)$_2$ (1.68 g, 2.39 mmol), CuI (456 mg, 2.39 mmol), N,N-dimethylformamide (24 mL) and triethylamine (4.85 g, 47.93 mmol) at −40° C. was introduced prop-1-yne (1.9 g, 47.42 mmol) for 30 min and the resulting mixture stirred at room temperature for 1 hr, and overnight at 75° C. The resulting mixture was diluted with ethyl acetate (100 mL). The resulting mixture was washed with water (3×25 mL). The resulting mixture was dried over anhydrous sodium sulfate and concentrated under vacuum. The resulting residue was purified on a silica gel column with ethyl acetate/petroleum ether (5/95) to yield methyl 5-fluoro-2-methyl-1-benzofuran-7-carboxylate as a white solid.

b) (5-Fluoro-2-methylbenzofuran-7-yl)methanol

To a solution of methyl 5-fluoro-2-methyl-1-benzofuran-7-carboxylate (2 g, 9.61 mmol), in tetrahydrofuran (70 mL) was added LAH (548 mg, 14.44 mmol) in portions at 0° C. The resulting solution was stirred for 30 min at 0° C. in a water/ice bath. The reaction was then quenched by the addition of Na$_2$SO$_4$.10H$_2$O (3 g). The solids were filtered out. The resulting mixture was concentrated under vacuum. The resulting residue was purified on a silica gel column with ethyl acetate/petroleum ether (40/60) to yield (5-fluoro-2-methylbenzofuran-7-yl)methanol as yellow oil.

c) (5-Fluoro-2-methylbenzofuran-7-yl)methyl methanesulfonate

Into a 100-mL round-bottom flask was placed (5-fluoro-2-methyl-1-benzofuran-7-yl)methanol (2.8 g, 15.54 mmol), dichloromethane (50 mL) and triethylamine (4.72 g, 46.64 mmol). To the resulting mixture was then added MsCl (4.47 g) dropwise with stirring at 0° C. The resulting solution was stirred for 3 h at 0° C. in a water/ice bath. The resulting solution was diluted with DCM (100 mL). The resulting mixture was washed with water (3×30 mL). The resulting mixture was dried over anhydrous sodium sulfate and concentrated under vacuum. The resulting residue was purified on a silica gel column with ethyl acetate/petroleum ether (10/90) to yield (5-fluoro-2-methyl-1-benzofuran-7-yl) methyl methanesulfonate as colorless oil.

d) Ethyl 3-(4-((5-fluoro-2-methylbenzofuran-7-yl) methoxy)-2,3-dimethylphenyl)propanoate Into a 50-mL round-bottom flask was placed ethyl 3-(4-hydroxy-2,3-dimethylphenyl)propanoate (2.15 g, 9.67 mmol) (prepared as described in U.S. Pat. Appl. Publ., 20110313003, 22 Dec. 2011), N,N-dimethylformamide (15 mL), potassium carbonate (4.01 g, 29.01 mmol), and (5-fluoro-2-methyl-1-benzofuran-7-yl)methyl methanesulfonate (2.5 g, 9.68 mmol). The resulting solution was stirred overnight at room temperature. The resulting solution was diluted with water (15 mL). The resulting solution was extracted with ethyl acetate (3×20 mL) and the organic layers combined and dried over anhydrous sodium sulfate and concentrated under vacuum. The resulting residue was purified on a silica gel column with ethyl acetate/petroleum ether (5/95) to yield ethyl 3-[4-[(5-fluoro-2-methyl-1-benzofuran-7-yl)methoxy]-2,3-dimethylphenyl]propanoate as a white solid.

e) 3-{4-[(5-Fluoro-2-methyl-1-benzofuran-7-yl) methoxy]-2,3-dimethylphenyl}propanoic acid Into a 150-mL round-bottom flask was placed ethyl 3-[4-[(5-fluoro-2-methyl-1-benzofuran-7-yl)methoxy]-2,3-dimethylphenyl]propanoate (3.5 g, 9.10 mmol), tetrahydrofuran (50 mL), water (50 mL) and LiOH (1.1 g, 45.93 mmol). The resulting solution was stirred overnight at room temperature. The resulting mixture was concentrated under vacuum and the pH of the solution adjusted to 4-5 with 1N HCl. The solids were collected by filtration. The resulting solid was dried in an oven under reduced pressure to yield 3-[4-[(5-fluoro-2-methyl-1-benzofuran-7-yl)methoxy]-2,3-dimethylphenyl]propanoic acid as a white solid.

$^1$H NMR: (300 MHz, CDCl$_3$): δ: 7.06-7.13 (m, 2H), 7.00 (d, J=8.4 Hz, 1H), 6.81 (d, J=8.4 Hz, 1H), 6.38 (s, 1H), 5.32 (s, 2H), 2.97 (t, J=7.5 Hz, 2H), 2.61 (t, J=7.2 Hz, 2H), 2.47 (s, 3H), 2.27 (s, 3H), 2.26 (s, 3H). Mass spectrum (ESI, m/z): Calculated for C$_{21}$H$_{21}$FO$_4$, 355.1 (M−H). found 355.1.

Example 2

3-(4-{[5-Fluoro-2-(3-methylbutyl)-1-benzofuran-7-yl]methoxy}-2,3-dimethylphenyl)propanoic acid

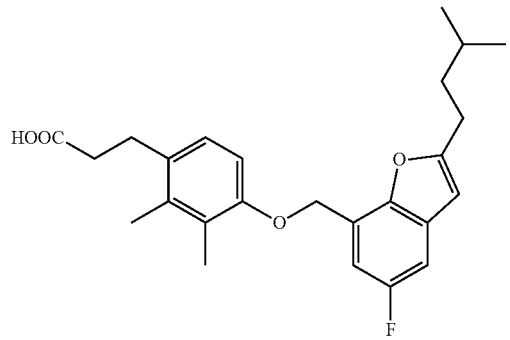 [SMILES: Cc1c(CCC(=O)O)ccc(OCc2cc(F)cc3cc(CCC(C)C)oc23)c1C]

a) Methyl 5-fluoro-2-isopentylbenzofuran-7-carboxylate

Into a 50-mL sealed tube, was placed methyl 3-bromo-5-fluoro-2-hydroxybenzoate (1 g, 4.02 mmol, prepared as in Example 5 step (b)), Pd(PPh$_3$)$_2$Cl$_2$ (282 mg, 0.40 mmol), CuI (76 mg, 0.40 mmol), N,N-dimethylformamide (8 mL), TEA (814 mg, 8.04 mmol) and 5-methylhex-1-yne (758 mg, 7.88 mmol). The resulting solution was stirred overnight at 75° C. The resulting solution was diluted with ethyl acetate (30 mL). The resulting mixture was washed with saturated brine (3×30 mL). The resulting mixture was concentrated under vacuum. The resulting residue was purified on a silica gel column with ethyl acetate/petroleum ether (1/30) to yield methyl 5-fluoro-2-(3-methylbutyl)-1-benzofuran-7-carboxylate as yellow oil.

b) (5-Fluoro-2-isopentylbenzofuran-7-yl)methanol

To a solution of methyl 5-fluoro-2-(3-methylbutyl)-1-benzofuran-7-carboxylate (300 mg, 1.14 mmol) in tetrahydrofuran (10 mL) was added LAH (129 mg, 3.40 mmol) in several batches at 0° C. The resulting solution was stirred for 1 h at 15° C. The reaction was then quenched by the addition of sodium sulfate 10H$_2$O (2 g). The solids were filtered out. The resulting mixture was concentrated under vacuum. The resulting residue was purified on a silica gel column with ethyl acetate/petroleum ether (1:30-1:10) to yield 200 mg (67%) of [5-fluoro-2-(3-methylbutyl)-1-benzofuran-7-yl]methanol as yellow oil.

c) Ethyl 3-(4-((5-fluoro-2-isopentylbenzofuran-7-yl)methoxy)-2,3-dimethylphenyl)propanoate Into a 50-mL 3-necked round-bottom flask purged and maintained with an inert atmosphere of nitrogen was placed [5-fluoro-2-(3-methylbutyl)-1-benzofuran-7-yl]methanol (50 mg, 0.19 mmol, 90%), ethyl 3-(4-hydroxy-2,3-dimethylphenyl)propanoate (70 mg, 0.31 mmol) (prepared as described in U.S. Pat. Appl. Publ., 20110313003, 22 Dec. 2011), PPh$_3$ (83 mg, 0.32 mmol), tetrahydrofuran (3 mL) and DEAD (55 mg, 0.32 mmol). The resulting solution was stirred for 3 h at 30° C. The resulting mixture was concentrated under vacuum. The resulting residue was purified on a silica gel column with PE/EtOAc (40/1) to yield ethyl 3-(4-[[5-fluoro-2-(3-methylbutyl)-1-benzofuran-7-yl]methoxy]-2,3-dimethylphenyl)propanoate as yellow oil.

d) 3-(4-{[5-Fluoro-2-(3-methylbutyl)-1-benzofuran-7-yl]methoxy}-2,3-dimethylphenyl)propanoic acid To a solution of ethyl 3-(4-[[5-fluoro-2-(3-methylbutyl)-1-benzofuran-7-yl]methoxy]-2,3-dimethylphenyl)propanoate (60 mg, 0.14 mmol) in tetrahydrofuran (3 mL) was added a solution of LiOH (60 mg, 2.51 mmol) in water (3 mL). The resulting solution was stirred overnight at 30° C. The resulting mixture was concentrated under vacuum. The pH value of the solution was adjusted to pH 5 with hydrogen chloride (2 N). The resulting solution was extracted with ethyl acetate (2×5 mL) of ethyl acetate and the organic layers combined and concentrated. The resulting residue was purified by RP-C18-HPLC to yield 3-(4-[[5-fluoro-2-(3-methylbutyl)-1-benzofuran-7-yl]methoxy]-2,3-dimethylphenyl)propanoic acid as a white solid.

$^1$H NMR: (300 MHz, CDCl$_3$) δ: 7.05-7.11 (m, 2H), 6.98 (d, J=8.4 Hz, 1H), 6.8 (d, J=8.4 Hz, 1H), 6.37 (s, 1H), 5.30 (s, 2H), 2.95 (t, J=8.4 Hz, 2H), 2.77 (d, J=7.5 Hz, 1H), 2.60 (t, J=8.4 Hz, 2H), 2.25 (s, 7H), 1.60-1.68 (m, 3H), 0.96 (d, J=6.0 Hz, 6H). Mass spectrum (ESI, m/z): Calculated for C$_{25}$H$_{29}$FO$_4$, 413 (M+H). found 413.

Example 3

3-(4-{[5-Fluoro-2-(2-methoxyethyl)-1-benzofuran-7-yl]methoxy}-2,3-dimethylphenyl)propanoic acid

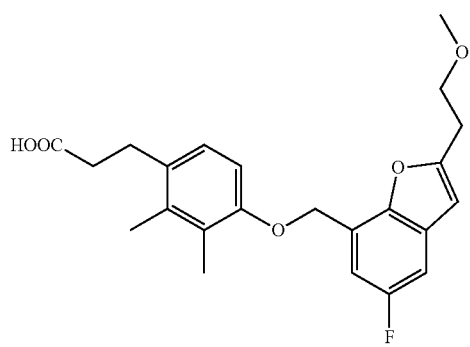 [SMILES: COCCc1cc2cc(F)cc(COc3ccc(CCC(=O)O)c(C)c3C)c2o1]

a) Methyl 5-fluoro-2-(2-hydroxyethyl)benzofuran-7-carboxylate

Into a 30-mL sealed tube purged and maintained with an inert atmosphere of nitrogen was placed methyl 3-bromo-5-fluoro-2-hydroxybenzoate (1.24 g, 4.98 mmol, prepared as described in Example 5, step (b)), but-3-yn-1-ol (700 mg, 9.99 mmol), Pd(PPh$_3$)$_2$Cl$_2$ (350 mg, 0.50 mmol), CuI (95 mg, 0.50 mmol), triethylamine (1.01 g, 9.98 mmol) and N,N-dimethylformamide (5 mL). The resulting solution was stirred for 21 h at 75° C. The reaction was then quenched by the addition of water. The resulting solution was extracted with ethyl acetate (3×10 mL) and the organic layers combined and concentrated under vacuum. The resulting residue was purified on a silica gel column with ethyl acetate/petroleum ether (21/79). The collected fractions were combined and concentrated under vacuum to yield methyl 5-fluoro-2-(2-hydroxyethyl)-1-benzofuran-7-carboxylate as a yellow solid. Mass spectrum (ESI, m/z): Calculated for C$_{12}$H$_{11}$FO$_4$, 239 (M+H). found 239.

b) Methyl 5-fluoro-2-(2-methoxyethyl)benzofuran-7-carboxylate

Into a 50-mL 3-necked round-bottom flask was placed methyl 5-fluoro-2-(2-hydroxyethyl)-1-benzofuran-7-carboxylate (500 mg, 2.10 mmol), N,N-dimethylformamide (10 mL), sodium hydride (150 mg, 3.75 mmol, 60%) and iodomethane (540 mg, 3.80 mmol). The resulting solution was stirred overnight at 30° C. The reaction was then quenched by the addition of water. The resulting solution was extracted with ethyl acetate (3×5 mL) and the organic layers combined. The resulting mixture was washed with sodium chloride (aq). The resulting residue was dried over anhydrous sodium sulfate. The resulting residue was purified on a silica gel column with ethyl acetate/petroleum ether (10/90). The resulting solution was decolorized by the addition of active carbon to yield methyl 5-fluoro-2-(2-methoxyethyl)-1-benzofuran-7-carboxylate as colorless oil. Mass spectrum (ESI, m/z): Calculated for C$_{13}$H$_{13}$FO$_4$, 253 (M+H). found 253.

c) 3-(4-{[5-Fluoro-2-(2-methoxyethyl)-1-benzofuran-7-yl]methoxy}-2,3-dimethylphenyl)propanoic acid The title compound was prepared by reacting methyl 5-fluoro-2-(2-methoxyethyl)benzofuran-7-carboxylate and ethyl 3-(4-hydroxy-2,3-dimethylphenyl)propanoate, according to the procedures as described in Example 2.

$^1$H NMR (300 MHz, CDCl$_3$) δ 7.14-7.07 (m, 2H), 6.98 (d, J=8.1 Hz, 1H), 6.80 (d, J=8.4 Hz, 1H), 6.48 (s, 1H), 5.30 (s, 2H), 3.75 (t, J=6.6 Hz, 2H), 3.39 (s, 3H), 3.05 (t, J=6.6 Hz, 2H), 2.95 (t, J=6.6 Hz, 2H), 2.61 (t, J=8.1 Hz, 2H), 2.25 (s, 6H). Mass spectrum (ESI, m/z): Calculated for C$_{23}$H$_{25}$FO$_5$, 423.2 (M+Na). found 423.2.

Example 4

3-{4-[(5-Fluoro-2-propyl-1-benzofuran-7-yl)methoxy]-2,3-dimethylphenyl}propanoic acid

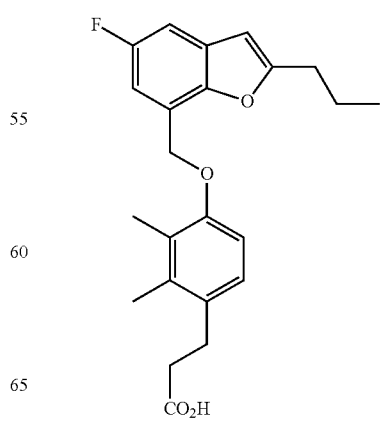

The title compound was prepared according to the procedures as described in Example 2 substituting pent-1-yne for 5-methylhex-1-yne in Step (a).

$^1$H NMR (300 MHz, CDCl$_3$) δ: 7.06-7.12 (m, 2H), 6.98 (d, J=8.4 Hz, 1H), 6.80 (d, J=8.4 Hz, 1H), 6.38 (s, 1H), 5.30 (s, 2H), 2.95 (t, J=8.0 Hz, 2H), 2.74 (t, J=8.0 Hz, 2H), 2.57-2.63 (m, 2H), 2.25 (s, 6H), 1.17-1.84 (m, 2H), 1.10 (t, J=7.4 Hz, 3H). Mass spectrum (ESI, m/z): Calculated for C$_{23}$H$_{25}$FO$_4$, 407.2 (M+Na). found 407.1.

Example 5

3-(4-{[5-Fluoro-2-(hydroxymethyl)-1-benzofuran-7-yl]methoxy}-2,3-dimethylphenyl)propanoic acid

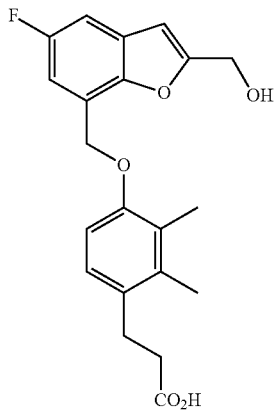 [SMILES: Cc1c(CCC(=O)O)ccc(OCc2cc(F)cc3cc(CO)oc23)c1C]

a) Methyl 5-fluoro-2-hydroxybenzoate

Into a 1-L round-bottom flask was placed 5-fluoro-2-hydroxybenzoic acid (20 g, 128.11 mmol), methanol (250 mL) and sulfuric acid (20 mL). The resulting solution was stirred overnight at 80° C. The resulting mixture was concentrated under vacuum. The resulting solution was diluted with ethyl acetate (300 mL). The resulting mixture was washed with sodium bicarbonate (3×100 mL). The resulting residue was dried over anhydrous sodium sulfate. The resulting residue was purified on a silica gel column with ethyl acetate/petroleum ether (95:5) to yield methyl 5-fluoro-2-hydroxybenzoate as a white solid. Mass spectrum (ESI, m/z): Calculated for C$_8$H$_7$FO$_3$, 172 (M+H). found 172.

b) Methyl 3-bromo-5-fluoro-2-hydroxybenzoate

To a solution of methyl 5-fluoro-2-hydroxybenzoate (14 g, 82.29 mmol) in methanol (400 mL) was added a solution of Br$_2$ (14.5 g, 90.73 mmol, 1.13 equiv) in methanol (200 mL). The resulting solution was stirred overnight at 15° C. The resulting solution was concentrated and purified by silica gel column chromatography with PE/EtOAc (95:5) to yield methyl 3-bromo-5-fluoro-2-hydroxybenzoate as a light yellow solid. Mass spectrum (ESI, m/z): Calculated for C$_8$H$_6$BrFO$_3$, 249 (M+H). found 249.

c) Methyl 5-fluoro-2-(((trimethylsilyl)oxy)methyl)benzofuran-7-carboxylate

A mixture of methyl 3-bromo-5-fluoro-2-hydroxybenzoate (1.86 g, 7.47 mmol), trimethyl(prop-2-yn-1-yloxy)silane (1.92 g, 14.97 mmol), Pd(PPh$_3$)$_2$Cl$_2$ (52.5 mg, 0.07 mmol), TEA (1.515 g, 14.97 mmol), CuI (142.5 mg, 0.75 mmol) and) in N,N-dimethylformamide (7.5 mL) was stirred for 1 h at 25° C. and then for 21 hr at 75° C. The resulting mixture was diluted with water (7.5 mL). The resulting solution was extracted with ethyl acetate (3×15 mL) and the organic layers combined and dried over anhydrous sodium sulfate. The resulting residue was purified on a silica gel column with ethyl acetate/petroleum ether (20:1~3:1) to yield methyl 5-fluoro-2-[[(trimethylsilyl)oxy]methyl]-1-benzofuran-7-carboxylate as light yellow oil. Mass spectrum (ESI, m/z): Calculated for C$_{14}$H$_{14}$FO$_4$Si, 297 (M+H). found 297.

d) Methyl 5-fluoro-2-(hydroxymethyl)benzofuran-7-carboxylate

To a solution of methyl 5-methyl-2-[[(trimethylsilyl)oxy]methyl]-1-benzofuran-7-carboxylate (2.96 g, 5.06 mmol, 50%) in tetrahydrofuran (60 mL) was added TBAF (5.24 g, 20.04 mmol). The resulting solution was stirred for 30 min at 25° C. The resulting mixture was concentrated under vacuum. The resulting mixture was washed with water (1×100 mL). The resulting solution was extracted with ethyl acetate (3×100 mL) and the organic layers combined. The resulting mixture was washed with brine (2×50 mL). The resulting residue was dried over anhydrous sodium sulfate and concentrated. The resulting residue was purified on a silica gel column with ethyl acetate/petroleum ether (20:1~2:1) to yield methyl 2-(hydroxymethyl)-5-methyl-1-benzofuran-7-carboxylate as light yellow oil. Mass spectrum (ESI, m/z): Calculated for C$_{11}$H$_9$FO$_4$, 225 (M+H). found 225.

e) Methyl 2-(((tert-butyldimethylsilyl)oxy)methyl)-5-fluorobenzofuran-7-carboxylate A mixture of 5-fluoro-2-(hydroxymethyl)-1-benzofuran-7-carboxylate (800 mg, 3.57 mmol), TBDMSCI (566.2 mg, 3.75 mmol), dichloromethane (20 mL) and imidazole (243 mg, 3.57 mmol) was stirred overnight at 20° C. The resulting mixture was washed with water (1×5 mL). The resulting solution was extracted with DCM (3×30 mL) and the organic layers combined and dried over anhydrous sodium sulfate. The resulting residue was purified on a silica gel column with ethyl acetate/petroleum ether (200:1~10:1) to yield methyl 2-[[(tert-butyldimethylsilyl)oxy]methyl]-5-fluoro-1-benzofuran-7-carboxylate as light yellow oil. Mass spectrum (ESI, m/z): Calculated for C$_{17}$H$_{23}$FO$_4$Si, 339 (M+H). found 339.

f) (2-(((Tert-butyldimethylsilyl)oxy)methyl)-5-fluorobenzofuran-7-yl)methanol

To a solution of methyl 2-[[(tert-butyldimethylsilyl)oxy]methyl]-5-fluoro-1-benzofuran-7-carboxylate (700 mg, 2.07 mmol) in tetrahydrofuran (40 mL) was added LiAlH$_4$ (236.1 mg, 6.22 mmol). The resulting solution was stirred for 5 min at 20° C. The reaction was then quenched by the addition of Na$_2$SO$_4$.10H$_2$O (500 mg). The solids were filtered out. The filtrate was purified on a silica gel column with ethyl acetate/petroleum ether (200:1~5:1) to yield (2-[[(tert-butyldimethylsilyl)oxy]methyl]-5-fluoro-1-benzofuran-7-yl)

methanol as light yellow oil. Mass spectrum (ESI, m/z): Calculated for $C_{16}H_{23}FO_3Si$, 311 (M+H). found 311.

g) Ethyl 3-(4-((2-(((tert-butyldimethylsilyl)oxy)methyl)-5-fluorobenzofuran-7-yl)methoxy)-2,3-dimethylphenyl)propanoate To a solution of (2-[[(tert-butyldimethylsilyl)oxy]methyl]-5-fluoro-1-benzofuran-7-yl)methanol (124 mg, 0.40 mmol) in tetrahydrofuran (2 mL) was added ethyl 3-(4-hydroxy-2,3-dimethylphenyl)propanoate (107 mg, 0.48 mmol), DEAD (84 mg, 0.48 mmol), and $PPh_3$ (126 mg, 0.48 mmol). The resulting solution was stirred overnight at 30° C. The resulting mixture was concentrated under vacuum. The resulting residue was purified on a silica gel column with ethyl acetate/petroleum ether (200:1~50:1) to yield ethyl 3-[4-[(2-[[(tert-butyldimethylsilyl)oxy]methyl]-5-fluoro-1-benzofuran-7-yl)methoxy]-2,3-dimethylphenyl]propanoate as colorless oil. Mass spectrum (ESI, m/z): Calculated for $C_{29}H_{39}FO_5Si$, 515 (M+H). found 515.

h) Ethyl 3-(4-((5-fluoro-2-(hydroxymethyl)benzofuran-7-yl)methoxy)-2,3-dimethylphenyl)propanoate To a solution of ethyl 3-[4-[(2-[[(tert-butyldimethylsilyl)oxy]methyl]-5-fluoro-1-benzofuran-7-yl)methoxy]-2,3-dimethylphenyl]propanoate (100 mg, 0.19 mmol) in tetrahydrofuran (5 mL) was added TBAF (105 mg, 0.40 mmol). The resulting solution was stirred for 1 h at 20° C. The resulting mixture was washed with water (1×5 mL). The resulting residue was dried over anhydrous sodium sulfate. The resulting residue was purified on a silica gel column with ethyl acetate/petroleum ether (20:1~4:1) to yield ethyl 3-(4-[[5-fluoro-2-(hydroxymethyl)-1-benzofuran-7-yl]methoxy]-2,3-dimethylphenyl)propanoate as a white solid. Mass spectrum (ESI, m/z): Calculated for $C_{23}H_{25}FO_5$, 401 (M+H). found 401.

i) 3-(4-((5-Fluoro-2-(hydroxymethyl)benzofuran-7-yl)methoxy)-2,3-dimethylphenyl)propanoic acid To a solution of ethyl 3-(4-[[5-fluoro-2-(hydroxymethyl)-1-benzofuran-7-yl]methoxy]-2,3-dimethylphenyl)propanoate (90 mg, 0.22 mmol) in tetrahydrofuran (5 mL) was added a solution of LiOH (90 mg, 3.76 mmol) in water (5 mL). The resulting solution was stirred for 14 h at 20° C. The resulting mixture was concentrated under vacuum. The pH of the solution was adjusted to pH 6 with hydrogen chloride (2 mol/L). The solids were collected by filtration to yield 3-(4-[[5-fluoro-2-(hydroxymethyl)-1-benzofuran-7-yl]methoxy]-2,3-dimethylphenyl)propanoic acid as a white solid.

$^1$H NMR (300 MHz, DMSO-d6) δ: 7.38-7.41 (dd, J1=2.7 Hz, J2=2.4 Hz, 1H), 7.18-7.12 (dd, J1=2.4 Hz, J2=2.7 Hz, 1H), 6.96 (d, J=8.4 Hz, 1H), 6.87 (d, J=8.4 Hz, 1H), 6.81 (s, 1H), 5.30 (s, 1H), 4.58 (s, 1H), 2.73-2.80 (m, 2H), 2.40 (t, J=7.4 Hz, 2H), 2.16 (s, 3H), 2.13 (s, 3H). Mass spectrum (ESI, m/z): Calculated for $C_{21}H_{21}FO_5$, 395.1 (M+Na). found 395.1.

Example 6

3-(4-{[5-Fluoro-2-(2-hydroxyethyl)-1-benzofuran-7-yl]methoxy}-2,3-dimethylphenyl)propanoic acid

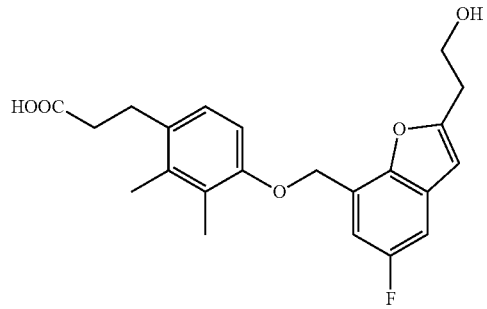 [SMILES: Cc1c(CCC(=O)O)ccc(OCc2cc(F)cc3cc(CCO)oc23)c1C]

The title compound was prepared according to the procedures as described in Example 5 substituting methyl 5-fluoro-2-(2-hydroxyethyl)benzofuran-7-carboxylate (prepared as described in Example 3 step (a)) for methyl 5-fluoro-2-(hydroxymethyl)-1-benzofuran-7-carboxylate in step (e).

$^1$H NMR (300 MHz, CDCl$_3$) δ: 7.18-7.13 (m, 2H), 7.01 (d, J=8.1 Hz, 1H), 6.84 (d, J=8.4 Hz, 1H), 6.55 (s, 1H), 5.340 (s, 2H), 4.04 (t, J=6.0 Hz, 2H), 3.09 (t, J=6.3 Hz, 2H), 2.98 (t, J=8.4 Hz, 2H), 2.64 (t, J=7.5 Hz, 2H), 2.28 (s, 6H). Mass spectrum (ESI, m/z): Calculated for $C_{22}H_{23}FO_5$, 409 (M+Na). found 409.

Example 7

3-{4-[(2-Cyclopentyl-5-fluoro-1-benzofuran-7-yl)methoxy]-2,3-dimethylphenyl}propanoic acid

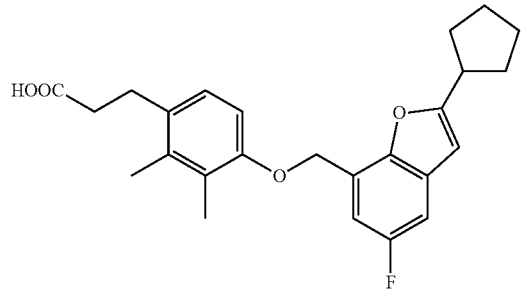 [SMILES: Cc1c(CCC(=O)O)ccc(OCc2cc(F)cc3cc(C4CCCC4)oc23)c1C]

The title compound was prepared according to the procedures as described in Example 2 substituting ethynylcyclopentane for 5-methylhex-1-yne in step (a).

$^1$H NMR (300 MHz, CDCl$_3$) δ: 7.06-7.11 (m, 2H), 6.98 (d, J=8.1 Hz, 1H), 6.81 (d, J=8.4 Hz, 1H), 6.37 (s, 1H), 5.30 (s, 2H), 3.16-3.24 (m, 1H), 2.95 (t, J=8.4 Hz, 2H), 2.60 (t, J=8.4 Hz, 2H), 2.25 (s, 6H), 1.99-2.11 (m, 2H), 1.69-1.80 (m, 9H). Mass spectrum (ESI, m/z): Calculated for $C_{25}H_{27}FO_4$, 433.2 (M+Na). found 433.0.

Example 8

3-(4-{[2-(Cyclopentylmethyl)-5-fluoro-1-benzofuran-7-yl]methoxy}-2,3-dimethylphenyl)propanoic acid

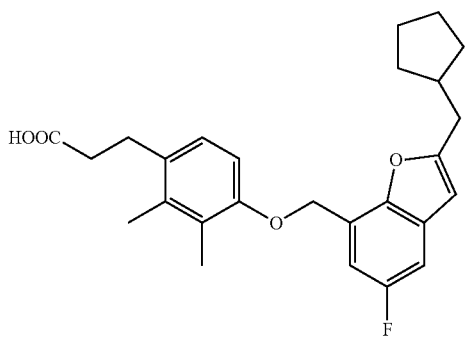 [SMILES: Cc1c(CCC(=O)O)ccc(OCc2cc(F)cc3cc(CC4CCCC4)oc23)c1C]

The title compound was prepared according to the procedures as described in Example 2 substituting prop-2-yn-1-ylcyclopentane for 5-methylhex-1-yne in step (a).

$^1$H NMR (300 MHz, CDCl$_3$) δ: 7.06-7.11 (m, 2H), 6.97 (d, J=8.1 Hz, 1H), 6.80 (d, J=8.4 Hz, 1H), 6.36 (s, 1H), 5.29 (s, 2H), 2.95 (t, J=8.4 Hz, 2H), 2.75 (d, J=7.2 Hz, 1H), 2.60 (t, J=8.4 Hz, 2H), 2.25-2.34 (m, 7H), 1.79-1.86 (m, 2H), 1.54-1.68 (m, 4H), 1.25-1.31 (m, 2H). Mass spectrum (ESI, m/z): Calculated for C$_{26}$H$_{29}$FO$_4$, 447 (M+Na). found 447.

Example 9

3-{4-[(2-Benzyl-5-fluoro-1-benzofuran-7-yl)methoxy]-2,3-dimethylphenyl}propanoic acid

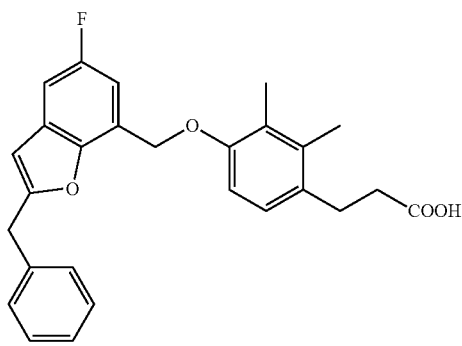 [SMILES: Cc1c(CCC(=O)O)ccc(OCc2cc(F)cc3cc(Cc4ccccc4)oc23)c1C]

The title compound was prepared according to the procedures as described in Example 2 substituting prop-2-yn-1-ylbenzene for 5-methylhex-1-yne in step (a).

$^1$H NMR (300 MHz, CDCl$_3$) δ: 7.25-7.36 (m, 5H), 7.04-7.13 (m, 2H), 6.95 (d, J=8.4 Hz, 1H), 6.77 (d, J=8.4 Hz, 1H), 6.34 (s, 2H), 4.11 (s, 2H), 2.94 (t, J=7.5 Hz, 2H), 2.59 (t, J=7.5 Hz, 2H), 2.23 (d, J=3.3 Hz, 6H). Mass spectrum (ESI, m/z): Calculated for C$_{27}$H$_{25}$FO$_4$, 431 (M−H). found 431.

Example 10

3-(4-{[5-Fluoro-2-(methoxymethyl)-1-benzofuran-7-yl]methoxy}-2,3-dimethylphenyl)propanoic acid

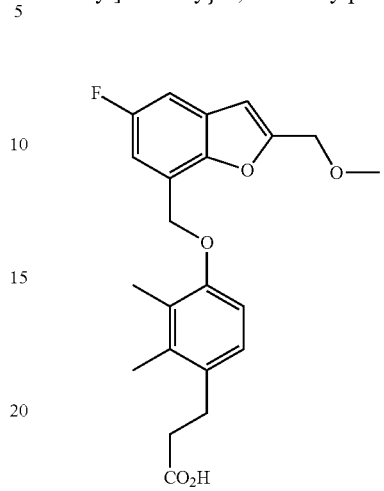

The title compound was prepared according to the procedures as described in Example 2 substituting methoxyethyne for 5-methylhex-1-yne in step (a).

$^1$H NMR (300 MHz, CDCl$_3$) δ: 7.42-7.45 (m, 1H), 7.23-7.27 (m, 1H), 6.86-6.95 (m, 3H), 5.31 (s, 2H), 4.55 (s, 2H), 2.72-2.80 (m, 3H), 2.50 (s, 3H), 2.38-2.43 (m, 1H), 2.16 (s, 3H), 2.12 (s, 3H). Mass spectrum (ESI, m/z): Calculated for C$_{22}$H$_{23}$FO$_5$, 409 (M+Na). found 409.

Example 11

3-(4-{[5-Fluoro-2-(1-methylethyl)-1-benzofuran-7-yl]methoxy}-2,3-dimethylphenyl)propanoic acid

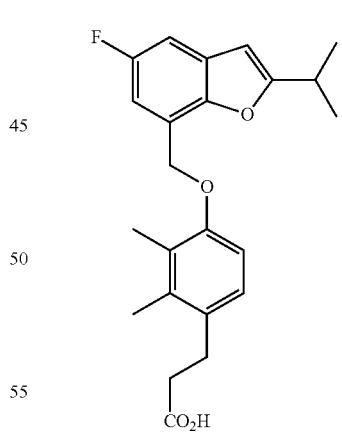

The title compound was prepared according to the procedures as described in Example 2 substituting 3-methylbut-1-yne for 5-methylhex-1-yne in step (a).

$^1$H NMR (300 MHz, CDCl$_3$) δ: 7.07-7.11 (m, 2H), 6.98 (d, J=8.4 Hz, 1H), 6.81 (d, J=8.4 Hz, 1H), 6.35 (s, 1H), 5.30 (s, 2H), 2.97-3.11 (m, 1H), 2.94 (t, J=8.0 Hz, 2H), 2.60 (t, J=8.0 Hz, 2H), 2.25 (s, 3H), 2.24 (s, 3H), 1.35 (s, 3H), 1.33 (s, 3H). Mass spectrum (ESI, m/z): Calculated for C$_{23}$H$_{25}$FO$_4$, 407.2 (M+Na). found 407.1.

Example 12

3-(4-{[5-Fluoro-2-(2-methylpropyl)-1-benzofuran-7-yl]methoxy}-2,3-dimethylphenyl)propanoic acid

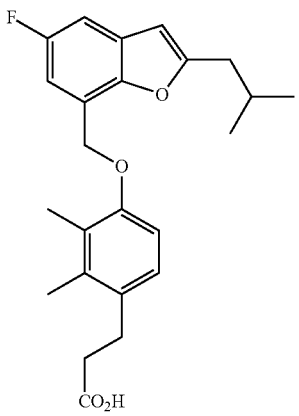 [SMILES: Cc1c(CCC(=O)O)ccc(OCc2cc(F)cc3cc(CC(C)C)oc23)c1C]

The title compound was prepared according to the procedures as described in Example 2 substituting 4-methylpent-1-yne for 5-methylhex-1-yne in step (a).

$^1$H NMR (300 MHz, CDCl$_3$) δ: 7.07-7.11 (m, 2H), 6.97 (d, J=8.4 Hz, 1H), 6.80 (d, J=8.4 Hz, 1H), 6.37 (s, 1H), 5.30 (s, 2H), 2.95 (t, J=8.0 Hz, 2H), 2.57-2.64 (m, 2H), 2.25 (s, 6H), 2.00-2.18 (m, 1H), 0.99 (s, 3H), 0.97 (s, 3H). Mass spectrum (ESI, m/z): Calculated for C$_{24}$H$_{27}$FO$_4$, 399 (M+Na). found 399.

Example 13

3-[4-({2-[2-(Acetylamino)ethyl]-5-fluoro-1-benzofuran-7-yl}methoxy)-2,3-dimethylphenyl]propanoic acid

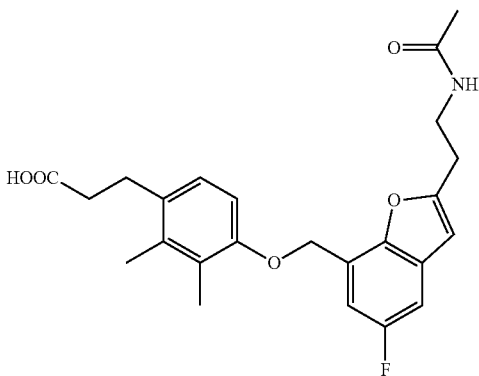 [SMILES: CC(=O)NCCc1cc2cc(F)cc(COc3ccc(CCC(=O)O)c(C)c3C)c2o1]

a) Ethyl 3-(4-((5-fluoro-2-(2-((methylsulfonyl)oxy)ethyl)benzofuran-7-yl)methoxy)-2,3-dimethylphenyl)propanoate Into a 100-mL 3-necked round-bottom flask purged and maintained with an inert atmosphere of nitrogen was placed ethyl 3-(4-[[5-fluoro-2-(2-hydroxyethyl)-1-benzofuran-7-yl]methoxy]-2,3-dimethylphenyl)propanoate (1.3 g, 3.14 mmol, prepared as described in Example 6), dichloromethane (20 mL), triethylamine (950 mg, 9.39 mmol) and MsCl (715 mg). The resulting solution was stirred overnight at 20° C. The reaction was then quenched by the addition of water. The resulting solution was extracted with ethyl acetate (3×10 mL) and the organic layers combined. The resulting residue was purified on a silica gel column with ethyl acetate/petroleum ether (1/20). The collected fractions were combined and concentrated under vacuum to yield 1 ethyl 3-[4-([5-fluoro-2-[2-(methanesulfonyloxy)ethyl]-1-benzofuran-7-yl]methoxy)-2,3-dimethylphenyl]propanoate as colorless oil. Mass spectrum (ESI, m/z): Calculated for C$_{25}$H$_{29}$FO$_7$S, 493 (M+H). found 493.

b) Ethyl 3-(4-((2-(2-azidoethyl)-5-fluorobenzofuran-7-yl)methoxy)-2,3-dimethylphenyl)propanoate Into a 100-mL round-bottom flask was placed ethyl 3-[4-([5-fluoro-2-[2-(methanesulfonyloxy)ethyl]-1-benzofuran-7-yl]methoxy)-2,3-dimethylphenyl]propanoate (1 g, 2.03 mmol), N,N-dimethylformamide (15 mL) and NaN$_3$ (132 mg, 2.03 mmol). The resulting solution was stirred overnight at 60° C. The reaction was then quenched by the addition of water. The resulting solution was extracted with ethyl acetate (3×10 mL) and the organic layers combined and concentrated under vacuum. The resulting residue was purified on a silica gel column with ethyl acetate/petroleum ether (1/2). The collected fractions were combined and concentrated under vacuum to yield ethyl 3-(4-[[2-(2-azidoethyl)-5-fluoro-1-benzofuran-7-yl]methoxy]-2,3-dimethylphenyl)propanoate as colorless oil. Mass spectrum (ESI, m/z): Calculated for C$_{24}$H$_{26}$FN3O$_4$, 440 (M+H). found 440.

c) Ethyl 3-(4-((2-(2-aminoethyl)-5-fluorobenzofuran-7-yl)methoxy)-2,3-dimethylphenyl)propanoate To a solution of ethyl 3-(4-[[2-(2-azidoethyl)-5-fluoro-1-benzofuran-7-yl]methoxy]-2,3-dimethylphenyl) propanoate (700 mg, 1.59 mmol) in MeOH (15 mL) was added Palladium on carbon (700 mg) and hydrogen and the resulting solution was stirred overnight at 20° C. The solids were filtered out. The resulting mixture was concentrated under vacuum to yield ethyl 3-(4-[[2-(2-aminoethyl)-5-fluoro-1-benzofuran-7-yl]methoxy]-2,3-dimethylphenyl)propanoate as colorless oil.

d) Ethyl 3-(4-((2-(2-acetamidoethyl)-5-fluorobenzofuran-7-yl)methoxy)-2,3-dimethylphenyl)propanoate Into a 8-mL vial was placed ethyl 3-(4-[[2-(2-aminoethyl)-5-fluoro-1-benzofuran-7-yl]methoxy]-2,3-dimethylphenyl)propanoate (50 mg, 0.12 mmol), dichloromethane (2 mL), triethylamine (36 mg, 0.36 mmol), and acetyl chloride (11 mg, 0.14 mmol). The resulting solution was stirred overnight at 20° C. The resulting mixture was concentrated under vacuum to yield ethyl 3-(4-[[2-(2-acetamidoethyl)-5-fluoro-1-benzofuran-7-yl]methoxy]-2,3-dimethylphenyl) propanoate as yellow oil. Mass spectrum (ESI, m/z): Calculated for C$_{26}$H$_{30}$FNO$_5$, 456 (M+H). found 456.

e) 3-[4-({2-[2-(Acetylamino)ethyl]-5-fluoro-1-benzofuran-7-yl}methoxy)-2,3-dimethylphenyl]propanoic acid To a solution of ethyl 3-(4-[[2-(2-acetamidoethyl)-5-fluoro-1-benzofuran-7-yl]methoxy]-2,3-dimethylphenyl) propanoate (40 mg, 0.09 mmol) in 1 mL of THF was added a solution of LiOH (40 mg, 1.67 mmol) in water (1 mL). The resulting solution was stirred overnight at 20° C. The resulting mixture was concentrated under vacuum. The resulting solution was extracted with ethyl acetate (2×1 mL) and the aqueous layers combined. The pH value of the solution was adjusted to pH 2 with hydrogen chloride (1 mol/L). The resulting solution was extracted with ethyl acetate (3×2 mL) and the organic layers combined and concentrated under vacuum. The resulting residue was purified by RP-C18-HPLC to yield 1.9 mg (5%) of 3-(4-[[2-(2-acetamidoethyl)-5-fluoro-1-benzofuran-7-yl]methoxy]-2,3-dimethylphenyl)propanoic acid as a white solid.

$^1$H NMR (300 MHz, DMSO) δ 12.06 (s, 1H), 8.03 (s, 1H), 7.36 (d, J=9.9 Hz, 1H), 7.19 (d, J=9.9 Hz, 1H), 6.98 (d, J=8.4 Hz, 1H), 6.90 (d, J=8.4 Hz, 1H), 6.72 (s, 1H), 5.32 (s, 1H), 3.43-3.37 (m, 2H), 2.94 (t, J=6.9 Hz, 2H), 2.80 (t, J=7.5 Hz, 2H), 2.45-2.18 (m, 2H), 2.18 (s, 6H), 1.81 (s, 3H). Mass spectrum (ESI, m/z): Calculated for $C_{24}H_{26}FNO_5$, 428 (M+H). found 428.

Example 14

3-{4-[(5-Fluoro-2-{2-[(methylsulfonyl)amino]ethyl}-1-benzofuran-7-yl)methoxy]-2,3-dimethylphenyl}propanoic acid

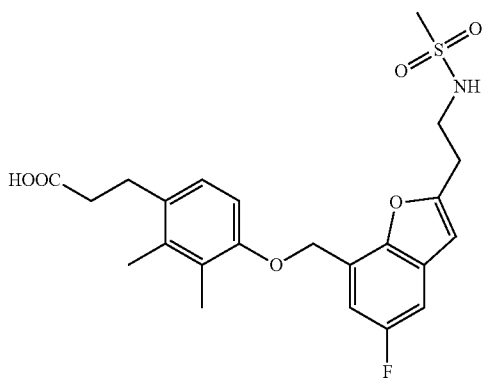 [SMILES: Cc1c(CCC(=O)O)ccc(OCc2cc(F)cc3cc(CCNS(C)(=O)=O)oc23)c1C]

a) Ethyl 3-(4-((5-fluoro-2-(2-(methylsulfonamido)ethyl)benzofuran-7-yl)methoxy)-2,3-dimethylphenyl)propanoate Into a 8-mL vial was placed ethyl 3-(4-[[2-(2-aminoethyl)-5-fluoro-1-benzofuran-7-yl]methoxy]-2,3-dimethylphenyl)propanoate (50 mg, 0.12 mmol, prepared as described in Example 13 step(c)), dichloromethane (2 mL), triethylamine (36 mg, 0.36 mmol) and methanesulfonyl chloride (16 mg, 0.14 mmol). The resulting solution was stirred overnight at 20° C. The resulting mixture was concentrated under vacuum to yield ethyl 3-(4-[[5-fluoro-2-(2-methanesulfonamidoethyl)-1-benzofuran-7-yl]methoxy]-2,3-dimethylphenyl)propanoate as yellow oil. Mass spectrum (ESI, m/z): Calculated for $C_{25}H_{30}FNO_6S$, 492 (M+H). found 492.

b) 3-{4-[(5-Fluoro-2-{2-[(methylsulfonyl)amino]ethyl}-1-benzofuran-7-yl)methoxy]-2,3-dimethylphenyl}propanoic acid The title compound was prepared according to the procedures as described in Example 1.

$^1$H NMR (300 MHz, DMSO) δ: 7.41-7.37 (m, 1H), 7.25-7.18 (m, 1H), 6.98 (d, J=8.4 Hz, 1H), 6.90 (d, J=8.4 Hz, 1H), 6.77 (s, 1H), 5.32 (s, 2H), 3.02 (t, J=7.2 Hz, 2H), 2.91 (s, 3H), 2.80 (t, J=7.2 Hz, 2H), 2.45-2.40 (m, 4H), 2.18-2.09 (m, 6H). Mass spectrum (ESI, m/z): Calculated for $C_{23}H_{26}FNO_6S$, 464 (M+H). found 464.

Example 15

3-[4-({2-[2-(Dimethylamino)ethyl]-5-fluoro-1-benzofuran-7-yl}methoxy)-2,3-dimethylphenyl]propanoic acid

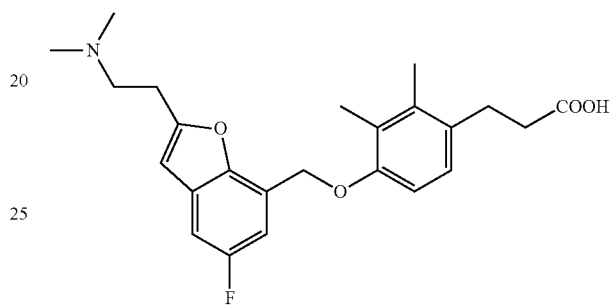

a) Ethyl 3-(4-((2-(2-(dimethylamino)ethyl)-5-fluorobenzofuran-7-yl)methoxy)-2,3-dimethylphenyl)propanoate Into a 8-mL vial was placed ethyl 3-[4-([5-fluoro-2-[2-(methanesulfonyloxy)ethyl]-1-benzofuran-7-yl]methoxy)-2,3-dimethylphenyl]propanoate (100 mg, 0.20 mmol, prepared as described in Example 13), dimethylamine (49 mg, 1.09 mmol), potassium carbonate (84 mg, 0.61 mmol) and N,N-dimethylformamide (2 mL). The resulting solution was stirred overnight at 40° C. The reaction was then quenched by the addition of water. The resulting solution was extracted with ethyl acetate (3×1 mL) and the organic layers combined. The resulting residue was purified on a silica gel column with ethyl acetate/petroleum ether (1/10). The collected fractions were combined and concentrated under vacuum to yield ethyl 3-[4-([2-[2-(dimethylamino)ethyl]-5-fluoro-1-benzofuran-7-yl]methoxy)-2,3-dimethylphenyl]propanoate as colorless oil. Mass spectrum (ESI, m/z): Calculated for $C_{26}H_{32}FNO_4$, 442 (M+H). found 442.

b) 3-[4-({2-[2-(Dimethylamino)ethyl]-5-fluoro-1-benzofuran-7-yl}methoxy)-2,3-dimethylphenyl]propanoic acid The title compound was prepared according to the procedures as described in Example 1.

$^1$H NMR (300 MHz, CDCl$_3$, ppm) δ: 9.62 (s, 1H), 7.45-742 (m, 1H), 7.267-7.22 (m, 1H), 6.91 (d, J=8.4 Hz, 2H), 6.91-6.86 (m, 2H), 5.32 (s, 2H), 3.53-3.48 (m, 2H), 3.31-3.26 (m, 2H), 2.88 (s, 6H), 2.81 (t, J=8.1 Hz, 3H), 2.43 (t, J=7.2 Hz, 3H), 2.18-2.16 (m, 6H). Mass spectrum (ESI, m/z): Calculated for $C_{24}H_{28}FNO_4$, 414 (M+H). found 464.

Example 16

3-{4-[(2-tert-Butyl-5-fluoro-1-benzofuran-7-yl)methoxy]-2,3-dimethylphenyl}propanoic acid

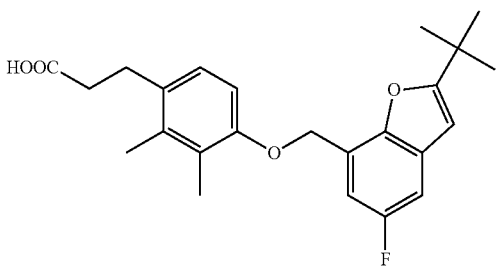 [SMILES: Cc1c(CCC(=O)O)ccc(OCc2cc(F)cc3cc(C(C)(C)C)oc23)c1C]

The title compound was prepared according to the procedures as described in Example 2 substituting 3,3-dimethylbut-1-yne for 5-methylhex-1-yne in step (a).

$^1$H NMR (300 MHz, CDCl3) δ: 7.09-7.15 (m, 2H), 7.00 (d, J=8.4 Hz, 1H), 6.86 (d, J=8.4 Hz, 1H), 6.37 (s, 1H), 5.33 (s, 2H), 2.97 (t, J=7.5 Hz, 1H), 2.62 (t, J=7.5 Hz, 1H), 2.27 (s, 6H), 1.39 (s, 9H). Mass spectrum (ESI, m/z): Calculated for $C_{24}H_{27}FO_4$, 399 (M+H). found 399 and 416 (M+H3O).

Example 17

3-{4-[(5-Ethoxy-2-ethyl-1-benzofuran-7-yl)methoxy]-2,3-dimethylphenyl}propanoic acid

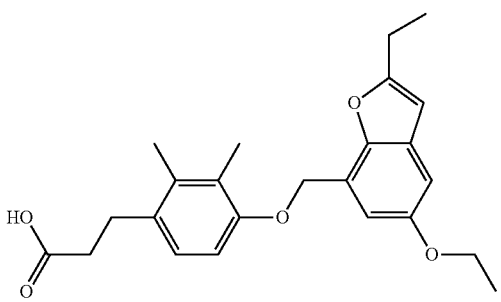 [SMILES: CCOc1cc(COc2ccc(CCC(=O)O)c(C)c2C)c2oc(CC)cc2c1]

a) Methyl 3-bromo-5-ethoxy-2-hydroxybenzoate

Into a 250-mL round-bottom flask was placed methyl 5-ethoxy-2-hydroxybenzoate (5 g, 27.45 mmol), methanol (100 mL) and Br$_2$ (4.83 g, 30.22 mmol). The resulting solution was stirred overnight at room temperature. The resulting mixture was concentrated under vacuum. The resulting solution was diluted with ethyl acetate (100 mL) and washed with Na$_2$SO$_3$ (aq) (3×20 mL). The resulting mixture was concentrated under vacuum. The resulting residue was purified on a silica gel column with ethyl acetate/petroleum ether (1:5) to yield methyl 3-bromo-5-ethoxy-2-hydroxybenzoate as a light yellow solid. Mass spectrum (ESI, m/z): Calculated for $C_{10}H_{11}BrO_4$, 275.0 (M+H). found 275.0.

b) Methyl 5-ethoxy-2-ethylbenzofuran-7-carboxylate

The title compound was prepared by reacting but-1-yne and methyl 3-bromo-5-ethoxy-2-hydroxybenzoate according to the procedure in Example 2 step (a).

c) (5-Ethoxy-2-ethylbenzofuran-7-yl)methyl methanesulfonate

The title compound was prepared by reacting methyl 3-bromo-5-ethoxy-2-hydroxybenzoate by LiAlH$_4$ reduction and mesylation according to the procedure in Example 1 step(b).

d) Ethyl 3-(4-((5-ethoxy-2-ethylbenzofuran-7-yl)methoxy)-2,3-dimethylphenyl)propanoate Into a 50-mL round-bottom flask was placed (5-ethoxy-2-ethyl-1-benzofuran-7-yl)methyl methanesulfonate (121 mg, 0.41 mmol), potassium carbonate (168 mg, 1.22 mmol), N,N-dimethylformamide (10 mL) and ethyl 3-(4-hydroxy-2,3-dimethylphenyl)propanoate (90 mg, 0.40 mmol). The resulting solution was stirred overnight at room temperature. The resulting solution was diluted with ethyl acetate (100 mL). The resulting mixture was washed with brine (3×20 mL). The resulting residue was dried over anhydrous sodium sulfate. The resulting mixture was concentrated under vacuum to yield ethyl 3-[4-[(5-ethoxy-2-ethyl-1-benzofuran-7-yl)methoxy]-2,3-dimethylphenyl]propanoate as colorless oil. Mass spectrum (ESI, m/z): Calculated for $C_{26}H_{32}O_5$, 425 (M+H). found 425.

e) 3-{4-[(5-Ethoxy-2-ethyl-1-benzofuran-7-yl)methoxy]-2,3-dimethylphenyl}propanoic acid The title compound was prepared according to the procedure as described in Example 1.

$^1$H NMR (300 MHz, CD$_3$Cl) δ: 6.98 (s, 1H), 6.96 (d, J=3.0 Hz, 1H), 6.91 (d, J=2.4 Hz, 1H), 6.83 (s, 1H), 6.81 (s, 1H), 6.32 (s, 1H), 5.28 (s, 2H), 4.03 (q, J=5.4 Hz, 2H), 2.95 (t, J=7.9 Hz, 2H), 2.77 (t, J=8.4 Hz, 2H), 2.59 (t, J=8.1 Hz, 2H), 2.24 (s, 6H), 1.41 (t, J=6.9 Hz, 3H), 1.32 (t, J=7.5 Hz, 3H). Mass spectrum (ESI, m/z): Calculated for $C_{24}H_{28}O_5$, 395 (M−H). found 395.

Example 18

3-(2,3-Dimethyl-4-{[2-propyl-5-(trifluoromethyl)-1-benzofuran-7-yl]methoxy}phenyl)propanoic acid

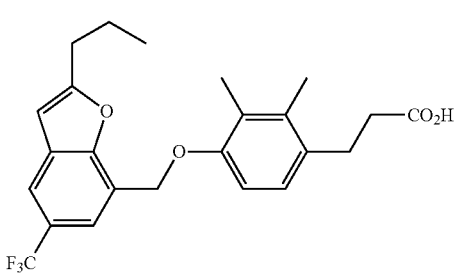 [SMILES: CCCc1cc2cc(C(F)(F)F)cc(COc3ccc(CCC(=O)O)c(C)c3C)c2o1]

a) 5-iodo-2-propylbenzofuran-7-carbaldehyde

The title compound was prepared by reacting 2-hydroxy-3,5-diiodobenzaldehyde and pent-1-yne according to the procedure in Example 2 step (a).

b) (5-Iodo-2-propylbenzofuran-7-yl)methanol

To a solution of 5-iodo-2-propyl-1-benzofuran-7-carbaldehyde (2.7 g, 8.60 mmol) in tetrahydrofuran (40 mL) was added LiBH$_4$ (570 mg, 25.91 mmol). The resulting solution was stirred for 30 min at 0° C. The reaction was then quenched by the addition of water (5 mL). The resulting mixture was concentrated under vacuum. The resulting solution was extracted with ethyl acetate (3×30 mL) and the organic layers combined and dried over sodium sulfate. The solids were filtered out. The resulting mixture was concentrated under vacuum. The resulting residue was purified on a silica gel column with petroleum ether/EtOAc (200:1~5:1) to yield (5-iodo-2-propyl-1-benzofuran-7-yl)methanol as a light yellow solid.

c) Ethyl 3-(4-((5-iodo-2-propylbenzofuran-7-yl)methoxy)-2,3-dimethylphenyl)propanoate The title compound was prepared by reacting 5-iodo-2-propyl-1-benzofuran-7-yl)methanol according to the procedure in Example 1.

d) Ethyl 3-(2,3-dimethyl-4-((2-propyl-5-(trifluoromethyl)benzofuran-7-yl)methoxy)phenyl)propanoate A mixture of ethyl 3-[4-[(5-iodo-2-propyl-1-benzofuran-7-yl)methoxy]-2,3-dimethylphenyl]propanoate (150 mg, 0.29 mmol), methyl 2,2-difluoro-2-(fluorosulfonyl)acetate (443 mg, 2.31 mmol) and CuI (438 mg, 2.30 mmol) in NMP/DMF (7/7 mL) was stirred for 18 h at 100° C. The resulting solution was diluted with water (15 mL). The resulting solution was extracted with ethyl acetate (3×30 mL) and the organic layers combined and dried over sodium sulfate. The solids were filtered out. The resulting mixture was concentrated under vacuum. The resulting residue was purified on a silica gel column with PE/EtOAc (200:1~10:1) to yield ethyl 3-(2,3-dimethyl-4-[[2-propyl-5-(trifluoromethyl)-1-benzofuran-7-yl]methoxy]phenyl)propanoate as light yellow oil.

e) 3-(2,3-Dimethyl-4-{[2-propyl-5-(trifluoromethyl)-1-benzofuran-7-yl]methoxy}phenyl)propanoic acid The title compound was prepared according to the procedures as described in Example 1.

$^1$H NMR (300 MHz, CDCl$_3$) δ7.73 (s, 1H), 7.60 (s, 1H), 6.98-7.01 (d, J=8.4 Hz, 1H), 6.82-6.85 (d, J=8.4 Hz, 1H), 6.48 (s, 1H), 5.33 (s, 2H), 2.93-2.98 (t, J=7.8 Hz, 2H), 2.75-2.80 (t, J=7.5 Hz, 2H), 2.58-2.63 (t, J=7.9 Hz, 2H), 2.24 (s, 6H), 1.72-1.85 (m, 2H), 0.99-1.04 (t, J=7.4 Hz, 3H). Mass spectrum (ESI, m/z): Calculated for C$_{24}$H$_{25}$F$_3$O$_4$, 433 (M−H). found 433.

Example 19

3-{4-[(5-Ethynyl-2-propyl-1-benzofuran-7-yl)methoxy]-2,3-dimethylphenyl}propanoic acid

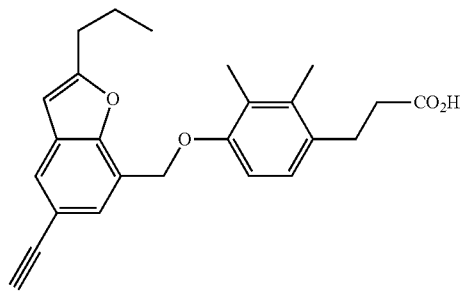 [SMILES: C#Cc1cc(COc2ccc(CCC(=O)O)c(C)c2C)c2oc(CCC)cc2c1]

a) Ethyl 3-(2,3-dimethyl-4-((2-propyl-5-((trimethylsilyl)ethynyl)benzofuran-7-yl)methoxy)phenyl)propanoate A mixture of ethyl 3-[4-[(5-iodo-2-propyl-1-benzofuran-7-yl)methoxy]-2,3-dimethylphenyl]propanoate (150 mg, 0.29 mmol, prepared as described in Example 18), ethynyltrimethylsilane (57 mg, 0.58 mmol), CuI (5.5 mg, 0.03 mmol), TEA (58 mg, 0.57 mmol), Pd(PPh$_3$)$_2$Cl$_2$ (21 mg, 0.10 equiv) in N,N-dimethylformamide (15 mL) was stirred for 18 h at 90° C. The resulting solution was diluted with water (15 mL). The resulting solution was extracted with ethyl acetate (3×30 mL) and the organic layers combined and dried over sodium sulfate. The solids were filtered out. The resulting mixture was concentrated under vacuum. The resulting residue was purified on a silica gel column with PE/EtOAc (200:1~10:1) to yield ethyl 3-[2,3-dimethyl-4-([2-propyl-5-[2-(trimethylsilyl)ethynyl]-1-benzofuran-7-yl]methoxy)phenyl]propanoate as light yellow oil.

b) Ethyl 3-(4-((5-ethynyl-2-propylbenzofuran-7-yl)methoxy)-2,3-dimethylphenyl)propanoate To a solution of ethyl 3-[2,3-dimethyl-4-([2-propyl-5-[2-(trimethylsilyl)ethynyl]-1-benzofuran-7-yl]methoxy)phenyl]propanoate (150 mg, 0.31 mmol) in tetrahydrofuran (10 mL) was added TBAF (0.6 mL, 2.00 equiv). The resulting solution was stirred for 1 h at 30° C. The resulting mixture was concentrated under vacuum. The resulting solution was diluted with water (5 mL). The resulting solution was extracted with ethyl acetate (3×15 mL) and the organic layers were combined and dried over anhydrous sodium sulfate. The solids were filtered out. The resulting mixture was concentrated under vacuum to yield ethyl 3-[4-[(5-ethynyl-2-propyl-1-benzofuran-7-yl)methoxy]-2,3-dimethylphenyl]propanoate as light yellow oil.

c) 3-{4-[(5-Ethynyl-2-propyl-1-benzofuran-7-yl)methoxy]-2,3-dimethylphenyl}propanoic acid The title compound was prepared by reacting ethyl 3-(4-((5-ethynyl-2-propylbenzofuran-7-yl)methoxy)-2,3-dimethylphenyl)propanoate according to the procedures in Example 1.

$^1$H NMR (300 MHz, CDCl$_3$) δ7.59 (s, 1H), 7.50 (s, 1H), 6.97-6.99 (d, J=8.4 Hz, 1H), 6.80-6.83 (d, J=8.4 Hz, 1H), 6.38 (s, 1H), 5.28 (s, 2H), 2.92-3.00 (m, 3H), 2.72-2.77 (t,

J=7.5 Hz, 2H), 2.57-2.63 (t, J=8.1 Hz, 2H), 2.24 (s, 6H), 1.71-1.83 (m, 2H), 0.98-1.03 (t, J=7.4 Hz, 3H). Mass spectrum (ESI, m/z): Calculated for $C_{25}H_{26}O_4$, 389 (M–H). found 389.

Example 20

3-{4-[(5-Chloro-2-ethyl-6-methyl-1-benzofuran-7-yl)methoxy]-2,3-dimethylphenyl}propanoic acid

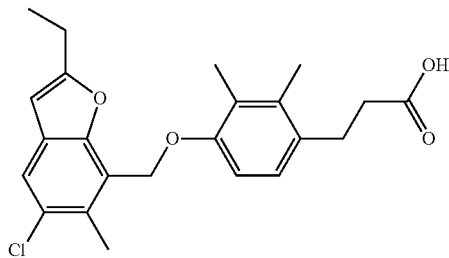 [SMILES: CCc1cc2cc(Cl)c(C)c(COc3ccc(CCC(=O)O)c(C)c3C)c2o1]

a) Methyl 2-hydroxy-6-methoxybenzoate

A mixture of 2-hydroxy-6-methoxybenzoic acid (20 g, 118.94 mmol), methanol (300 mL) and sulfuric acid (5 mL) was heated to reflux overnight. The resulting mixture was concentrated under vacuum. The resulting residue was purified on a silica gel column with ethyl acetate/hexane (1/30) to yield methyl 2-hydroxy-6-methoxybenzoate as colorless oil.

b) Methyl 3-chloro-6-hydroxy-2-methoxybenzoate

Into a 500-mL round-bottom flask was placed methyl 2-hydroxy-6-methoxybenzoate (15 g, 82.34 mmol), $CH_3CN$ (200 mL), NCS (10.9 g, 81.63 mmol) and $CF_3COOH$ (20 mL). The resulting solution was stirred for 3 h at 25° C. The resulting mixture was concentrated under vacuum. The resulting solution was diluted with ethyl acetate (300 mL). (300 mL) The resulting mixture was washed with brine (300 mL), $NaHCO_3$(aq) (300 mL) and brine (300 mL). The resulting residue was purified on a silica gel column with EtOAc/PE (1/30) to yield methyl 3-chloro-6-hydroxy-2-methoxybenzoate as colorless oil.

c) Methyl 3-bromo-5-chloro-2-hydroxy-6-methoxybenzoate

Into a 500-mL round-bottom flask was placed methyl 3-chloro-6-hydroxy-2-methoxybenzoate (10.7 g, 49.40 mmol), $CH_3CN$ (200 mL) and NBS (6.59 g, 3.42 mmol). The resulting solution was stirred for 3 h at 75° C. The resulting mixture was concentrated under vacuum. The resulting residue was purified on a silica gel column with ethyl acetate/petroleum ether (30/1-1/10) to yield methyl 3-bromo-5-chloro-2-hydroxy-6-methoxybenzoate as a yellow solid.

d) Methyl 5-chloro-2-ethyl-6-methoxybenzofuran-7-carboxylate

Into a 150-mL sealed tube was placed methyl 3-bromo-5-chloro-2-hydroxy-6-methoxybenzoate (10 g, 33.84 mmol), $Pd(PPh_3)_2Cl_2$ (5.7 g, 8.12 mmol), CuI (772 mg, 4.05 mmol), N,N-dimethylformamide (80 mL), triethylamine (8.1 g, 80.05 mmol), and but-1-yne (4.3 g, 79.50 mmol). The resulting mixture was stirred overnight at 75° C. The reaction was then quenched by the addition of water (100 mL). The resulting solution was extracted with ethyl acetate (3×100 mL) and the organic layers combined. The resulting mixture was washed with brine (3×200 mL). The resulting mixture was concentrated under vacuum. The resulting residue was purified on a silica gel column with ethyl acetate/petroleum ether (1/50-1/30) to methyl 5-chloro-2-ethyl-6-methoxy-1-benzofuran-7-carboxylate as brown oil.

e) 5-Chloro-2-ethyl-6-hydroxybenzofuran-7-carboxylic acid

To a solution of methyl 5-chloro-2-ethyl-6-methoxy-1-benzofuran-7-carboxylate (7 g, 26.05 mmol) in dichloromethane (200 mL) was added $BBr_3$ (14 mL) at –70° C. The resulting solution was stirred for 1 h at 25° C. The reaction was then quenched by the addition of water (300 mL). The resulting solution was extracted with ethyl acetate (2×200 mL) and the organic layers combined. The resulting mixture was washed with brine (3×300 mL). The resulting residue was dried over sodium sulfate and concentrated under vacuum to yield 5-chloro-2-ethyl-6-hydroxy-1-benzofuran-7-carboxylic acid as brown oil.

f) Methyl 5-chloro-2-ethyl-6-hydroxybenzofuran-7-carboxylate

Into a 250-mL round bottom flask, was placed 5-chloro-2-ethyl-6-hydroxy-1-benzofuran-7-carboxylic acid (4 g, 16.62 mmol), methanol (100 mL) and sulfuric acid (5 mL). The resulting solution was heated to reflux overnight. The resulting mixture was concentrated under vacuum. The resulting residue was purified on a silica gel column with ethyl acetate/petroleum ether (1/30-20/1) to yield methyl 5-chloro-2-ethyl-6-hydroxy-1-benzofuran-7-carboxylate as a yellow solid.

g) Methyl 5-chloro-2-ethyl-6-(((trifluoromethyl)sulfonyl)oxy)benzofuran-7-carboxylate To a mixture of methyl 5-chloro-2-ethyl-6-hydroxy-1-benzofuran-7-carboxylate (1 g, 3.93 mmol), dichloromethane (20 mL) and triethylamine (1.2 g, 11.86 mmol) was added $Tf_2O$ (2.2 g, 7.80 mmol). The resulting solution was stirred for 3 h at 25° C. The reaction was then quenched by the addition of water (20 mL). The resulting solution was extracted with DCM (2×20 mL) and the organic layers combined and concentrated under vacuum. The resulting residue was purified on a silica gel column with ethyl acetate/petroleum ether (1/30) to yield methyl 5-chloro-2-ethyl-6-[(trifluoromethane)sulfonyloxy]-1-benzofuran-7-carboxylate as a yellow solid.

h) Methyl 5-chloro-2-ethyl-6-methylbenzofuran-7-carboxylate

Into a 10-mL sealed tube was placed methyl 5-chloro-2-ethyl-6-[(trifluoromethane)sulfonyloxy]-1-benzofuran-7-carboxylate (300 mg, 0.78 mmol), methylboronic acid (186 mg, 3.11 mmol), tetrahydrofuran (5 mL), $K_3PO_4$ (655 mg, 3.09 mmol), and $Pd(dppf)Cl_2$ (113 mg, 0.15 mmol). The resulting solution was stirred overnight at 75° C. The resulting mixture was concentrated under vacuum. The resulting residue was purified on a silica gel column with ethyl acetate/petroleum ether (1/30-1/10) to yield methyl 5-chloro-2-ethyl-6-methyl-1-benzofuran-7-carboxylate as colorless oil.

i) (5-Chloro-2-ethyl-6-methylbenzofuran-7-yl)methanol

To a solution of methyl 5-chloro-2-ethyl-6-methyl-1-benzofuran-7-carboxylate (200 mg, 0.79 mmol) in tetrahydrofuran (10 mL) was added LAH (36 mg, 0.95 mmol, 1.20 equiv) in several batches at 0-5° C. The resulting solution was stirred for 1 h at 25° C. The reaction was then quenched by the addition of $Na_2SO_4.10H_2O$ (1 g). The solids were filtered out. The resulting mixture was concentrated under vacuum. The resulting residue was purified on a silica gel column with ethyl acetate/petroleum ether (1/30-1/5) to yield (5-chloro-2-ethyl-6-methyl-1-benzofuran-7-yl)methanol as a yellow solid.

j) Ethyl 3-(4-((5-chloro-2-ethyl-6-methylbenzofuran-7-yl)methoxy)-2,3-dimethylphenyl)propanoate Into a 50-mL round-bottom flask purged and maintained with an inert atmosphere of nitrogen was placed (5-chloro-2-ethyl-6-methyl-1-benzofuran-7-yl)methanol (100 mg, 0.45 mmol), ethyl 3-(4-hydroxy-2,3-dimethylphenyl)propanoate (148 mg, 0.67 mmol), toluene (5 mL), ADDP (223 mg, 0.89 mmol) and n-$Bu_3P$ (180 mg, 0.89 mmol). The resulting solution was stirred overnight at 60° C. The resulting mixture was concentrated under vacuum. The resulting solution was diluted with diethyl ether (3 mL). The solids were filtered out. The resulting residue was purified on a silica gel column with PE/EtOAc (30/1).concentrated under vacuum to yield ethyl 3-[4-[(5-chloro-2-ethyl-6-methyl-1-benzofuran-7-yl)methoxy]-2,3-dimethylphenyl] propanoate as yellow oil.

k) 3-{[(5-Chloro-2-ethyl-6-methyl-1-benzofuran-7-yl)methoxy]-2,3-dimethylphenyl}propanoic acid To a solution of ethyl 3-[4-[(5-chloro-2-ethyl-6-methyl-1-benzofuran-7-yl)methoxy]-2,3-dimethylphenyl]propanoate (120 mg, 0.28 mmol,) in tetrahydrofuran (2 mL) was added a solution of LiOH (120 mg, 5.01 mmol) in water (2 mL). The resulting solution was stirred overnight at 40° C. The pH was adjusted to pH 5 with hydrogen chloride (2 mol/L). The resulting solution was extracted with ethyl acetate (2×5 mL) and the organic layers combined and concentrated under vacuum. The resulting residue was purified by RP-C18-HPLC to yield 3-[4-[(5-chloro-2-ethyl-6-methyl-1-benzofuran-7-yl)methoxy]-2,3-dimethylphenyl] propanoic acid as a white solid.

$^1$H NMR (300 MHz, $CDCl_3$) δ: 7.48 (s, 1H), 6.92-7.03 (m, 2H), 6.30 (s, 1H), 5.32 (s, 2H), 2.95 (t, J=7.8 Hz, 2H), 2.73-2.81 (m, 2H), 2.60 (t, J=7.2 Hz, 2H), 2.50 (s, 3H), 2.22 (s, 3H), 2.14 (s, 2H), 1.315 (t, J=7.8 Hz, 3H). Mass spectrum (ESI, m/z): Calculated for $C_{23}H_{25}ClO_4$, 399 (M–H). found 399.

Example 21

3-{4-[(2-Carbamoyl-5-fluoro-1-benzofuran-7-yl) methoxy]-2,3-dimethylphenyl}propanoic acid

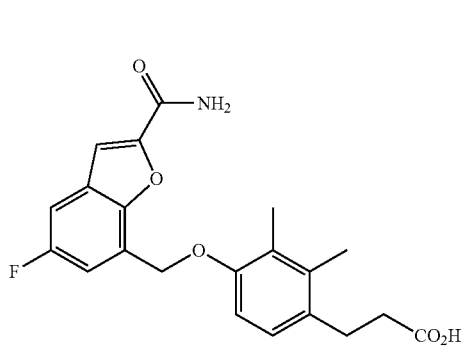 [SMILES: Cc1c(CCC(=O)O)ccc(OCc2cc(F)cc3cc(C(N)=O)oc23)c1C]

a) 5-Fluoro-2-hydroxy-3-methylbenzaldehyde

Into a 1000-mL round-bottom flask was placed 4-fluoro-2-methylphenol (52.5 g, 416.24 mmol), trifluoroacetic acid (320 mL) and methenamine (103 g). The resulting residue was stirred at 100° C. overnight. To this was added sulfuric acid (50 mL, 50%) and water (300 mL) and the resulting solution was stirred for 4 h at 20° C. The resulting mixture was washed with $H_2O$. The resulting solution was extracted with ethyl acetate (3×50 mL) and the organic layers combined. The resulting mixture was washed with $NH_4HCO_3$ (aq). The resulting residue was dried over anhydrous sodium sulfate and concentrated under vacuum to yield 5-fluoro-2-hydroxy-3-methylbenzaldehyde as a yellow solid.

b) Ethyl 5-fluoro-7-methylbenzofuran-2-carboxylate

Into a 100-mL round-bottom flask was placed 5-fluoro-2-hydroxy-3-methylbenzaldehyde (3 g, 19.46 mmol), ethyl 2-bromoacetate (4 g, 23.95 mmol), potassium carbonate (8.28 g, 59.91 mmol) and $CH_3CN$ (40 mL). The resulting solution was stirred for 60 h at 70° C. The solids were filtered out. The resulting mixture was concentrated under vacuum. The resulting residue was purified on a silica gel column with ethyl acetate/petroleum ether (8/92). The collected fractions were combined and concentrated under vacuum to yield ethyl 5-fluoro-7-methyl-1-benzofuran-2-carboxylate as colorless oil.

c) 5-Fluoro-7-methylbenzofuran-2-carboxylic acid

To a solution of ethyl 5-fluoro-7-methyl-1-benzofuran-2-carboxylate (3.2 g, 14.40 mmol) in 20 mL of THF was added a solution of LiOH (3.2 g, 133.61 mmol) in water (20 mL). The resulting solution was stirred overnight at 25° C. The resulting mixture was concentrated under vacuum. The pH value of the solution was adjusted to pH 3 with hydrogen chloride (1 mol/L). The solids were collected by filtration. The solid was dried in an oven under reduced pressure to yield 5-fluoro-7-methyl-1-benzofuran-2-carboxylic acid as a white solid.

d) 5-Fluoro-7-methylbenzofuran-2-carboxamide

Into a 100-mL round-bottom flask was placed 5-fluoro-7-methyl-1-benzofuran-2-carboxylic acid (1 g, 5.15 mmol), tetrahydrofuran (15 mL) and carbonyl diimidazole (920 mg, 5.67 mmol) and the mixture was stirred for 2 h at room temperature. NH$_3$(g) was introduced and the mixture was stirred for 1 hr. The reaction was then quenched by the addition of water. The resulting solution was extracted with ethyl acetate (3×10 mL) and the organic layers combined and dried over anhydrous sodium sulfate and concentrated under vacuum to yield 5-fluoro-7-methyl-1-benzofuran-2-carboxamide as yellow oil.

e) 5-Fluoro-7-methylbenzofuran-2-carbonitrile

Into a 50-mL round-bottom flask was placed 5-fluoro-7-methyl-1-benzofuran-2-carboxamide (400 mg, 0.52 mmol), N,N-dimethylformamide (10 mL) and trichloro-1,3,5-triazine (2.2 g, 11.93 mmol) and the mixture stirred overnight at 25° C. The reaction was then quenched by the addition of water. The resulting solution was extracted with ethyl acetate (3×5 mL) and the organic layers combined and concentrated under vacuum. The resulting residue was purified on a silica gel column with ethyl acetate/petroleum ether (10/90). The collected fractions were combined and concentrated under vacuum to yield 5-fluoro-7-methyl-1-benzofuran-2-carbonitrile as a white solid.

f) 7-(Bromomethyl)-5-fluorobenzofuran-2-carbonitrile

Into a 50-mL round-bottom flask was placed 5-fluoro-7-methyl-1-benzofuran-2-carbonitrile (100 mg, 0.57 mmol), CCl$_4$ (5 mL), NBS (111 mg, 0.62 mmol) and AlBN (9 mg, 0.05 mmol). The resulting solution was stirred for 16 hr at 70° C. The resulting mixture was concentrated under vacuum. The resulting residue was purified on a silica gel column with ethyl acetate/petroleum ether (2/98). The collected fractions were combined and concentrated under vacuum to yield 7-(bromomethyl)-5-fluoro-1-benzofuran-2-carbonitrile as a yellow solid.

g) Ethyl 3-(4-((2-cyano-5-fluorobenzofuran-7-yl)methoxy)-2,3-dimethylphenyl)propanoate Into a 8-mL vial was placed 7-(bromomethyl)-5-fluoro-1-benzofuran-2-carbonitrile (60 mg, 0.24 mmol), ethyl 3-(4-hydroxy-2,3-dimethylphenyl)propanoate (63 mg, 0.28 mmol), potassium carbonate (40 mg, 0.29 mmol) and CH$_3$CN (2 mL). The resulting solution was stirred overnight at 60° C. The resulting mixture was concentrated under vacuum. The resulting residue was purified on a silica gel column with ethyl acetate/petroleum ether (10/90). The collected fractions were combined and concentrated under vacuum to yield ethyl 3-[4-[(2-cyano-5-fluoro-1-benzofuran-7-yl)methoxy]-2,3-dimethylphenyl]propanoate as a white solid.

h) 3-{4-[(2-Carbamoyl-5-fluoro-1-benzofuran-7-yl)methoxy]-2,3-dimethylphenyl}propanoic acid Into a 50-mL round-bottom flask was placed ethyl 3-[4-[(2-cyano-5-fluoro-1-benzofuran-7-yl)methoxy]-2,3-dimethylphenyl]propanoate (50 mg, 0.13 mmol), LiOH (50 mg, 2.09 mmol), tetrahydrofuran (2 mL) and water (2 mL). The resulting solution was stirred overnight at 30° C. The pH value of the solution was adjusted to pH 2 with hydrogen chloride (1 mol/L). The resulting solution was extracted with ethyl acetate (3×1 mL) and the organic layers combined and concentrated under vacuum. The resulting residue was purified by RP-C18-HPLC to yield 3-[4-[(2-carbamoyl-5-fluoro-1-benzofuran-7-yl)methoxy]-2,3-dimethylphenyl] propanoic acid as a white solid.

$^1$H NMR (300 MHz, CDCl$_3$) δ 12.09v(s, 1H), 8.17 (s, 1H), 7.78 (s, 1H), 7.57 (t, J=5.4 Hz, 2H), 7.38 (d, J=9.6 Hz, 1H), 6.98-6.88 (m, 2H), 5.39 (s, 2H), 2.78 (t, J=7.5 Hz, 2H), 2.41 (t, J=7.2 Hz, 2H), 2.27 (s, 6H). Mass spectrum (ESI, m/z): Calculated for C$_{21}$H$_{20}$FNO$_5$, 408.1 (M+Na). found 408.1.

Example 22

7-{[4-(2-Carboxyethyl)-2,3-dimethylphenoxy]methyl}-5-fluoro-1-benzofuran-2-carboxylic acid

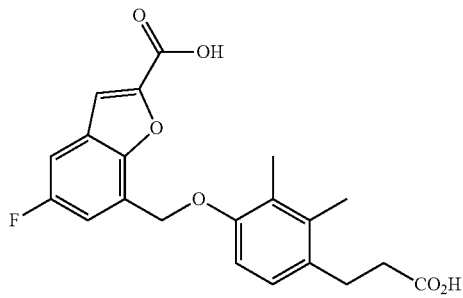 [SMILES: Cc1c(CCC(=O)O)ccc(OCc2cc(F)cc3cc(C(=O)O)oc23)c1C]

Into a 50-mL round-bottom flask was placed ethyl 3-[4-[(2-cyano-5-fluoro-1-benzofuran-7-yl)methoxy]-2,3-dimethylphenyl]propanoate (50 mg, 0.13 mmol, prepared as described in Example 21), LiOH (50 mg, 2.09 mmol), tetrahydrofuran (2 mL), and water (2 mL). The resulting solution was stirred overnight at 30° C. The pH value of the solution was adjusted to pH 2 with hydrogen chloride (1 mol/L). The resulting solution was extracted with ethyl acetate (3×1 mL) and the organic layers combined and concentrated under vacuum. The resulting residue was purified by RP-C18-HPLC to yield 7-[4-(2-carboxyethyl)-2,3-dimethylphenoxymethyl]-5-fluoro-1-benzofuran-2-carboxylic acid as a white solid.

$^1$H NMR (300 MHz, CDCl$_3$) δ: 7.68 (s, 1H), 7.60-7.56 (m, 1H), 7.45 (d, J=9.6 Hz, 1H), 6.97-6.88 (m, 2H), 5.35 (s, 2H), 2.78 (t, J=7.5 Hz, 2H), 2.40 (t, J=7.2 Hz, 2H), 2.26 (s, 6H). Mass spectrum (ESI, m/z): Calculated for C$_{21}$H$_{19}$FO$_6$, 409.1 (M+Na). found 409.1.

Example 23

3-{4-[(5-Chloro-2-ethyl-6-methoxy-1-benzofuran-7-yl)methoxy]-2,3-dimethylphenyl}propanoic acid

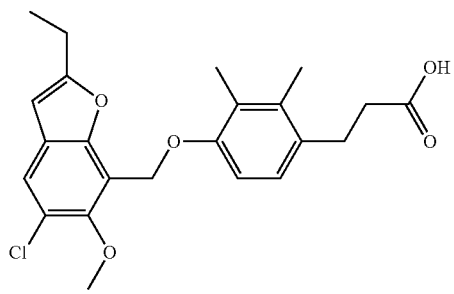 [SMILES: CCc1cc2cc(Cl)c(OC)c(COc3ccc(CCC(=O)O)c(C)c3C)c2o1]

The title compound was prepared by reacting methyl 5-chloro-2-ethyl-6-methoxybenzofuran-7-carboxylate (prepared as described in Example 20) according to the procedure in Example 1.

$^1$H NMR (300 MHz, CDCl$_3$) δ: 7.50 (s, 1H), 6.97-7.07 (m, 2H), 6.32 (s, 1H), 5.29 (s, 2H), 3.94 (s, 3H), 2.98 (t, J=8.4 Hz, 2H), 2.76-2.79 (m, 2H), 2.67 (t, J=8.7 Hz, 2H), 2.24 (s, 3H), 2.16 (s, 3H), 1.31 (t, J=8.2 Hz, 3H). Mass spectrum (ESI, m/z): Calculated for C$_{23}$H$_{25}$ClO$_5$, 415 (M−H). found 415.

Example 24

3-(4-{[5-(Dimethylcarbamoyl)-2-propyl-1-benzofuran-7-yl]methoxy}-2,3-dimethylphenyl)propanoic acid

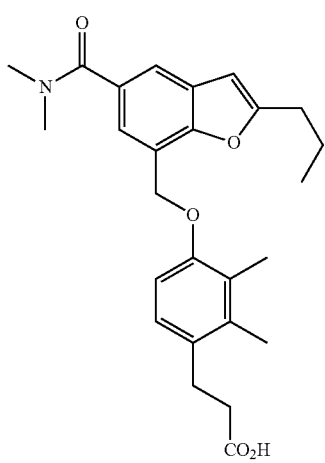 [SMILES: CCCc1cc2cc(C(=O)N(C)C)cc(COc3ccc(CCC(=O)O)c(C)c3C)c2o1]

a) Ethyl 3-(4-((5-(dimethylcarbamoyl)-2-propylbenzofuran-7-yl)methoxy)-2,3-dimethylphenyl)propanoate To a mixture of ethyl 3-[4-[(5-iodo-2-propyl-1-benzofuran-7-yl)methoxy]-2,3-dimethylphenyl]propanoate (150 mg, 0.29 mmol, prepared as described in Example 18), dimethylamine (0.72 mL, 5.00 equiv), Pd(PPh$_3$)$_2$Cl$_2$ (12.2 mg, 0.02 mmol) in N,N-dimethylformamide (5 mL) was added CO(gas). The resulting solution was stirred for 18 h at 25-30° C. The resulting solution was diluted with water (10 mL). The resulting solution was extracted with ethyl acetate (3×10 mL) and the organic layers combined and dried over sodium sulfate. The solids were filtered out. The resulting mixture was concentrated under vacuum. The resulting residue was purified on a silica gel column with PE/EtOAc (5/1) to yield ethyl 3-(4-[[5-(dimethylcarbamoyl)-2-propyl-1-benzofuran-7-yl]methoxy]-2,3-dimethylphenyl)propanoate as light yellow oil.

b) Ethyl 3-(4-((5-(dimethylcarbamoyl)-2-propylbenzofuran-7-yl)methoxy)-2,3-dimethylphenyl)propanoate To a mixture ethyl 3-(4-[[5-(dimethylcarbamoyl)-2-propyl-1-benzofuran-7-yl]methoxy]-2,3-dimethylphenyl)propanoate (120 mg, 0.26 mmol) in tetrahydrofuran (5 mL) was added a solution of LiOH (120 mg, 5.01 mmol) in water (5 mL). The resulting solution was stirred for 18 h at 25° C. The resulting mixture was concentrated under vacuum. The pH was adjusted to pH 6 with hydrogen chloride (2 mol/L). The solids were collected by filtration to yield 3-(4-[[5-(dimethylcarbamoyl)-2-propyl-1-benzofuran-7-yl]methoxy]-2,3-dimethylphenyl)propanoic acid as a white solid.

$^1$H NMR (300 MHz, CDCl$_3$) δ7.52 (s, 1H), 7.36 (s, 1H), 6.94-6.97 (d, J=8.4 Hz, 1H), 6.78-6.81 (d, J=8.4 Hz, 1H), 6.43 (s, 1H), 5.33 (s, 2H), 2.91-2.98 (m, 6H), 2.74-2.79 (m, 4H), 2.55-2.60 (t, J=7.8 Hz, 2H), 2.20 (s, 6H), 1.75-1.85 (m, 2H), 0.99-1.04 (t, J=7.4 Hz, 3H). Mass spectrum (ESI, m/z): Calculated for C$_{26}$H$_{31}$NO$_5$, 438 (M+H). found 438.

Example 25

3-{4-[(5-Iodo-2-propyl-1-benzofuran-7-yl)methoxy]-2,3-dimethylphenyl}propanoic acid

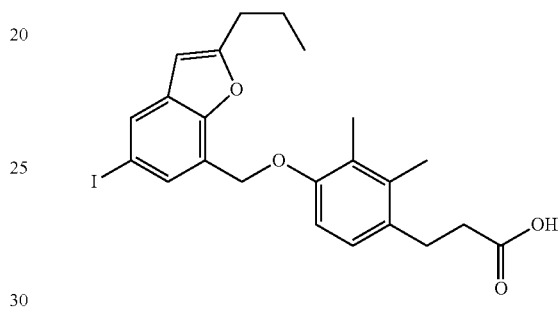

To a mixture of ethyl 3-[4-[(5-iodo-2-propyl-1-benzofuran-7-yl)methoxy]-2,3-dimethylphenyl]propanoate (50 mg, 0.10 mmol, prepared as described in Example 18) in tetrahydrofuran (5 mL) was added a solution of LiOH (50 mg) in water (5 mL). The resulting solution was stirred for 18 h at 25-30° C. The resulting mixture was concentrated under vacuum. The pH value of the solution was adjusted to pH 6 with hydrogen chloride (2 mol/L). The solids were collected by filtration to 3-[4-[(5-iodo-2-propyl-1-benzofuran-7-yl)methoxy]-2,3-dimethylphenyl]propanoic acid as a white solid.

$^1$H NMR (300 MHz, CDCl$_3$) δ: 7.76 (s, 1H), 7.66 (s, 1H), 6.96-6.99 (d, J=8.4 Hz, 1H), 6.79-6.82 (d, J=8.4 Hz, 1H), 6.34 (s, 1H), 5.25 (s, 2H), 2.92-2.98 (t, J=8.0 Hz, 2H), 2.71-2.76 (t, J=7.4 Hz, 2H), 2.58-2.63 (t, J=8.0 Hz, 2H), 2.23 (s, 6H), 1.70-1.82 (m, 2H), 0.97-1.03 (t, J=7.4 Hz, 3H). Mass spectrum (ESI, m/z): Calculated for C$_{23}$H$_{25}$IO$_4$, 491 (M−H). found 491.

Example 26

3-{4-[(2-Cyano-5-fluoro-1-benzofuran-7-yl)methoxy]-2,3-dimethylphenyl}propanoic acid

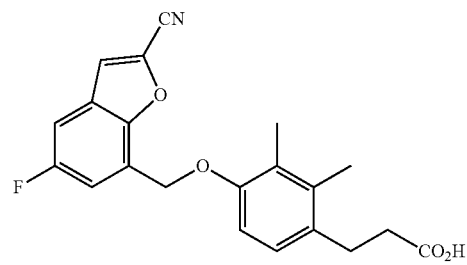 [SMILES: Cc1c(CCC(=O)O)ccc(OCc2cc(F)cc3cc(C#N)oc23)c1C]

a) (E)-Tert-butyl 3-(4-(benzyloxy)-2,3-dimethylphenyl)acrylate

A mixture of 1-(benzyloxy)-4-bromo-2,3-dimethylbenzene (14.4 g, 49.45 mmol), butyl prop-2-enoate (31.7 g, 247.33 mmol), PdCl$_2$ (0.88 g), (tolyl)$_3$P (3.01 g), DIEA (19.2 g, 148.56 mmol) and N,N-dimethylformamide (200 mL) was stirred overnight at 80° C. The resulting solution was diluted with ethyl acetate (800 mL). The resulting mixture was washed with water (3×200 mL) and brine (1×200 mL). The resulting residue was dried over anhydrous sodium sulfate and concentrated under vacuum. The resulting residue was purified on a silica gel column with ethyl acetate/petroleum ether (1/99) to yield (E)-tert-butyl 3-(4-(benzyloxy)-2,3-di methylphenyl)acrylate as yellow oil.

b) Tert-butyl 3-(4-hydroxy-2,3-dimethylphenyl)propanoate

Into a 250-mL round-bottom flask was placed tert-butyl (2E)-3-[4-(benzyloxy)-2,3-dimethylphenyl]prop-2-enoate (10 g, 29.55 mmol), methanol (100 mL), palladium on carbon (10 g) and H$_2$(gas). The resulting solution was stirred overnight at room temperature. The resulting mixture was concentrated under vacuum to yield tert-butyl 3-(4-hydroxy-2,3-dimethylphenyl)propanoate as a white solid.

c) Tert-butyl 3-(4-((2-cyano-5-fluorobenzofuran-7-yl)methoxy)-2,3-dimethylphenyl)propanoate A mixture of 7-(bromomethyl)-5-fluoro-1-benzofuran-2-carbonitrile (20 mg, 0.08 mmol, prepared as described in Example 21, step f), tert-butyl 3-(4-hydroxy-2,3-dimethylphenyl)propanoate (23 mg, 0.09 mmol), potassium carbonate (22 mg, 0.16 mmol) and CH$_3$CN (1 mL) was stirred overnight at 60° C. The resulting mixture was concentrated under vacuum. The resulting residue was purified on a silica gel column with ethyl acetate/petroleum ether (20/80). The collected fractions were combined and concentrated under vacuum to yield tert-butyl 3-[4-[(2-cyano-5-fluoro-1-benzofuran-7-yl)methoxy]-2,3-dimethylphenyl]propanoate as colorless oil.

d) 3-{4-[(2-Cyano-5-fluoro-1-benzofuran-7-yl)methoxy]-2,3-dimethylphenyl}propanoic acid A mixture of tert-butyl 3-[4-[(2-cyano-5-fluoro-1-benzofuran-7-yl)methoxy]-2,3-dimethylphenyl]propanoate (20 mg, 0.05 mmol), trifluoroacetic acid (0.25 mL), and dichloromethane (1 mL) was stirred for 1 h at 30° C. The resulting mixture was concentrated under vacuum. The resulting residue was purified by RP-C18-HPLC to yield 3-[4-[(2-cyano-5-fluoro-1-benzofuran-7-yl)methoxy]-2,3-dimethylphenyl]propanoic acid as a white solid.

$^1$H NMR (300 MHz, CDCl$_3$) δ" 7.46 (s, 2H), 7.31-7.28 (m, 1H), 6.99 (d, J=7.2 Hz, 2H), 6.76 (d, J=7.2 Hz, 1H), 5.34 (s, 2H), 2.96 (t, J=7.5 Hz, 2H), 2.60 (t, J=7.2 Hz, 2H), 2.26 (s, 6H). Mass spectrum (ESI, m/z): Calculated for C$_{21}$H$_{18}$FNO$_4$, 366 (M−H). found 366.

Example 27

3-(4-{[2-Ethyl-5-(trifluoromethoxy)-1-benzofuran-7-yl]methoxy}-5-fluoro-2-propylphenyl)propanoic acid

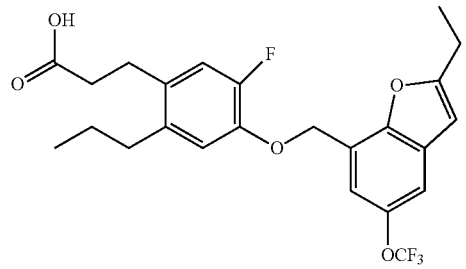 [SMILES: CCCc1cc(OCc2cc(OC(F)(F)F)cc3cc(CC)oc23)c(F)cc1CCC(=O)O]

The title compound was prepared by reacting (2-propyl-5-(trifluoromethoxy)benzofuran-7-yl)methanol (prepared as described in Example 89 step(e)) and ethyl 3-(5-fluoro-4-hydroxy-2-propylphenyl)propanoate (prepared as described in U.S. Pat. Appl. Publ., 20110313003, 22 Dec. 2011), according to procedure in Example 1.

$^1$H NMR: (300 MHz, CDCl$_3$, ppm) δ: 7.26 (s, 1H), 7.24-7.29 (m, 1H), 6.84-6.93 (m, 2H), 6.41 (s, 1H), 5.38 (s, 2H), 2.78-2.91 (m, 4H), 2.58-2.63 (m, 2H), 2.48-2.53 (m, 2H), 1.49-1.59 (m, 2H), 1.34 (t, J=7.5 Hz, 3H), 0.918 (t, J=7.2 Hz, 3H). Mass spectrum (ESI, m/z): Calculated for C$_{24}$H$_{24}$F$_4$O$_5$, 467.2 (M−H). found 467.2.

Example 28

3-[4-{[2-Ethyl-5-(trifluoromethoxy)-1-benzofuran-7-yl]methoxy}-5-fluoro-2-(3-methylbutyl)phenyl]propanoic acid

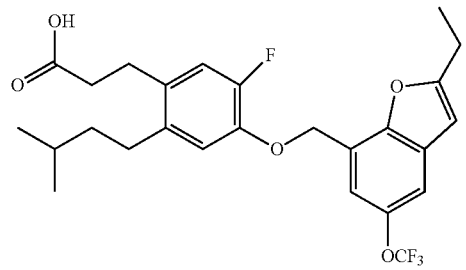 [SMILES: CCc1cc2cc(OC(F)(F)F)cc(COc3cc(CCC(C)C)c(CCC(=O)O)cc3F)c2o1]

a) (E)-1-Fluoro-2-methoxy-4-(3-methylbut-1-en-1-yl)benzene

A mixture of isobutyltriphenylphosphonium bromide (19 g, 47.58 mmol), tetrahydrofuran (100 mL), sodium hydride (1.9 g, 79.17 mmol) and 4-fluoro-3-methoxybenzaldehyde (5 g, 32.44 mmol) was stirred for 3 h at room temperature. The reaction was then quenched by the addition of water (100 mL). The resulting solution was extracted with ethyl acetate (3×100 mL) and the organic layers combined and dried over anhydrous sodium sulfate and concentrated under vacuum. The resulting residue was purified on a silica gel column with ethyl acetate/petroleum ether (1/50-1/30) to yield (E)-1-fluoro-2-methoxy-4-(3-methylbut-1-en-1-yl) benzene as colorless oil.

b) 1-Fluoro-4-isopentyl-2-methoxybenzene

To a 100-mL round-bottom flask was placed (E)-1-fluoro-2-methoxy-4-(3-methylbut-1-en-1-yl)benzene (3.3 g, 16.99 mmol), palladium on carbon (330 mg), methanol (30 mL) and a balloon of hydrogen. The resulting solution was stirred for 2 h at room temperature, filtered and concentrated to yield 1-fluoro-2-methoxy-4-(3-methylbutyl)benzene as colorless oil.

c) 5-Fluoro-2-isopentyl-4-methoxybenzaldehyde

A mixture of 1-fluoro-2-methoxy-4-(3-methylbutyl)benzene (2.9 g, 14.78 mmol), dichloromethane (40 mL), TiCl$_4$ (5 g, 26.60 mmol) and dichloro(methoxy)methane (1.69 g, 14.70 mmol) was stirred for 2 h at room temperature. The reaction was then quenched by the addition of 40 mL of water. The resulting solution was extracted with DCM (40 mL) and the organic layers combined and concentrated under vacuum. The resulting residue was purified on a silica gel column with ethyl acetate/petroleum ether (1/50-1/30) to yield 5-fluoro-4-methoxy-2-(3-methylbutyl)benzaldehyde as a yellow solid.

d) (E)-ethyl 3-(5-fluoro-2-isopentyl-4-methoxyphenyl)acrylate

A mixture of (carbethoxymethylene)triphenylphosphorane (5.297 g, 15.20 mmol), 5-fluoro-4-methoxy-2-(3-methylbutyl)benzaldehyde (3.1 g, 13.82 mmol), and toluene (50 mL) was stirred overnight at 90° C. The resulting mixture was concentrated under vacuum. The resulting residue was purified on a silica gel column with ethyl acetate/petroleum ether (1/50-1/30) to yield ethyl (2E)-3-[5-fluoro-4-methoxy-2-(3-methylbutyl)phenyl]prop-2-enoate as yellow oil.

e) Ethyl 3-(5-fluoro-2-isopentyl-4-methoxyphenyl)propanoate

To a mixture of ethyl (2E)-3-[5-fluoro-4-methoxy-2-(3-methylbutyl)phenyl]prop-2-enoate (3.5 g, 11.89 mmol), methanol (100 mL) and palladium on carbon (3 g) was added a balloon of hydrogen and the mixture stirred for 2 h at room temperature to yield ethyl 3-[5-fluoro-4-methoxy-2-(3-methylbutyl)phenyl]propanoate as yellow oil.

f) Ethyl 3-(5-fluoro-4-hydroxy-2-isopentylphenyl)propanoate

To a solution of ethyl 3-[5-fluoro-4-methoxy-2-(3-methylbutyl)phenyl]propanoate (3.2 g, 10.80 mmol) in dichloromethane (100 mL) was added BBr$_3$ (8 mL) dropwise with stirring at −40° C. The resulting solution was stirred for 2 h at room temperature. The reaction was then quenched by the addition of water (100 mL). The resulting solution was extracted with DCM (2×100 mL) and the organic layers combined and dried over anhydrous sodium sulfate and concentrated under vacuum. The resulting residue was purified on a silica gel column with ethyl acetate/petroleum ether (1/50-1/30) to yield ethyl 3-(5-fluoro-4-hydroxy-2-isopentylphenyl)propanoate as colorless oil.

g) 3-[4-{[2-Ethyl-5-(trifluoromethoxy)-1-benzofuran-7-yl]methoxy}-5-fluoro-2-(3-methylbutyl)phenyl]propanoic acid The title compound was prepared by reacting ethyl 3-(5-fluoro-4-hydroxy-2-isopentylphenyl)propanoate according to Example 27.

$^1$H NMR: (300 MHz, CDCl$_3$, ppm) δ: 7.29 (s, 1H), 7.23 (s, 1H), 6.92-6.82 (m, 2H), 6.41 (s, 1H), 5.38 (s, 2H), 2.91-2.77 (m, 4H), 2.63-2.61 (m, 2H), 2.58-2.51 (m, 1H), 1.39-1.31 (m, 5H), 0.93-0.90 (m, 6H). Mass spectrum (ESI, m/z): Calculated for C$_{26}$H$_{28}$F$_4$O$_5$, 495 (M−H). found 495.

Example 29

3-(7-{[2-Ethyl-5-(trifluoromethoxy)-1-benzofuran-7-yl]methoxy}-2,3-dihydro-1H-inden-4-yl)propanoic acid

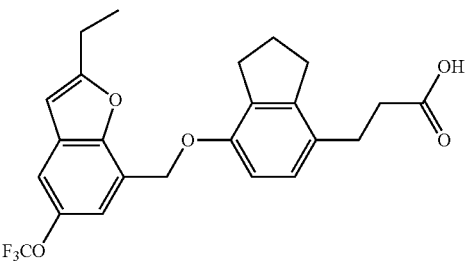 [SMILES: CCc1cc2cc(OC(F)(F)F)cc(COc3ccc(CCC(=O)O)c4c3CCC4)c2o1]

The title compound was prepared by reacting (2-propyl-5-(trifluoromethoxy)benzofuran-7-yl)methanol (prepared as described in Example 89 step(e)) and ethyl 3-(7-hydroxy-2,3-dihydro-1H-inden-4-yl)propanoate (prepared as described in U.S. Pat. Appl. Publ., 20110313003, 22 Dec. 2011) according to the procedure in Example 1.

$^1$H NMR: (300 MHz, CDCl$_3$, ppm) δ: 7.28-7.24 (m, 2H), 6.95 (d, J=8.4 Hz, 1H), 6.76 (d, J=8.4 Hz, 1H), 5.34 (s, 2H), 2.98-2.86 (m, 6H), 2.83-2.77 (m, 2H), 2.63 (t, J=7.5 Hz, 2H), 2.15-2.08 (m, 2H), 1.34 (t, J=7.5 Hz, 3H). Mass spectrum (ESI, m/z): Calculated for C$_{24}$H$_{23}$F$_3$O$_5$, 447 (M−H). found 447.

Example 30

3-[4-{[2-Ethyl-5-(trifluoromethoxy)-1-benzofuran-7-yl]methoxy}-5-fluoro-2-(2-methylpropyl)phenyl]propanoic acid

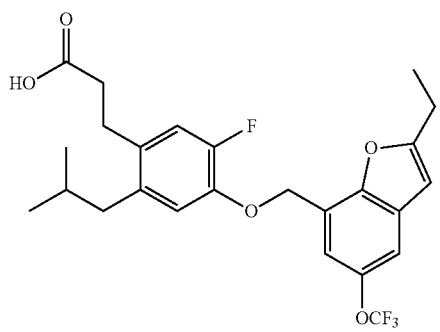 [SMILES: CCc1cc2cc(OC(F)(F)F)cc(COc3cc(CC(C)C)c(CCC(=O)O)cc3F)c2o1]

a) 1-Fluoro-2-methoxy-4-(2-methylprop-1-en-1-yl)benzene

Into a 100-mL round-bottom flask purged and maintained with an inert atmosphere of nitrogen was placed isopropyltriphenylphosphonium iodide (9.6 g, 22.21 mmol), tetrahydrofuran (40 mL) and sodium hydride (900 mg, 22.50 mmol, 60%) and the resulting solution was stirred for 1 h at room temperature. To the resulting mixture was then added 4-fluoro-3-methoxybenzaldehyde (2.3 g, 14.92 mmol) and the mixture was stirred overnight at room temperature. The reaction was then quenched by the addition of water (40 mL). The resulting solution was extracted with ethyl acetate (3×40 mL) and the organic layers combined and dried over anhydrous sodium sulfate and concentrated under vacuum. The resulting residue was purified on a silica gel column with ethyl acetate/petroleum ether (1/50-1/30) to yield 1-fluoro-2-methoxy-4-(2-methylprop-1-en-1-yl)benzene as colorless oil b) Ethyl 3-(5-fluoro-4-hydroxy-2-isobutylphenyl)propanoate

The title compound was prepared according to procedures in Example 28 substituting 1-fluoro-2-methoxy-4-(2-methylprop-1-en-1-yl)benzene for (E)-1-fluoro-2-methoxy-4-(3-methylbut-1-en-1-yl)benzene in step (b).

c) 3-[4-{[2-Ethyl-5-(trifluoromethoxy)-1-benzofuran-7-yl]methoxy}-5-fluoro-2-(2-methylpropyl)phenyl]propanoic acid The title compound was prepared by reacting (2-propyl-5-(trifluoromethoxy)benzofuran-7-yl)methanol (prepared as described in Example 89) and ethyl 3-(5-fluoro-4-hydroxy-2-isobutylphenyl)propanoate according to the procedures in Example 1.

$^1$H NMR: (300 MHz, CDCl$_3$, ppm) δ: 7.28 (s, 1H), 7.23 (s, 1H), 6.90 (d, J=12.3 Hz, 1H), 6.78 (d, J=12.3 Hz, 1H), 6.41 (s, 1H), 5.38 (s, 2H), 2.89-2.78 (m, 4H), 2.62-2.57 (m, 2H), 2.38 (d, J=7.2 Hz, 2H), 1.77-1.68 (m, 1H), 1.36-1.25 (m, 3H), 0.85-0.83 (m, 6H). Mass spectrum (ESI, m/z): Calculated for C$_{25}$H$_{26}$F$_4$O$_5$, 481 (M−H). found 481.

Example 31

3-{7-[(5-Chloro-2-ethyl-1-benzofuran-7-yl)methoxy]-2,3-dihydro-1H-inden-4-yl}propanoic acid

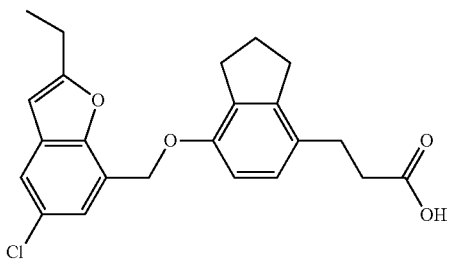 [SMILES: CCc1cc2cc(Cl)cc(COc3ccc(CCC(=O)O)c4c3CCC4)c2o1]

The title compound was prepared by reacting (5-chloro-2-ethylbenzofuran-7-yl)methanol (prepared as described in Example 88 step(b)) and ethyl 3-(7-hydroxy-2,3-dihydro-1H-inden-4-yl)propanoate (prepared as described in U.S. Pat. Appl. Publ., 20110313003, 22 Dec. 2011) according to the procedure in Example 20 step (j).

$^1$H NMR: (300 MHz, CDCl$_3$) δ: 7.43 (d, J=2.1 Hz, 1H), 7.32 (d, J=2.1 Hz, 1H), 6.96 (d, J=8.4 Hz, 1H), 6.76 (d, J=8.1 Hz, 1H), 6.36 (s, 1H), 5.32 (s, 2H), 2.78-3.00 (m, 8H), 2.64 (t, J=8.4 Hz, 2H), 2.01-2.16 (m, 3H), 2.16 (s, 3H), 1.34 (t, J=7.5 Hz, 3H). Mass spectrum (ESI, m/z): Calculated for C$_{23}$H$_{23}$ClO$_4$, 397 (M−H). found 397.

Example 32

3-{4-[(2-Acetyl-5-fluoro-1-benzofuran-7-yl)methoxy]-2,3-dimethylphenyl}propanoic acid

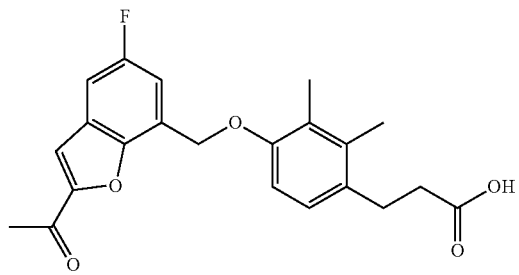 [SMILES: CC(=O)c1cc2cc(F)cc(COc3ccc(CCC(=O)O)c(C)c3C)c2o1]

a) 3-Bromo-5-fluoro-2-hydroxybenzaldehyde

A mixture of 2-bromo-4-fluorophenol (5 g, 26.18 mmol), trifluoroacetic acid (60 mL), and hexamethylemetetramine (3.68 g, 26.29 mmol) was stirred overnight at 80° C. The resulting solution was extracted with ethyl acetate (2×20 mL) and the organic layers combined. The resulting mixture was washed with H$_2$O. The resulting mixture was washed with sodium bicarbonate (aq). The resulting residue was dried over anhydrous sodium sulfate and concentrated under vacuum to yield 3-bromo-5-fluoro-2-hydroxybenzaldehyde as a yellow solid.

b) 1-(7-Bromo-5-fluorobenzofuran-2-yl)ethanone

Into a 100-mL round-bottom flask was placed 3-bromo-5-fluoro-2-hydroxybenzaldehyde (2 g, 9.13 mmol), 1-chloropropan-2-one (1.1 g, 11.89 mmol), potassium carbonate (2.25 g, 16.28 mmol), and N,N-dimethylformamide (20 mL) and the resulting solution was stirred for 2 h at 80° C. The reaction was then quenched by the addition of water. The resulting solution was extracted with ethyl acetate (2×20 mL) and the organic layers combined. The resulting mixture was washed with sodium chloride (aq). The resulting mixture was concentrated under vacuum. The resulting residue was purified on a silica gel column with ethyl acetate/petroleum ether (10/90). The collected fractions were combined and concentrated under vacuum to yield 1-(7-bromo-5-fluoro-1-benzofuran-2-yl)ethan-1-one as yellow oil.

c) Methyl 2-acetyl-5-fluorobenzofuran-7-carboxylate

To a mixture of 1-(7-bromo-5-fluoro-1-benzofuran-2-yl)ethan-1-one (2.2 g, 8.56 mmol), Pd(dppf)$_2$Cl$_2$ (1 g, 1.23 mmol), triethylamine (5 g, 49.41 mmol) and methanol (30 mL) was introduced CO (g). The resulting solution was stirred overnight at 60° C. The resulting mixture was concentrated under vacuum. The resulting residue was purified on a silica gel column with ethyl acetate/petroleum ether (20/80). The collected fractions were combined and concentrated under vacuum to yield methyl 2-acetyl-5-fluoro-1-benzofuran-7-carboxylate as a yellow solid.

d) Methyl 5-fluoro-2-(2-methyl-1,3-dioxolan-2-yl) benzofuran-7-carboxylate

Into a 100-mL round-bottom flask was placed methyl 2-acetyl-5-fluoro-1-benzofuran-7-carboxylate (500 mg, 2.12 mmol), ethane-1,2-diol (5 g, 80.56 mmol), TsOH (40 mg, 0.23 mmol) and toluene (10 mL) and the mixture was stirred overnight at 70° C. The resulting mixture was concentrated under vacuum. The resulting residue was purified on a silica gel column with ethyl acetate/petroleum ether (30/70). The collected fractions were combined and concentrated under vacuum to yield methyl 5-fluoro-2-(2-methyl-1,3-dioxolan-2-yl)-1-benzofuran-7-carboxylate as yellow oil.

e) (5-Fluoro-2-(2-methyl-1,3-dioxolan-2-yl)benzofuran-7-yl)methanol

To a solution of methyl 5-fluoro-2-(2-methyl-1,3-dioxolan-2-yl)-1-benzofuran-7-carboxylate (400 mg, 1.43 mmol) in tetrahydrofuran (10 mL) was added LAH (163 mg, 4.30 mmol) and the resulting solution was stirred for 2 h at 30° C. The reaction was then quenched by the addition of sodium sulfate.10H$_2$O. The solids were filtered out. The resulting mixture was concentrated under vacuum to yield [5-fluoro-2-(2-methyl-1,3-dioxolan-2-yl)-1-benzofuran-7-yl]methanol as yellow oil.

f) 1-(5-Fluoro-7-(hydroxymethyl)benzofuran-2-yl) ethanone

Into a 8-mL vial was placed [5-fluoro-2-(2-methyl-1,3-dioxolan-2-yl)-1-benzofuran-7-yl]methanol (30 mg, 0.12 mmol), acetone (1 mL), and hydrogen chloride (1N) (1 mL). The resulting solution was stirred for 2 h at 30° C. The resulting solution was extracted with ethyl acetate (3×1 mL) and the organic layers combined and concentrated under vacuum. The resulting residue was purified on a silica gel column with ethyl acetate/petroleum ether (35/65). The collected fractions were combined and concentrated under vacuum to yield 1-[5-fluoro-7-(hydroxymethyl)-1-benzofuran-2-yl]ethan-1-one as a white solid.

g) (2-Acetyl-5-fluorobenzofuran-7-yl)methyl methanesulfonate

Into a 8-mL vial was placed 1-[5-fluoro-7-(hydroxymethyl)-1-benzofuran-2-yl]ethan-1-one (20 mg, 0.10 mmol), dichloromethane (1 mL), methanesulfonyl chloride (20 mg, 0.17 mmol), and triethylamine (30 mg, 0.30 mmol) and the mixture was stirred overnight at 30° C. The reaction was then quenched by the addition of water. The resulting solution was extracted with ethyl acetate (3×1 mL) and the organic layers combined and dried over anhydrous sodium sulfate and concentrated under vacuum to yield (2-acetyl-5-fluoro-1-benzofuran-7-yl)methyl methanesulfonate as yellow oil.

h) Tert-butyl 3-(4-((2-acetyl-5-fluorobenzofuran-7-yl)methoxy)-2,3-dimethylphenyl)propanoate A mixture of (2-acetyl-5-fluoro-1-benzofuran-7-yl) methyl methanesulfonate (30 mg, 0.10 mmol), tert-butyl 3-(4-hydroxy-2,3-dimethylphenyl)propanoate (28 mg, 0.11 mmol, prepared as described in Example 22), and potassium carbonate (45 mg, 0.33 mmol), in N,N-dimethylformamide (1 mL) was stirred overnight at 30° C. The resulting solution was diluted with of H$_2$0. The resulting solution was extracted with ethyl acetate (2×1 mL) and the organic layers combined. The resulting solution was extracted with of ethyl acetate and the organic layers combined. The resulting residue was purified by preparative-TLC with ethyl acetate/ petroleum ether (1/5). The resulting solution was extracted with of ethyl acetate and the organic layers combined to yield tert-butyl 3-[4-[(2-acetyl-5-fluoro-1-benzofuran-7-yl) methoxy]-2,3-dimethylphenyl]propanoate as yellow oil.

i) 3-{4-[(2-Acetyl-5-fluoro-1-benzofuran-7-yl) methoxy]-2,3-dimethylphenyl}propanoic acid A mixture of tert-butyl 3-[4-[(2-acetyl-5-fluoro-1-benzofuran-7-yl)methoxy]-2,3-dimethylphenyl]propanoate (20 mg, 0.05 mmol), dichloromethane (1 mL) and trifluoroacetic acid (0.2 mL) was stirred for 3 h at 30° C. The resulting mixture was concentrated and purified by RP-C18-HPLC to yield 3-[4-[(2-acetyl-5-fluoro-1-benzofuran-7-yl)methoxy]-2,3-dimethylphenyl]propanoic acid as a white solid.

$^1$H NMR: (300 MHz, CDCl$_3$) δ: 7.50 (s, 1H), 7.44-7.43 (m, 1H), 7.32-7.29 (m, 2H), 6.95 (d, J=8.1 Hz, 1H), 6.80 (d, J=8.1 Hz, 1H), 5.39 (s, 2H), 2.98-2.99 (m, 2H), 2.78-2.61 (m, 5H), 2.13-2.17 (m, 6H). Mass spectrum (ESI, m/z): Calculated for C$_{22}$H$_{21}$FO$_5$, 383 (M–H). found 383.

Example 33

3-(4-{[5-(Difluoromethoxy)-2-ethyl-1-benzofuran-7-yl]methoxy}-2,3-dimethylphenyl)propanoic acid

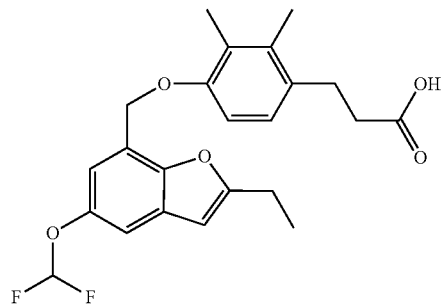 [SMILES: CCc1cc2cc(OC(F)F)cc(COc3ccc(CCC(=O)O)c(C)c3C)c2o1]

a) Methyl 3-bromo-2-hydroxy-5-methoxybenzoate

To a solution of methyl 2-hydroxy-5-methoxybenzoate (10 g, 54.89 mmol) in methanol (150 g, 4.68 mol) was added Br$_2$ (10.4 g, 65.08 mmol) and the resulting solution was stirred overnight at room temperature. The resulting mixture was concentrated under vacuum and diluted with ethyl acetate (100 mL) and washed with Na$_2$S$_2$O$_3$ (aq) (3×50 mL). The resulting residue was purified on a silica gel column with ethyl acetate/petroleum ether (1:3) to yield methyl 3-bromo-2-hydroxy-5-methoxybenzoate as yellow oil.

b) Methyl 2-ethyl-5-methoxybenzofuran-7-carboxylate

A mixture of methyl 3-bromo-2-hydroxy-5-methoxybenzoate (10.3 g, 39.45 mmol), N,N-dimethylformamide (100 mL), TEA (8.0 g, 79.06 mmol), CuI (750 mg, 3.94 mmol), Pd(PPh$_3$)$_2$Cl$_2$ (2.77 g, 3.95 mmol) and but-1-yne (4.28 g, 79.13 mmol) was stirred overnight at 80° C. The resulting solution was diluted with ethyl acetate (300 mL). The resulting mixture was washed with brine (3×50 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield methyl 2-ethyl-5-methoxy-1-benzofuran-7-carboxylate as yellow oil c) Methyl 2-ethyl-5-hydroxybenzofuran-7-carboxylate

To a solution of methyl 2-ethyl-5-methoxy-1-benzofuran-7-carboxylate (1.5 g, 6.40 mmol) in dichloromethane (50 mL) was added BBr$_3$ (3.2 g) at −78° C. The resulting solution was stirred for 30 min at room temperature. The reaction was then quenched by the addition of water (15 mL). The resulting solution was diluted with DCM (100 mL). The resulting mixture was washed with brine (3×40 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield methyl 2-ethyl-5-hydroxy-1-benzofuran-7-carboxylate as yellow oil.

d) Methyl 5-(difluoromethoxy)-2-ethyl-1-benzofuran-7-carboxylate

Into a 25-mL round-bottom flask was placed methyl 2-ethyl-5-hydroxy-1-benzofuran-7-carboxylate (280 mg, 1.27 mmol), 1,4-dioxane (15 mL), water (0.5 mL), sodium hydroxide (153 mg, 3.83 mmol), tetrabutylammonium iodide (469.6 mg, 1.27 mmol), and chlorodifluoromethane (219 mg, 2.53 mmol) and the mixture was stirred overnight at room temperature. The resulting mixture was concentrated under vacuum. The resulting solution was diluted with ethyl acetate (50 mL). The resulting mixture was washed with brine (3×10 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield methyl 5-(difluoromethoxy)-2-ethyl-1-benzofuran-7-carboxylate as colorless oil.

e) 3-(4-{[5-(Difluoromethoxy)-2-ethyl-1-benzofuran-7-yl]methoxy}-2,3-dimethylphenyl)propanoic acid The title compound was prepared by reacting methyl 5-(difluoromethoxy)-2-ethyl-1-benzofuran-7-carboxylate and ethyl 3-(4-hydroxy-2,3-dimethylphenyl)propanoate (prepared as described in U.S. Pat. Appl. Publ., 20110313003, 22 Dec. 2011) according to procedure in Example 1.

$^1$H NMR: (300 MHz, CD$_3$Cl) δ: 7.19 (d, J=2.7 Hz, 2H), 6.99 (d, J=8.4 Hz, 1H), 6.82 (d, J=10.8 Hz, 1H), 6.49 (t, J=74.4 Hz, 1H), 6.40 (s, 1H), 6.32 (s, 1H), 5.31 (s, 2H), 2.96 (t, J=7.8 Hz, 2H), 2.82 (q, J$_1$=7.5 Hz, J$_2$=1.2 Hz, 2H), 2.61 (t, J=8.4 Hz, 2H), 2.26 (s, 6H), 1.35 (t, J=7.5 Hz, 3H). Mass spectrum (ESI, m/z): Calculated for C$_{23}$H$_{24}$F$_2$O$_5$, 317 (M−H). found 417.

Example 34

3-{2,3-Dimethyl-4-[(2-propyl-5-prop-1-yn-1-yl-1-benzofuran-7-yl)methoxy]phenyl}propanoic acid

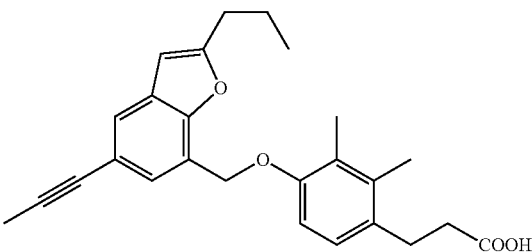 [SMILES: CC#Cc1cc(COc2ccc(CCC(=O)O)c(C)c2C)c2oc(CCC)cc2c1]

a) Ethyl 3-(2,3-dimethyl-4-((5-(prop-1-yn-1-yl)-2-propylbenzofuran-7-yl)methoxy)phenyl)propanoate To a mixture of ethyl 3-[4-[(5-iodo-2-propyl-1-benzofuran-7-yl)methoxy]-2,3-dimethylphenyl]propanoate (520 mg, 1.00 mmol, prepared as described in Example 18), CuI (15 mg, 0.08 mmol), Pd(PPh$_3$)$_2$Cl$_2$ (54 mg), and triethylamine (1 mL) in MeCN (2 mL) was added prop-1-yne (15.4 mg, 0.38 mmol) dropwise with stirring at −78° C. The resulting solution was stirred overnight at 25° C. The resulting solution was diluted with ethyl acetate (20 mL). The solids were filtered out. The resulting mixture was concentrated under vacuum. The resulting residue was purified on a silica gel column with ethyl acetate/petroleum ether (10/90). The collected fractions were combined and concentrated under vacuum to yield ethyl 3-(2,3-dimethyl-4-[[5-(prop-1-yn-1-yl)-2-propyl-1-benzofuran-7-yl]methoxy]phenyl)propanoate as light yellow oil.

b) 3-{2,3-Dimethyl-4-[(2-propyl-5-prop-1-yn-1-yl-1-benzofuran-7-yl)methoxy]phenyl}propanoic acid The title compound was prepared according to procedure as described in Example 1.

$^1$H NMR: (300 MHz, CDCl$_3$) δ: 7.47 (s, 1H), 7.39 (s, 1H), 6.99 (d, J=8.4 Hz, 1H), 6.83 (d, J=8.4 Hz, 1H), 6.35 (s, 1H), 5.26 (s, 2H), 2.95 (t, J=8.1 Hz, 2H), 2.73 (t, J=7.2 Hz, 2H), 2.59 (t, J=7.5 Hz, 2H), 2.21 (s, 6H), 2.05 (s, 3H), 1.80-1.82 (m, 2H), 1.03 (t, J=7.2 Hz, 3H), 1.35 (t, J=7.5 Hz, 3H). Mass spectrum (ESI, m/z): Calculated for C$_{26}$H$_{28}$O$_4$, 403 (M−H). found 403.

Example 35

3-{4-[(5-Chloro-2,6-diethyl-1-benzofuran-7-yl)methoxy]-2,3-dimethylphenyl}propanoic acid

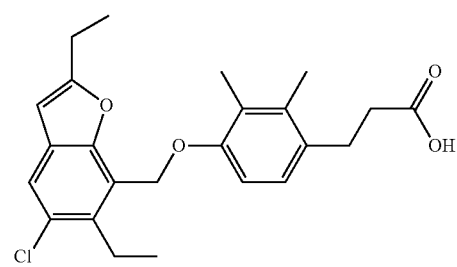 [SMILES: CCc1cc2cc(Cl)c(CC)c(COc3ccc(CCC(=O)O)c(C)c3C)c2o1]

a) Methyl 5-chloro-2,6-diethylbenzofuran-7-carboxylate

A mixture of methyl 5-chloro-2-ethyl-6-[(trifluoromethane)sulfonyloxy]-1-benzofuran-7-carboxylate (200 mg, 0.52 mmol, prepared as described in Example 20 step g), tetrahydrofuran (4 mL), Pd(dppf)Cl$_2$ (37 mg, 0.05 mmol), LiCl (150 mg, 3.57 mmol), and diethylzinc (310 mg, 2.51 mmol) was stirred overnight at 60° C. The resulting mixture was concentrated under vacuum. The resulting residue was purified on a silica gel column with ethyl acetate/petroleum ether (1/30-1/20) to yield methyl 5-chloro-2,6-diethyl-1-benzofuran-7-carboxylate as yellow oil.

b) 3-{4-[(5-Chloro-2,6-diethyl-1-benzofuran-7-yl)methoxy]-2,3-dimethylphenyl}propanoic acid The title compound was prepared by reacting methyl 5-chloro-2,6-diethyl-1-benzofuran-7-carboxylate according to procedure in Example 1.

$^1$H NMR: (300 MHz, CDCl$_3$) δ: 7.43 (s, 1H), 6.85-6.97 (m, 2H), 6.24 (s, 1H), 5.19 (s, 2H), 2.86-2.89 (m, 4H), 2.573-2.68 (m, 4H), 2.15 (s, 3H), 2.06 (s, 3H), 1.14-1.25 (m, 6H). Mass spectrum (ESI, m/z): Calculated for C$_{24}$H$_{27}$ClO$_4$, 413 (M–H). found 413.

Example 36

3-{4-[(5-Chloro-6-ethoxy-2-ethyl-1-benzofuran-7-yl)methoxy]-2,3-dimethylphenyl}propanoic acid

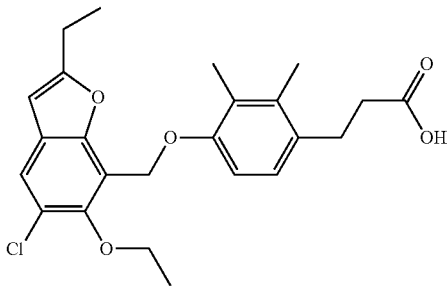 [SMILES: CCOc1c(Cl)cc2cc(CC)oc2c1COc1ccc(CCC(=O)O)c(C)c1C]

a) Methyl 5-chloro-6-ethoxy-2-ethylbenzofuran-7-carboxylate

Into a 8-mL vial, was placed methyl 5-chloro-2-ethyl-6-hydroxy-1-benzofuran-7-carboxylate (100 mg, 0.39 mmol, prepared as described in Example 20, step(e)), acetone (2 mL), bromoethane (0.5 mL), Cs$_2$CO$_3$ (639 mg, 1.96 mmol). The resulting solution was stirred overnight at 60° C. The reaction was then quenched by the addition of water (5 mL). The resulting solution was extracted with ethyl acetate (2×5 mL) and the organic layers combined and concentrated under vacuum. The resulting residue was purified on a silica gel column with P/E (30/1-20/1) to yield methyl 5-chloro-6-ethoxy-2-ethyl-1-benzofuran-7-carboxylate as yellow oil.

b) 3-{4-[(5-Chloro-6-ethoxy-2-ethyl-1-benzofuran-7-yl)methoxy]-2,3-dimethylphenyl}propanoic acid The title compound was prepared by reacting methyl 5-chloro-6-ethoxy-2-ethyl-1-benzofuran-7-carboxylate according to procedure in Example 1.

$^1$H NMR: (300 MHz, CDCl$_3$) δ: 7.49 (s, 1H), 6.96-7.06 (m, 2H), 6.31 (s, 1H), 5.29 (s, 2H), 4.09-4.16 (m, 2H), 2.97 (t, J=7.5 Hz, 2H), 2.73-2.81 (m, 2H), 2.63 (t, J=7.5 Hz, 2H), 2.27 (s, 3H), 2.15 (s, 3H), 1.41 (t, J=7.2 Hz, 3H), 1.309 (t, J=7.2 Hz, 5H). Mass spectrum (ESI, m/z): Calculated for C$_{24}$H$_{27}$ClO$_5$, 429 (M–H). found 429.

Example 37

3-(4-{[5-Chloro-2-ethyl-6-(2-methoxyethoxy)-1-benzofuran-7-yl]methoxy}-2,3-dimethylphenyl)propanoic acid

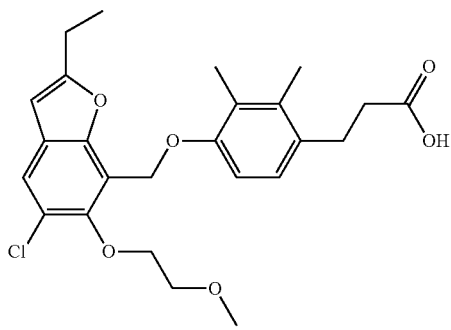 [SMILES: CCc1cc2cc(Cl)c(OCCOC)c(COc3ccc(CCC(=O)O)c(C)c3C)c2o1]

The title compound was prepared according to the procedure as described in Example 36 substituting 1-bromo-2-methoxyethane for bromoethane in step (a).

$^1$H NMR: (300 MHz, CDCl$_3$) δ: 7.46 (s, 1H), 6.95-7.03 (m, 2H), 6.29 (s, 1H), 5.31 (s, 2H), 4.20 (t, J=4.8 Hz, 2H), 3.70 (t, J=4.5 Hz, 2H), 3.36 (s, 3H), 2.95 (t, J=7.8 Hz, 2H), 2.70-2.78 (m, 2H), 2.59 (t, J=7.5 Hz, 2H), 2.20 (s, 3H), 2.12 (s, 3H), 1.28 (t, J=7.5 Hz, 3H), 1.30 (t, J=7.2 Hz, 5H). Mass spectrum (ESI, m/z): Calculated for C$_{25}$H$_{29}$ClO$_6$, 459 (M–H). found 459.

Example 38

3-(4-{[5-Chloro-2-ethyl-6-(2,2,2-trifluoroethoxy)-1-benzofuran-7-yl]methoxy}-2,3-dimethylphenyl)propanoic acid

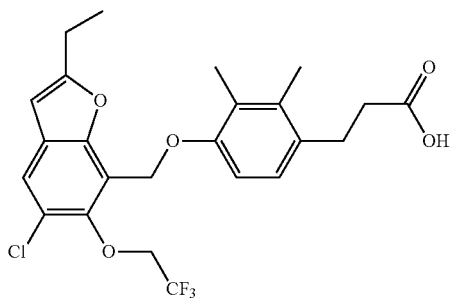 [SMILES: CCc1cc2cc(Cl)c(OCC(F)(F)F)c(COc3ccc(CCC(=O)O)c(C)c3C)c2o1]

The title compound was prepared according to procedure as described in Example 36 substituting trifluoromethyl trifluoromethanesulfonate for bromoethane and potassium carbonate for cesium carbonate.

$^1$H NMR: (300 MHz, CDCl$_3$) δ: 7.51 (s, 1H), 6.94-7.05 (m, 2H), 6.34 (s, 1H), 5.32 (s, 2H), 4.42-4.50 (m, 2H), 2.97 (t, J=7.5 Hz, 2H), 2.75-2.82 (m, 2H), 2.64 (t, J=7.5 Hz, 2H), 2.23 (s, 3H), 2.14 (s, 3H), 1.32 (t, J=7.5 Hz, 3H). Mass spectrum (ESI, m/z): Calculated for $C_{24}H_{24}ClF_3O_5$, 483 (M−H). found 483.

Example 39

3-(4-{[5-Chloro-2-ethyl-6-(1-methylethoxy)-1-benzofuran-7-yl]methoxy}-2,3-dimethylphenyl)propanoic acid

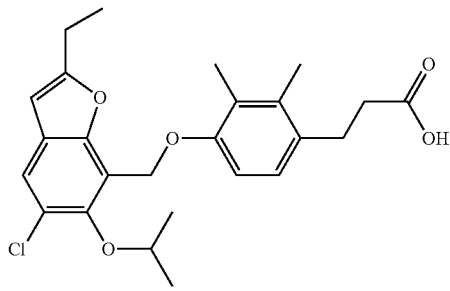 [SMILES: CCc1cc2cc(Cl)c(OC(C)C)c(COc3ccc(CCC(=O)O)c(C)c3C)c2o1]

The title compound was prepared according to procedure as described in Example 36 substituting 2-bromopropane for bromoethane.

$^1$H NMR: (300 MHz, CDCl$_3$) δ: 7.49 (s, 1H), 7.05 (d, J=8.4 Hz, 1H), 6.95 (d, J=8.4 Hz, 1H), 6.31 (s, 1H), 5.27 (s, 2H), 4.51-4.59 (m, 2H), 2.98 (t, J=7.5 Hz, 2H), 2.72-2.79 (m, 2H), 2.63 (t, J=7.5 Hz, 2H), 2.24 (s, 3H), 2.15 (s, 3H), 1.28-1.36 (m, 9H). Mass spectrum (ESI, m/z): Calculated for $C_{25}H_{29}ClO_5$, 443 (M−H). found 443.

Example 40

3-{4-[(6-Ethoxy-2-ethyl-1-benzofuran-7-yl)methoxy]-2,3-dimethylphenyl}propanoic acid

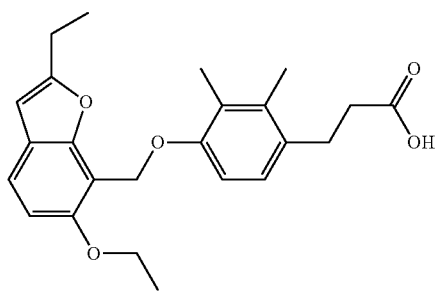 [SMILES: CCOc1ccc2cc(CC)oc2c1COc1ccc(CCC(=O)O)c(C)c1C]

a) Methyl 5-chloro-6-ethoxy-2-ethylbenzofuran-7-carboxylate

Into a 8-mL vial was placed methyl 5-chloro-2-ethyl-6-hydroxy-1-benzofuran-7-carboxylate (100 mg, 0.39 mmol), acetone (2 mL), bromoethane (0.5 mL) and Cs$_2$CO$_3$ (639 mg, 1.96 mmol) and the resulting solution was stirred overnight at 60° C. The reaction was then quenched by the addition of water (5 mL). The resulting solution was extracted with ethyl acetate (2×5 mL) and the organic layers combined and concentrated under vacuum. The resulting residue was purified on a silica gel column with P/E (30/1-20/1) to yield methyl 5-chloro-6-ethoxy-2-ethyl-1-benzofuran-7-carboxylate as yellow oil.

b) (6-Ethoxy-2-ethylbenzofuran-7-yl)methanol

To a solution of methyl 5-chloro-6-ethoxy-2-ethyl-1-benzofuran-7-carboxylate (100 mg, 0.35 mmol) in tetrahydrofuran (3 mL) was added LAH (40 mg, 1.05 mmol) in several batches. The resulting solution was stirred for 2 h at 25° C. The reaction was then quenched by the addition of Na$_2$SO$_4$.10H$_2$O (1 g). The solids were filtered out. The resulting mixture was concentrated under vacuum. The resulting residue was purified on a silica gel column with ethyl acetate/petroleum ether (1/30-1/5) to yield (5-chloro-6-ethoxy-2-ethyl-1-benzofuran-7-yl)methanol and (6-ethoxy-2-ethylbenzofuran-7-yl)methanol as yellow oil.

c) 3-{4[(6-Ethoxy-2-ethyl-1-benzofuran-7-yl)methoxy]-2,3-dimethylphenyl}propanoic acid The title compound was prepared by reacting (6-ethoxy-2-ethylbenzofuran-7-yl)methanol according to Example 1.

$^1$H NMR: (300 MHz, CDCl$_3$) δ: 7.35 (d, J=8.4 Hz, 1H), 7.01 (s, 2H), 6.85 (d, J=8.4 Hz, 1H), 6.30 (s, 1H), 5.33 (s, 2H), 4.08-4.15 (m, 2H), 2.96 (t, J=7.5 Hz, 2H), 2.73-2.80 (m, 2H), 2.61 (t, J=7.5 Hz, 2H), 2.22 (s, 3H), 2.17 (s, 3H), 1.38-1.43 (t, J=6.9 Hz, 3H), 1.31 (t, J=7.5 Hz, 3H). Mass spectrum (ESI, m/z): Calculated for $C_{24}H_{28}O_5$, 395 (M−H). found 395.

Example 41

3-(4-{[5-Chloro-2-ethyl-6-(2-methylpropoxy)-1-benzofuran-7-yl]methoxy}-2,3-dimethylphenyl)propanoic acid

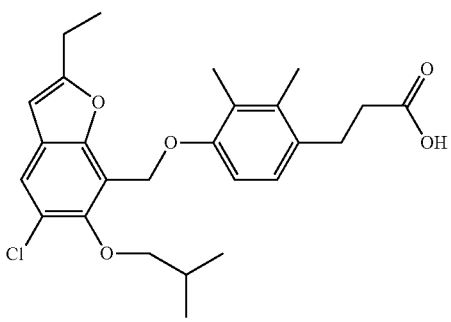 [SMILES: CCc1cc2cc(Cl)c(OCC(C)C)c(COc3ccc(CCC(=O)O)c(C)c3C)c2o1]

The title compound was prepared according to procedure as described in Example 36 substituting 1-bromo-2-methylpropane for bromoethane.

$^1$H NMR: (300 MHz, CDCl$_3$) δ: 7.48 (s, 1H), 6.94-7.05 (m, 2H), 6.31 (s, 1H), 5.28 (s, 2H), 3.82 (d, J=6.6 Hz, 1H), 2.97 (t, J=7.2 Hz, 2H), 2.73-2.80 (m, 2H), 2.64 (t, J=7.5 Hz, 2H), 2.23 (s, 3H), 2.15 (s, 3H), 1.31 (t, J=7.5 Hz, 3H), 1.02 (d, J=6.9 Hz, 6H). Mass spectrum (ESI, m/z): Calculated for $C_{26}H_{31}ClO_5$, 457 (M−H). found 457.

Example 42

3-(4-{[6-(Benzyloxy)-5-chloro-2-ethyl-1-benzofuran-7-yl]methoxy}-2,3-dimethylphenyl)propanoic acid

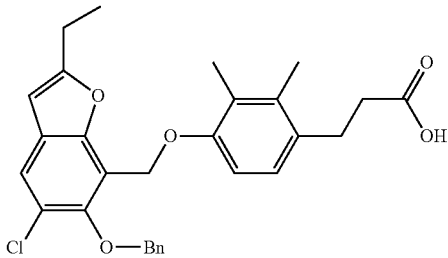 [SMILES: CCc1cc2cc(Cl)c(OCc3ccccc3)c(COc3ccc(CCC(=O)O)c(C)c3C)c2o1]

The title compound was prepared according to procedure as described in Example 36 substituting benzyl bromide for bromoethane. $^1$H NMR: (300 MHz, CDCl$_3$) δ: 7.53 (s, 1H), 7.42-7.45 (m, 2H), 7.32-7.34 (m, 2H), 7.01 (d, J=8.7 Hz, 1H), 6.89 (d, J=8.1 Hz, 1H), 6.34 (s, 1H), 5.25 (s, 2H), 5.08 (s, 2H), 2.97 (t, J=7.8 Hz, 2H), 2.74-2.82 (m, 2H), 2.62 (t, J=7.5 Hz, 2H), 2.22 (s, 3H), 2.14 (s, 3H), 1.32 (t, J=7.5 Hz, 3H). Mass spectrum (ESI, m/z): Calculated for C$_{29}$H$_{29}$ClO$_5$, 491 (M−H). found 491.

Example 43

3-(4-{[5-Chloro-6-(difluoromethoxy)-2-ethyl-1-benzofuran-7-yl]methoxy}-2,3-dimethylphenyl)propanoic acid

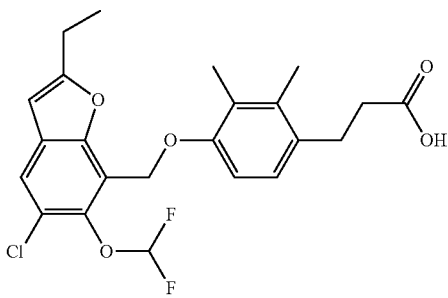 [SMILES: CCc1cc2cc(Cl)c(OC(F)F)c(COc3ccc(CCC(=O)O)c(C)c3C)c2o1]

a) Methyl 5-chloro-6-(difluoromethoxy)-2-ethylbenzofuran-7-carboxylate

Into a 25-mL round-bottom flask purged and maintained with an inert atmosphere of CF$_2$Cl was placed methyl 5-chloro-2-ethyl-6-hydroxy-1-benzofuran-7-carboxylate (100 mg, 0.39 mmol, prepared as described in Example 20, step(e)), 1,4-dioxane (3 mL), a solution of sodium hydroxide (47 mg, 1.18 mmol) in water (0.2 mL) and tetrabutylammonium iodide (145 mg, 0.39 mmol). The resulting solution was stirred overnight at 25° C. The resulting mixture was concentrated under vacuum. The resulting residue was purified on a silica gel column with P/E (30/1-20/1) to yield methyl 5-chloro-6-(difluoromethoxy)-2-ethyl-1-benzofuran-7-carboxylate as yellow oil.

b) 3-(4-{[5-Chloro-6-(difluoromethoxy)-2-ethyl-1-benzofuran-7-yl]methoxy}-2,3-dimethylphenyl)propanoic acid The title compound was prepared according to procedure as described in Example 1 using methyl 5-chloro-6-(difluoromethoxy)-2-ethyl-1-benzofuran-7-carboxylate.

$^1$H NMR: (300 MHz, CDCl$_3$) δ: 7.56 (s, 1H), 7.04 (d, J=8.4 Hz, 1H), 6.94 (d, J=8.4 Hz, 1H), 6.61 (t, J=74.7 Hz, 1H), 6.36 (s, 1H), 5.33 (s, 2H), 2.97 (t, J=7.5 Hz, 2H), 2.76-2.83 (m, 2H), 2.62 (t, J=7.5 Hz, 2H), 2.23 (s, 3H), 2.15 (s, 3H), 1.32 (t, J=7.5 Hz, 3H). Mass spectrum (ESI, m/z): Calculated for C$_{23}$H$_{23}$ClF$_2$O$_5$, 451 (M−H). found 451.

Example 44

3-(4-{[6-(Difluoromethoxy)-2-ethyl-1-benzofuran-7-yl]methoxy}-2,3-dimethylphenyl)propanoic acid

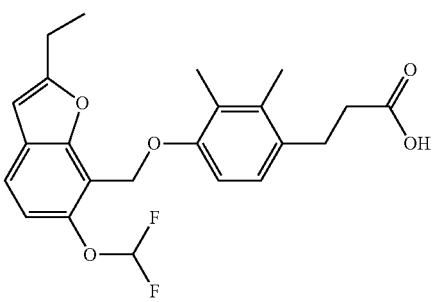 [SMILES: CCc1cc2ccc(OC(F)F)c(COc3ccc(CCC(=O)O)c(C)c3C)c2o1]

a) (6-(Difluoromethoxy)-2-ethylbenzofuran-7-yl)methanol

To a solution of methyl 5-chloro-6-(difluoromethoxy)-2-ethyl-1-benzofuran-7-carboxylate (80 mg, 0.26 mmol) in tetrahydrofuran (3 mL) was added LAH (30 mg, 0.79 mmol) in several batches. The resulting solution was stirred for 2 h at 25° C. The reaction was then quenched by the addition of Na$_2$SO$_4$.10H$_2$O (1 g). The solids were filtered out. The resulting mixture was concentrated under vacuum. The resulting residue was purified on a silica gel column with ethyl acetate/petroleum ether (1/30-1/5) to yield [5-chloro-6-(difluoromethoxy)-2-ethyl-1-benzofuran-7-yl]methanol and (6-(difluoromethoxy)-2-ethylbenzofuran-7-yl)methanol as yellow oil.

b) 3-(4-{[6-(Difluoromethoxy)-2-ethyl-1-benzofuran-7-yl]methoxy}-2,3-dimethylphenyl)propanoic acid The title compound was prepared according to procedure as described in Example 1 using (6-(difluoromethoxy)-2-ethylbenzofuran-7-yl)methanol.

$^1$H NMR: (300 MHz, CDCl$_3$) δ: 7.44 (d, J=8.4 Hz, 1H), 6.95-7.10 (m, 3H), 6.51 (t, J=74.9 Hz, 1H), 6.39 (s, 1H), 5.32 (s, 2H), 2.96 (t, J=7.5 Hz, 2H), 2.76-2.84 (m, 2H), 2.62 (t, J=7.5 Hz, 2H), 2.23 (s, 3H), 2.15 (s, 3H), 1.33 (t, J=7.5

Hz, 3H). Mass spectrum (ESI, m/z): Calculated for $C_{23}H_{24}F_2O_5$, 418 (M−H). found 418.

Example 45

3-(2,3-Dimethyl-4-{[2-propyl-5-(3,3,3-trifluoroprop-1-yn-1-yl)-1-benzofuran-7-yl]methoxy}phenyl)propanoic acid

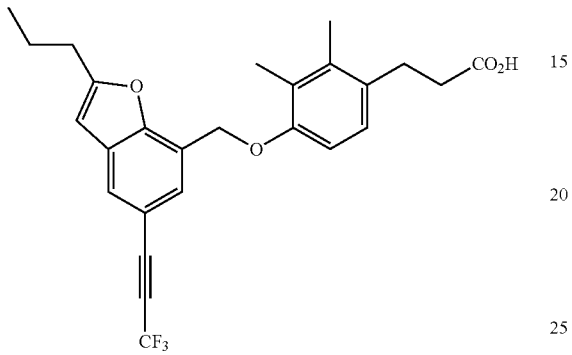

a) Ethyl 3-(2,3-dimethyl-4-((2-propyl-5-(3,3,3-trifluoroprop-1-yn-1-yl)benzofuran-7-yl)methoxy)phenyl)propanoate To a solution of disopropylamine (128 mg) in tetrahydrofuran (10 mL) at −78° C. was added n-BuLi (0.5 mL, 2.5N) and the resulting solution was stirred for 15 min. To this solution was added 2-bromo-3,3,3-trifluoroprop-1-ene (100.6 mg, 0.58 mmol), and $ZnCl_2$.TMEDA (159 mg), and the mixture was stirred for 30 min at −78° C. Ethyl 3-[4-[(5-iodo-2-propyl-1-benzofuran-7-y)methoxy]-2,3-dimethylphenyl]propanoate (200 mg, 0.38 mmol, prepared as described in Example 18) and $Pd(PPh_3)_4$ (22 mg, 0.02 mmol) were then added and the mixture stirred for 30 min at room temperature and then at 80° C. overnight. The resulting mixture was concentrated under vacuum, diluted with ethyl acetate (40 mL), and washed with brine (3×10 mL). The resulting residue was dried over anhydrous sodium sulfate and concentrated under vacuum. The resulting residue was purified on a silica gel column with ethyl acetate/petroleum ether (1:5) to yield ethyl 3-(2,3-dimethyl-4-((2-propyl-5-(3,3,3-trifluoroprop-1-yn-1-yl)benzofuran-7-yl)methoxy)phenyl)propanoate.

b) 3-(2,3-Dimethyl-4-{[2-propyl-5-(3,3,3-trifluoroprop-1-yn-1-yl)-1-benzofuran-7-yl]methoxy}phenyl)propanoic acid The title compound was prepared by hydrolysis of the ester prepared in step (b) above according to the procedure as described in Example 1.

$^1$H NMR: (400 MHz, $CD_3OD$) δ 7.79 (s, 1H), 7.56 (s, 1H), 6.99 (d, J=8.4 Hz, 1H), 6.85 (d, J=8.4 Hz, 1H), 6.61 (s, 1H), 5.33 (s, 2H), 2.91 (t, J=8.0 Hz, 2H), 2.82 (t, J=7.6 Hz, 2H), 2.51 (t, J=8.0 Hz, 2H), 2.25 (s, 3H), 1.86-1.63 (m, 2H), 1.08 (t, J=7.2 Hz, 3H). Mass spectrum (ESI, m/z): Calculated for $C_{26}H_{25}F_3O_4$, 457 (M−H). found 457.

Example 46

3-{4-[(5-Chloro-2-ethyl-6-phenoxy-1-benzofuran-7-yl)methoxy]-2,3-dimethylphenyl}propanoic acid

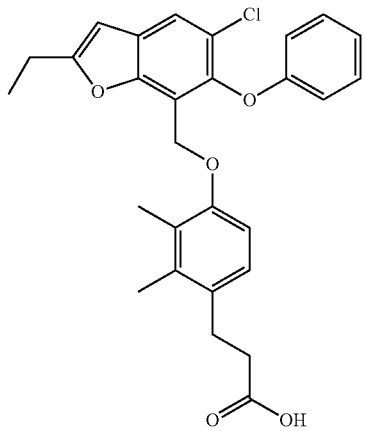 [SMILES: CCc1cc2cc(Cl)c(Oc3ccccc3)c(COc3ccc(CCC(=O)O)c(C)c3C)c2o1]

a) Methyl 5-chloro-2-ethyl-6-phenoxybenzofuran-7-carboxylate

Into a 25-mL round-bottom flask purged and maintained with an inert atmosphere of nitrogen, was placed methyl 5-chloro-2-ethyl-6-hydroxy-1-benzofuran-7-carboxylate (300 mg, 1.18 mmol, prepared in Example 20 step f), $CH_3CN$ (8 mL), 2-(trimethylsilyl)phenyl trifluoromethanesulfonate (703 mg, 2.36 mmol), and CsF (535 mg, 3.54 mmol) the resulting mixture was heated to reflux overnight. The reaction was then quenched by the addition of water (10 mL). The resulting solution was extracted with ethyl acetate (2×10 mL) acetate and the organic layers combined and concentrated under vacuum. The resulting residue was purified on a silica gel column with P/E (30/1-10/1) to yield methyl 5-chloro-2-ethyl-6-phenoxy-1-benzofuran-7-carboxylate as yellow oil.

b) 3-{4-[(5-Chloro-2-ethyl-6-phenoxy-1-benzofuran-7-yl)methoxy]-2,3-dimethylphenyl}propanoic acid The title compound was prepared by reacting methyl 5-chloro-2-ethyl-6-phenoxy-1-benzofuran-7-carboxylate according to the procedure as described in Example 1.

$^1$H NMR: (300 MHz, $CDCl_3$) δ: 7.57 (s, 1H), 721-7.27 (m, 2H), 6.92-7.01 (m, 2H), 6.78-6.84 (m, 3H), 6.38 (s, 1H), 5.16 (s, 2H), 2.92 (t, J=7.5 Hz, 2H), 2.77-2.84 (m, 2H), 2.57 (t, J=7.5 Hz, 2H), 2.20 (s, 3H), 2.11 (s, 3H), 1.34 (t, J=7.5 Hz, 3H). Mass spectrum (ESI, m/z): Calculated for $C_{28}H_{27}ClO_5$, 501 (M+Na). found 501.

Example 47

3-(4-{[5-(Difluoromethoxy)-2-methyl-1-benzofuran-7-yl]methoxy}-2,3-dimethylphenyl)propanoic acid

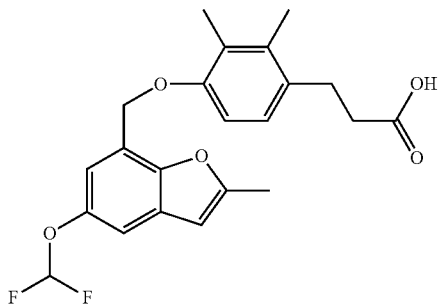 [SMILES: Cc1cc2cc(OC(F)F)cc(COc3ccc(CCC(=O)O)c(C)c3C)c2o1]

a) Methyl 5-methoxy-2-methylbenzofuran-7-carboxylate

Into a 150-mL sealed tube was placed methyl 3-bromo-2-hydroxy-5-methoxybenzoate (3.0 g, 11.49 mmol, prepared as described in Example 33 step a), Pd(PPh$_3$)$_2$Cl$_2$ (0.805 g), CuI (219 mg, 1.15 mmol), TEA (2.33 g, 23.03 mmol) and N,N-dimethylformamide (50 mL). The resulting residue was cooled to −78° C. and prop-1-yne (923 mg, 23.04 mmol) was introduced. The resulting mixture was stirred overnight at 80° C. The resulting solution was diluted with EtOAc and washed with brine (3×50 mL). The resulting residue was dried over anhydrous sodium sulfate, concentrated, and the residue was purified by silica gel chromatography to yield methyl 5-methoxy-2-methyl-1-benzofuran-7-carboxylate as a yellow solid.

b) Methyl 5-hydroxy-2-methylbenzofuran-7-carboxylate

Into a 50-mL 3-necked round-bottom flask purged and maintained with an inert atmosphere of nitrogen, was placed methyl 5-methoxy-2-methyl-1H-indene-7-carboxylate (500 mg, 2.29 mmol), dichloromethane (20 mL). To the resulting mixture was then added BBr$_3$ (1.13 g) at −78° C. The resulting solution was stirred for 30 min at room temperature. The reaction was then quenched by the addition of water (5 mL). The resulting solution was diluted with DCM (30 mL). The resulting mixture was washed with brine (3×10 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield methyl 5-hydroxy-2-methyl-1H-indene-7-carboxylate as a yellow solid.

c) Methyl 5-(difluoromethoxy)-2-methylbenzofuran-7-carboxylate

Into a 50-mL round-bottom flask purged and maintained with an inert atmosphere of chlorodifluoromethane was placed methyl 5-hydroxy-2-methyl-1-benzofuran-7-carboxylate (310 mg, 1.50 mmol), 1,4-dioxane (10 mL), water (1 mL), sodium hydroxide (182.4 mg, 4.56 mmol) and tetrabutylammonium iodide (561 mg, 1.52 mmol). The resulting solution was stirred overnight at room temperature. The resulting mixture was concentrated under vacuum. The resulting solution was diluted with ethyl acetate (50 mL). The resulting mixture was washed with brine (3×10 mL). The solid was dried in an oven under reduced pressure. The solids were filtered out. The resulting mixture was concentrated under vacuum. The resulting residue was purified on a silica gel column with ethyl acetate/petroleum ether (1:4) to yield methyl 5-(difluoromethoxy)-2-methyl-1-benzofuran-7-carboxylate as a light yellow solid.

d) 3-(4-{[5-(Difluoromethoxy)-2-methyl-1-benzofuran-7-yl]methoxy}-2,3-dimethylphenyl)propanoic acid The title compound was prepared by reacting methyl 5-(difluoromethoxy)-2-methylbenzofuran-7-carboxylate according to Example 1.

$^1$H NMR: (400 MHz, CD$_3$Cl) δ: 7.19 (d, J=4.8 Hz, 2H), 7.01 (d, J=8.0 Hz, 1H), 6.82 (d, J=11.2 Hz, 1H), 6.50 (t, J=74.4 Hz, 1H), 6.41 (s, 1H), 5.32 (s, 2H), 2.98 (t, J=8.0 Hz, 2H), 2.62 (t, J=8.0 Hz, 2H), 2.49 (s, 3H), 2.27 (s, 6H). Mass spectrum (ESI, m/z): Calculated for C$_{22}$H$_{22}$F$_2$O$_5$, 403 (M−H). found 403.

Example 48

3-(4-{[5-(Difluoromethoxy)-2-propyl-1-benzofuran-7-yl]methoxy}-2,3-dimethylphenyl)propanoic acid

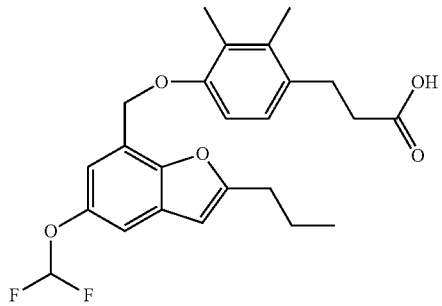 [SMILES: CCCc1cc2cc(OC(F)F)cc(COc3ccc(CCC(=O)O)c(C)c3C)c2o1]

The title compound was prepared according to the procedure as described in Example 47 substituting pent-1-yne for prop-1-yne in step (a).

$^1$H NMR: (300 MHz, CD$_3$Cl) δ: 7.19 (d, J=5.4 Hz, 2H), 6.99 (d, J=8.4 Hz, 1H), 6.82 (d, J=8.4 Hz, 1H), 6.49 (d, J=74.4 Hz, 1H), 6.41 (s, 1H), 5.31 (s, 2H), 2.96 (t, J=7.5 Hz, 2H), 2.76 (t, J=7.5 Hz, 2H), 2.61 (t, J=7.8 Hz, 2H), 2.25 (s, 6H), 1.82-1.75 (m, 2H), 1.02 (t, J=7.5 Hz, 3H). Mass spectrum (ESI, m/z): Calculated for C$_{24}$H$_{26}$F$_2$O$_5$, 431 (M−H). found 431.

Example 49

3-{4-[(5-Chloro-2-methyl-1-benzofuran-7-yl)methoxy]-2,3-dimethylphenyl}propanoic acid

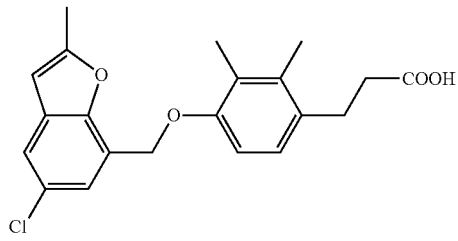 [SMILES: Cc1cc2cc(Cl)cc(COc3ccc(CCC(=O)O)c(C)c3C)c2o1]

a) Methyl 3-bromo-5-chloro-2-hydroxybenzoate

Into a 1-L round-bottom flask was placed methyl 5-chloro-2-hydroxybenzoate (16 g, 85.75 mmol), methanol (200 mL) and Br$_2$ (16.5 g, 103.25 mmol) and the resulting mixture was stirred for 10 min at 20° C. The solids were collected by filtration, then washed with methanol to yield methyl 3-bromo-5-chloro-2-hydroxybenzoate as a white powder.

b) Methyl 5-chloro-2-methylbenzofuran-7-carboxylate

Into a 80-mL tube was placed methyl 3-bromo-5-chloro-2-hydroxybenzoate (3 g, 11.30 mmol), Pd(Ph$_3$P)$_2$Cl$_2$ (0.791 g), CuI (215 mg, 1.13 mmol), TEA (2.28 g, 22.53 mmol), N,N-dimethylformamide (30 mL), and prop-1-yne (950 mg, 23.71 mmol). The resulting solution was stirred overnight at 80° C. The resulting mixture was extracted with ethyl acetate (100 mL), and the washed with brine. The resulting mixture was concentrated and the residue was purified on a silica gel column to yield methyl 5-chloro-2-methyl-1-benzofuran-7-carboxylate as a yellow solid.

c) 3-{4-[(5-Chloro-2-methyl-1-benzofuran-7-yl)methoxy]-2,3-dimethylphenyl}propanoic acid The title compound was prepared by reacting methyl 5-chloro-2-methyl-1-benzofuran-7-carboxylate according to the procedure as described in Example 1.

$^1$H NMR: (300 MHz, CD$_3$OD) δ: 7.39 (d, J=1.8, 1H), 7.24 (d, J=1.8, 1H), 6.93 (d, J=8.4 Hz, 1H), 6.77 (d, J=8.4 Hz, 1H), 6.44 (s, 1H), 5.24 (s, 2H), 2.89-2.83 (m, 2H), 2.48-2.43 (m, 5H), 2.20 (s, 3H), 2.17 (s, 3H). Mass spectrum (ESI, m/z): Calculated for C$_{21}$H$_{21}$ClO$_4$, 371 (M−H). found 371.

Example 50

3-(4-{[5-(1,1-Difluoroethyl)-2-propyl-1-benzofuran-7-yl]methoxy}-2,3-dimethylphenyl)propanoic acid

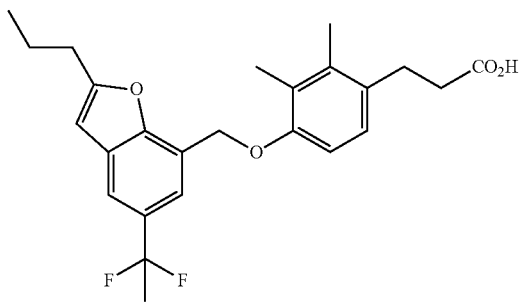 [SMILES: CCCc1cc2cc(C(C)(F)F)cc(COc3ccc(CCC(=O)O)c(C)c3C)c2o1]

a) Ethyl 3-(4-((5-acetyl-2-propylbenzofuran-7-yl)methoxy)-2,3-dimethylphenyl)propanoate Into a 5-mL flask was placed ethyl 3-[4-[(5-iodo-2-propyl-1-benzofuran-7-yl)methoxy]-2,3-dimethylphenyl]propanoate (20 mg, 0.04 mmol, prepared as described in Example 18), N,N-dimethylformamide (1 mL), LiCl (8 mg), DIPEA (10 mg), Pd$_2$(dba)$_3$ (0.5 mg), and acetyl acetate (20 mg, 0.20 mmol). The resulting mixture was irradiated with microwave radiation for 1 h at 150° C. The resulting solution was diluted with ethyl acetate (20 mL), and washed with brine (3×10 mL). The resulting residue was dried over anhydrous sodium sulfate and solids were filtered out. The resulting mixture was concentrated under vacuum and the residue was purified by silica gel chromatography to yield ethyl 3-[4-[(5-acetyl-2-propyl-1-benzofuran-7-yl)methoxy]-2,3-dimethylphenyl]propanoate as a white solid.

b) Ethyl 3-(4-((5-(1,1-difluoroethyl)-2-propylbenzofuran-7-yl)methoxy)-2,3-dimethylphenyl)propanoate Into a 8-mL vial purged and maintained with an inert atmosphere of nitrogen was placed ethyl 3-[4-[(5-acetyl-2-propyl-1-benzofuran-7-yl)methoxy]-2,3-dimethylphenyl]propanoate (170 mg, 0.39 mmol) and DAST (0.5 mL) in [C$_8$min][PF$_6$] (2 mL). The resulting solution was stirred overnight at 55° C. The resulting solution was diluted with ethyl acetate (50 mL). The resulting mixture was washed with brine (3×10 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield ethyl 3-(4-[[5-(1,1-difluoroethyl)-2-propyl-1-benzofuran-7-yl]methoxy]-2,3-dimethylphenyl)propanoate as colorless oil.

c) 3-(4-{[5-(1,1-Difluoroethyl)-2-propyl-1-benzofuran-7-yl]methoxy}-2,3-dimethylphenyl)propanoic acid Into a 8-mL vial was placed ethyl 3-(4-[[5-(1,1-difluoroethyl)-2-propyl-1-benzofuran-7-yl]methoxy]-2,3-dimethylphenyl)propanoate (30 mg, 0.07 mmol), LiOH (30 mg, 1.25 mmol), tetrahydrofuran (2 mL), and water (2 mL). The resulting solution was stirred overnight at room temperature. The resulting mixture was concentrated under vacuum. The pH of the solution was adjusted to pH 4-5 with hydrogen chloride (1 mol/L). The resulting solution was extracted with ethyl acetate (3×20 mL) and the organic layers combined and concentrated under vacuum to yield 2 3-(4-[[5-(1,1-difluoroethyl)-2-propyl-1-benzofuran-7-yl]methoxy]-2,3-dimethylphenyl)propanoic acid as a white solid.

$^1$H NMR: (400 MHz, CD$_3$Cl) δ 7.63 (s, 1H), 7.54 (s, 1H), 7.02 (t, J=4.8 Hz, 1H), 6.87 (d, J=8.4 Hz, 1H), 6.46 (s, 1H), 5.34 (s, 2H), 2.98 (t, J=8.0 Hz, 2H), 2.78 (t, J=7.6 Hz, 2H), 2.63 (t, J=5.4 Hz, 2H), 2.26 (d, J=4.4 Hz, 6H), 1.99 (t, J=18.0 Hz, 3H), 1.85-1.75 (m, 2H), 1.03 (t, J=7.2 Hz, 3H). Mass spectrum (ESI, m/z): Calculated for C$_{25}$H$_{28}$F$_2$O$_4$, 429 (M−H). found 429.

Example 51

3-{2,3-Dimethyl-4-[(6-methylfuro[2,3-f][1,3]benzodioxol-4-yl)methoxy]phenyl}propanoic acid

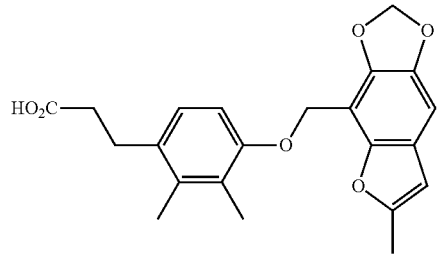 [SMILES: Cc1cc2cc3c(c(COc4ccc(CCC(=O)O)c(C)c4C)c2o1)OCO3]

a) 5-(Methoxymethoxy)benzo[d][1,3]dioxole

Into a 250-mL round-bottom flask was placed 2,3-dihydro-1,4-benzodioxin-6-ol (6 g, 39.44 mmol), tetrahydrofuran (100 mL). To the resulting mixture was then added sodium hydride (1.56 g, 65.00 mmol) at 0-5° C. The resulting residue was stirred for 30 min at 0° C. To the resulting mixture was then added bromo(methoxy)methane (8.08 g, 64.66 mmol). The resulting solution was stirred overnight at room temperature. The resulting mixture was concentrated under vacuum. The resulting solution was diluted with ethyl acetate (100 mL). The resulting mixture was washed with brine (3×50 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield 6-(methoxymethoxy)-2,3-dihydro-1,4-benzodioxine as colorless oil.

b) 5-(Methoxymethoxy)benzo[d][1,3]-dioxole-4-carbaldehyde

Into a 250-mL round-bottom flask purged and maintained with an inert atmosphere of nitrogen was placed 5-(methoxymethoxy)-2H-1,3-benzodioxole (6.6 g, 36.23 mmol), tetrahydrofuran (150 mL), BuLi (22 mL, 36.23 mmol), TMEDA (4.26 g, 36.66 mmol) and N,N-dimethylformamide (4.02 g). The resulting solution was stirred overnight at room temperature. The reaction was then quenched by the addition of water (1 mL). The resulting mixture was concentrated under vacuum. The resulting solution was diluted with ethyl acetate (200 mL). The resulting mixture was washed with brine (3×40 mL). The solid was dried in an oven under reduced pressure. The solids were filtered out. The resulting mixture was concentrated under vacuum. The resulting residue was purified on a silica gel column with ethyl acetate/petroleum ether (1:3) to yield 5-(methoxymethoxy)-2H-1,3-benzodioxole-4-carbaldehyde as a yellow solid.

c) 5-Hydroxybenzo[d][1,3]-dioxole-4-carbaldehyde

Into a 250-mL round-bottom flask was placed 5-(methoxymethoxy)-2H-1,3-benzodioxole-4-carbaldehyde (7 g, 33.30 mmol), dichloromethane (100 mL) and trifluoroacetic acid (5 mL). The resulting solution was stirred for 1 h at 0° C. The resulting solution was diluted with DCM (100 mL). The resulting mixture was washed with brine (3×50 mL). The resulting residue was dried over anhydrous sodium sulfate. The solids were filtered out. The resulting mixture was concentrated under vacuum. The resulting residue was purified on a silica gel column with ethyl acetate/petroleum ether (1:1) to yield 5-hydroxy-2H-1,3-benzodioxole-4-carbaldehyde as colorless oil.

d) 6-Bromo-5-hydroxybenzo[d][1,3]-dioxole-4-carbaldehyde

Into a 250-mL round-bottom flask was placed 5-hydroxy-2H-1,3-benzodioxole-4-carbaldehyde (3.1 g, 18.66 mmol), methanol (150 mL) and Br$_2$ (3.53 g, 22.09 mmol). The resulting solution was stirred for 30 min at room temperature. The resulting mixture was concentrated under vacuum. The resulting solution was diluted with ethyl acetate (150 mL). The resulting mixture was washed with Na$_2$SO$_3$ (3×40 mL). The resulting residue was dried over anhydrous sodium sulfate. The resulting mixture was concentrated under vacuum. The resulting residue was purified on a silica gel column with ethyl acetate/petroleum ether (1:2) to yield 6-bromo-5-hydroxy-2H-1,3-benzodioxole-4-carbaldehyde as a yellow solid.

e) 6-Methyl-[1,3]dioxolo[4,5-f]benzofuran-4-carbaldehyde

Into a 100-mL sealed tube was placed 6-bromo-5-hydroxy-2H-1,3-benzodioxole-4-carbaldehyde (1.1 g, 4.49 mmol), N,N-dimethylformamide (30 mL), CuI (85 mg, 0.45 mmol), TEA (907 mg, 8.96 mmol) and Pd(PPh$_3$)$_2$Cl$_2$ (314 mg, 0.45 mmol). To the resulting mixture was then added prop-1-yne (359 mg, 8.96 mmol) at −78° C. The resulting solution was stirred overnight at 80° C. in an oil bath. The resulting solution was diluted with ethyl acetate (100 mL). The resulting mixture was washed with sodium chloride(aq) (3×20 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield 6-methyl-[1,3]dioxolo[4,5-f]benzofuran-4-carbaldehyde as colorless oil.

f) (6-Methyl-[1,3]dioxolo[4,5-f]benzofuran-4-yl)methanol

Into a 8-mL vial was placed 6-methyl-[1,3]dioxolo[4,5-f]benzofuran-4-carbaldehyde (50 mg, 0.24 mmol), tetrahydrofuran (2 mL) and LiAlH$_4$ (28 mg, 0.74 mmol) at 0-5° C. The resulting solution was stirred for 30 min at 0° C. The reaction was then quenched by the addition of water (1 mL). The resulting solution was diluted with ethyl acetate (20 mL). The resulting mixture was washed with brine (3×10 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield (6-methyl-[1,3]dioxolo[4,5-f]benzofuran-4-yl)methanol as a yellow solid.

g) 3-{2,3-Dimethyl-4-[(6-methylfuro[2,3-f][1,3]benzodioxol-4-yl)methoxy]phenyl}propanoic acid The title compound was prepared by reacting 6-methyl-[1,3]dioxolo[4,5-f]benzofuran-4-yl)methanol according to the procedures as described in Example 1.
$^1$H NMR: (300 MHz, CDCl$_3$) δ: 7.01 (d, J=8.4 Hz, 1H), 6.93 (d, J=8.4 Hz, 1H), 6.85 (s, 1H), 6.27 (s, 1H), 6.00 (s, 2H), 5.27 (s, 2H), 2.96 (t, J=7.5 Hz, 2H), 2.64-2.59 (m, 2H), 2.42 (s, 3H), 2.24 (s, 3H), 2.20 (s, 3H). Mass spectrum (ESI, m/z): Calculated for C$_{22}$H$_{22}$O$_6$, 381 (M−H). found 381.

Example 52

3-{2,3-Dimethyl-4-[(2-methyl-5-prop-1-yn-1-yl-1-benzofuran-7-yl)methoxy]phenyl}propanoic acid

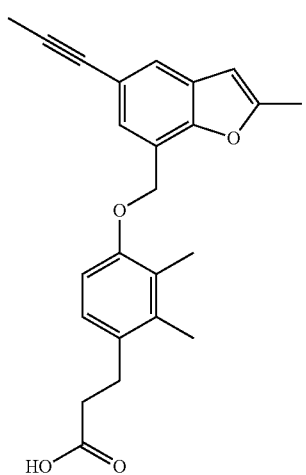 [SMILES: CC#Cc1cc(COc2ccc(CCC(=O)O)c(C)c2C)c2oc(C)cc2c1]

a) 2-Methyl-5-(prop-1-yn-1-yl)benzofuran-7-carbaldehyde

Into a 5-mL sealed tube was placed 2-hydroxy-3,5-diiodobenzaldehyde (500 mg, 1.34 mmol), $Cu_2O$ (115 mg, 0.80 mmol) and pyridine (3 mL). This was followed by the addition of prop-1-yne (160 mg, 3.99 mmol) dropwise with stirring at −78° C. The resulting solution was stirred overnight at 120° C. The resulting solution was diluted with ethyl acetate (20 mL). The solids were filtered out. The resulting mixture was concentrated under vacuum. The resulting residue was purified on a silica gel column with ethyl acetate/petroleum ether (10/90). The collected fractions were combined and concentrated under vacuum to yield 2-methyl-5-(prop-1-yn-1-yl)-1-benzofuran-7-carbaldehyde as colorless oil.

b) (2-Methyl-5-(prop-1-yn-1-yl)benzofuran-7-yl)methanol

Into a 100-mL round-bottom flask was placed 2-methyl-5-(prop-1-yn-1-yl)-1-benzofuran-7-carbaldehyde (50 mg, 0.25 mmol), tetrahydrofuran (10 mL) and LAH (19 mg, 0.50 mmol) in portions at 0° C. The resulting solution was stirred for 2 h at 25° C. The reaction was then quenched by the addition of $Na_2SO_4 \cdot 10H_2O$ (100 mg). The solids were filtered out. The resulting mixture was concentrated under vacuum. The resulting residue was purified on a silica gel column with ethyl acetate/petroleum ether (40/60). The collected fractions were combined and concentrated under vacuum to yield (2-methyl-5-(prop-1-yn-1-yl)benzofuran-7-yl)methanol as colorless oil.

c) 3-{2,3-Dimethyl-4-[(2-methyl-5-prop-1-yn-1-yl-1-benzofuran-7-yl)methoxy]phenyl}propanoic acid Into a 100-mL round-bottom flask purged and maintained with an inert atmosphere of nitrogen was placed (2-methyl-5-(prop-1-yn-1-yl)benzofuran-7-yl)methanol (70 mg, 0.35 mmol), ethyl 3-(4-hydroxy-2,3-dimethylphenyl)propanoate (116 mg, 0.52 mmol), $Bu_3P$ (177 mg), ADDP (185 mg, 0.74 mmol) and toluene (30 mL). The resulting solution was stirred overnight at 60° C. The resulting mixture was concentrated under vacuum. The resulting solution was diluted with diethyl ether (30 mL). The solids were filtered out. The resulting mixture was concentrated under vacuum. The resulting residue was purified on a silica gel column with ethyl acetate/petroleum ether (10/90). The collected fractions were combined and concentrated under vacuum to yield ethyl 3-(2,3-dimethyl-4-[[2-methyl-5-(prop-1-yn-1-yl)-1-benzofuran-7-yl]methoxy]phenyl)propanoate as colorless oil.

$^1$H NMR: (300 MHz, $CD_3OD$) δ: 7.44 (s, 1H), 7.30 (s, 1H), 6.98 (d, J=6.3 Hz, 1H), 6.83 (d, J=6.3 Hz, 1H), 6.45 (s, 1H), 5.26 (s, 2H), 2.91 (t, J=5.7 Hz, 2H), 2.51 (t, J=6 Hz, 2H), 2.47 (s, 3H), 2.28 (s, 3H), 2.25 (s, 3H), 2.02 (s, 3H). Mass spectrum (ESI, m/z): Calculated for $C_{24}H_{24}O_4$, 375 (M−H). found 375.

Example 53

3-{4-[(5-Chloro-2,6-dimethyl-1-benzofuran-7-yl)methoxy]-2,3-dimethylphenyl}propanoic acid

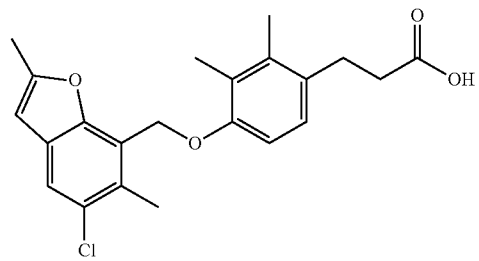 [SMILES: Cc1cc2cc(Cl)c(C)c(COc3ccc(CCC(=O)O)c(C)c3C)c2o1]

The title compound was prepared according to the procedure as described in Example 20 substituting prop-1-yne for but-1-yne in step (d).

$^1$H NMR: (300 MHz, $CDCl_3$) δ: 7.62 (s, 1H), 6.93-7.05 (m, 2H), 6.32 (s, 1H), 5.32 (s, 2H), 2.98 (t, J=7.2 Hz, 2H), 2.63 (t, J=8.4 Hz, 2H), 2.51 (s, 3H), 2.45 (s, 3H), 2.24 (s, 3H), 2.15 (s, 3H). Mass spectrum (ESI, m/z): Calculated for $C_{22}H_{23}ClO_4$, 385 (M−H). found 385.

Example 54

3-{4-[(5-Chloro-2,6-dimethyl-1-benzofuran-7-yl)methoxy]-3,5-difluorophenyl}propanoic acid

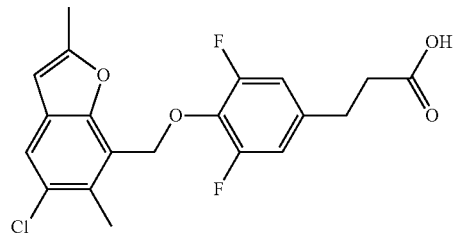 [SMILES: Cc1cc2cc(Cl)c(C)c(COc3c(F)cc(CCC(=O)O)cc3F)c2o1]

The title compound was prepared according to the procedure as described in Example 53 substituting ethyl 3-(3,5-difluoro-4-hydroxyphenyl)propanoate (prepared as described in U.S. Pat. Appl. Publ., 20110313003, 22 Dec. 2011) for ethyl 3-(4-hydroxy-2,3-dimethylphenyl)propanoate.

$^1$H NMR: (300 MHz, $CD_3OD$) δ: 7.49 (s, 1H), 6.84 (d, J=9.3 Hz, 2H), 6.36 (s, 1H), 5.47 (s, 2H), 2.84 (t, J=7.5 Hz, 2H), 2.54-2.59 (m, 5H), 2.39 (s, 3H). Mass spectrum (ESI, m/z): Calculated for $C_{20}H_{17}ClF_2O_4$, 393 (M−H). found 393.

Example 55

3-{4-[(2,2-Difluoro-6-methylfuro[2,3-f][1,3]benzo-dioxol-4-yl)methoxy]-2,3-dimethylphenyl}propanoic acid

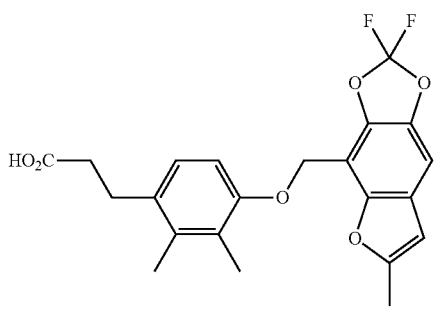 [SMILES: Cc1cc2cc3c(c(COc4ccc(CCC(=O)O)c(C)c4C)c2o1)OC(F)(F)O3]

a) 2,2-Difluorobenzo[d][1,3]dioxol-5-ol

Into a 250-mL round-bottom flask was placed (2,2-difluoro-2H-1,3-benzodioxol-5-yl)boronic acid (5 g, 24.76 mmol), $H_2O_2$ (50 mL) and tetrahydrofuran (100 mL). The resulting solution was stirred overnight at room temperature. The resulting mixture was concentrated under vacuum. The resulting solution was extracted with ethyl acetate (3×30 mL) acetate and the organic layers combined and concentrated under vacuum. The resulting residue was purified on a silica gel column with ethyl acetate/petroleum ether (1:1) to yield 2,2-difluoro-2H-1,3-benzodioxol-5-ol as yellow oil.

b) 2,2-Difluoro-5-(methoxymethoxy)benzo[d][1,3] dioxole

Into a 250-mL round-bottom flask was placed 2,2-difluoro-2H-1,3-benzodioxol-5-ol (4.2 g, 24.12 mmol), tetrahydrofuran (100 mL) and sodium hydride (1.5 g, 62.50 mmol) and the mixture was stirred for 1 hr at 0° C. Bromo(methoxy)methane (4.49 g, 35.93 mmol) was then added and the resulting solution was stirred overnight at room temperature. The reaction was then quenched by the addition of water (5 mL). The resulting mixture was concentrated under vacuum. The resulting solution was diluted with ethyl acetate (100 mL). The resulting mixture was washed with brine (3×30 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield 2,2-difluoro-5-(methoxymethoxy)-2H-1,3-benzodioxole as yellow oil.

c) 2,2-Difluoro-5-(methoxymethoxy)benzo[d][1,3] dioxole-4-carbaldehyde

Into a 250-mL round-bottom flask purged and maintained with an inert atmosphere of nitrogen was placed 2,2-difluoro-5-(methoxymethoxy)-2H-1,3-benzodioxole (4.4 g, 20.17 mmol), tetrahydrofuran (50 mL). To the resulting mixture was then added n-BuLi (18.9 mL) and the mixture was stirred for 15 min at −78° C. To the resulting mixture was then added TMEDA (2.3 g, 19.79 mmol) and N,N-dimethylformamide (2.2 g, 30.10 mmol) and the resulting solution was stirred overnight at room temperature. The reaction was then quenched by the addition of water (1 mL). The resulting mixture was concentrated under vacuum. The resulting solution was diluted with ethyl acetate (150 mL). The resulting mixture was washed with brine (3×40 mL). The resulting residue was dried over anhydrous sodium sulfate. The solids were filtered out. The resulting mixture was concentrated under vacuum. The resulting residue was purified on a silica gel column with ethyl acetate/petroleum ether (1:2) to yield 2,2-difluoro-5-(methoxymethoxy)-2H-1,3-benzodioxole-4-carbaldehyde as yellow oil.

d) 2,2-Difluoro-5-(methoxymethoxy)benzo[d][1,3] dioxole-4-carboxylic acid

Into a 250-mL round-bottom flask was placed 2,2-difluoro-5-(methoxymethoxy)-2H-1,3-benzodioxole-4-carbaldehyde (4.0 g, 16.25 mmol), $Ag_2O$ (5.6 g) and sodium hydroxide (5% aq) (100 mL). The resulting solution was stirred overnight at room temperature. The solids were filtered out. The pH value of the solution was adjusted to pH 2-3 with hydrogen chloride (6 mol/L). The resulting solution was extracted with ethyl acetate (3×50 mL) and the organic layers combined and dried over anhydrous sodium sulfate. The solids were filtered out. The resulting mixture was concentrated under vacuum. The resulting residue was purified on a silica gel column with ethyl acetate/petroleum ether (1:1) to yield 2,2-difluoro-5-(methoxymethoxy)-2H-1,3-benzodioxole-4-carboxylic acid as yellow oil.

e) Methyl 2,2-difluoro-5-(methoxymethoxy)benzo [d][1,3]dioxole-4-carboxylate Into a 250-mL round-bottom flask was placed 2,2-difluoro-5-(methoxymethoxy)-2H-1,3-benzodioxole-4-carboxylic acid (3.2 g, 12.21 mmol), methanol (100 mL) and azidotrimethylsilane (2.08 g, 18.05 mmol). The resulting solution was stirred for 3 h at 0° C. The resulting mixture was concentrated under vacuum. The resulting solution was diluted with ethyl acetate (100 mL). The resulting mixture was washed with brine (3×40 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield methyl 2,2-difluoro-5-(methoxymethoxy)-2H-1,3-benzodioxole-4-carboxylate as a yellow solid.

f) Methyl 2,2-difluoro-5-hydroxybenzo[d][1,3]diox-ole-4-carboxylate

Into a 250-mL round-bottom flask was placed methyl 2,2-difluoro-5-(methoxymethoxy)-2H-1,3-benzodioxole-4-carboxylate (3.0 g, 10.86 mmol), dichloromethane (100 mL) and $CF_3COOH$ (10 mL) was then added at 0-5° C. in an ice/water bath. The resulting solution was stirred for 2 h at 0° C. The resulting mixture was washed with brine (3×50 mL). The resulting residue was dried over anhydrous sodium sulfate. The solids were filtered out. The resulting mixture was concentrated under vacuum. The resulting residue was purified on a silica gel column with ethyl acetate/petroleum ether (1:1) to yield methyl 2,2-difluoro-5-hydroxy-2H-1,3-benzodioxole-4-carboxylate as a yellow solid.

g) Methyl 6-bromo-2,2-difluoro-5-hydroxybenzo[d] [1,3]dioxole-4-carboxylate

Into a 100-mL round-bottom flask was placed methyl 2,2-difluoro-5-hydroxy-2H-1,3-benzodioxole-4-carboxylate (800 mg, 3.45 mmol), methanol (30 mL) and Br$_2$ (707 mg, 4.42 mmol) was then added at 0-5° C. in an ice/water bath. The resulting solution was stirred for 3 h at 0° C. The resulting mixture was concentrated under vacuum. The resulting solution was diluted with ethyl acetate (50 mL). The resulting mixture was washed with brine (3×15 mL). The resulting residue was dried over anhydrous sodium sulfate. The solids were filtered out. The resulting mixture was concentrated under vacuum. The resulting residue was purified on a silica gel column with ethyl acetate/petroleum ether (1:2) to yield methyl 6-bromo-2,2-difluoro-5-hydroxy-2H-1,3-benzodioxole-4-carboxylate as a brown solid.

h) Methyl 2,2-difluoro-6-methyl-[1,3]dioxolo[4,5-f]benzofuran-4-carboxylate

Into a 50-mL sealed tube was placed methyl 6-bromo-2,2-difluoro-5-hydroxy-2H-1,3-benzodioxole-4-carboxylate (760 mg, 2.44 mmol), CuI (47 mg, 0.25 mmol), Pd(PPh$_3$)$_2$Cl$_2$ (172 mg, 0.25 mmol), TEA (495 mg, 4.89 mmol) and N,N-dimethylformamide (15 mL). To the resulting mixture was then added prop-1-yne (196 mg, 4.89 mmol) at −78° C. The resulting solution was stirred overnight at 75° C. The resulting solution was diluted with ethyl acetate (50 mL). The resulting mixture was washed with brine (3×15 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield methyl 2,2-difluoro-6-methyl-[1,3]dioxolo[4,5-f]benzofuran-4-carboxylate as a yellow solid.

i) 3-{4-[(2,2-Difluoro-6-methylfuro[2,3-f][1,3]benzodioxol-4-yl)methoxy]-2,3-dimethylphenyl}propanoic acid The title compound was prepared by reacting methyl 2,2-difluoro-6-methyl-[1,3]dioxolo[4,5-f]benzofuran-4-carboxylate according to procedure in Example 20.
$^1$H NMR: (300 MHz, CD$_3$OD) δ: 7.26 (s, 1H), 6.99 (d, J=6.3 Hz, 2H), 6.90 (d, J=6.3 Hz, 2H), 5.35 (s, 2H), 2.91 (t, J=6.0 Hz, 2H), 2.56-2.47 (m, 5H), 2.21 (s, 3H), 2.14 (s, 3H). Mass spectrum (ESI, m/z): Calculated for C$_{22}$H$_{20}$F$_2$O$_6$, 417 (M−H). found 417.

Example 56

3-{2,3-Dimethyl-4-[(7-methyl-2,3-dihydrofuro[2,3-g][1,4]benzodioxin-5-yl)methoxy]phenyl}propanoic acid

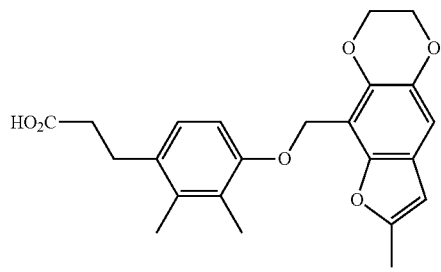 [SMILES: Cc1cc2cc3c(c(COc4ccc(CCC(=O)O)c(C)c4C)c2o1)OCCO3]

The title compound was prepared according to the procedure described in Example 55 substituting 2,3-dihydro-1,4-benzodioxin-6-ol for 2,2-difluorobenzo[d][1,3]dioxol-5-ol in step (b).

$^1$H NMR: (300 MHz, CD$_3$OD) δ: 6.98-6.89 (m, 3H), 6.28 (s, 1H), 5.22 (s, 2H), 4.27-4.22 (m, 4H), 2.89 (t, J=7.5 Hz, 2H), 2.49 (t, J=7.5 Hz, 2H), 2.38 (s, 3H), 2.281 (s, 3H), 2.03 (s, 3H). Mass spectrum (ESI, m/z): Calculated for C$_{23}$H$_{24}$O$_6$, 395 (M−H). found 395.

Example 57

3-{4-[(5-Chloro-2-methyl-1-benzothiophen-7-yl)methoxy]-2,3-dimethylphenyl}propanoic acid

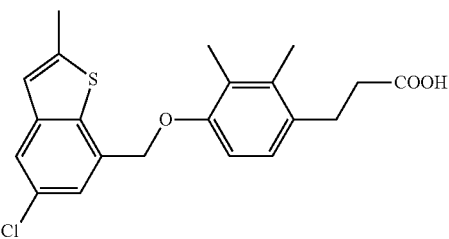 [SMILES: Cc1cc2cc(Cl)cc(COc3ccc(CCC(=O)O)c(C)c3C)c2s1]

a) Ethyl 2-((2-bromo-4-chlorophenyl)thio)propanoate

Into a 250-mL round-bottom flask was placed 2-bromo-4-chlorobenzene-1-thiol (5 g, 22.37 mmol), acetone (100 mL), ethyl 2-bromopropanoate (12 g, 66.29 mmol), and potassium carbonate (9.2 g, 66.57 mmol). The resulting solution was heated to reflux overnight. The reaction was then quenched by the addition of water (200 mL). The resulting solution was extracted with ethyl acetate (2×200 mL) and the organic layers combined and concentrated under vacuum. The resulting residue was purified on a silica gel column with ethyl acetate/petroleum ether (1/100-1/10) to yield ethyl 2-[(2-bromo-4-chlorophenyl)sulfanyl]propanoate as colorless oil.

b) 2-((2-Bromo-4-chlorophenyl)thio)propanal

Into a 100-mL 3-necked round-bottom flask purged and maintained with an inert atmosphere of nitrogen was placed ethyl 2-[(2-bromo-4-chlorophenyl)sulfanyl]propanoate (4 g, 12.36 mmol) and dichloromethane (100 mL). To the resulting mixture was then added DIBAL-H (24 mL) at −70° C. The resulting solution was stirred for 30 min at −70° C. The reaction was then quenched by the addition of water (40 mL). The solids were filtered out. The resulting solution was extracted with ethyl acetate (3×50 mL) and the organic layers combined and concentrated under vacuum. The resulting residue was purified on a silica gel column with EtOAc/PE (1/100-1/30) to yield 2-[(2-bromo-4-chlorophenyl)sulfanyl]propanal as colorless oil.

c) 7-Bromo-5-chloro-2-methylbenzo[b]thiophene

Into a 100-mL round-bottom flask was placed PPA (10 mL) and 2-[(2-bromo-4-chlorophenyl)sulfanyl]propanal (1.2 g, 4.29 mmol) and the mixture was heated at 150° C. for 45 min. The resulting residue was cooled to room temperature. The reaction was then quenched by the addition of water (20 mL). The resulting solution was extracted with ethyl acetate (2×20 mL) and the organic layers combined and concentrated under vacuum. The resulting residue was purified on a silica gel column with ethyl acetate/petroleum ether (1/100-1/10) to yield 7-bromo-5-chloro-2-methyl-1-benzothiophene as a yellow solid.

d) Methyl 5-chloro-2-methylbenzo[b]thiophene-7-carboxylate

Into a 100-mL round-bottom flask purged and maintained with an inert atmosphere of nitrogen was placed 7-bromo-5-chloro-2-methyl-1-benzothiophene (900 mg, 3.44 mmol), methanol (20 mL), triethylamine (1 g, 9.88 mmol) and Pd(dppf)Cl$_2$ (504 mg, 0.69 mmol). The resulting solution was stirred overnight at 60° C. The resulting mixture was concentrated under vacuum. The resulting residue was purified on a silica gel column with P/E (100/1-10/1) to yield methyl 5-chloro-2-methyl-1-benzothiophene-7-carboxylate as a white solid.

e) 3-{4-[(5-Chloro-2-methyl-1-benzothiophen-7-yl)methoxy]-2,3-dimethylphenyl}propanoic acid The title compound was prepared according to the procedure as described in Example 20 from 5-chloro-2-methyl-1-benzothiophene-7-carboxylate.

$^1$H NMR: (300 MHz, CD$_3$OD) δ: 7.61 (s, 1H), 7.31 (s, 1H), 7.01 (s, 1H), 6.91 (d, J=8.1 Hz, 1H), 6.73 (d, J=7.5 Hz, 1H), 5.16 (s, 2H), 2.85 (t, J=7.5 Hz, 2H), 2.55 (s, 3H), 2.45 (t, J=7.5 Hz, 2H), 2.15 (s, 6H). Mass spectrum (ESI, m/z): Calculated for C$_{21}$H$_{21}$ClO$_3$S, 387 (M−H). found 387.

Example 58

3-{4-[(5-Chloro-2-methyl-1-benzothiophen-7-yl)methoxy]-3,5-difluorophenyl}propanoic acid

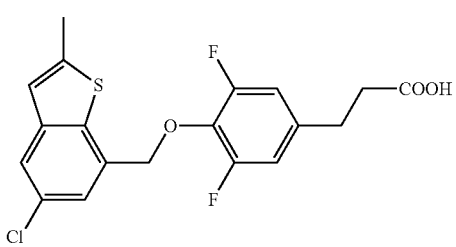 [SMILES: Cc1cc2cc(Cl)cc(COc3c(F)cc(CCC(=O)O)cc3F)c2s1]

The title compound was prepared according to the procedure as described in Example 57 substituting ethyl 3-(3,5-difluoro-4-hydroxyphenyl)propanoate (prepared as described in U.S. Pat. Appl. Publ., 20110313003, 22 Dec. 2011) for ethyl 3-(4-hydroxy-2,3-dimethylphenyl)propanoate.

$^1$H NMR: (300 MHz, CD$_3$OD) δ: 7.62 (s, 1H), 7.28 (s, 1H), 7.00 (s, 1H), 6.81-6.89 (m, 2H), 5.22 (s, 2H), 2.82 (t, J=7.2 Hz, 2H), 2.52-2.57 (m, 5H), 1.71-1.80 (m, 2H). Mass spectrum (ESI, m/z): Calculated for C$_{19}$H$_{15}$ClF$_2$O$_3$S, 395 (M−H). found 395.

Example 59

3-{4-[(5-Chloro-2-methyl-1-benzothiophen-7-yl)methoxy]-3,5-difluorophenyl}propan-1-ol

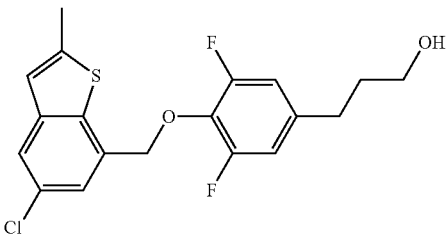 [SMILES: Cc1cc2cc(Cl)cc(COc3c(F)cc(CCCO)cc3F)c2s1]

To a solution of ethyl 3-[4-[(5-chloro-2-methyl-1-benzothiophen-7-yl)methoxy]-3,5-difluorophenyl]propanoate (100 mg, 0.24 mmol, prepared as described in Example 58) in tetrahydrofuran (5 mL) was added LAH (8.9 mg, 0.23 mmol). The resulting solution was stirred for 30 min at 0° C. The reaction was then quenched by the addition of Na$_2$SO$_4$.10H$_2$O (500 mg). The solids were filtered out. The resulting mixture was concentrated under vacuum and the resulting residue was purified by reversed-phase-(C$_{18}$)-HPLC to yield 3-[4-[(5-chloro-2-methyl-1-benzothiophen-7-yl)methoxy]-3,5-difluorophenyl]propan-1-ol as a white solid. $^1$H NMR: (300 MHz, CD$_3$OD) δ: 7.70 (s, 1H), 7.40 (s, 1H), 7.01 (s, 1H), 6.77-6.85 (m, 2H), 5.23 (s, 2H), 3.51 (t, J=6.3 Hz, 2H), 2.56-2.63 (m, 5H), 1.71-1.80 (m, 2H).

Example 60

3-[2,3-Dimethyl-4-({2-methyl-5-[3-(methylsulfonyl)prop-1-yn-1-yl]-1-benzofuran-7-yl}methoxy)phenyl]propanoic acid

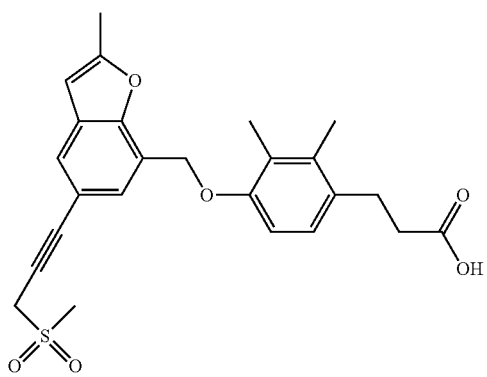 [SMILES: Cc1cc2cc(C#CCS(C)(=O)=O)cc(COc3ccc(CCC(=O)O)c(C)c3C)c2o1]

a) 3-(2,3-Dimethyl-4-((2-methyl-5-(3-(methylthio)prop-1-yn-1-yl)benzofuran-7-yl)methoxy)phenyl)propanoic acid To a solution of ethyl 3-[2,3-dimethyl-4-([2-methyl-5-[3-(methylsulfanyl)prop-1-yn-1-yl]-1-benzofuran-7-yl]methoxy)phenyl]propanoate (100 mg, 0.22 mmol, prepared as described in Example 61) in tetrahydrofuran (2 mL) was added a solution of LiOH (100 mg, 4.18 mmol) in water (2 mL). The resulting residue was stirred overnight at 25° C.

and the pH was adjusted to pH 5 with hydrogen chloride (2 mol/L). The resulting residue was extracted with ethyl acetate (3×10 mL) and the organic layers combined and dried over anhydrous sodium sulfate and concentrated under vacuum to yield 3-[2,3-dimethyl-4-([2-methyl-5-[3-(methylsulfanyl)prop-1-yn-1-yl]-1-benzofuran-7-yl]methoxy) phenyl]propanoic acid as yellow oil.

b) 3-[2,3-Dimethyl-4-({2-methyl-5-[3-(methylsulfonyl)prop-1-yn-1-yl]-1-benzofuran-7-yl}methoxy) phenyl]propanoic acid Into a 50-mL round bottom flask was placed 3-[2,3-dimethyl-4-([2-methyl-5-[3-(methylsulfanyl)prop-1-yn-1-yl]-1-benzofuran-7-yl]methoxy)phenyl]propanoic acid (120 mg, 0.28 mmol), dichloromethane (3 mL) and m-CPBA (98 mg, 0.57 mmol). The resulting solution was stirred for 1 h at 25° C. The resulting mixture was concentrated under vacuum and purified by RP-C18-HPLC to yield 3-(4-[[5-(3-methanesulfonylprop-1-yn-1-yl)-2-methyl-1-benzofuran-7-yl]methoxy]-2,3-dimethylphenyl)propanoic acid as a white solid.

$^1$H NMR: (300 MHz, CD$_3$OD) δ: 7.61 (s, 1H), 7.44 (s, 1H), 7.05 (s, 1H), 6.97 (d, J=8.4 Hz, 1H), 6.82 (d, J=8.1 Hz, 1H), 6.52 (s, 1H), 5.29 (s, 2H), 3.56 (s, 2H), 3.09 (s, 3H), 2.91 (t, J=7.5 Hz, 2H), 2.42-2.60 (m, 5H), 2.32 (s, 3H), 2.21 (s, 3H). Mass spectrum (ESI, m/z): Calculated for C$_{25}$H$_{26}$O$_6$S, 481 (M+Na). found 481.

Example 61

3-[2,3-Dimethyl-4-({2-methyl-5-[3-(methylsulfonyl) propyl]benzofuran-7-yl}methoxy)phenyl]propanoic acid

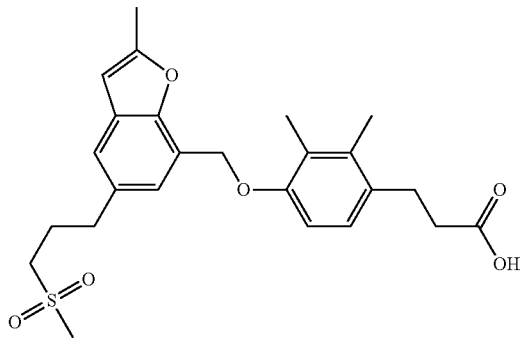 [SMILES: Cc1cc2cc(CCCS(C)(=O)=O)cc(COc3ccc(CCC(=O)O)c(C)c3C)c2o1]

a) 5-Iodo-2-methylbenzofuran-7-carbaldehyde

Into a 50-mL sealed tube was placed 2-hydroxy-3,5-diiodobenzaldehyde (2 g, 5.35 mmol), pyridine (10 mL), Cu$_2$O (460 mg, 3.21 mmol) and a solution of prop-1-yne (212 mg, 5.29 mmol, 0.99 equiv) in pyridine (prepared at −78° C., 5 mL). The resulting solution was stirred for 1 h at 120° C. The resulting solution was diluted with ethyl acetate (10 mL). The resulting solution was extracted with ethyl acetate (3×20 mL) and the organic layers combined. The resulting mixture was washed with brine (3×30 mL). The resulting mixture was concentrated under vacuum. The resulting residue was purified on a silica gel column with ethyl acetate/petroleum ether (1/30-1/20) to yield 5-iodo-2-methyl-1-benzofuran-7-carbaldehyde as a yellow solid.

b) 2-Methyl-5-(3-(methylthio)prop-1-yn-1-yl)benzofuran-7-carbaldehyde

Into a 50-mL sealed tube was placed 5-iodo-2-methyl-1-benzofuran-7-carbaldehyde (1.2 g, 4.19 mmol), 3-(methylsulfanyl)prop-1-yne (724 mg, 8.40 mmol), Pd(PPh$_3$)$_2$Cl$_2$ (147 mg, 0.21 mmol), CuI (80 mg, 0.42 mmol), N,N-dimethylformamide (20 mL) and TEA (1.27 g, 12.55 mmol). The resulting solution was stirred overnight at 80° C. The reaction was then quenched by the addition of water (10 mL). The resulting solution was extracted with ethyl acetate (3×20 mL) and the organic layers combined. The resulting mixture was washed with brine (3×30 mL). The resulting mixture was concentrated under vacuum. The resulting residue was purified on a silica gel column with PE/EtOAc (30/1-20/1) to yield 2-methyl-5-[3-(methylsulfanyl)prop-1-yn-1-yl]-1-benzofuran-7-carbaldehyde as yellow oil.

c) Ethyl 3-(2,3-dimethyl-4-((2-methyl-5-(3-(methylthio)prop-1-yn-1-yl)benzofuran-7-yl)methoxy)phenyl)propanoate The title compound was prepared by reduction of 2-methyl-5-[3-(methylsulfanyl)prop-1-yn-1-yl]-1-benzofuran-7-carbaldehyde aldehyde with LiAlH$_4$ and coupled to ethyl 3-(4-hydroxy-2,3-dimethylphenyl)propanoate according to the procedure in Example 20.

d) Ethyl 3-(2,3-dimethyl-4-((2-methyl-5-(3-(methylthio)propyl)benzofuran-7-yl)methoxy)phenyl)propanoate Into a 50-mL round bottom flask purged and maintained with an inert atmosphere of H$_2$ was placed ethyl 3-[2,3-dimethyl-4-([2-methyl-5-[3-(methylsulfanyl)prop-1-yn-1-yl]-1-benzofuran-7-yl]methoxy)phenyl]propanoate (150 mg, 0.33 mmol), ethyl acetate (5 mL) and palladium on carbon (150 mg). The resulting solution was stirred for 4 h at 25° C. The solids were filtered out. The resulting mixture was concentrated under vacuum to yield ethyl 3-[2,3-dimethyl-4-([2-methyl-5-[3-(methylsulfanyl)propyl]-1-benzofuran-7-yl]methoxy)phenyl]propanoate as yellow oil.

e) 3-(2,3-Dimethyl-4-((2-methyl-5-(3-(methylthio) propyl)benzofuran-7-yl)methoxy)phenyl)propanoic acid To a solution of ethyl 3-[2,3-dimethyl-4-[2-methyl-5-[3-(methylsulfanyl)propyl]-1-benzofuran-7-yl]methoxy)phenyl]propanoate (130 mg, 0.29 mmol) in tetrahydrofuran (2 mL) was added a solution of LiOH (130 mg, 5.43 mmol) in water (2 mL). The resulting solution was stirred overnight at 25° C. The pH value of the solution was adjusted to pH 5 with hydrogen chloride (2 mol/L). The resulting solution was extracted with ethyl acetate (3×10 mL) and the organic layers combined and dried over anhydrous sodium sulfate and concentrated under vacuum to yield 3-[2,3-dimethyl-4-([2-methyl-5-[3-(methylsulfanyl)propyl]-1-benzofuran-7-yl]methoxy)phenyl]propanoic acid as yellow oil.

f) 3-[2,3-Dimethyl-4-({2-methyl-5-[3-(methylsulfonyl)propyl]-1-benzofuran-7-yl}methoxy)phenyl] propanoic acid Into a 50-mL round-bottom flask was placed 3-[2,3-dimethyl-4-([2-methyl-5-[3-(methylsulfanyl)propyl]-1-benzofuran-7-yl]methoxy)phenyl]propanoic acid (100 mg, 0.23 mmol), dichloromethane (3 mL) and m-CPBA (80 mg, 0.46 mmol). The resulting solution was stirred for 2 h at 25° C. The resulting mixture was concentrated under vacuum. The resulting residue was purified by RP-HPLC (C18) to yield 3-(4-[[5-(3-methanesulfonylpropyl)-2-methyl-1-benzofuran-7-yl]methoxy]-2,3-dimethylphenyl)propanoic acid as a white solid.

$^1$H NMR: (300 MHz, CD$_3$OD) δ: 7.19 (s, 1H), 7.14 (s, 1H), 7.05 (s, 1H), 6.84 (d, J=8.4 Hz, 1H), 6.71 (d, J=8.4 Hz, 1H), 6.32 (s, 1H), 5.17 (s, 2H), 2.71-2.97 (m, 8H), 2.34-2.66 (m, 5H), 1.93-2.11 (m, 10H). Mass spectrum (ESI, m/z): Calculated for C$_{25}$H$_{30}$O$_6$S, 481 (M+Na). found 481.

Example 62

3-{4-[(6-Chloro-2-methyl-1-benzothiophen-4-yl)methoxy]-2,3-dimethylphenyl}propanoic acid

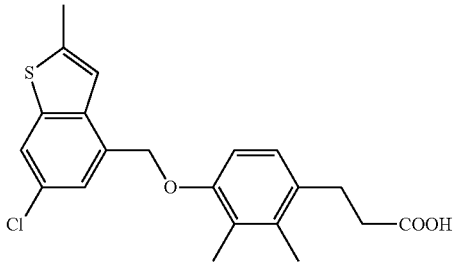 [SMILES: Cc1cc2c(COc3ccc(CCC(=O)O)c(C)c3C)cc(Cl)cc2s1]

a) 3-Bromo-5-chlorobenzenethiol

Into a 250-mL round-bottom flask was placed 3-bromo-5-chlorobenzene-1-sulfonyl chloride (3.8 g, 13.11 mmol), PPh$_3$ (12 g, 45.75 mmol), tetrahydrofuran (200 mL) and water (10 mL). The resulting solution was stirred overnight at 50° C. The resulting solution was diluted with sodium hydroxide (100 mL). The resulting mixture was washed with ethyl acetate (2×200 mL). The pH value of the solution was adjusted to pH 3 with hydrogen chloride (6 mol/L). The resulting solution was extracted with ethyl acetate (2×300 mL) and the organic layers combined and dried over anhydrous sodium sulfate and concentrated under vacuum to yield 3-bromo-5-chlorobenzene-1-thiol as red oil.

b) Ethyl 2-((3-bromo-5-chlorophenyl)thio)propanoate

Into a 250-mL round-bottom flask was placed 3-bromo-5-chlorobenzene-1-thiol (8.8 g, 39.37 mmol), ethyl 2-bromopropanoate (21.4 g, 118.21 mmol), potassium carbonate (16.4 g, 118.66 mmol), and acetone (100 mL). The resulting solution was stirred overnight at 60° C. The resulting solution was diluted with water (50 mL). The resulting solution was extracted with ethyl acetate (3×50 mL) and the organic layers combined and dried over anhydrous sodium sulfate. The solids were filtered out. The resulting mixture was concentrated under vacuum. The resulting residue was purified on a silica gel column with ethyl acetate/petroleum ether (5/95). The collected fractions were combined and concentrated under vacuum to yield ethyl 2-((3-bromo-5-chlorophenyl)thio)propanoate as yellow oil.

c) 2-((3-Bromo-5-chlorophenyl)thio)propanal

To a solution of ethyl 2-[(3-bromo-5-chlorophenyl)sulfanyl]propanoate (2 g, 6.18 mmol) in toluene (20 mL) was added DIBAL (6.2 mL, 1 mol/L) dropwise with stirring at −78° C. The resulting solution was stirred for 30 min at −78° C. The reaction was then quenched by the addition of water (20 mL). The solids were filtered out. The resulting solution was extracted with ethyl acetate (4×20 mL) and the organic layers combined and dried over anhydrous sodium sulfate. The solids were filtered out. The resulting mixture was concentrated under vacuum. The resulting residue was purified on a silica gel column with ethyl acetate/petroleum ether (5/95). The collected fractions were combined and concentrated under vacuum to yield 2-[(3-bromo-5-chlorophenyl)sulfanyl]propanal as yellow oil.

d) 4-Bromo-6-chloro-2-methylbenzo[b]thiophene

Into a 50-mL round-bottom flask was placed PPA (5 mL) and 2-[(3-bromo-5-chlorophenyl)sulfanyl]propanal (1.2 g, 4.29 mmol) was added dropwise with stirring at 150° C. in 30 min. The resulting solution was stirred for 30 min at 150° C. The reaction was then quenched by the addition of water (20 mL). The resulting solution was extracted with ethyl acetate (3×20 mL) and the organic layers combined and dried over anhydrous sodium sulfate. The solids were filtered out. The resulting mixture was concentrated under vacuum. The resulting residue was purified on a silica gel column with ethyl acetate/petroleum ether (1/99). The collected fractions were combined and concentrated under vacuum to yield 4-bromo-6-chloro-2-methyl-1-benzothiophene as a white solid.

e) 3-{4-[(6-Chloro-2-methyl-1-benzothiophen-4-yl)methoxy]-2,3-dimethylphenyl}propanoic acid The title compound was prepared according to the procedure as described in Example 57 substituting 4-bromo-6-chloro-2-methylbenzo[b]thiophene for 7-bromo-5-chloro-2-methyl-1-benzothiophene in step (d).

$^1$H NMR: (300 MHz, CDCl$_3$) δ: 7.71 (s, 1H), 7.39 (s, 1H), 7.16 (s, 1H), 6.99 (d, J=6.3 Hz, 1H), 6.75 (d, J=6.3 Hz, 1H), 5.11 (s, 2H), 2.98 (t, J=6 Hz, 2H), 2.60-2.64 (m, 5H), 2.26 (s, 3H), 2.23 (s, 3H). Mass spectrum (ESI, m/z): Calculated for C$_{21}$H$_{21}$ClO$_3$S, 387 (M−H). found 387.

Example 63

3-{4-[(6-Chloro-2-methyl-1-benzothiophen-4-yl)methoxy]-3,5-difluorophenyl}propanoic acid

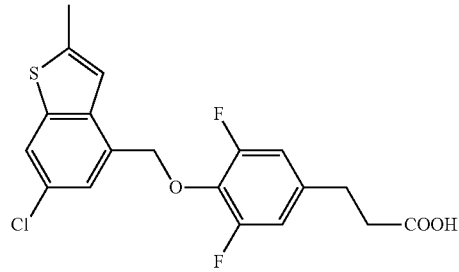 [SMILES: Cc1cc2c(COc3c(F)cc(CCC(=O)O)cc3F)cc(Cl)cc2s1]

The title compound was prepared according to the procedure as described in Example 62 substituting ethyl 3-(3, 5-difluoro-4-hydroxyphenyl)propanoate for ethyl 3-(4-hydroxy-2,3-dimethylphenyl)propanoate.

$^1$H NMR: (300 MHz, CD$_3$OD) δ: 7.74 (s, 1H), 7.42 (s, 1H), 7.17 (s, 1H), 6.91 (d, J=6.9 Hz, 2H), 5.18 (s, 2H), 2.88 (t, J=5.7 Hz, 2H), 2.57-2.62 (m, 5H). Mass spectrum (ESI, m/z): Calculated for C$_{19}$H$_{15}$ClF$_2$O$_3$S, 395 (M−H). found 395.

Example 64

3-{4-[(6-Chloro-2-methyl-1-benzothiophen-4-yl)methoxy]-3,5-difluorophenyl}propan-1-ol

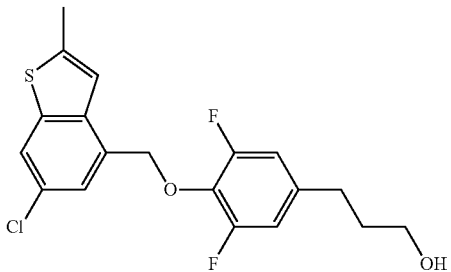 [SMILES: Cc1cc2c(COc3c(F)cc(CCCO)cc3F)cc(Cl)cc2s1]

The title compound was prepared by reacting 3-{4-[(6-chloro-2-methyl-1-benzothiophen-4-yl)methoxy]-3,5-difluorophenyl}propanoic acid (prepared as described in Example 63) according to procedure in Example 59.

$^1$H NMR: (300 MHz, CD$_3$OD) δ: 7.74 (s, 1H), 7.41 (s, 1H), 7.17 (s, 1H), 6.86 (d, J=7.2 Hz, 2H), 5.18 (s, 2H), 3.56 (t, J=4.5 Hz, 2H), 2.62-2.66 (m, 5H), 1.76-1.83 (m, 2H).

Example 65

3-{4-[(2-tert-Butyl-6-chloro-1,3-benzothiazol-4-yl)methoxy]-2,3-dimethylphenyl}propanoic acid

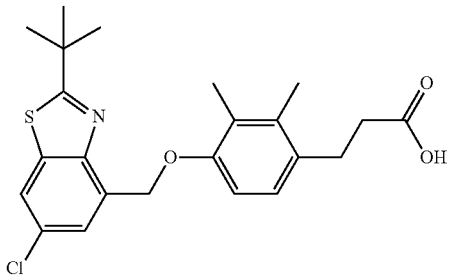 [SMILES: Cc1c(CCC(=O)O)ccc(OCc2cc(Cl)cc3sc(C(C)(C)C)nc23)c1C]

a) 2-Amino-3-bromo-5-chlorobenzenethiol

The title compound was prepared according to the procedure as described in Example 66 substituting 2-bromo-4-chloroaniline for 2-bromo-4-fluoroaniline.

b) 4-Bromo-2-(tert-butyl)-6-chlorobenzo[d]thiazole

Into a 100-mL round-bottom flask was placed 2-amino-3-bromo-5-chlorobenzene-1-thiol (400 mg, 1.68 mmol), NMP (10 mL) and 2,2-dimethylpropanoyl chloride (403 mg, 3.34 mmol). The resulting solution was stirred for 1 h at 130° C. The reaction was then quenched by the addition of water (10 mL). The resulting solution was extracted with ethyl acetate (3×10 mL) of ethyl acetate and the organic layers combined. The resulting mixture was washed with brine (3×20 mL). The resulting mixture was concentrated under vacuum. The resulting residue was purified on a silica gel column with ethyl acetate/petroleum ether (1/30-1/10) to yield 4-bromo-2-tert-butyl-6-chloro-1,3-benzothiazole as yellow oil.

c) Methyl 2-tert-butyl-6-chloro-1,3-benzothiazole-4-carboxylate

Into a 100-mL round-bottom flask was placed 4-bromo-2-tert-butyl-6-chloro-1,3-benzothiazole (150 mg, 0.49 mmol), methanol (10 mL), Pd(dppf)Cl$_2$ (72 mg, 0.10 mmol) and triethylamine (149 mg, 1.47 mmol). CO (g) was introduced and the resulting solution was stirred overnight at 60° C. The resulting mixture was concentrated under vacuum. The product was purified by TLC(PE/EtOAc=5/1), to yield methyl 2-tert-butyl-6-chloro-1,3-benzothiazole-4-carboxylate as a solid.

d) (2-Tert-butyl-6-chloro-1,3-benzothiazol-4-yl)methanol

To a solution of methyl 2-tert-butyl-6-chloro-1,3-benzothiazole-4-carboxylate (120 mg, 0.42 mmol) in ether (2 mL) was added LAH (16 mg, 0.42 mmol) at 0° C. The resulting solution was stirred for 30 min at 0° C. The reaction was then quenched by addition of sodium sulfate.10H$_2$O (500 mg). The solids were filtered out. The resulting residue was concentrated under vacuum. Then the product was purified by preparative TLC plate (PE/EA=5/1) to yield (2-tert-butyl-6-chloro-1,3-benzothiazol-4-yl)methanol as yellow oil.

e) 3-{4-[(2-tert-Butyl-6-chloro-1,3-benzothiazol-4-yl)methoxy]-2,3-dimethylphenyl}propanoic acid The title compound was prepared by reacting (2-tert-butyl-6-chloro-1,3-benzothiazol-4-yl)methanol according to the procedure as described in Example 20 step (j).

$^1$H NMR: (300 MHz, DMSO) δ: 8.21 (s, 1H), 7.59 (s, 1H), 6.94 (d, J=8.4 Hz, 1H), 6.88 (d, J=8.4 Hz, 1H), 5.48 (s, 2H), 2.77 (t, J=7.5 Hz, 2H), 2.39 (d, J=8.1 Hz, 1H), 2.15 (s, 6H), 1.47 (s, 9H). Mass spectrum (ESI, m/z): Calculated for C$_{23}$H$_{26}$ClNO$_3$S, 432 (M+H). found 431.

Example 66

3-{4-[(2-Ethyl-6-fluoro-1,3-benzothiazol-4-yl)methoxy]-2,3-dimethylphenyl}propanoic acid

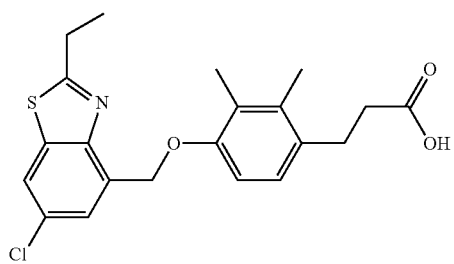 [SMILES: CCc1nc2c(COc3ccc(CCC(=O)O)c(C)c3C)cc(Cl)cc2s1]

a) 4-Bromo-6-fluorobenzo[d]thiazol-2-amine

To a solution of 2-bromo-4-fluoroaniline (10 g, 52.63 mmol) and NH$_4$SCN (20 g) in acetic acid (80 mL) was added a solution of Br$_2$ (9.2 g, 57.57 mmol) in acetic acid (20 mL) at 0-5° C. The resulting solution was stirred for 2 h at 0° C. The resulting solution was diluted with water (200 mL). The pH of the solution was adjusted to pH 7-8 with sodium hydroxide (10%) and the resulting residue collected by filtration to yield 4-bromo-6-fluoro-1,3-benzothiazol-2-amine as a yellow solid.

b) 4-Bromo-6-fluorobenzo[d]thiazole

Into a 500-mL round-bottom flask was placed 4-bromo-6-fluoro-1,3-benzothiazol-2-amine (12.0 g, 48.57 mmol), 1,4-dioxane (100 mL) and 3-methylbutyl nitrite (31 g, 264.63 mmol). The resulting solution was stirred for 1 h at 60° C. The resulting mixture was concentrated under vacuum and the residue was purified by silica gel column chromatography to yield 4-bromo-6-fluoro-1,3-benzothiazole as a yellow solid.

c) 2-Amino-3-bromo-5-fluorobenzenethiol

Into a 100-mL round-bottom flask was placed 4-bromo-6-fluoro-1,3-benzothiazole (2.0 g, 8.62 mmol), ethanol (20 mL) and NH$_2$NH$_2$.H$_2$O (1.7 g). The resulting solution was stirred for 2 h at 80° C. The resulting mixture was concentrated under vacuum and the residue was purified by silica gel column chromatography to yield 2-amino-3-bromo-5-fluorobenzene-1-thiol as yellow oil.

d) 4-Bromo-2-ethyl-6-fluorobenzo[d]thiazole

Into a 100-mL round-bottom flask was placed 2-amino-3-bromo-5-fluorobenzene-1-thiol (800 mg, 3.60 mmol), NMP (20 mL) and propanoyl chloride (667 mg, 7.21 mmol). The resulting solution was stirred for 1.5 h at 130° C. The resulting solution was diluted with ethyl acetate (100 mL). The resulting mixture was washed with brine (3×30 mL). The resulting residue was dried over anhydrous sodium sulfate. The solids were filtered out. The resulting mixture was concentrated under vacuum and the residue was purified by silica gel column chromatography to yield 4-bromo-2-ethyl-6-fluorobenzo[d]thiazole as colorless oil.

e) Methyl 2-ethyl-6-fluorobenzo[d]thiazole-4-carboxylate

Into a 100-mL round-bottom flask was placed 4-bromo-2-ethyl-6-fluorobenzo[d]thiazole (320 mg, 1.23 mmol), methanol (20 mL), TEA (373 mg, 3.69 mmol), and Pd(dppf)Cl$_2$ (135 mg). CO (g) was introduced and the resulting solution was stirred overnight at 60° C. The resulting mixture was concentrated under vacuum and the residue was purified by silica gel chromatograph to yield of methyl 2-ethyl-6-fluorobenzo[d]thiazole-4-carboxylate as a colorless oil.

f) 3-{4-[(2-Ethyl-6-fluoro-1,3-benzothiazol-4-yl)methoxy]-2,3-dimethylphenyl}propanoic acid The title compound was prepared by reacting methyl 2-ethyl-6-fluorobenzo[d]thiazole-4-carboxylate according to the procedure as described in Example 1.

$^1$H NMR: (300 MHz, DMSO): 7.95 (dd, J$_1$=8.7 Hz, J$_2$=2.7 Hz, 1H), 7.40 (dd, J$_1$=9.9 Hz, J$_2$=2.7 Hz, 1H), 6.94 (d, J=8.4 Hz, 1H), 6.83 (d, J=8.4 Hz, 1H), 5.49 (s, 2H), 3.14 (q, J$_1$=15.0 Hz, J$_2$=7.5 Hz, 2H), 2.77 (t, J=7.2 Hz, 2H), 2.40 (t, J=7.5 Hz, 2H), 1.38 (t, J=7.5 Hz, 3H). Mass spectrum (ESI, m/z): Calculated for C$_{21}$H$_{22}$FNO$_3$S, 388 (M+H). found 388.

Example 67

3-(4-{[6-chloro-2-(1-methylethyl)-1,3-benzothiazol-4-yl]methoxy}-2,3-dimethylphenyl)propanoic acid

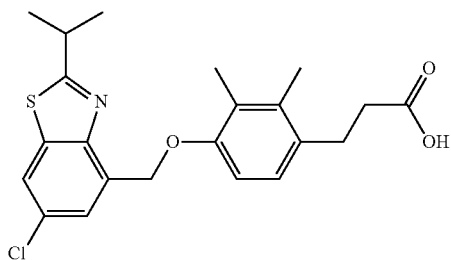 [SMILES: Cc1c(CCC(=O)O)ccc(OCc2cc(Cl)cc3sc(C(C)C)nc23)c1C]

a) 4-Bromo-6-chloro-2-isopropylbenzo[d]thiazole

Into a 100-mL round-bottom flask was placed 2-amino-3-bromo-5-chlorobenzene-1-thiol (400 mg, 1.68 mmol, prepared as described in Example 65), NMP (10 mL) and 2-methylpropanoyl chloride (359 mg, 3.37 mmol). The resulting solution was stirred for 1 h at 130° C. The reaction was then quenched by the addition of water (10 mL). The resulting solution was extracted with ethyl acetate (3×10 mL) and the organic layers combined. The resulting mixture was washed with brine (3×20 mL). The resulting mixture was concentrated under vacuum. The resulting residue was purified on a silica gel column with ethyl acetate/petroleum ether (1/30-1/10) to yield 4-bromo-6-chloro-2-isopropyl-benzo[d]thiazole as a light yellow oil.

b) 3-(4-{[6-chloro-2-(1-methylethyl)-1,3-benzothiazol-4-yl]methoxy}-2,3-dimethylphenyl)propanoic acid The title compound was prepared by reacting 4-bromo-6-chloro-2-isopropylbenzo[d]thiazole according to the procedure as described in Example 65.

$^1$H NMR: (300 MHz, DMSO) δ: 8.21 (s, 1H), 7.58 (s, 1H), 6.94 (d, J=8.4 Hz, 1H), 6.85 (d, J=8.4 Hz, 1H), 5.48 (s, 2H), 3.40-3.49 (m, 1H), 2.77 (t, J=8.1 Hz, 2H), 2.40 (d, J=8.4 Hz, 2H), 2.16 (s, 6H), 1.42 (s, 3H), 1.40 (s, 3H). Mass spectrum (ESI, m/z): Calculated for C$_{22}$H$_{24}$ClNO$_3$S, 416 (M−H). found 416.

Example 68

3-{4-[(2-tert-butyl-6-fluoro-1,3-benzothiazol-4-yl)methoxy]-2,3-dimethylphenyl}propanoic acid

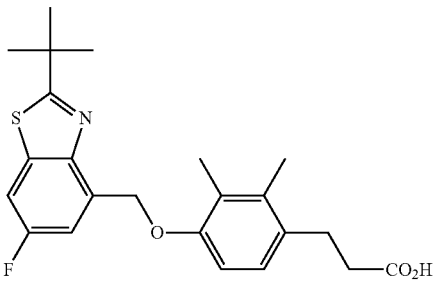 [SMILES: Cc1c(CCC(=O)O)ccc(OCc2cc(F)cc3sc(C(C)(C)C)nc23)c1C]

a) 4-Bromo-2-(tert-butyl)-6-fluorobenzo[d]thiazole

Into a 100-mL round-bottom flask was placed 2-amino-3-bromo-5-fluorobenzene-1-thiol (800 mg, 3.60 mmol, prepared as described in Example 66), NMP (10 mL) and 2,2-dimethylpropanoyl chloride (872 mg, 7.23 mmol). The resulting solution was stirred for 1.5 h at 130° C. The resulting solution was diluted with ethyl acetate (100 mL). The resulting mixture was washed with brine (3×30 mL). The resulting residue was dried over anhydrous sodium sulfate. The solids were filtered out. The resulting mixture was concentrated under vacuum. The resulting residue was purified onto a silica gel column with ethyl acetate/petroleum ether (1:5) to yield 4-bromo-2-tert-butyl-6-fluoro-1,3-benzothiazole as yellow oil.

b) 3-{4-[(2-tert-butyl-6-fluoro-1,3-benzothiazol-4-yl)methoxy]-2,3-dimethylphenyl}propanoic acid The title compound was prepared by reacting 4-bromo-2-(tert-butyl)-6-fluorobenzo[d]thiazole according to the procedure as described in Example 65.

$^1$H NMR: (300 MHz, DMSO) δ: 7.95 (dd, $J_1$=8.7 Hz, $J_2$=2.7 Hz, 1H), 7.42 (dd, $J_1$=9.9 Hz, $J_2$=2.7 Hz, 1H), 6.93 (d, J=8.1 Hz, 1H), 6.87 (d, J=8.4 Hz, 1H), 5.49 (s, 2H), 2.77 (t, J=7.5 Hz, 2H), 2.38 (t, J=7.5 Hz, 2H), 2.16 (s, 6H), 1.47 (s, 9H). Mass spectrum (ESI, m/z): Calculated for $C_{23}H_{26}FNO_3S$, 416 (M−H). found 416.

Example 69

3-[4-({5-Chloro-2-methyl-6-[3-(methylsulfonyl)propyl]-1-benzofuran-7-yl}methoxy)-2,3-dimethylphenyl]propanoic acid

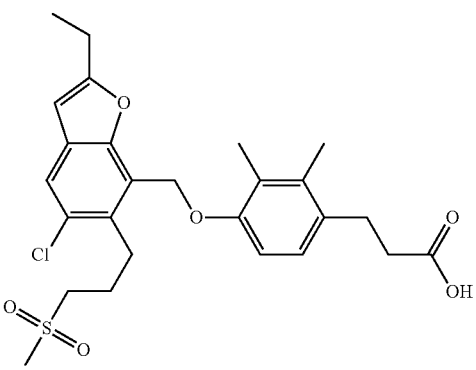 [SMILES: CCc1cc2cc(Cl)c(CCCS(C)(=O)=O)c(COc3ccc(CCC(=O)O)c(C)c3C)c2o1]

a) Methyl 5-chloro-2-methyl-6-(((trifluoromethyl)sulfonyl)oxy)benzofuran-7-carboxylate The title compound was prepared according to the procedure as described in Example 20 substituting prop-1-yne for but-1-yne in step (d).

b) Methyl 5-chloro-2-methyl-6-(3-((trimethylsilyl)oxy)prop-1-en-1-yl)benzofuran-7-carboxylate A mixture of methyl 5-chloro-2-methyl-6-[(trifluoromethane)sulfonyloxy]-1-benzofuran-7-carboxylate (1 g, 2.68 mmol), DMF (10 mL), trimethyl([[(2E)-3-(tetramethyl-1,3,2-dioxaborolan-2-yl)prop-2-en-1-yl]oxy])silane (1.37 g, 5.35 mmol), $Pd(OAc)_2$ (60 mg, 0.27 mmol), 2-dicyclohexylphosphino-2',6'-dimethoxybiphenyl (220 mg, 0.54 mmol), $K_3PO_4$ (1.4 g, 6.60 mmol) and water (1 mL). The resulting solution was stirred overnight at 70° C. The reaction was then quenched by the addition of water (20 mL). The resulting solution was extracted with ethyl acetate (3×30 mL) and the organic layers combined. The resulting mixture was washed with brine (3×50 mL). The resulting mixture was concentrated under vacuum. The resulting residue was purified on a silica gel column with PE/EtOAc (30/1-10/1) to yield methyl 5-chloro-2-methyl-6-[(1E)-3-[(trimethylsilyl)oxy]prop-1-en-1-yl]-1-benzofuran-7-carboxylate as yellow oil.

c) Methyl 5-chloro-6-(3-hydroxyprop-1-en-1-yl)-2-methylbenzofuran-7-carboxylate Into a 100-mL round flask was placed methyl 5-chloro-2-methyl-6-[(1 E)-3-[(trimethylsilyl)oxy]prop-1-en-1-yl]-1-benzofuran-7-carboxylate (800 mg, 2.27 mmol), tetrahydrofuran (10 mL) and TBAF(1N) (5 mL). The resulting solution was stirred for 4 h at 25° C. The resulting mixture was concentrated under vacuum. The resulting residue was purified on a silica gel column with PE/EtOAc (30/1-5/1) to yield methyl 5-chloro-6-[(1E)-3-hydroxyprop-1-en-1-yl]-2-methyl-1-benzofuran-7-carboxylate as a white solid.

d) Methyl 5-chloro-2-methyl-6-(3-((methylsulfonyl)oxy)prop-1-en-1-yl)benzofuran-7-carboxylate Into a 50-mL round flask was placed methyl 5-chloro-6-[(1E)-3-hydroxyprop-1-en-1-yl]-2-methyl-1-benzofuran-7-carboxylate (100 mg, 0.36 mmol), dichloromethane (3 mL), triethylamine (108 mg, 1.07 mmol) and MsCl (81 mg, 0.71 mmol). The resulting solution was stirred for 2 h at 25° C. The reaction was then quenched by the addition of water (10 mL). The resulting solution was extracted with DCM (3×10 mL) and the organic layers combined. The resulting mixture was washed with brine (3×30 mL). The resulting residue was dried over sodium sulfate and concentrated under vacuum to methyl 5-chloro-6-[(1E)-3-(methanesulfonyloxy)prop-1-en-1-yl]-2-methyl-1-benzofuran-7-carboxylate as yellow oil.

e) Methyl 5-chloro-2-methyl-6-(3-(methylthio)prop-1-en-1-yl)benzofuran-7-carboxylate Into a 50-mL round bottom flask, was placed methyl 5-chloro-6-[(1E)-3-(methanesulfonyloxy)prop-1-en-1-yl]-2-methyl-1-benzofuran-7-carboxylate (80 mg, 0.22 mmol), N,N-dimethylformamide (2 mL), $CH_3SNa$ (78 mg, 1.11 mmol), $Cs_2CO_3$ (362 mg, 1.11 mmol). The resulting solution was stirred for 1 h at 25° C. The reaction was then quenched by the addition of water (10 mL). The resulting solution was extracted with ethyl acetate (3×10 mL) and the organic layers combined. The resulting mixture was washed with brine (3×20 mL). The resulting mixture was concentrated under vacuum. The resulting residue was purified on a silica gel column with PE/EtOAc (30/1-10/1) to yield methyl 5-chloro-2-methyl-6-[(1E)-3-(methylsulfanyl)prop-1-en-1-yl]-1-benzofuran-7-carboxylate as brown oil.

f) Methyl 5-chloro-2-methyl-6-(3-(methylthio)propyl)benzofuran-7-carboxylate

Into a 50-mL round bottom flask was placed methyl 5-chloro-2-methyl-6-[(1E)-3-(methylsulfanyl)prop-1-en-1-yl]-1-benzofuran-7-carboxylate (40 mg, 0.13 mmol), tetrahydrofuran (2 mL) and palladium on carbon (40 mg). Hydrogen (gas) was introduced and the mixture was stirred for 4 h at 25° C. The solids were filtered out. The resulting mixture was concentrated under vacuum to yield methyl 5-chloro-2-methyl-6-[3-(methylsulfanyl)propyl]-1-benzofuran-7-carboxylate as colorless oil.

g) 3-(4-((5-Chloro-2-ethyl-6-(3-(methylthio)propyl)benzofuran-7-yl)methoxy)-2,3-dimethylphenyl)propanoic acid The title compound was prepared by reacting methyl 5-chloro-2-methyl-6-(3-(methylthio)propyl)benzofuran-7-carboxylate by LiAlH$_4$ reduction, coupling and hydrolysis according to the procedure as described in Example 20.

h) 3-[4-({5-Chloro-2-methyl-6-[3-(methylsulfonyl)propyl]-1-benzofuran-7-yl}-methoxy)-2,3-dimethylphenyl]propanoic acid Into a 25-mL round-bottom flask was placed 3-[4-([5-chloro-2-methyl-6-[3-(methylsulfanyl)propyl]-1-benzofuran-7-yl]methoxy)-2,3-dimethylphenyl]propanoic acid (15 mg, 0.03 mmol), dichloromethane (1 mL) and m-CPBA (11 mg, 0.06 mmol). The resulting solution was stirred for 2 h at 25° C. The resulting mixture was concentrated under vacuum and purified by RP-C18-HPLC to yield 3-(4-[[5-chloro-6-(3-methanesulfonylpropyl)-2-methyl-1-benzofuran-7-yl]methoxy]-2,3-dimethylphenyl)propanoic acid as a off-white solid.
$^1$H NMR: (300 MHz, CD$_3$OD) δ: 7.57 (s, 1H), 6.97-7.04 (m, 2H), 6.47 (s, 1H), 5.35 (s, 2H), 3.09-3.20 (m, 4H), 2.86-2.95 (m, 5H), 2.43-2.54 (m, 5H), 2.27 (s, 3H), 2.10-2.22 (m, 5H). Mass spectrum (ESI, m/z): Calculated for C$_{25}$H$_{29}$ClO$_6$S, 491 (M−H). found 491.

Example 70

3-{4-[(6-Chloro-2-ethyl-1,3-benzothiazol-4-yl)methoxy]-2,3-dimethylphenyl}propanoic acid

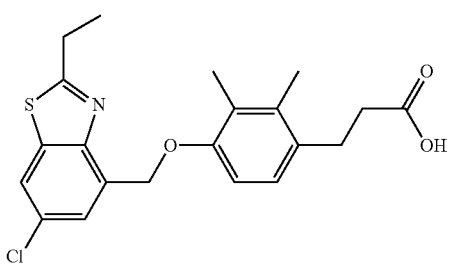 [SMILES: CCc1nc2c(COc3ccc(CCC(=O)O)c(C)c3C)cc(Cl)cc2s1]

a) (6-Chloro-2-ethylbenzo[d]thiazol-4-yl)methanol

The title compound was prepared according to the procedure as described in Example 65 step (b) substituting propanoyl chloride for 2,2-dimethylpropanoyl chloride.

b) 3-{4-[(6-Chloro-2-ethyl-1,3-benzothiazol-4-yl)methoxy]-2,3-dimethylphenyl}propanoic acid The title compound was prepared by reacting 6-chloro-2-ethylbenzo[d]thiazol-4-yl)methanol according to the procedure as described in Example 20 step (j).
$^1$H NMR: (300 MHz, DMSO) δ: 8.19 (s, 1H), 7.56 (s, 1H), 6.94 (d, J=8.1 Hz, 1H), 6.83 (d, J=8.4 Hz, 1H), 5.48 (s, 2H), 3.12-3.19 (m, 2H), 2.77 (t, J=8.1 Hz, 2H), 2.40 (t, J=8.1 Hz, 2H), 2.16 (s, 6H), 1.38 (t, J=7.5 Hz, 3H). Mass spectrum (ESI, m/z): Calculated for C$_{21}$H$_{22}$ClNO$_3$S, 404 (M+H). found 404.

Example 71

3-(4-{[6-Chloro-2-(2-methylpropyl)-1,3-benzothiazol-4-yl]methoxy}-2,3-dimethylphenyl)propanoic acid

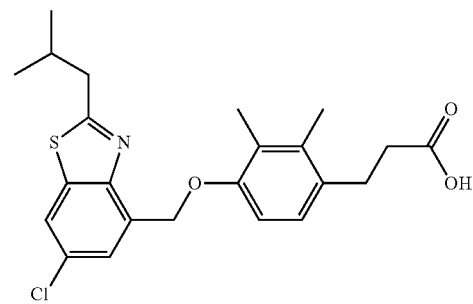 [SMILES: Cc1c(CCC(=O)O)ccc(OCc2cc(Cl)cc3sc(CC(C)C)nc23)c1C]

The title compound was prepared according to the procedure as described in Example 65 substituting 3-methylbutanoyl chloride for 2,2-dimethylpropanoyl chloride in step (b).
$^1$H NMR: (300 MHz, DMSO) δ: 8.19 (s, 1H), 7.57 (s, 1H), 6.31 (d, J=8.7 Hz, 1H), 6.84 (d, J=8.4 Hz, 1H), 5.48 (s, 2H), 3.01 (d, J=6.9 Hz, 2H), 2.77 (t, J=7.5 Hz, 2H), 2.39 (t, J=7.5 Hz, 2H), 2.14-2.17 (m, 7H), 1.00 (s, 3H), 0.09 (s, 3H). Mass spectrum (ESI, m/z): Calculated for C$_{23}$H$_{26}$ClNO$_3$S, 432 (M+H). found 432.

Example 72

3-(4-{[6-Fluoro-2-(1-methylethyl)-1,3-benzothiazol-4-yl]methoxy}-2,3-dimethylphenyl)propanoic acid

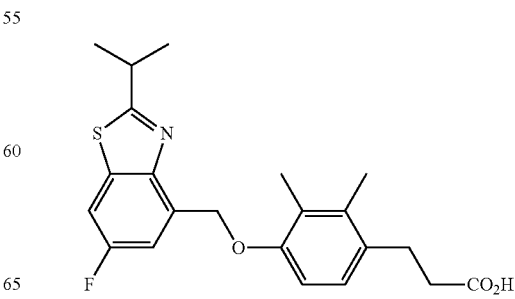

a) 4-Bromo-6-fluoro-2-isopropylbenzo[d]thiazole

Into a 50-mL round-bottom flask was placed 2-amino-3-bromo-5-fluorobenzene-1-thiol (800 mg, 3.60 mmol, prepared as described in Example 66), NMP (10 mL), and 2-methylpropanoyl chloride (771 mg, 7.24 mmol). The resulting solution was stirred for 1.5 h at 130° C. The resulting solution was diluted with ethyl acteate (100 mL). The resulting mixture was washed with brine (3×30 mL). The resulting residue was dried over anhydrous sodium sulfate. The solids were filtered out. The resulting mixture was concentrated under vacuum. The resulting residue was purified on a silica gel column with ethyl acetate/petroleum ether (1:5) to 4-bromo-6-fluoro-2-(propan-2-yl)-1,3-benzothiazole as yellow oil.

b) 3-(4-{[6-Fluoro-2-(1-methylethyl)-1,3-benzothiazol-4-yl]methoxy}-2,3-dimethylphenyl)propanoic acid The title compound was prepared by reacting 4-bromo-6-fluoro-2-(propan-2-yl)-1,3-benzothiazole according to the procedure as described in Example 65.

$^1$H NMR: (300 MHz, DMSO) δ: 7.95 (d, J=6.9 Hz, 1H), 7.41 (d, J=9.6 Hz, 1H), 6.94 (d, J=8.4 Hz, 1H), 6.85 (d, J=8.4 Hz, 1H), 5.49 (s, 2H), 3.48-3.39 (m, 1H), 2.80-2.72 (m, 2H), 2.50-2.37 (m, 2H), 2.16 (s, 6H), 1.41 (d, J=6.3 Hz, 6H). Mass spectrum (ESI, m/z): Calculated for $C_{22}H_{24}FNO_3S$, 400 (M−H). found 400.

Example 73

3-[4-{[2-Methyl-5-(trifluoromethoxy)-1-benzofuran-7-yl]methoxy}-2-(trifluoromethyl)phenyl]propanoic acid

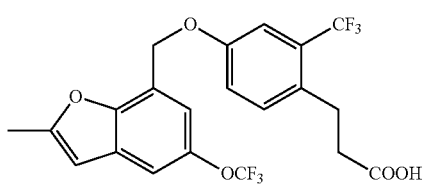 [SMILES: Cc1cc2cc(OC(F)(F)F)cc(COc3ccc(CCC(=O)O)c(C(F)(F)F)c3)c2o1]

a) Methyl 2-hydroxy-5-(trifluoromethoxy)benzoate

To a solution of 2-hydroxy-5-(trifluoromethoxy)benzoic acid (2.2 g, 9.90 mmol) in dichloromethane (10 mL) and methanol (2 mL) at 0° C. was added tms-diazomethane (2M) (5 mL) dropwise and the solution was stirred for 3 h at 25° C. The reaction was then quenched by the addition of water. The resulting solution was extracted with DCM (3×10 mL) and the organic layers combined and concentrated under vacuum. The resulting residue was purified on a silica gel column with ethyl acetate/petroleum ether (10/90). The collected fractions were combined and concentrated under vacuum to yield methyl 2-hydroxy-5-(trifluoromethoxy)benzoate as colorless oil.

b) Methyl 3-bromo-2-hydroxy-5-(trifluoromethoxy)benzoate

Into a 50-mL round-bottom flask was placed methyl 2-hydroxy-5-(trifluoromethoxy)benzoate (1 g, 4.23 mmol), CH$_3$CN (20 mL) and NBS (1.5 g, 8.43 mmol). The resulting solution was stirred overnight at 75° C. in an oil bath. The resulting mixture was concentrated under vacuum. The resulting residue was purified on a silica gel column with ethyl acetate/petroleum ether (2/98). The collected fractions were combined and concentrated under vacuum to yield methyl 3-bromo-2-hydroxy-5-(trifluoromethoxy)benzoate as yellow oil.

c) Methyl 2-methyl-5-(trifluoromethoxy)benzofuran-7-carboxylate

Into a 50-mL pressure tank reactor was placed methyl 3-bromo-2-hydroxy-5-(trifluoromethoxy)benzoate (1.2 g, 3.81 mmol), prop-1-yne (300 mg, 7.49 mmol), Pd(PPh$_3$)$_2$Cl$_2$ (268 mg, 0.38 mmol), CuI (73 mg, 0.38 mmol), triethylamine (760 mg, 7.51 mmol) and N,N-dimethylformamide (10 mL). The resulting solution was stirred overnight at 75° C. in an oil bath. The resulting solution was diluted with water. The resulting solution was extracted with ethyl acetate (3×15 mL) and the organic layers combined. The resulting mixture was washed with water (2×15 mL). The resulting mixture was concentrated under vacuum. The resulting residue was purified on a silica gel column with ethyl acetate/petroleum ether (10/90). The collected fractions were combined and concentrated under vacuum to yield methyl 2-methyl-5-(trifluoromethoxy)-1-benzofuran-7-carboxylate as a yellow solid.

d) Ethyl 3-(4-hydroxy-2-(trifluoromethyl)phenyl)propanoate

The title compound was prepared according to the procedure as described in Example 86 substituting 4-bromo-3-(trifluoromethyl)phenol for 4-bromo-2,3-difluorophenol in step (a).

e) 3-[4-{[2-Methyl-5-(trifluoromethoxy)-1-benzofuran-7-yl]methoxy}-2-(trifluoromethyl)phenyl] propanoic acid The title compound was prepared by reacting methyl 2-methyl-5-(trifluoromethoxy)-1-benzofuran-7-carboxylate and ethyl 3-(4-hydroxy-2-(trifluoromethyl)phenyl)propanoate according to the procedure as described in Example 1.

$^1$H NMR: (300 MHz, CD$_3$OD) δ: 7.52-7.24 (m, 5H), 6.58 (s, 1H), 5.42 (s, 2H), 3.04 (t, J=7.2 Hz, 2H), 2.57 (t, J=7.5 Hz, 2H), 2.51 (s, 3H). Mass spectrum (ESI, m/z): Calculated for $C_{21}H_{16}F_6O_5$, 461 (M−H). found 461.

Example 74

3-(4-((5-cyano-2-ethylbenzofuran-7-yl)methoxy)-2,3-dimethylphenyl)propanoic acid

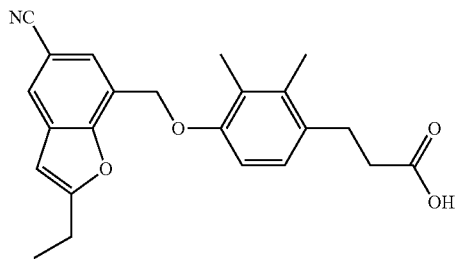 [SMILES: CCc1cc2cc(C#N)cc(COc3ccc(CCC(=O)O)c(C)c3C)c2o1]

Step A: Ethyl 3-(4-((5-bromo-2-ethylbenzofuran-7-yl)methoxy)-2,3-dimethylphenyl)propanoate Ethyl 3-(4-((5-bromo-2-ethylbenzofuran-7-yl)methoxy)-2,3-dimethylphenyl)propanoate was prepared according to the procedure as described in Example 83, substituting methyl 5-bromo-2-ethylbenzofuran-7-carboxylate (prepared as described in Example 101, step (a)) for methyl 2-ethyl-5-fluorobenzofuran-7-carboxylate in step (c).

Step B: Ethyl 3-(4-((5-cyano-2-ethylbenzofuran-7-yl)methoxy)-2,3-dimethylphenyl)propanoate A mixture of ethyl 3-(4-((5-bromo-2-ethylbenzofuran-7-yl)methoxy)-2,3-dimethylphenyl)propanoate (300 mg, 0.65 mmol), zinc cyanide (77 mg, 0.65 mmol) and Pd(PPh$_3$)$_4$ (75 mg, 0.065 mmol) in NMP (6 mL) was heated to 120° C. for 75 min in a microwave reactor. The mixture was cooled to room temperature and diluted with EtOAc. The EtOAc solution was washed with water, and brine and dried over Na$_2$SO$_4$. EtOAc was removed under vacuum and the resulting residue was purified by silica gel column chromatography to yield ethyl 3-(4-((5-cyano-2-ethylbenzofuran-7-yl)methoxy)-2,3-dimethylphenyl)propanoate.

Step C: 3-(4-((5-Cyano-2-ethylbenzofuran-7-yl)methoxy)-2,3-dimethylphenyl)propanoic acid 3-(4-((5-Cyano-2-ethylbenzofuran-7-yl)methoxy)-2,3-dimethylphenyl)propanoic acid was prepared from ethyl 3-(4-((5-cyano-2-ethylbenzofuran-7-yl)methoxy)-2,3-dimethylphenyl)propanoate by hydrolysis with sodium hydroxide according to the procedure as described in Example 86 step (e).
$^1$H NMR (CHLOROFORM-d) δ: 7.77 (d, J=1.5 Hz, 1H), 7.66 (d, J=1.5 Hz, 1H), 6.99 (d, J=8.3 Hz, 1H), 6.78 (d, J=8.6 Hz, 1H), 6.48 (s, 1H), 5.33 (s, 2H), 2.91-3.00 (m, 2H), 2.80-2.90 (m, 2H), 2.58-2.65 (m, 2H), 2.26 (s, 6H), 1.36 (t, 3H). Mass spectrum (ESI, m/z): Calcd. for C$_{23}$H$_{23}$NO$_4$, 777.3 (M2+Na). found 777.3.

Example 75

3-(6-((2-ethyl-5-fluorobenzofuran-7-yl)methoxy)-2-methylpyridin-3-yl)propanoic acid

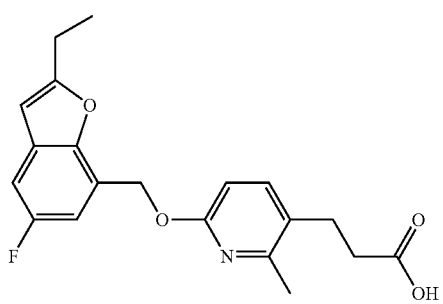 [SMILES: CCc1cc2cc(F)cc(COc3ccc(CCC(=O)O)c(C)n3)c2o1]

Step A: Ethyl 3-(6-fluoro-2-methylpyridin-3-yl)propanoate

Ethyl 3-(6-fluoro-2-methylpyridin-3-yl)propanoate was prepared according to the procedure described in Example 86 steps (a and b) substituting 3-bromo-6-fluoro-2-methylpyridine for 4-bromo-2,3-difluorophenol.

Step B: 3-(6-((2-Ethyl-5-fluorobenzofuran-7-yl)methoxy)-2-methylpyridin-3-yl)propanoic acid 3-(6-((2-Ethyl-5-fluorobenzofuran-7-yl)methoxy)-2-methylpyridin-3-yl)propanoic acid was prepared from ethyl 3-(6-fluoro-2-methylpyridin-3-yl)propanoate and (2-ethyl-5-fluorobenzofuran-7-yl)methanol (prepared as described Example 83 (c)) according to the procedure as described in Example 96.
$^1$H NMR (MeOD) δ: 7.49 (d, J=8.6 Hz, 1H), 7.13 (dd, J=8.6, 2.5 Hz, 1H), 7.05 (dd, J=10.1, 2.5 Hz, 1H), 6.65 (d, J=8.6 Hz, 1H), 6.48 (s, 1H), 5.56 (s, 2H), 2.88 (t, J=7.8 Hz, 2H), 2.78-2.85 (m, 2H), 2.52-2.58 (m, 2H), 2.45 (s, 3H), 1.34 (t, 3H). Mass spectrum (ESI, m/z): Calcd. for C$_{20}$H$_{20}$FNO$_4$, 358.1 (M+H). found 358.0.

Example 76

3-(4-{[6-Fluoro-2-(2-methylpropyl)-1,3-benzothiazol-4-yl]methoxy}-2,3-dimethylphenyl)propanoic acid

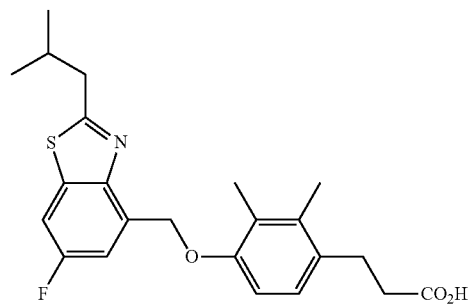 [SMILES: Cc1c(CCC(=O)O)ccc(OCc2cc(F)cc3sc(CC(C)C)nc23)c1C]

The title compound was prepared according to the procedure as described in Example 68 substituting 3-methylbutanoyl chloride for 2,2-dimethylpropanoyl chloride.
$^1$H NMR: (300 MHz, DMSO) δ: 7.96 (dd, J=6.3 Hz, 2.1 Hz, 1H), 7.42 (dd, J=7.5 Hz, 1.8 Hz, 1H), 6.94 (d, J=6.3 Hz, 1H), 6.85 (d, J=6.3 Hz, 1H), 5.51 (s, 2H), 3.02 (d, J=6.4 Hz, 2H), 2.78 (t, J=6.3 Hz, 2H), 2.41 (t, J=6.0 Hz, 2H), 2.21-2.11 (m, 7H), 1.01 (s, 6H). Mass spectrum (ESI, m/z): Calculated for C$_{23}$H$_{26}$FNO$_3$S, 414 (M−H). found 414.

Example 77

3-(4-((5-Chloro-2-(2-fluorovinyl)benzofuran-7-yl)methoxy)-2,3-dimethylphenyl)propanoic acid (mixture of E/Z)

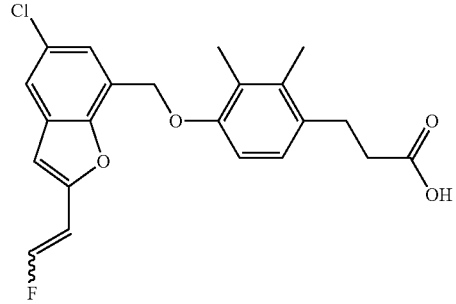 [SMILES: Cc1c(CCC(=O)O)ccc(OCc2cc(Cl)cc3cc(C=CF)oc23)c1C]

3-(4-((5-Chloro-2-(2-fluorovinyl)benzofuran-7-yl)methoxy)-2,3-dimethylphenyl)propanoic acid (mixture of E/Z) was prepared according to the procedure as described in Example 116 using ethyl 3-(4-((5-chloro-2-(2-fluorovinyl)benzofuran-7-yl)methoxy)-2,3-dimethylphenyl)propanoate (prepared as described in Example 112).

$^1$H NMR (CHLOROFORM-d) δ: 7.27-7.56 (m, 3H), 6.49-7.03 (m, 3H), 5.69-6.39 (m, 1H), 5.22-5.32 (m, 2H), 2.87-3.03 (m, 2H), 2.61 (t, J=7.8 Hz, 2H), 2.18-2.30 (m, 6H).

Example 78

3-(4-{[6-Fluoro-2-(trifluoromethyl)-1,3-benzothiazol-4-yl]methoxy}-2,3-dimethylphenyl)propanoic acid

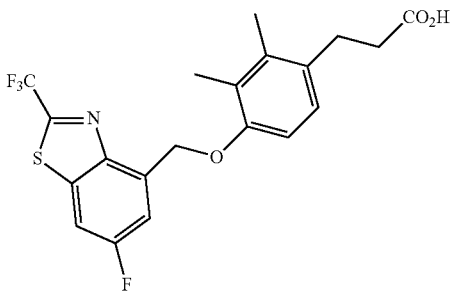 [SMILES: Cc1c(CCC(=O)O)ccc(OCc2cc(F)cc3sc(C(F)(F)F)nc23)c1C]

a) 4-Bromo-6-fluoro-2-(trifluoromethyl)benzo[d]thiazole

Into a 100-mL round-bottom flask was placed 2-amino-3-bromo-5-fluorobenzene-1-thiol (800 mg, 3.60 mmol, prepared as described in Example 66), NMP (10 mL) and trifluoroacetyl 2,2,2-trifluoroacetate (1.5 g, 7.14 mmol). The resulting solution was stirred for 1.5 h at 130° C. The resulting solution was diluted with ethyl acetate (100 mL). The resulting mixture was washed with brine (3×30 mL). The resulting residue was dried over anhydrous sodium sulfate. The solids were filtered out. The resulting mixture was concentrated under vacuum. The resulting residue was purified on a silica gel column with ethyl acetate/petroleum ether (1:10) to yield 4-bromo-6-fluoro-2-(trifluoromethyl)-1,3-benzothiazole as yellow oil.

b) Methyl 6-fluoro-2-(trifluoromethyl)benzo[d]thiazole-4-carboxylate

Into a 100-mL round-bottom flask was placed 4-bromo-6-fluoro-2-(trifluoromethyl)-1,3-benzothiazole (300 mg, 1.00 mmol), methanol (20 mL), TEA (303 mg, 2.99 mmol), and Pd(dppf)Cl$_2$ (110 mg, 0.15 mmol). CO(g) was introduced and the mixture was stirred overnight at 60° C. The resulting mixture was concentrated under vacuum. The resulting residue was purified on a silica gel column with ethyl acetate/petroleum ether (1:5) to yield methyl 6-fluoro-2-(trifluoromethyl)-1,3-benzothiazole-4-carboxylate as yellow oil.

c) (6-Fluoro-2-(trifluoromethyl)-2,3-dihydrobenzo[d]thiazol-4-yl)methanol

The title compound was prepared by reacting methyl 6-fluoro-2-(trifluoromethyl)benzo[d]thiazole-4-carboxylate using LiAlH$_4$ reduction according to the procedure as described in Example 1.

d) (6-Fluoro-2-(trifluoromethyl)benzo[d]thiazol-4-yl)methanol

Into a 25-mL round-bottom flask was placed [6-fluoro-2-(trifluoromethyl)-2,3-dihydro-1,3-benzothiazol-4-yl]methanol (100 mg, 0.39 mmol), dichloromethane (10 mL), and tetrachlorocyclohexa-2,5-diene-1,4-dione (194 mg, 0.79 mmol). The resulting solution was stirred for 30 min at 25° C. The resulting mixture was concentrated under vacuum. The resulting residue was purified on a silica gel column with ethyl acetate/hexane (1:4) to yield [6-fluoro-2-(trifluoromethyl)-1,3-benzothiazol-4-yl]methanol as yellow oil.

e) Tert-butyl 3-(4-(((6-fluoro-2-(trifluoromethyl)benzo[d]thiazol-4-yl)methoxy)-2,3-dimethylphenyl)propanoate Into a 25-mL round-bottom flask purged and maintained with an inert atmosphere of nitrogen was placed [6-fluoro-2-(trifluoromethyl)-1,3-benzothiazol-4-yl]methanol (40 mg, 0.16 mmol), tert-butyl 3-(4-hydroxy-2,3-dimethylphenyl)propanoate (60 mg, 0.24 mmol, prepared as described in Example 26), ADDP (87 mg, 0.35 mmol), Bu$_3$P (48 mg) and toluene (10 mL). The resulting solution was stirred overnight at 60° C. The resulting mixture was concentrated under vacuum. The resulting residue was purified on a silica gel column with ethyl acetate/petroleum ether (1:10) to yield tert-butyl 3-(4-[[6-fluoro-2-(trifluoromethyl)-1,3-benzothiazol-4-yl]methoxy]-2,3-dimethylphenyl)propanoate as a white solid.

f) 3-(4-{[6-Fluoro-2-(trifluoromethyl)-1,3-benzothiazol-4-yl]methoxy}-2,3-dimethylphenyl)propanoic acid Into a 25-mL round-bottom flask was placed tert-butyl 3-(4-[[6-fluoro-2-(trifluoromethyl)-1,3-benzothiazol-4-yl]methoxy]-2,3-dimethylphenyl)propanoate (50 mg, 0.10 mmol), dichloromethane (10 mL) and trifluoroacetic acid (2 mL). The resulting solution was stirred overnight at 25° C. The resulting solution was diluted with DCM (10 mL). The resulting mixture was washed with brine (3×5 mL). The resulting residue was dried over anhydrous sodium sulfate. The solids were filtered out. The resulting mixture was concentrated under vacuum to yield 3-(4-[[6-fluoro-2-(trifluoromethyl)-1,3-benzothiazol-4-yl]methoxy]-2,3-dimethylphenyl)propanoic acid as a off-white solid.

$^1$H NMR: (400 MHz, DMSO) δ: 7.95 (dd, J=8.4 Hz, 2.8 Hz, 1H), 7.42 (dd, J=9.6 Hz, 2.4 Hz, 1H), 6.96 (d, J=8.4 Hz, 1H), 6.89 (d, J=8.4 Hz, 1H), 5.58 (s, 2H), 2.77 (t, J=8.4 Hz, 2H), 2.41 (t, J=8.4 Hz, 2H), 2.18 (s, 3H), 2.17 (s, 3H). Mass spectrum (ESI, m/z): Calculated for C$_{20}$H$_{17}$F$_4$NO$_3$S, 426 (M−H). found 426.

Example 79

3-(4-{[6-Chloro-2-(trifluoromethyl)-1,3-benzothiazol-4-yl]methoxy}-2,3-dimethylphenyl)propanoic acid

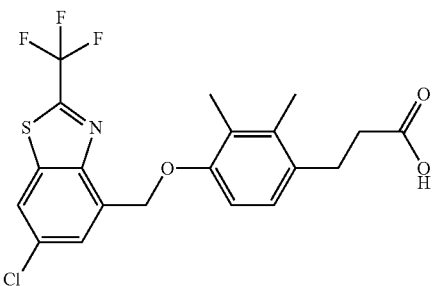 [SMILES: Cc1c(CCC(=O)O)ccc(OCc2cc(Cl)cc3sc(C(F)(F)F)nc23)c1C]

The title compound was prepared according to the procedure as described in Example 78 substituting 2-amino-3-bromo-5-chlorobenzene-1-thiol (prepared as described in Example 65) for 2-amino-3-bromo-5-fluorobenzene-1-thiol.

$^1$H NMR: (300 MHz, DMSO) δ: 8.51 (s, 1H), 7.81 (s, 1H), 6.86-6.97 (m, 2H), 5.55 (s, 2H), 2.78 (t, J=7.2 Hz, 2H), 2.40 (d, J=7.2 Hz, 1H), 2.16 (s, 6H). Mass spectrum (ESI, m/z): Calculated for $C_{20}H_{17}ClF_3NO_3S$, 442 (M−H). found 442.

Example 80

3-{4-[(5-Chloro-2-methyl-1,3-benzothiazol-7-yl)methoxy]-2,3-dimethylphenyl}propanoic acid

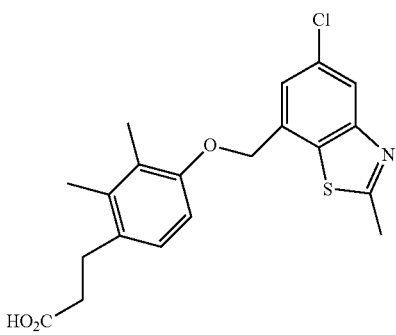 [SMILES: Cc1nc2cc(Cl)cc(COc3ccc(CCC(=O)O)c(C)c3C)c2s1]

a) Ethyl 2,5-dichloro-3-nitrobenzoate

Into a 100-mL round-bottom flask was placed 2,5-dichloro-3-nitrobenzoic acid (1 g, 4.24 mmol), potassium carbonate (2.34 g, 16.93 mmol), acetone, and diethyl sulfate (1.6 g, 10.38 mmol). The resulting solution was stirred for 1 h at 55° C. The resulting mixture was concentrated under vacuum. The resulting residue was purified on a silica gel column with ethyl acetate/petroleum ether (1:10) to yield ethyl 2,5-dichloro-3-nitrobenzoate as colorless oil.

b) Ethyl 2-(benzylthio)-5-chloro-3-nitrobenzoate

Into a 100-mL round-bottom flask purged and maintained with an inert atmosphere of nitrogen, was placed ethyl 2,5-dichloro-3-nitrobenzoate (1.1 g, 4.17 mmol), N,N-dimethylformamide (20 mL), potassium carbonate (1.73 g, 12.52 mmol) and phenylmethanethiol (570 mg, 4.59 mmol). The resulting solution was stirred for 6 h at 90° C. The resulting solution was diluted with ethyl acetate (100 mL). The resulting mixture was washed with brine (3×30 mL). The resulting residue was dried over anhydrous sodium sulfate. The solids were filtered out. The resulting mixture was concentrated under vacuum. The resulting residue was purified on a silica gel column with ethyl acetate/petroleum ether (1:5) to yield ethyl 2-(benzylsulfanyl)-5-chloro-3-nitrobenzoate as a solid.

c) Ethyl 3-amino-2-(benzylthio)-5-chlorobenzoate

Into a 100-mL round-bottom flask was placed ethyl 2-(benzylsulfanyl)-5-chloro-3-nitrobenzoate (1.2 g, 3.41 mmol), ethanol (30 mL), Fe (1.9 g) and NH4Cl(aq) (10 mL). The resulting mixture was stirred for 6 h at 60° C. The resulting mixture was concentrated under vacuum. The resulting solution was diluted with ethyl acetate (100 mL). The resulting residue was dried over anhydrous sodium sulfate. The solids were filtered out. The resulting mixture was concentrated under vacuum. The resulting residue was purified on a silica gel column with ethyl acetate/petroleum ether (1:3) to yield ethyl 3-amino-2-(benzylthio)-5-chlorobenzoate as yellow oil.

d) 3-Amino-5-chloro-2-mercaptobenzoic acid

Into a 100-mL round-bottom flask purged and maintained with an inert atmosphere of nitrogen was placed ethyl 3-amino-2-(benzylsulfanyl)-5-chlorobenzoate (800 mg, 2.49 mmol), tot (30 mL) and $AlCl_3$ (1.32 g). The resulting solution was stirred overnight at 30° C. The resulting mixture was concentrated under vacuum. The resulting residue was purified on a silica gel column with dichloromethane/methanol (10:1) to yield 3-amino-5-chloro-2-mercaptobenzoic acid as a yellow solid.

e) 5-Chloro-2-methylbenzo[d]thiazole-7-carboxylic acid

Into a 100-mL round-bottom flask was placed 3-amino-5-chloro-2-mercaptobenzoic acid (600 mg, 2.76 mmol), NMP (10 mL) and acetyl chloride (433 mg, 5.52 mmol). The resulting solution was stirred for 2 h at 130° C. The resulting solution was diluted with ethyl acetate (100 mL). The resulting mixture was washed with brine (3×30 mL). The resulting residue was dried over anhydrous sodium sulfate. The solids were filtered out. The resulting mixture was concentrated under vacuum to yield 5-chloro-2-methyl-1,3-benzothiazole-7-carboxylic acid as yellow oil.

f) (5-Chloro-2-methylbenzo[d]thiazol-7-yl)methanol

To a solution of 5-chloro-2-methyl-1,3-benzothiazole-7-carboxylic acid (380 mg, 1.67 mmol) in diethyl ether (20 mL) was added $LiAlH_4$ (127 mg, 3.35 mmol) at 0-5° C. The resulting solution was stirred for 30 min at 0° C. The reaction was then quenched by the addition of water (1 mL). The resulting mixture was concentrated under vacuum. The resulting residue was purified on a silica gel column with ethyl acetate/petroleum ether (1:2) to yield (5-chloro-2-methyl-1,3-benzothiazol-7-yl)methanol as a yellow solid.

g) 3-{4-[(5-Chloro-2-methyl-1,3-benzothiazol-7-yl)methoxy]-2,3-dimethylphenyl}propanoic acid The title compound was prepared by reacting (5-chloro-2-methyl-1,3-benzothiazol-7-yl)methanol according to the procedure as described in Example 1.

$^1$H NMR (DMSO-d$_6$) δ: 12.08 (s, 1H), 7.99 (d, J=1.7 Hz, 1H), 7.64 (d, J=1.5 Hz, 1H), 6.90-6.99 (m, 1H), 6.78-6.87 (m, 1H), 5.31 (s, 2H), 2.82 (s, 3H), 2.73-2.81 (m, 2H), 2.40 (t, J=7.8 Hz, 2H), 2.19 (s, 3H), 2.17 (s, 3H). Mass spectrum (ESI, m/z): Calculated for C$_{20}$H$_{20}$ClNO$_3$S, 388 (M–H). found 388.

Example 81

3-(4-((5-chloro-2-methyl-2H-indazol-7-yl)methoxy)-2,3-dimethylphenyl)propanoic acid

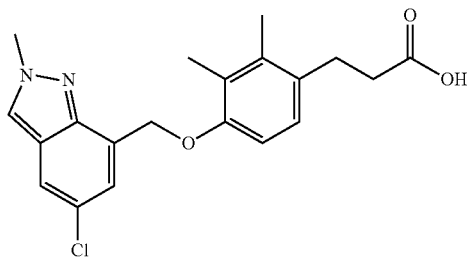 [SMILES: Cc1c(CCC(=O)O)ccc(OCc2cc(Cl)cc3cn(C)nc23)c1C]

a) 5-chloro-2-methyl-2H-indazole-7-carbaldehyde and 5-chloro-1-methyl-1H-indazole-7-carbaldehyde A solution of commercially available 5-chloro-1H-indazole-7-carbaldehyde (344 mg, 1.90 mmol) in dry DMF (5 mL) was added carefully to a suspension of NaH (56 mg, 2.22 mmol) in dry DMF (15 mL) and stirred for 30 minutes at ambient temperature. Methyl iodide (140 μL, 2.25 mmol) was added and the reaction mixture stirred overnight. The next day, the solution was cautiously poured onto water and extracted with diethyl ether. Washing of the organic layer with brine, followed by concentration in vacuo and purification of the residue by flash chromatography (SiO$_2$, 10-100% dcm/heptanes) yielded the title mixture of isomers (ca. 60:40 based on integration of the aldehyde NMR signals) as a residue, which was used in the next step without further separation.

b) (5-Chloro-2-methyl-2H-indazol-7-yl)methanol and (5-chloro-1-methyl-1H-indazol-7-yl)methanol The residue prepared in step (a) above (368 mg, 1.89 mmol) was dissolved in dry THF (12 mL) and treated with a solution of lithium aluminum-tri-tert-butoxyhydride (2.50 mL, 2.50 mmol, 1 M in THF) under argon. After stirring the resulting mixture at room temperature for 4 h, a saturated solution of sodium tartrate was added and the resulting mixture stirred at room temperature. The resulting mixture was extracted with diethyl ether, then concentrated in vacuo and purified of the residue by flash chromatography (SiO$_2$, step gradient: DCM->10% diethyl ether/DCM->diethyl ether) to yield the title compounds, as separated residues.

(5-chloro-2-methyl-2H-indazol-7-yl)methanol: $^1$H NMR (MeOD) δ: 8.14 (s, 1H), 7.57 (s, 1H), 7.28 (s, 1H), 4.97 (s, 2H), 4.19 (s, 3H).

(5-chloro-1-methyl-1H-indazol-7-yl)methanol: $^1$H NMR (MeOD) δ: 7.94 (s, 1H), 7.68 (s, 1H), 7.32 (s, 1H), 4.97 (s, 2H), 4.32 (s, 3H).

c) Ethyl 3-(4-((5-chloro-2-methyl-2H-indazol-7-yl)methoxy)-2,3-dimethylphenyl)-propanoate Into a 40 mL vial equipped with a septum cap and stirbar was placed (5-chloro-2-methyl-2H-indazol-7-yl)methanol (28.8 mg, 0.146 mmol), ethyl 3-(4-hydroxy-2,3-dimethylphenyl)-propanoate (69.4 mg, 0.312 mmol), triphenylphosphine (88 mg, 0.336 mmol) and dry THF (12 mL). The vial was cooled to 0° C. under argon and treated dropwise with diisopropylazodicarboxylate (70 μL, 0.338 mmol). The resulting mixture was allowed to warm to room temperature overnight, then concentrated in vacuo. The resulting residue was purified by by flash chromatography (SiO$_2$, 50% ether/heptane) to yield the title compound as a residue.

$^1$H NMR (CHLOROFORM-d) δ: 7.87 (s, 1H), 7.55 (s, 1H), 7.41 (s, 1H), 6.95 (d, J=8.3 Hz, 1H), 6.81 (d, J=8.3 Hz, 1H), 5.46 (s, 2H), 4.18-4.26 (m, 3H), 4.14 (q, J=7.1 Hz, 2H), 2.85-2.97 (m, 2H), 2.53 (t, J=8.1 Hz, 2H), 2.31 (s, 3H), 2.26 (s, 3H), 1.25 (t, J=7.1 Hz, 3H).

d) 3-(4-((5-Chloro-2-methyl-2H-indazol-7-yl)methoxy)-2,3-dimethylphenyl)propanoic acid Into a 20 mL scintillation vial was placed ethyl 3-(4-((5-chloro-2-methyl-2H-indazol-7-yl)methoxy)-2,3-dimethylphenyl)-propanoate (16 mg, 0.0399 mmol) followed by potassium hydroxide (100 μL, 0.25 mmol, 2.5 M aqueous), THF (10 mL) methanol (2 mL) and water (2 mL). The resulting mixture was stirred overnight at ambient temperature and then the pH was adjusted to pH~4 by the addition of aqueous HCl. The resulting mixture was extracted with ethyl acetate, the organic layer was dried (MgSO$_4$) and then concentrated in vacuo to yield the title compound as a white solid.

$^1$H NMR (ACETONITRILE-d$_3$) δ: 8.10 and 8.05 (s, 1H), 7.65-7.69 and 7.56-7.63 (s, 1H), 7.29-7.33 and 7.20 (s, 1H), 6.91-6.99 (m, 1H), 6.78-6.86 (m, 1H), 5.44-5.48 and 5.38-5.44 (m, 2H), 4.17-4.20 and 4.12-4.17 (m, 3H), 2.81-2.89 (m, 2H), 2.46-2.53 (m, 2H), 2.22 (s, 3H) Note: other methyl group buried under water peak.

Example 82

3-(4-((5-chloro-1-methyl-1H-indazol-7-yl)methoxy)-2,3-dimethylphenyl)propanoic acid

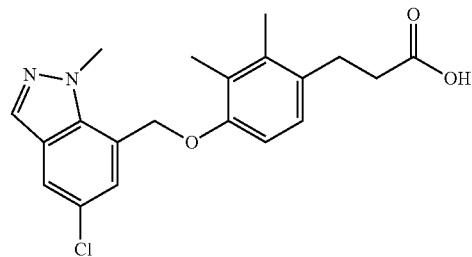 [SMILES: Cc1c(CCC(=O)O)ccc(OCc2cc(Cl)cc3cnn(C)c23)c1C]

a) Ethyl 3-(4-((5-chloro-1-methyl-1H-indazol-7-yl)methoxy)-2,3-dimethylphenyl)-propanoate Into a 40 mL vial equipped with a septum cap and stirbar was placed (5-chloro-1-methyl-1H-indazol-7-yl)methanol (76 mg, 0.387 mmol, prepared as described in Example 81 step b), ethyl 3-(4-hydroxy-2,3-dimethylphenyl)-propanoate (86 mg, 0.389 mmol), triphenylphosphine (107 mg, 0.408 mmol) and dry THF (12 mL). The vial was cooled to 0° C. under argon and treated dropwise with diisopropylazodicarboxylate (80 µL, 0.386 mmol). The resulting mixture was allowed to warm to room temperature overnight, then concentrated in vacuo. The resulting residue was purified flash chromatography (SiO$_2$, 50% ether/heptane) to yield the title compound as a residue.

$^1$H NMR (CHLOROFORM-d) δ: 7.94 (s, 1H), 7.70 (s, 1H), 7.34 (s, 1H), 7.03 (d, J=8.3 Hz, 1H), 6.81 (d, J=8.3 Hz, 1H), 5.26 (s, 2H), 4.22 (s, 3H), 4.15 (q, J=7.1 Hz, 2H), 2.95 (t, J=7.9 Hz, 2H), 2.55 (t, J=7.9 Hz, 2H), 2.23 (s, 3H), 2.12 (s, 3H), 1.26 (t, 3H).

b) 3-(4-((5-chloro-1-methyl-1H-indazol-7-yl)methoxy)-2,3-dimethylphenyl)propanoic acid Into a 20 mL vial was placed ethyl 3-(4-((5-chloro-1-methyl-1H-indazol-7-yl)methoxy)-2,3-dimethylphenyl)-propanoate (70 mg, 0.175 mmol) followed by potassium hydroxide (300 µL, 0.75 mmol, 2.5 M aqueous), THF (10 mL) methanol (2 mL) and water (2 mL). The resulting mixture was stirred overnight at ambient temperature and then the pH was adjusted to pH~4 by the addition of aqueous HCl. The resulting mixture was extracted with ethyl acetate, the organic layer was dried (MgSO$_4$) and concentration in vacuo to yield the title compound as a white solid.

$^1$H NMR (ACETONITRILE-d$_3$) δ: 7.96 (s, 1H), 7.77 (s, 1H), 7.42 (s, 1H), 6.98-7.08 (m, 1H), 6.86-6.95 (m, 1H), 5.39 (s, 2H), 4.19 (s, 3H), 2.83-2.92 (m, 2H), 2.46-2.55 (m, 2H), 2.20 (s, 3H), 2.09 (s, 3H).

Example 83

3-(4-((2-ethyl-5-fluorobenzofuran-7-yl)methoxy)-2,3-dimethylphenyl)propanoic acid

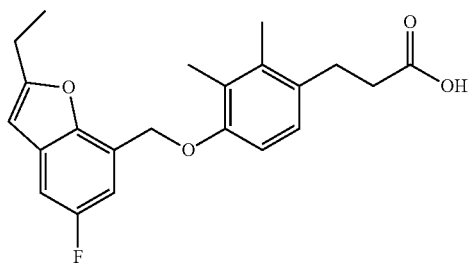 [SMILES: CCc1cc2cc(F)cc(COc3ccc(CCC(=O)O)c(C)c3C)c2o1]

a) Methyl 3-bromo-5-fluoro-2-hydroxybenzoate

A 1-L round bottom flask was charged with methyl 5-fluoro-2-hydroxybenzoate (9.40 g, 55.25 mmol) and methanol (320 mL). A solution of bromine (3.21 mL, 62.43 mmol) and methanol (140 mL) was added dropwise via an addition funnel. The resulting mixture was stirred at room temperature overnight. The resulting mixture was concentrated in vacuo and purified using the Analogix IF-280, 400 g column, 95:5 Heptane:EtOAc to yield Methyl 3-bromo-5-fluoro-2-hydroxybenzoate.

$^1$H NMR (CHLOROFORM-d) δ: 7.17-7.22 (m, 1H), 6.93-6.96 (m, 1H), and 3.49 (s, 3H).

b) Methyl 2-ethyl-5-fluorobenzofuran-7-carboxylate

A 20 mL sealed tube was charged with methyl 3-bromo-5-fluoro-2-hydroxybenzoate (1.39 g, 4.01 mmol) and DMF (4.0 mL). The resulting mixture was cooled using a dry ice and acetone bath to −78° C. To the resulting mixture was then bubbled 1-butyne for 10 minutes. To the resulting mixture was then added copper iodide (76.5 mg, 0.402 mmol) and Pd(PPh$_3$)$_2$Cl$_2$ (281.8 mg, 0.402 mmol). The resulting mixture was flushed with argon, the tube was sealed and the mixture stirred at room temperature for 1 h, then heated to 75° C. and stir overnight. The resulting mixture was concentrated in vacuo and purified using the Analogix IF-280, 150 g column, 95:5-90:10 Heptane:EtOAc to yield methyl 2-ethyl-5-fluorobenzofuran-7-carboxylate.

$^1$H NMR (CHLOROFORM-d) δ: 7.52-7.58 (m, 1H), 7.28-7.34 (m, 1H), 6.40 (s, 1H), 3.89 (s, 3H), 2.82 (q, J=7.8 Hz, J=11.7 Hz, 2H) and 1.35 (t, J=7.8 Hz, 3H).

c) (2-ethyl-5-fluorobenzofuran-7-yl)methanol

A 20 mL vial was charged with methyl 2-ethyl-5-fluorobenzofuran-7-carboxylate (200 mg, 0.90 mmol) and 2.4 mL of dichloromethane. The resulting mixture was cooled using a dry ice and acetone bath to −78° C. To the resulting mixture was then added dropwise via syringe a dichloromethane solution of DIBAL (3.60 mL, 3.60 mmol). The resulting mixture was warmed to room temperature over 20 minutes. The resulting mixture was poured into aqueous sodium hydroxide solution (50 mL). The layers were separated and the aqueous layer extracted three more times with ethyl acetate (100 mL each time). The organic layers were dried with magnesium sulfate, filtered through CELITE and concentrate in vacuo to yield (2-ethyl-5-fluorobenzofuran-7-yl)methanol, which was used without further purification.

$^1$H NMR (CHLOROFORM-d) δ: 7.04-7.08 (m, 1H), 6.95-7.02 (m, 1H), 6.35 (s, 1H), 4.94-4.99 (m, 2H), 2.80 (q, J=7.8 Hz, J=11.7 Hz, 2H) and 1.33 (t, J=7.8 Hz, 3H).

d) Ethyl 3-(4-((2-ethyl-5-fluorobenzofuran-7-yl)methoxy)-2,3-dimethylphenyl)propanoate A 10 mL round bottom flask was charged with ethyl 3-(4-hydroxy-2,3-dimethylphenyl)propanoate (389.0 mg, 1.79 mmol), (2-ethyl-5-fluorobenzofuran-7-yl)methanol (174.0 mg, 0.896 mmol), triphenylphosphine (367.0 mg, 1.40 mmol) and tetrahydrofuran (1.26 mL). The resulting mixture was cooled using an ice/water bath. to the resulting mixture was then added a 40% wt solution of diethyl azodicarboxylate (0.66 mL, 1.44 mmol) was added dropwise. The resulting mixture was allowed to warm to room temperature with stirring overnight. The resulting mixture was concentrated in vacuo and purified using the Analogix IF-280, 40 g column, 95:5-90:10 Heptane:EtOAc to yield ethyl 3-(4-((2-ethyl-5-fluorobenzofuran-7-yl)methoxy)-2,3-dimethylphenyl)propanoate.

$^1$H NMR (CHLOROFORM-d) δ: 7.02-7.13 (m, 2H), 6.91-7.00 (m, 1H), 6.73-6.82 (m, 1H), 6.35 (s, 1H), 5.28 (s, 2H), 4.13 (q, J=7.8 Hz, J=11.7 Hz, 2H), 2.87-2.96 (m, 2H), 2.80 (q, J=7.8 Hz, J=11.7 Hz, 2H), 2.47-2.56 (m, 2H), 2.25 (s, 3H), 2.23 (s, 3H), 1.33 (t, J=7.8 Hz, 3H) and 1.24 (t, J=7.8 Hz, 3H).

e) 3-(4-((2-ethyl-5-fluorobenzofuran-7-yl)methoxy)-2,3-dimethylphenyl)propanoic acid A 10 mL round bottom flask was charged with ethyl 3-(4-((2-ethyl-5-fluorobenzofuran-7-yl)methoxy)-2,3-dimethylphenyl)propanoate (243.5 mg, 0.611 mmol), tetrahydrofuran (5.1 mL), water (2.1 mL), and lithium hydroxide (256.4 mg, 6.11 mmol). The resulting mixture was stirred at room temperature overnight. The resulting mixture was then washed with diethyl ether. The resulting residue was then acidified with 2N HCl. The resulting mixture was extracted with ethyl acetate (2×100 mL). The organic layers were dried with magnesium sulfate, filter and concentrate in vacuo. The resulting residue was purified using the Analogix IF-280, 40 g column, 90:10-50:50 Heptane:EtOAc to yield 3-(4-((2-ethyl-5-fluorobenzofuran-7-yl)methoxy)-2,3-dimethylphenyl)propanoic acid.

$^1$H NMR (CHLOROFORM-d) δ: 7.06-7.14 (m, 2H), 6.96-7.02 (m, 1H), 6.77-6.83 (m, 1H), 6.38 (s, 1H), 5.30 (s, 2H), 2.90-3.00 (m, 2H), 2.80 (q, J=7.8 Hz, J=11.7 Hz, 2H), 2.56-2.65 (m, 2H), 2.26 (s, 3H), 2.25 (s, 3H), and 1.37 (t, J=7.8 Hz, 3H); LC/MS (ES+) m/z 371 (M+1).

Example 84

3-(4-((5-fluoro-2-(trifluoromethyl)benzofuran-7-yl)methoxy)-2,3-dimethylphenyl)propanoic acid

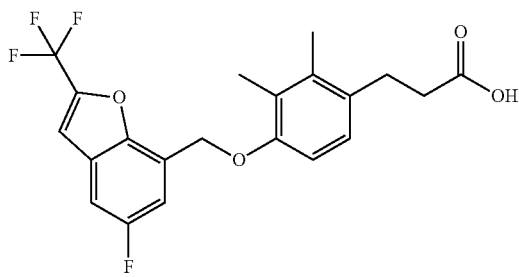 [SMILES: Cc1c(CCC(=O)O)ccc(OCc2cc(F)cc3cc(C(F)(F)F)oc23)c1C]

a) Methyl 5-fluoro-2-(trifluoromethyl)benzofuran-7-carboxylate

A 20 mL sealed tube was charged with methyl 3-bromo-5-fluoro-2-hydroxybenzoate (1.39 g, 4.01 mmol, prepared as described in Example 83) and 4.0 mL of dimethylformamide. The resulting mixture was cooled using a dry ice and acetone bath to −78° C. Inot the resulting mixture was then bubbled 3,3,3-trifluoroprop-1-yne for 10 minutes; followed by addition of copper iodide (76.5 mg, 0.402 mmol) and Pd(PPh$_3$)$_2$Cl$_2$ (281.8 mg, 0.402 mmol). The reaction mixture was flushed with argon, the tube sealed and the resulting mixture stirred at room temperature for 1 h, then heated to 75° C. and stirred overnight. The resulting mixture was concentrated in vacuo and the resulting residue using the Analogix IF-280, 150 g column, 95:5-90:10 Heptane:EtOAc to yield methyl 5-fluoro-2-(trifluoromethyl)benzofuran-7-carboxylate, which was used directly in the next step.

b) (5-fluoro-2-(trifluoromethyl)benzofuran-7-yl)methanol

A 50 mL round bottom flask was charged with methyl 5-fluoro-2-(trifluoromethyl)benzofuran-7-carboxylate (1.05 g, 4.00 mmol) and 10.5 mL of dichloromethane. The resulting mixture was cooled using a dry ice and acetone bath to −78° C. To the resulting mixture was then added dropwise via syringe a dichloromethane solution of DIBAL (16.0 mL, 16.0 mmol). The resulting mixture was warmed to room temperature over 20 minutes, then poured into aqueous sodium hydroxide solution (50 mL). The layers were separated, and the aqueous layer extracted three more times with ethyl acetate (100 mL each time). The organic layers were dried with magnesium sulfate, filtered through CELITE and concentrated in vacuo to yield (5-fluoro-2-(trifluoromethyl)benzofuran-7-yl)methanol, which was used without further purification.

$^1$H NMR (CHLOROFORM-d) δ: 7.56-7.61 (m, 1H), 7.51-7.55 (m, 1H), 6.30-6.36 (m, 1H), and 4.94-5.03 (m, 2H).

c) Ethyl 3-(4-((5-fluoro-2-(trifluoromethyl)benzofuran-7-yl)methoxy)-2,3-dimethylphenyl)propanoate A 10 mL round bottom flask was charged with ethyl 3-(4-hydroxy-2,3-dimethylphenyl)propanoate (1.71 g, 7.69 mmol), (5-fluoro-2-(trifluoromethyl)benzofuran-7-yl)methanol (900.0 mg, 3.84 mmol), triphenylphosphine (1.57 g, 6.00 mmol) and tetrahydrofuran (5.4 mL). The resulting mixture was cooled using an ice/water bath. A 40% wt solution of diethyl azodicarboxylate (2.8 mL, 6.19 mmol) was then added dropwise and the resulting mixture allowed to warm to room temperature with stirring overnight. The resulting mixture was concentrated in vacuo and the resulting residue purified using the Analogix IF-280, 150 g column, 95:5-90:10 Heptane:EtOAc to yield ethyl 3-(4-((5-fluoro-2-(trifluoromethyl)benzofuran-7-yl)methoxy)-2,3-dimethylphenyl)propanoate.

$^1$H NMR (CHLOROFORM-d) δ: 6.93-7.05 (m, 3H), 6.65-6.72 (m, 2H), 5.08 (s, 2H), 4.13 (q, J=7.8 Hz, J=11.7 Hz, 2H), 2.86-2.96 (m, 2H), 2.47-2.57 (m, 2H), 2.24 (s, 6H), and 1.25 (t, J=7.8 Hz, 3H).

d) 3-(4-((5-fluoro-2-(trifluoromethyl)benzofuran-7-yl)methoxy)-2,3-dimethylphenyl)propanoic acid A 50 mL round bottom flask was charged with ethyl 3-(4-((5-fluoro-2-(trifluoromethyl)benzofuran-7-yl)methoxy)-2,3-dimethylphenyl)propanoate (215.6 mg, 0.492 mmol), tetrahydrofuran (4.1 mL), water (1.7 mL), and lithium hydroxide (206 mg, 4.92 mmol). The resulting mixture was stirred at room temperature overnight. The resulting mixture was washed with diethyl ether. The resulting residue was then acidified with 2N HCl. The resulting mixture was extracted with ethyl acetate (2×100 mL). The organic layers were dried with magnesium sulfate, filtered and concentrated in vacuo. The resulting residue was purified using the Analogix IF-280, 40 g column, 90:10-50:50 Heptane:EtOAc to yield 3-(4-((5-fluoro-2-(trifluoromethyl)benzofuran-7-yl)methoxy)-2,3-dimethylphenyl)propanoic acid.

$^1$H NMR (CHLOROFORM-d) δ: 6.94-7.05 (m, 3H), 6.66-6.74 (m, 2H), 5.08 (s, 2H), 2.90-2.98 (m, 2H), 2.55-2.65 (m, 2H), and 2.25 (s, 6H); LC/MS (ES+) m/z 434 (M+Na).

Example 85

3-(4-((3,5-difluoro-2-methylbenzofuran-7-yl)methoxy)-2,3-dimethylphenyl)propanoic acid

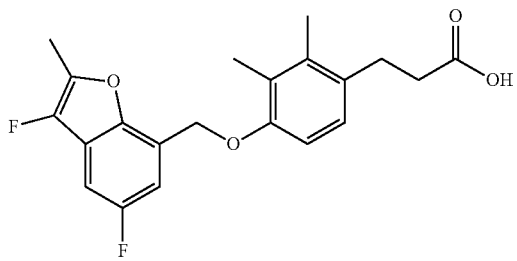 [SMILES: Cc1oc2c(COc3ccc(CCC(=O)O)c(C)c3C)cc(F)cc2c1F]

a) Methyl 5-fluoro-2-methylbenzofuran-7-carboxylate

A 20 mL sealed tube was charged with methyl 3-bromo-5-fluoro-2-hydroxybenzoate (1.39 g, 4.01 mmol) and 4.0 mL of dimethylformamide. The resulting mixture was cooled using a dry ice and acetone bath to −78° C. Inot the resulting mixture was then bubbled propyne for 10 minutes, followed by addition of copper iodide (76.5 mg, 0.402 mmol) and PdCl$_2$(Ph$_3$P)$_2$ (281 mg, 0.402 mmol). The resulting mixture was flushed with argon, the tube sealed and the resulting mixture stirred at room temperature for 1 h, then heated to 75° C. and stirred overnight. The resulting mixture was concentrated in vacuo and the resulting residue purified using the Analogix IF-280, 150 g column, 95:5 Heptane:EtOAc to yield methyl 5-fluoro-2-methylbenzofuran-7-carboxylate, which was used directly in the next step.

$^1$H NMR (CHLOROFORM-d) δ: 7.50-7.59 (m, 1H), 7.28-7.36 (m, 1H), 6.40 (s, 1H), 3.98 (s, 3H), and 2.52 (s, 3H).

b) Methyl 2-bromo-3,5-difluoro-2-methyl-2,3-dihydrobenzofuran-7-carboxylate A polypropylene tube was charged with N-bromosuccinimide (222.3 mg, 1.25 mmol) and diethyl ether (6.0 mL) and 70% pyridinium poly(hydrogen fluoride) solution (1.20 mL, 0.961 mmol). The tube was flushed with argon and cooled using a dry ice and acetone bath to −78° C. A solution of methyl 5-fluoro-2-methylbenzofuran-7-carboxylate (200 mg, 0.961 mmol) in diethyl ether (1.0 mL) was added slowly. The resulting residue was stirred and allowed to warm to room temperature overnight. The resulting mixture was poured into ice water and extract with diethyl ether. The resulting mixture was washed with saturated sodium bicarbonate and the organic layers dried with magnesium sulfate, filtered through CELITE and concentrated in vacuo to yield methyl 2-bromo-3,5-difluoro-2-methyl-2,3-dihydrobenzofuran-7-carboxylate, which was used without further purification.

$^1$H NMR (CHLOROFORM-d) δ: 7.58-7.65 (m, 1H), 7.28-7.35 (m, 1H), 5.29 (d, J=15.2 Hz, 1H), 3.94 (s, 3H) and 2.12 (d, J=18.2 Hz, 3H).

c) Methyl 3,5-difluoro-2-methylbenzofuran-7-carboxylate

A 50 mL round bottom flask was charged with methyl 2-bromo-3,5-difluoro-2-methyl-2,3-dihydrobenzofuran-7-carboxylate (300 mg, 0.977 mmol) and 9.8 mL of dimethylsulfoxide. To the resulting mixture was then added 1,8-diazobicycloundec-7-ene (0.29 mL, 1.95 mmol) and the mixture stirred at room temperature overnight. The resulting mixture was diluted with diethyl ether and washed with saturated aqueous ammonium chloride. The organic layers were dried with magnesium sulfate, filtered through CELITE and concentrated in vacuo to yield methyl 3,5-difluoro-2-methylbenzofuran-7-carboxylate, which was used without further purification.

$^1$H NMR (CHLOROFORM-d) δ: 7.59-7.67 (m, 1H), 7.26-7.34 (m, 1H), 4.00 (s, 3H), and 2.55 (s, 3H).

d) (3,5-difluoro-2-methylbenzofuran-7-yl)methanol

A 50 mL round bottom flask was charged with methyl 3,5-difluoro-2-methylbenzofuran-7-carboxylate (280 mg, 1.24 mmol) and 3.3 mL of dichloromethane. The resulting mixture was cooled using a dry ice and acetone bath to −78° C. To the resulting mixture was then added dropwise via syringe a dichloromethane solution of DIBAL (5.0 mL, 5.0 mmol). The resulting mixture was warmed to room temperature over 20 minutes, then poured into aqueous sodium hydroxide solution (50 mL). The layers were separated and the aqueous layer extracted three more times with ethyl acetate (100 mL each time). The organic layers were dried with magnesium sulfate, filtered through CELITE and concentrated in vacuo to yield (3,5-difluoro-2-methylbenzofuran-7-yl)methanol, which was used without further purification.

e) Ethyl 3-(4-((3,5-difluoro-2-methylbenzofuran-7-yl)methoxy)-2,3-dimethylphenyl)propanoate A 50 mL round bottom flask was charged with ethyl 3-(4-hydroxy-2,3-dimethylphenyl)propanoate (0.875 g, 3.94 mmol), (3,5-difluoro-2-methylbenzofuran-7-yl)methanol (390 mg mg, 1.97 mmol), triphenylphosphine (0.805 g, 3.07 mmol) and tetrahydrofuran (2.8 mL). The resulting mixture was cooled using an ice/water bath. To the resulting mixture was then added a 40% wt solution of diethyl azodicarboxylate (1.4 mL, 3.17 mmol) dropwise and the mixture allowed to warm to room temperature with stirring overnight. The resulting mixture was concentrated in vacuo and the resulting residue purified using the Analogix IF-280, 40 g column, 95:5-90:10 Heptane:EtOAc to yield ethyl 3-(4-((3,5-difluoro-2-methylbenzofuran-7-yl)methoxy)-2,3-dimethylphenyl)propanoate.

$^1$H NMR (CHLOROFORM-d) δ: 7.12-7.18 (m, 1H), 6.99-7.05 (m, 1H), 6.71-6.77 (m, 1H), 6.61-6.67 (m, 1H), 5.25 (s, 2H), 4.13 (q, J=7.8 Hz, J=11.7 Hz, 2H), 2.85-2.96 (m, 2H), 2.47-2.56 (m, 2H), 2.42 (s, 3H), 2.24 (s, 3H), 2.20 (s, 3H), and 1.25 (t, J=7.8 Hz, 3H).

f) 3-(4-((3,5-difluoro-2-methylbenzofuran-7-yl)methoxy)-2,3-dimethylphenyl)propanoic acid A 100 mL round bottom flask was charged with ethyl 3-(4-((3,5-difluoro-2-methylbenzofuran-7-yl)methoxy)-2,3-dimethylphenyl)propanoate (209.6 mg, 0.521 mmol), tetrahydrofuran (4.3 mL), water (1.8 mL), and lithium hydroxide (219 mg, 5.21 mmol). The resulting mixture was stirred at room temperature rt overnight. The resulting mixture was washed with diethyl ether. The resulting residue was then acidified with 2N HCl. The resulting mixture was extracted with ethyl acetate (2×100 mL). The organic layers were dried with magnesium sulfate, filtered and concentrated in vacuo. The resulting residue was purified using the Analogix IF-280, 40 g column, 90:10-50:50 Heptane:EtOAc to yield 3-(4-((3,5-difluoro-2-methylbenzofuran-7-yl)methoxy)-2,3-dimethylphenyl)propanoic acid.

$^1$H NMR (CHLOROFORM-d) δ: 7.14-7.20 (m, 1H), 7.03-7.07 (m, 1H), 6.73-6.80 (m, 1H), 6.64-6.70 (m, 1H), 5.29 (s, 2H), 2.89-2.97 (m, 2H), 2.55-2.64 (m, 2H), 2.45 (s, 3H), and 2.25 (s, 6H); LC/MS (ES+) m/z 375 (M+1).

Example 86

3-{4-[(2,3-Dimethyl-1-benzofuran-4-yl)methoxy]-2,3-difluorophenyl}propanoic acid

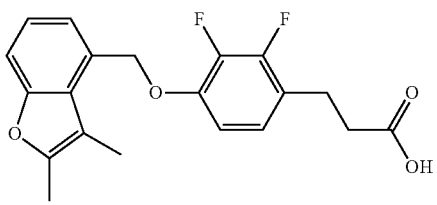 [SMILES: Cc1oc2cccc(COc3ccc(CCC(=O)O)c(F)c3F)c2c1C]

a) (E)-Ethyl 3-(2,3-difluoro-4-hydroxyphenyl)acrylate

A mixture of 4-bromo-2,3-difluorophenol (14.37 g, 66 mmol), TEA (33 mL, 237.4 mmol), ethyl acrylate (22.33 mL, 204.35 mmol), Pd(OAc)$_2$ (0.77 g, 3.45 mmol) and tri-o-tolylphosphine (1.40 g, 4.61 mmol) in DMF (30 mL) in a pressure tube was degassed/refilled with argon and then heated at 110° C. overnight. The resulting residue was cooled to room temperature, EtOAc was added and the mixture stirred for 30 min. The resulting residue was filtered through a pad of CELITE and the filtrate was evaporated under vacuum. The resulting residue was acidified with 2N HCl to pH~2 and extracted with EtOAc. The combined organic fractions were washed with water, brine and dried over Na$_2$SO$_4$. The solvent was evaporated under vacuum and the residue was purified by silica column chromatography (40-50% EtOAc/heptane) to yield (E)-ethyl 3-(2,3-difluoro-4-hydroxyphenyl)acrylate as a yellow solid.

$^1$H NMR (400 MHz, CHLOROFORM-d) δ ppm 1.34 (t, J=7.1 Hz, 3 H), 4.27 (q, J=7.1 Hz, 2 H), 6.45 (d, J=16.2 Hz, 1 H), 6.76 -6.87 (m, 1 H), 7.15 -7.24 (m, 1 H), 7.70 (d, J=16.2 Hz, 1 H).

b) Ethyl 3-(2,3-difluoro-4-hydroxyphenyl)propanoate

To a solution of (E)-ethyl 3-(2,3-difluoro-4-hydroxyphenyl)acrylate (5.10 g, 20.58 mmol) in ethanol (100 mL) in a Parr bottle was added Pd/C (10%, 1.5 g). The vessel was charged with hydrogen (40PSI) and shaken overnight. The catalyst was removed by filtration and the filtrate concentrated in vacuo to yield ethyl 3-(2,3-difluoro-4-hydroxyphenyl)propanoate.

c) (2,3-Dimethylbenzofuran-4-yl)methanol

A solution of methyl 2,3-dimethylbenzofuran-4-carboxylate (2 g, 9.79 mmol, prepared as described in PCT Publication WO 2008/038251) in DCM was cooled to −78° C. To the resulting solution was then added DIBAL (1 M, 39.2 mL, 39.2 mmol) dropwise. The resulting solution was stirred for 2 h at −78° C. and allowed to warm to room temperature. The resulting solution was cooled in an ice bath and quenched with saturated NH$_4$Cl and stirred for 1 h. The organic layer was decanted and the aqueous layer was extracted three times with DCM. The combined organic layers were washed with NaOH solution (1.0 M) and brine, then dried over Na$_2$SO$_4$ and concentrated in vacuo to yield an oil. The oil was purified by column chromatography to yield (2,3-dimethylbenzofuran-4-yl)methanol.

d) Ethyl 3-(4-((2,3-dimethylbenzofuran-4-yl)methoxy)-2,3-difluorophenyl)propanoate A solution of (2,3-dimethylbenzofuran-4-yl)methanol (76.5 mg, 0.43 mmol), ethyl 3-(2,3-difluoro-4-hydroxyphenyl)propanoate (100 mg, 0.43 mmol) and PPh$_3$ (114 mg, 0.43 mmol) in THF was cooled in an ice bath and treated with diethylazodicarboxylate (68 uL, 0.43 mmol). The resulting solution was stirred and allowed to warm to room temperature over 18 h. The solvent was removed under vacuum and the residue was purified by silica preparative TLC to yield ethyl 3-(4-((2,3-dimethylbenzofuran-4-yl)methoxy)-2,3-difluorophenyl)propanoate.

e) 3-(4-((2,3-dimethylbenzofuran-4-yl)methoxy)-2,3-difluorophenyl)propanoic acid A solution of ethyl 3-(4-((2,3-dimethylbenzofuran-4-yl)methoxy)-2,3-difluorophenyl)propanoate (120 mg, 0.31 mmol) in MeOH was treated with NaOH (5M, 0.62 mL, 3.1 mmol) and the resulting solution was stirred for 18 h. Methanol was removed under vacuum and the residue was neutralized with 2N HCl and then extracted with EtOAc. The solvent was removed under vacuum to yield 3-(4-((2,3-dimethylbenzofuran-4-yl)methoxy)-2,3-difluorophenyl)propanoic acid.

$^1$H NMR (CHLOROFORM-d) δ: 7.35 (d, J=7.8 Hz, 1H), 7.03-7.14 (m, 2H), 6.76-6.82 (m, 2H), 5.46 (s, 2H), 2.57-2.65 (m, 2H), 2.38 (s, 3H), 2.37 (s, 3H), 2.30 (t, 2H).

Example 87

3-{2,3-Difluoro-4-[(2-methyl-1-benzofuran-4-yl)methoxy]phenyl}propanoic acid

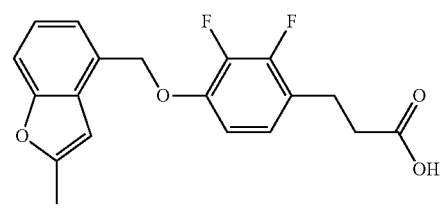 [SMILES: Cc1cc2c(COc3ccc(CCC(=O)O)c(F)c3F)cccc2o1]

a) Methyl 3-(prop-2-yn-1-yloxy)benzoate

To a solution of methyl 3-hydroxybenzoate (7.0 g, 46 mmol) in DMF was added K$_2$CO$_3$ (9.9 g, 71.8 mmol) and propargyl bromide (8.2 g, 66.7 mmol). The resulting suspension was stirred for 18 h, diluted with water and extracted with EtOAc (×2). The organic layers were combined, dried over sodium sulfate, filtered and concentrated in vacuo. The resulting residue was purified by chromatography (0-20% EtOAc/heptane) to yield methyl 3-(prop-2-yn-1-yloxy)benzoate.

$^1$H NMR (400 MHz, CHLOROFORM-d) δ ppm 2.55 (t, J=2.4 Hz, 1H), 3.91 (s, 3H), 4.73 (d, J=2.4 Hz, 2H), 7.17 (dt, J=6.7, 1.5 Hz, 1H), 7.36 (t, J=7.9 Hz, 1H), 7.63 (dd, J=2.7, 1.5 Hz, 1H), 7.65-7.71 (m, 1H).

b) Methyl 2-methylbenzofuran-4-carboxylate

A solution of methyl 3-(prop-2-yn-1-yloxy)benzoate (2.2 g, 11.7 mmol), and CsF (2.3 g, 15.4 mmol) in N,N-diethylaniline (20 mL) was refluxed for 5 h. The reaction mixture was cooled to room temp and diluted with EtOAc. The EtOAc solution was extracted with 2N HCl (×3). The organic fraction was washed with brine, dried over $Na_2SO_4$ and evaporated. The resulting residue was purified by silica gel column chromatography to yield methyl 2-methylbenzofuran-4-carboxylate.

c) (2-Methylbenzofuran-4-yl)methanol

A solution of methyl 2-methylbenzofuran-4-carboxylate (0.73 g, 3.84 mmol, prepared as described in ISHIKAWA, T., et al., Heterocycles, 1994, pp 371-80, Vol. 39(1)) in DCM was cooled to −78° C. To the resulting mixture was then added DIBAL (1M, 15.4 mL, 15.4 mmol) dropwise. The resulting solution was stirred for 20 min at −78° C. and allowed to warm to room temperature. The resulting solution was poured into a mixture of 1N NaOH and ice and extracted with EtOAc. The combined organic fractions were washed with NaOH solution (1.0M) and brine, dried over $Na_2SO_4$ and concentrated in vacuo to yield an oil which was purified by column chromatography to yield (2-methylbenzofuran-4-yl)methanol.

d) Ethyl 3-(2,3-difluoro-4-((2-methyl benzofuran-4-yl)methoxy)phenyl)propanoate

A solution of (2-methylbenzofuran-4-yl)methanol (70.5 mg, 0.43 mmol), ethyl 3-(2,3-difluoro-4-hydroxyphenyl)propanoate (100 mg, 0.43 mmol, prepared as described in Example 86) and $PPh_3$ (114 mg, 0.43 mmol) in THF was cooled in an ice bath and treated with diethylazodicarboxylate (68 uL, 0.43 mmol). The resulting solution was stirred and allowed to warm to room temperature over 18 h. The solvent was removed under vacuum and the residue was purified by silica preparative TLC to yield ethyl 3-(2,3-difluoro-4-((2-methylbenzofuran-4-yl)methoxy)phenyl)propanoate.

e) 3-(2,3-Difluoro-4-((2-methylbenzofuran-4-yl)methoxy)phenyl)propanoic acid

A solution of ethyl 3-(2,3-difluoro-4-((2-methylbenzofuran-4-yl)methoxy)phenyl)propanoate (116 mg, 0.31 mmol) in MeOH was treated with NaOH (5M, 0.62 mL, 3.1 mmol) and the resulting solution was stirred for 18 h. Methanol was removed under vacuum and the residue was neutralized with 2N HCl and extracted with EtOAc. The solvent was removed under vacuum to yield 3-(2,3-difluoro-4-((2-methylbenzofuran-4-yl)methoxy)phenyl)propanoic acid.

$^1$H NMR (400 MHz, CHLOROFORM-d) δ ppm 2.39-2.49 (m, 5H), 2.76 (t, J=7.7 Hz, 2H), 5.33 (s, 2H), 6.56 (s, 1H), 6.74-6.90 (m, 2H), 7.13-7.22 (m, 2H), 7.36-7.42 (m, 1H). ESI-MS (m/z): Calculated for $C_{19}H_{16}F_2O_4$: 369.1 (M+Na). found: 369.1.

Example 88

3-{4-[(5-Chloro-2-ethyl-1-benzofuran-7-yl)methoxy]-2,3-dimethylphenyl}propanoic acid

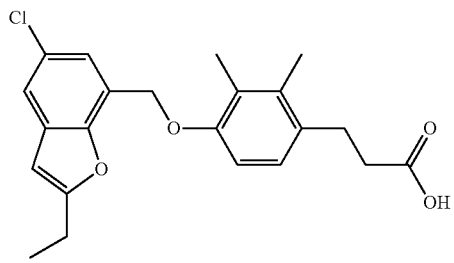

a) 5-chloro-2-ethylbenzofuran-7-carbaldehyde

A 20-mL sealed tube was charged with 5-chloro-2-hydroxy-3-iodobenzaldehyde (5 g, 12.7 mmol, 72%), dichlorobis(triphenylphosphine)palladium (0.89 g, 1.27 mmol), copper(I)iodide (0.24 g, 1.27 mmol), TEA (3.5 mL, 25.5 mmol) and 12.7 mL of DMF. The tube was flushed with argon, but-1-yne (1.4 g, 25.5 mmol) was introduced, and the resulting mixture stirred for 1 h at room temperature and at 75° C. overnight. The resulting residue was cooled to room temperature, concentrated in vacuo and purified using the silica column chromatography to yield 5-chloro-2-ethylbenzofuran-7-carbaldehyde.

b) (5-Chloro-2-ethylbenzofuran-7-yl)methanol

To a solution of 5-chloro-2-ethylbenzofuran-7-carbaldehyde (390 mg, 1.87 mmol) in MeOH cooled in an ice bath was added sodium borohydride (85 mg, 2.24 mmol). The resulting mixture was stirred at room temperature for 2 h. The resulting residue was extracted with EtOAc, dried over $Na_2SO_4$ and purified by silica gel column chromatography to yield b) (5-Chloro-2-ethylbenzofuran-7-yl)methanol.

c) 3-{4-[(5-Chloro-2-ethyl-1-benzofuran-7-yl)methoxy]-2,3-dimethylphenyl}propanoic acid The title compound was prepared by reacting (5-chloro-2-ethylbenzofuran-7-yl)methanol according to the procedure as described in Example 2.

$^1$H NMR (MeOD) δ: 7.41 (d, J=2.0 Hz, 1H), 7.32 (d, J=2.0 Hz, 1H), 6.99 (d, J=8.6 Hz, 1H), 6.82 (d, J=8.6 Hz, 1H), 6.39 (s, 1H), 5.29 (s, 2H), 2.89-2.98 (m, 2H), 2.82 (q, J=7.6 Hz, 2H), 2.50-2.57 (m, 2H), 2.25 (s, 3H), 2.25 (s, 3H), 1.35 (t, 3H). Mass spectrum (ESI, m/z): Calculated for $C_{22}H_{23}ClO_4$, 409.1 (M+Na). found 409.0.

Example 89

3-(4-{[2-Ethyl-5-(trifluoromethoxy)-1-benzofuran-7-yl]methoxy}-2,3-dimethylphenyl)propanoic acid

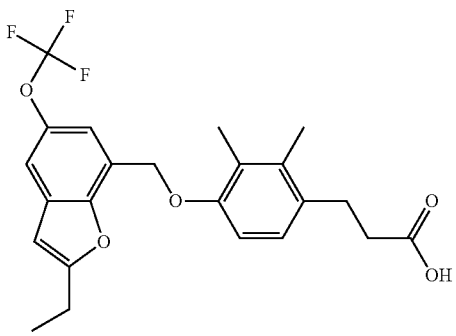 [SMILES: CCc1cc2cc(OC(F)(F)F)cc(COc3ccc(CCC(=O)O)c(C)c3C)c2o1]

a) 2-Methoxy-5-(trifluoromethoxy)benzaldehyde

To a solution of 1-methoxy-4-(trifluoromethoxy)benzene (25 g, 130.1 mmol) in 500 mL of DCM at −78° C. was added titanium(IV)tetrachloride over a period of 1 minute. The resulting mixture was stirred for 30 minutes and dichloromethylmethyl ether (27.5 mL, 294.9 mmol) was added. The ice bath was allowed to expire and the mixture was stirred at room temperature overnight. The resulting residue was poured carefully into water and extracted with three portions of DCM. The combined extracts were washed with water and brine, dried ($Na_2SO_4$), and concentrated. The resulting residue was purified by flash column chromatography to yield 2-methoxy-5-(trifluoromethoxy)benzaldehyde.

b) 2-Hydroxy-5-(trifluoromethoxy)benzaldehyde

To a solution of 2-methoxy-5-(trifluoromethoxy)benzaldehyde (19.5 g, 88.6 mmol) in DCM at −78° C. was added boron tribromide (17.6 mL, 186.0 mmol) over a period of ca.1 min. The resulting mixture was stirred for 1 hour, the cooling bath was replaced with an ice bath and the mixture was stirred for 1 hour. The resulting residue was slowly poured on to ice and extracted with DCM (×2). The extracts were dried ($Na_2SO_4$) and concentrated. The resulting residue was purified by silica column chromatography to yield 2-hydroxy-5-(trifluoromethoxy)benzaldehyde.

c) 2-Hydroxy-3-iodo-5-(trifluoromethoxy)benzaldehyde

A solution of 2-hydroxy-5-(trifluoromethoxy)benzaldehyde (20 g, 97.0 mmol) and NIS (54.6 g, 242.7 mmol) in DMF (196 mL) was stirred at room temperature under Argon for 48 hr. The DMF was removed under vacuum and the residue taken up in EtOAc and washed with 1N HCl, sodium thiosulfate and sat NaCl. The organic layer was dried over $Na_2SO_4$ and evaporated. The resulting residue was purified by silica gel chromatography (0 to 30% EtOAc/hept over 20 min) to yield 2-hydroxy-3-iodo-5-(trifluoromethoxy)benzaldehyde.

d) 2-Propyl-5-(trifluoromethoxy)benzofuran-7-carbaldehyde

The title compound was prepared by reacting 2-hydroxy-3-iodo-5-(trifluoromethoxy)benzaldehyde according to the procedure as described in Example 88 step (a) substituting pent-1-yne for but-1-yne.

e) (2-Propyl-5-(trifluoromethoxy)benzofuran-7-yl)methanol

The title compound was prepared by reacting 2-propyl-5-(trifluoromethoxy)benzofuran-7-carbaldehyde by reduction with $NaBH_4$ according to the procedure as described in Example 88 step (b).

f) 3-(4-{[2-Ethyl-5-(trifluoromethoxy)-1-benzofuran-7-yl]methoxy}-2,3-dimethylphenyl)propanoic acid The title compound was prepared by reacting (2-propyl-5-(trifluoromethoxy)benzofuran-7-yl)methanol according to the procedure described in Example 2.

$^1$H NMR (CHLOROFORM-d) δ: 7.29 (s, 1H), 7.26 (s, 1H), 6.99 (d, J=8.6 Hz, 1H), 6.82 (d, J=8.6 Hz, 1H), 6.42 (s, 1H), 5.31 (s, 2H), 2.91-2.99 (m, 2H), 2.81 (q, J=7.6 Hz, 2H), 2.56-2.64 (m, 2H), 2.25 (s, 6H), 1.34 (t, 3H). Mass spectrum (ESI, m/z): Calculated for $C_{23}H_{23}F_3O_5$, 437.1 (M+H). found 437.0.

Example 90

3-{4-[(2-Ethyl-5-fluoro-1-benzofuran-7-yl)methoxy]-2,3-difluorophenyl}propanoic acid

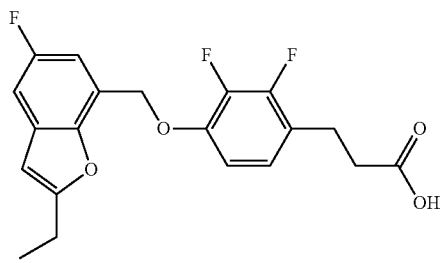 [SMILES: CCc1cc2cc(F)cc(COc3ccc(CCC(=O)O)c(F)c3F)c2o1]

The title compound was prepared according to the procedure as described in Example 83 substituting ethyl 3-(2,3-difluoro-4-hydroxyphenyl)propanoate (prepared as described in Example 86) for ethyl 3-(4-hydroxy-2,3-dimethylphenyl)propanoate.

$^1$H NMR (CHLOROFORM-d) δ: 7.12 (dd, J=8.3, 2.8 Hz, 1H), 7.05 (dd, J=9.6, 2.5 Hz, 1H), 6.77-6.90 (m, 2H), 6.36 (s, 1H), 5.43 (s, 2H), 2.80-2.87 (m, 2H), 2.77 (q, 2H), 2.47-2.56 (m, 2H), 1.30 (t, J=7.6 Hz, 3H). Mass spectrum (ESI, m/z): Calculated for $C_{20}H_{17}F_3O_4$, 401.1 (M+Na). found 401.0.

Example 91

3-{4-[(2-Ethyl-5-fluoro-1-benzofuran-7-yl)methoxy]-3,5-difluorophenyl}propanoic acid

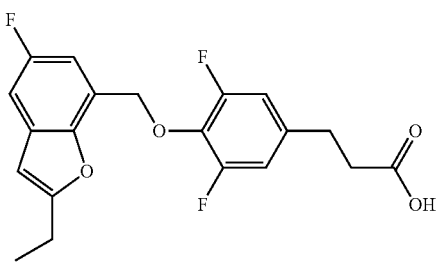 [SMILES: CCc1cc2cc(F)cc(COc3c(F)cc(CCC(=O)O)cc3F)c2o1]

The title compound was prepared according to the procedure as described in Example 83 substituting ethyl 3-(3,5-difluoro-4-hydroxyphenyl)propanoate (prepared as described in U.S. Pat. Appl. Publ., 20110313003, 22 Dec. 2011) for ethyl 3-(4-hydroxy-2,3-dimethylphenyl)propanoate.

$^1$H NMR (CHLOROFORM-d) δ: 7.10 (d, J=9.1 Hz, 2H), 6.69-6.80 (m, 2H), 6.34 (s, 1H), 5.40 (s, 2H), 2.83-2.92 (m, 2H), 2.77 (q, J=7.6 Hz, 2H), 2.60-2.70 (m, 2H), 1.31 (t, 3H). Mass spectrum (ESI, m/z): Calculated for $C_{20}H_{17}F_3O_4$, 401.1 (M+Na). found 401.0.

Example 92

3-{6-[(2-Ethyl-5-fluoro-1-benzofuran-7-yl)methoxy]-2-(trifluoromethyl)pyridin-3-yl}propanoic acid

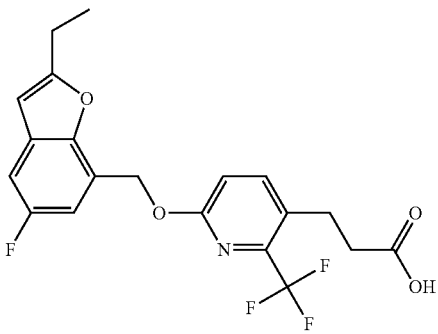 [SMILES: CCc1cc2cc(F)cc(COc3ccc(CCC(=O)O)c(C(F)(F)F)n3)c2o1]

a) 6-Chloro-3-iodo-2-(trifluoromethyl)pyridine

A solution of LDA (1.8 M, 24.5 mL) in THF was cooled to −78° C. and a solution of 2-chloro-6-(trifluoromethyl)pyridine (4 g, 22.0 mmol) in THF was added dropwise. The solution was stirred at −78° C. for 1.5 h. To the resulting mixture was then added a solution of iodine (5.6 g, 22.0 mmol) in THF dropwise over 30 min. The solution was stirred at −78° C. for 45 min, then quenched with 2M HCl. The resulting mixture was extracted with $Et_2O$ (2×). The combined organic extracts were washed with sodium thiosulfate, sat $NaHCO_3$, brine and dried over $Na_2SO_4$ to yield 6-chloro-3-iodo-2-(trifluoromethyl)pyridine.

b) (E)-Ethyl 3-(6-chloro-2-(trifluoromethyl)pyridin-3-yl)acrylate

The title compound was prepared according to the procedure as described in Example 86 step (a) substituting 6-chloro-3-iodo-2-(trifluoromethyl)pyridine for 4-bromo-2,3-difluorophenol.

c) (E)-Ethyl 3-(6-((2-ethyl-5-fluorobenzofuran-7-yl)methoxy)-2-(trifluoromethyl)pyridin-3-yl)acrylate To a solution of (2-ethyl-5-fluorobenzofuran-7-yl)methanol (362 mg, 1.86 mmol, prepared as described in Example 83) in DMF was added NaH (60%, 80 mg, 2.02 mmol) and the mixture stirred at room temperature for 1 hr. To the resulting solution was then added (E)-ethyl 3-(6-chloro-2-(trifluoromethyl)pyridin-3-yl)acrylate (434 mg, 1.55 mmol) dropwise and the resulting mixture stirred at room temperature for 72 h. DMF was removed under vacuum and the residue taken up in sat $NH_4Cl$ and extracted into EtOAc. The organic fraction was concentrated and the resulting residue purified by silica gel column chromatography to yield (E)-ethyl 3-(6-((2-ethyl-5-fluorobenzofuran-7-yl)methoxy)-2-(trifluoromethyl)pyridin-3-yl)acrylate.

d) Ethyl 3-(6-((2-ethyl-5-fluorobenzofuran-7-yl)methoxy)-2-(trifluoromethyl)pyridin-3-yl)propanoate To a solution of (E)-ethyl 3-(6-((2-ethyl-5-fluorobenzofuran-7-yl)methoxy)-2-(trifluoromethyl)pyridin-3-yl)acrylate (230 mg, 0.53 mmol) in EtOAc was added bis(norbornadiene)rhodium(I)tetrafluoroborate (24 mg, 0.06 mmol) and the resulting mixture stirred under a $H_2$ (balloon) atmosphere for 3 h. The resulting residue was concentrated and purified by silica gel column chromatography to yield ethyl 3-(6-((2-ethyl-5-fluorobenzofuran-7-yl)methoxy)-2-(trifluoromethyl)pyridin-3-yl)propanoate.

d) 3-{6-[(2-Ethyl-5-fluoro-1-benzofuran-7-yl)methoxy]-2-(trifluoromethyl)pyridin-3-yl}propanoic acid The title compound was prepared by reacting ethyl 3-(6-((2-ethyl-5-fluorobenzofuran-7-yl)methoxy)-2-(trifluoromethyl)pyridin-3-yl)propanoate according to the procedure described Example 1.

$^1$H NMR (MeOH) δ: 7.74 (d, J=7.6 Hz, 1H), 7.30 (d, J=7.1 Hz, 1H), 7.16 (dd, J=8.6, 2.5 Hz, 1H), 7.11 (dd, J=9.9, 2.8 Hz, 1H), 6.48 (t, J=1.0 Hz, 1H), 5.69 (s, 2H), 2.95 (t, J=7.6 Hz, 2H), 2.82 (q, J=7.6 Hz, 2H), 2.58-2.68 (m, 2H), 1.32 (t, 3H). Mass spectrum (ESI, m/z): Calculated for $C_{20}H_{17}F_4NO_4$, 412.1 (M+H). found 412.0.

Example 93

3-{4-[(6-Ethyl-2,2-dimethyl-2,3-dihydrobenzo[1,2-b:4,5-b']difuran-4-yl)methoxy]-2,3-dimethylphenyl}propanoic acid

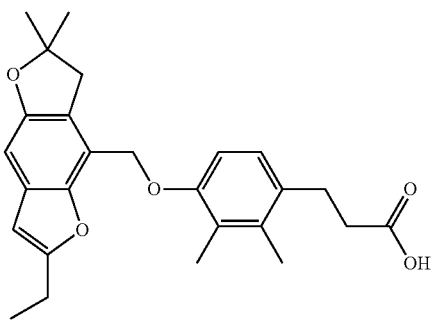 [SMILES: CCc1cc2cc3c(c(COc4ccc(CCC(=O)O)c(C)c4C)c2o1)CC(C)(C)O3]

a) Methyl 2-ethyl-5-((2-methylallyl)oxy)benzofuran-7-carboxylate

To a solution of methyl 2-ethyl-5-hydroxybenzofuran-7-carboxylate (0.61 g, 2.77 mmol, prepared as described in Example 33) in DMF (15 mL) was added potassium carbonate (0.84 g, 6.10 mmol) and 3-chloro-2-methylprop-1-ene (0.63 mL, 6.10 mmol). The resulting suspension was heated at 70° C. for 18 h, and then cooled to room temperature and solids filtered and washed with EtOAc. The EtOAc solution was washed with water, brine, and dried over sodium sulfate, filtered and concentrated in vacuo. The resulting residue was purified by silica gel chromatography to yield methyl 2-ethyl-5-((2-methylallyl)oxy)benzofuran-7-carboxylate.

b) Methyl 2-ethyl-5-hydroxy-6-(2-methylallyl)benzofuran-7-carboxylate

Neat methyl 2-ethyl-5-((2-methylallyl)oxy)benzofuran-7-carboxylate (0.72 g, 2.63 mmol) was heated at 192° C. for 18 hr. The resulting mixture was cooled and the resulting residue purified by silica column chromatography to yield methyl 2-ethyl-5-hydroxy-6-(2-methylallyl)benzofuran-7-carboxylate.

c) Methyl 6-ethyl-2,2-dimethyl-2,3-dihydrobenzo[1,2-b:4,5-b']difuran-4-carboxylate A mixture of methyl 2-ethyl-5-hydroxy-6-(2-methylallyl)benzofuran-7-carboxylate (0.20 g, 0.73 mmol) in formic acid was heated at 100° C. for 18 hr. The formic acid was removed under vacuum and the residue dissolved in MeOH and treated with TMS-diazomethane until a yellow color persisted. The resulting residue was concentrated and purified by silica gel column chromatography to yield methyl 6-ethyl-2,2-dimethyl-2,3-dihydrobenzo[1,2-b:4,5-b']difuran-4-carboxylate.

d) (6-Ethyl-2,2-dimethyl-2,3-dihydrobenzo[1,2-b:4,5-b']difuran-4-yl)methanol The title compound was prepared by reacting methyl 6-ethyl-2,2-dimethyl-2,3-dihydrobenzo[1,2-b:4,5-b']difuran-4-carboxylate with DIBAL according to the procedure as described in Example 86 step (c).

e) 4-(Chloromethyl)-6-ethyl-2,2-dimethyl-2,3-dihydrobenzo[1,2-b:4,5-b']difuran A mixture of (6-ethyl-2,2-dimethyl-2,3-dihydrobenzo[1,2-b:4,5-b']difuran-4-yl)methanol (40 mg, 0.16 mmol) and thionyl chloride (0.014 mL, 0.19 mmol) in methylene chloride (2.8 mL) were stirred at room temperature under argon for 4 hours. The resulting residue was concentrated and used in the next step without further purification.

f) Ethyl 3-(4-((6-ethyl-2,2-dimethyl-2,3-dihydrobenzo[1,2-b:4,5-b']difuran-4-yl)methoxy)-2,3-dimethylphenyl)propanoate A mixture of 4-(chloromethyl)-6-ethyl-2,2-dimethyl-2,3-dihydrobenzo[1,2-b:4,5-b']difuran (43 mg, 0.16 mmol), ethyl 3-(4-hydroxy-2,3-dimethylphenyl)propanoate (72 mg, 0.32 mmol) and cesium carbonate (137 mg, 0.42 mmol) in acetonitrile (2.9 mL) was heated at 70° C. under Ar overnight. The resulting residue was filtered and the filtrate was concentrated and diluted with EtOAc, washed with brine, and dried over $Na_2SO_4$. The resulting residue was purified by preparative TLC to yield ethyl 3-(4-((6-ethyl-2,2-dimethyl-2,3-dihydrobenzo[1,2-b:4,5-b']difuran-4-yl)methoxy)-2,3-dimethylphenyl)propanoate.

g) 3-{4-[(6-Ethyl-2,2-dimethyl-2,3-dihydrobenzo[1,2-b:4,5-b']difuran-4-yl)methoxy]-2,3-dimethylphenyl}propanoic acid The title compound was prepared by reacting ethyl 3-(4-((6-ethyl-2,2-dimethyl-2,3-dihydrobenzo[1,2-b:4,5-b']difuran-4-yl)methoxy)-2,3-dimethylphenyl)propanoate according to the procedure as described in Example 1.
$^1$H NMR (CHLOROFORM-d) δ: 6.94-7.01 (m, 1H), 6.86 (d, J=8.1 Hz, 1H), 6.75 (s, 1H), 6.29 (s, 1H), 5.25 (s, 2H), 3.12 (s, 2H), 2.90-2.99 (m, 2H), 2.75 (q, J=7.4 Hz, 2H), 2.55-2.65 (m, 2H), 2.23 (s, 3H), 2.17 (s, 3H), 1.47 (s, 6H), 1.30 (t, J=7.6 Hz, 3H). Mass spectrum (ESI, m/z): Calculated for $C_{26}H_{30}O_5$, 423.2 (M+H). found 423.0.

Example 94

3-{4-[(5-Chloro-2-propyl-1-benzofuran-7-yl)methoxy]-2,3-dimethylphenyl}propanoic acid

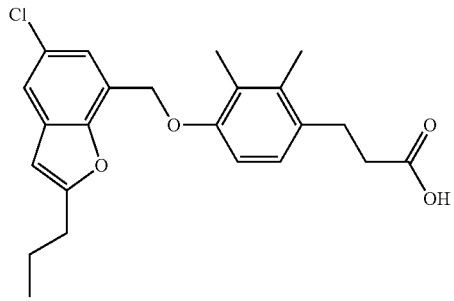 [SMILES: CCCc1cc2cc(Cl)cc(COc3ccc(CCC(=O)O)c(C)c3C)c2o1]

a) Methyl 5-chloro-2-hydroxy-3-iodobenzoate

A solution of methyl 5-chloro-2-hydroxybenzoate (2 g, 10.7 mmol) and NIS (6.0 g, 26.8 mmol) in DMF (22 mL) was stirred at room temperature under Ar for 48 hr. DMF was removed under vacuum and the residue taken up in EtOAc and washed with 1N HCl, sodium thiosulfate and sat NaCl. The organic layer was dried over $Na_2SO_4$ and evaporated. The resulting residue was purified by silica gel column chromatography (0 to 30% EtOAc in heptane over 20 min) to yield methyl 5-chloro-2-hydroxy-3-iodobenzoate.

b) Methyl 5-chloro-2-propylbenzofuran-7-carboxylate

The title compound was prepared by reacting methyl 5-chloro-2-hydroxy-3-iodobenzoate according to the procedure as described in Example 83 substituting 1-pentyne for 1-butyne in step (b).

c) (5-Chloro-2-propylbenzofuran-7-yl)methanol

The title compound was prepared by reacting methyl 5-chloro-2-propylbenzofuran-7-carboxylate according to the procedure as described in Example 83 step (c).

d) 3-{4-[(5-Chloro-2-propyl-1-benzofuran-7-yl)methoxy]-2,3-dimethylphenyl}propanoic acid The title compound was prepared by reacting (5-chloro-2-propylbenzofuran-7-yl)methanol according to the procedure as described in Example 83.

$^1$H NMR (CHLOROFORM-d) δ: 7.40 (s, 1H), 7.33 (s, 1H), 6.98 (d, J=8.3 Hz, 1H), 6.81 (d, J=8.3 Hz, 1H), 6.36 (s, 1H), 5.28 (s, 2H), 2.95 (t, J=7.8 Hz, 2H), 2.74 (t, J=7.3 Hz, 2H), 2.57-2.66 (m, 2H), 2.25 (s, 6H), 1.70-1.83 (m, 2H), 1.01 (t, 3H). Mass spectrum (ESI, m/z): Calculated for $C_{23}H_{25}ClO_4$, 423.1 (M+Na). found 423.0.

Example 95

3-(4-{[2-(Difluoromethyl)-5-fluoro-1-benzofuran-7-yl]methoxy}-2,3-dimethylphenyl)propanoic acid

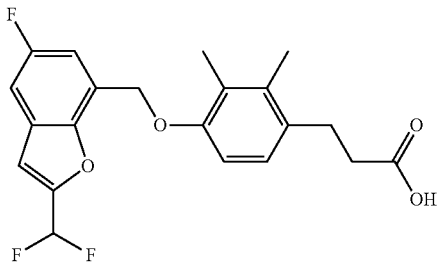 [SMILES: Cc1c(CCC(=O)O)ccc(OCc2cc(F)cc3cc(C(F)F)oc23)c1C]

a) Methyl 3-(4-((5-fluoro-2-(hydroxymethyl)benzofuran-7-yl)methoxy)-2,3-dimethylphenyl)propanoate A solution of 3-(4-((5-fluoro-2-(hydroxymethyl)benzofuran-7-yl)methoxy)-2,3-dimethylphenyl)propanoic acid (30 mg, 0.08 mmol, prepared as described in Example 5) in MeOH was cooled in an ice bath and treated with TMS-diazomethane until a permanent yellow color was obtained. Excess diazomethane was quenched with AcOH and solvent evaporated. The resulting residue was used in the next step without further purification.

b) Methyl 3-(4-((5-fluoro-2-formylbenzofuran-7-yl)methoxy)-2,3-dimethylphenyl)propanoate To a solution of methyl 3-(4-((5-fluoro-2-(hydroxymethyl)benzofuran-7-yl)methoxy)-2,3-dimethylphenyl)propanoate (31 mg, 0.08 mmol) in DCM (2 mL) was added Dess-Martin periodinane (40 mg, 0.09 mmol) and the resulting mixture stirred for 4 hr at room temperature. The resulting residue was diluted with EtOAc and washed with sat $Na_2CO_3$. The resulting residue was purified by prep-TLC to yield methyl 3-(4-((5-fluoro-2-formylbenzofuran-7-yl)methoxy)-2,3-dimethylphenyl)propanoate.

c) Methyl 3-(4-((2-(difluoromethyl)-5-fluorobenzofuran-7-yl)methoxy)-2,3-dimethylphenyl)propanoate To a solution of methyl 3-(4-((5-fluoro-2-formylbenzofuran-7-yl)methoxy)-2,3-dimethylphenyl)propanoate (30 mg, 0.08 mmol) in methanol was added bis(2-methoxyethyl)aminosulfur trifluoride (0.04 mL, 0.23 mmol) and the mixture stirred for 18 hr. the solution was concentrated and purified by preparative TLC to yield methyl 3-(4-((2-(difluoromethyl)-5-fluorobenzofuran-7-yl)methoxy)-2,3-dimethylphenyl)propanoate.

d) 3-(4-{[2-(Difluoromethyl)-5-fluoro-1-benzofuran-7-yl]methoxy}-2,3-dimethylphenyl)propanoic acid The title compound was prepared by reacting methyl 3-(4-((2-(difluoromethyl)-5-fluorobenzofuran-7-yl)methoxy)-2,3-dimethylphenyl)propanoate according to the procedure as described in Example 1.

$^1$H NMR (CHLOROFORM-d) δ: 7.32 (dd, J=9.6, 2.0 Hz, 1H), 7.23-7.25 (m, 1H), 7.04 (s, 1H), 6.99 (d, J=8.6 Hz, 1H), 6.79 (d, J=8.6 Hz, 1H), 6.75 (t, J=54.4 Hz, 1H), 5.34 (s, 2H), 2.90-3.00 (m, 2H), 2.56-2.66 (m, 2H), 2.26 (s, 3H), 2.24 (s, 3H). Mass spectrum (ESI, m/z): Calculated for $C_{21}H_{19}F_3O_4$, 415.1 (M+Na). found 415.0.

Example 96

3-{6-[(2-Ethyl-5-fluoro-1-benzofuran-7-yl)methoxy]-4-methylpyridin-3-yl}propanoic acid

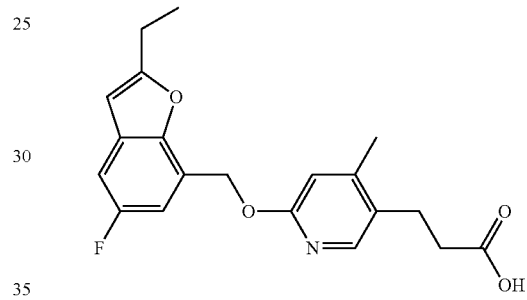

a) Ethyl 3-(6-fluoro-4-methylpyridin-3-yl)propanoate

The title compound was prepared according to the procedure as described in Example 86 substituting 5-bromo-2-fluoro-4-methylpyridine for 4-bromo-2,3-difluorophenol in step (a).

b) Ethyl 3-(6-((2-ethyl-5-fluorobenzofuran-7-yl)methoxy)-4-methylpyridin-3-yl)propanoate To a solution of (2-ethyl-5-fluorobenzofuran-7-yl)methanol (314 mg, 1.62 mmol, prepared as described in Example 83) in DMF was added NaH (60%, 70 mg, 1.75 mmol) and the resulting mixture stirred at room temperature for 1 hr. To the resulting solution (ethyl 3-(6-fluoro-4-methylpyridin-3-yl)propanoate (284 mg, 1.35 mmol) in DMF was added dropwise and the mixture stirred at room temperature for 72 h. DMF was removed under vacuum and the residue was purified by silica gel column chromatography to yield ethyl 3-(6-((2-ethyl-5-fluorobenzofuran-7-yl)methoxy)-4-methylpyridin-3-yl)propanoate.

c) 3-{6-[(2-Ethyl-5-fluoro-1-benzofuran-7-yl)methoxy]-4-methylpyridin-3-yl}propanoic acid The title compound was prepared by reacting ethyl 3-(6-((2-ethyl-5-fluorobenzofuran-7-yl)methoxy)-4-methylpyridin-3-yl)propanoate according to the procedure as described in Example 1.

¹H NMR (MeOD) δ: 7.96 (s, 1H), 7.12 (dd, J=8.6, 2.5 Hz, 1H), 7.05 (dd, J=9.6, 2.5 Hz, 1H), 6.84 (s, 1H), 6.42 (s, 1H), 5.59 (s, 2H), 2.93 (t, J=7.8 Hz, 2H), 2.81 (q, J=7.6 Hz, 2H), 2.60 (t, J=7.6 Hz, 2H), 2.38 (s, 3H), 1.28-1.43 (m, 3H). Mass spectrum (ESI, m/z): Calculated for C₂₀H₂₀FNO₄, 358.1 (M+H). found 358.0.

Example 97

3-{6-[(5-Chloro-2-propyl-1-benzofuran-7-yl)methoxy]-4-methylpyridin-3-yl}propanoic acid

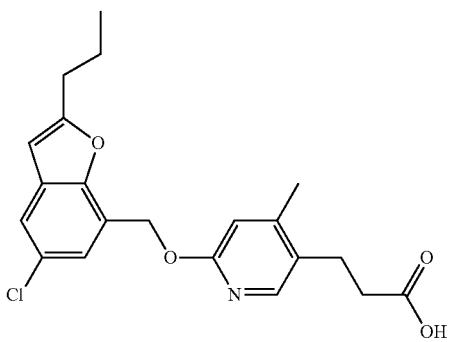 [SMILES: CCCc1cc2cc(Cl)cc(COc3cc(C)c(CCC(=O)O)cn3)c2o1]

The title compound was prepared according to the procedure as described in Example 96 substituting (5-chloro-2-propylbenzofuran-7-yl)methanol (prepared as described in Example 94) for (2-ethyl-5-fluorobenzofuran-7-yl)methanol.

¹H NMR (CHLOROFORM-d) δ: 8.22 (s, 1H), 7.43 (d, J=2.0 Hz, 1H), 7.27 (s, 1H), 6.90 (s, 1H), 6.36 (s, 1H), 5.60 (s, 2H), 2.94 (t, J=7.3 Hz, 2H), 2.73 (t, J=7.3 Hz, 2H), 2.63-2.70 (m, 2H), 2.42 (s, 3H), 1.76 (sxt, J=7.5 Hz, 2H), 1.00 (t, J=7.3 Hz, 3H). Mass spectrum (ESI, m/z): Calculated for C₂₁H₂₂ClNO₄, 388.1 (M+H). found 388.0.

Example 98

3-(2,3-Dimethyl-4-{[2-propyl-5-(trifluoromethoxy)-1-benzofuran-7-yl]methoxy}phenyl)propanoic acid

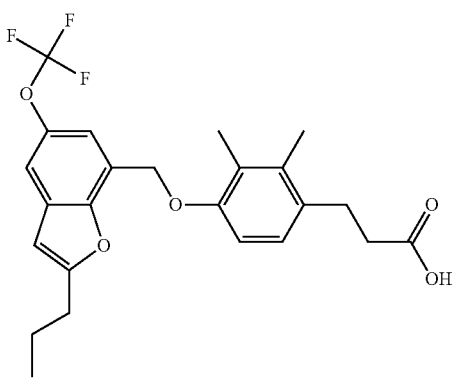 [SMILES: CCCc1cc2cc(OC(F)(F)F)cc(COc3ccc(CCC(=O)O)c(C)c3C)c2o1]

The title compound was prepared according to the procedure as described in Example 89 substituting pent-1-yne for but-1-yne.

¹H NMR (CHLOROFORM-d) δ: 7.24-7.31 (m, 1H), 6.99 (d, J=8.1 Hz, 1H), 6.82 (d, J=8.6 Hz, 1H), 6.42 (s, 1H), 5.31 (s, 2H), 2.91-3.00 (m, 2H), 2.76 (t, J=7.6 Hz, 2H), 2.56-2.66 (m, 2H), 2.25 (s, 6H), 1.78 (sxt, J=7.4 Hz, 2H), 1.02 (t, 3H). Mass spectrum (ESI, m/z): Calculated for C₂₄H₂₅F₃O₅, 451.2 (M+H). found 451.0.

Example 99

3-(2,3-Dimethyl-4-{[2-methyl-5-(trifluoromethoxy)-1-benzofuran-7-yl]methoxy}phenyl)propanoic acid

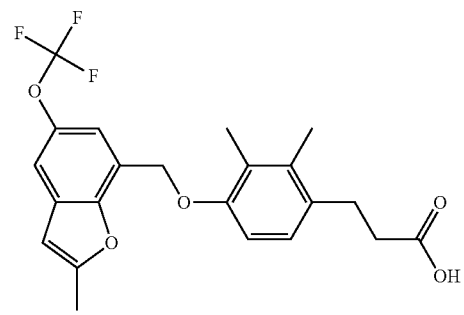 [SMILES: Cc1cc2cc(OC(F)(F)F)cc(COc3ccc(CCC(=O)O)c(C)c3C)c2o1]

The title compound was prepared according to the procedure as described in Example 89 substituting prop-1-yne for but-1-yne.

¹H NMR (CHLOROFORM-d) δ: 7.22-7.30 (m, 2H), 6.99 (d, J=8.6 Hz, 1H), 6.80 (d, J=8.1 Hz, 1H), 6.41 (d, J=1.0 Hz, 1H), 5.30 (s, 2H), 2.90-2.99 (m, 2H), 2.56-2.66 (m, 2H), 2.47 (s, 3H), 2.25 (s, 6H). Mass spectrum (ESI, m/z): Calculated for C₂₂H₂₁F₃O₅, 423.1 (M+H). found 423.0.

Example 100

3-{4-[(5-Chloro-2-propyl-1-benzofuran-7-yl)methoxy]-3-cyano-2-methylphenyl}propanoic acid

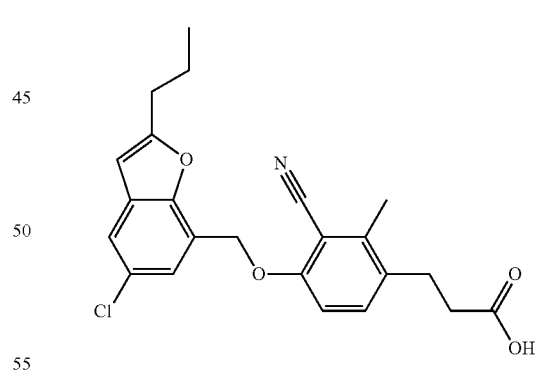

a) 3-Bromo-6-fluoro-2-methylbenzonitrile

To a cooled (0° C.) solution of 2-fluoro-6-methylbenzonitrile (2 g, 14.8 mmol) in concentrated sulfuric acid (40 mL) was added NBS (2.7 g, 15.6 mmol). The resulting residue was stirred at 0° C. for 3 hrs and poured into ice-water (400 mL). The resulting solution was extracted three times with EtOAc (80 mL) and the combined organic layers were washed with water and brine, dried over anhydrous sodium sulfate, filtered and concentrated. The resulting residue was purified by silica gel flash chromatography to yield 3-bromo-6-fluoro-2-methylbenzonitrile.

b) Ethyl 3-(3-cyano-4-fluoro-2-methylphenyl)propanoate

The title compound was prepared by reacting 3-bromo-6-fluoro-2-methylbenzonitrile according to the procedure as described in Example 86.

c) 3-{4-[(5-Chloro-2-propyl-1-benzofuran-7-yl)methoxy]-3-cyano-2-methylphenyl}propanoic acid The title compound was prepared by reacting ethyl 3-(3-cyano-4-fluoro-2-methylphenyl)propanoate and (5-chloro-2-propylbenzofuran-7-yl)methanol (prepared as described in Example 94) according to the procedures as described in Example 96.

$^1$H NMR (CHLOROFORM-d) δ: 7.41 (d, J=2.0 Hz, 1H), 7.32 (d, J=1.8 Hz, 1H), 7.23-7.25 (m, 1H), 6.83 (d, J=8.6 Hz, 1H), 6.37 (s, 1H), 5.42 (s, 2H), 2.92 (t, J=7.7 Hz, 2H), 2.76 (t, J=7.5 Hz, 2H), 2.60 (t, J=7.7 Hz, 2H), 2.51 (s, 3H), 1.78 (sxt, 2H), 1.02 (t, J=7.5 Hz, 3H). Mass spectrum (ESI, m/z): Calculated for $C_{23}H_{22}ClNO_4$, 431.1 (M+H). found 431.0.

Example 101

3-{4-[(5-Bromo-2-ethyl-1-benzofuran-7-yl)methoxy]-2,3-dimethylphenyl}propanoic acid

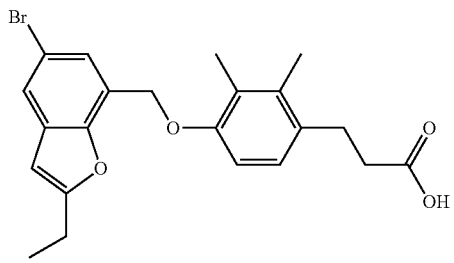

a) Methyl 5-bromo-2-ethylbenzofuran-7-carboxylate

The title compound was prepared according to the procedure as described in Example 83 step (b) substituting methyl 5-bromo-2-hydroxy-3-iodobenzoate for methyl 3-bromo-5-fluoro-2-hydroxybenzoate b) 3-{4-[(5-Bromo-2-ethyl-1-benzofuran-7-yl)methoxy]-2,3-dimethylphenyl}propanoic acid The title compound was prepared by reacting methyl 5-bromo-2-ethylbenzofuran-7-carboxylate according to the procedure as described in Example 83.

$^1$H NMR (MeOD) δ: 7.57 (d, J=2.0 Hz, 1H), 7.45 (d, J=1.8 Hz, 1H), 6.99 (d, J=8.3 Hz, 1H), 6.82 (d, J=8.3 Hz, 1H), 6.40 (s, 1H), 5.29 (s, 2H), 2.89-2.99 (m, 2H), 2.82 (q, J=7.6 Hz, 2H), 2.49-2.59 (m, 2H), 2.26 (s, 3H), 2.25 (s, 3H), 1.35 (t, J=7.5 Hz, 3H). Mass spectrum (ESI, m/z): Calculated for $C_{22}H_{23}BrO_4$, 431.1 (M+H). found 431.0.

Example 102

3-{4-[(5-Fluoro-2,3-dimethyl-1-benzofuran-7-yl)methoxy]-2,3-dimethylphenyl}propanoic acid

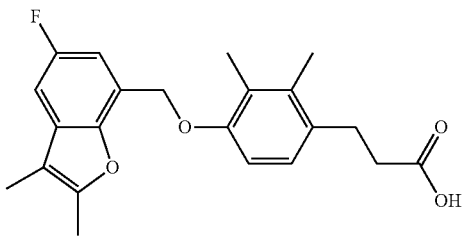 [SMILES: Cc1oc2c(COc3ccc(CCC(=O)O)c(C)c3C)cc(F)cc2c1C]

a) 3-(2-Bromo-4-fluorophenoxy)butan-2-one

A mixture of 2-bromo-4-fluorophenol (5 g, 26.2 mmol), potassium carbonate (10.8 g, 78.5 mmol), 3-chlorobutan-2-one (2.6 mL, 26.2 mmol), and potassium iodide (1.2 g, 7.4 mmol) in acetonitrile (20 mL) was heated to 70° C. and stirred for 18 h. The resulting residue was cooled to room temperature and the solids removed by filtration. The filtrate was concentrated under vacuum and the residue taken up in EtOAc and washed with water and saturated NaCl. The solution was dried over $Na_2SO_4$ and evaporated and the residue purified by silica gel chromatography to yield 3-(2-bromo-4-fluorophenoxy)butan-2-one.

b) 7-Bromo-5-fluoro-2,3-dimethylbenzofuran 3-(2-Bromo-4-fluorophenoxy)butan-2-one (4 g, 15.3 mmol) was added in portions to sulfuric acid (2 mL) at 30° C. and stirred for 6 hr. The resulting residue was cooled to room temperature and poured on to ice. The resulting aq. mixture was extracted with EtOAc. The EtOAc fraction was washed with 1N NaOH, water and saturated NaCl. The EtOAc fraction was dried over $Na_2SO_4$ and evaporated and the residue purified by silica gel chromatography to yield 7-bromo-5-fluoro-2,3-dimethylbenzofuran.

c) 5-Fluoro-2,3-dimethylbenzofuran-7-carbaldehyde

To a solution of 7-bromo-5-fluoro-2,3-dimethylbenzofuran (1.56 g, 6.42 mmol) in THF (30 mL) at −78° C. was added n-BuLi (1.6M hex, 4.41 mL). After stirring at this temperature for 30 min DMF (2.5 mL, 32.09 mmol) was added and the mixture was stirred for 1 h and then warmed to room temperature. Aqueous $NH_4Cl$ was added and the aqueous phase was extracted with EtOAc. The EtOAc phase was dried over $MgSO_4$, filtered, and evaporated under reduced pressure. The resulting residue was purified by silica gel chromatography to yield 5-fluoro-2,3-dimethylbenzofuran-7-carbaldehyde.

d) 3-{4-[(5-Fluoro-2,3-dimethyl-1-benzofuran-7-yl)methoxy]-2,3-dimethylphenyl}propanoic acid The title compound was prepared by reacting 5-fluoro-2,3-dimethylbenzofuran-7-carbaldehyde according to the procedure as described in Example 88.

$^1$H NMR (CHLOROFORM-d) δ: 7.09 (dd, J=9.9, 2.3 Hz, 1H), 6.95-7.03 (m, 2H), 6.79 (d, J=8.6 Hz, 1H), 5.29 (s, 2H), 2.95 (t, J=7.8 Hz, 2H), 2.56-2.65 (m, 2H), 2.39 (s, 3H), 2.25

(s, 3H), 2.25 (s, 3H), 2.13 (s, 3H). Mass spectrum (ESI, m/z): Calculated for $C_{22}H_{23}FO_4$, 371.1 (M+H). found 471.0.

Example 103

3-(7-{[2-Methyl-5-(trifluoromethoxy)-1-benzofuran-7-yl]methoxy}-2,3-dihydro-1H-inden-4-yl)propanoic acid

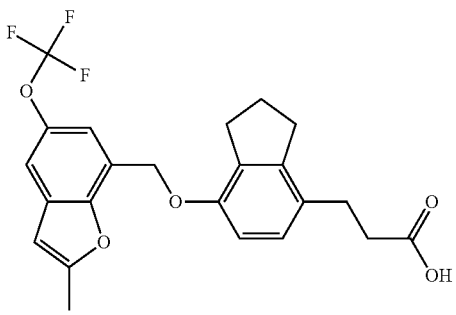 [SMILES: Cc1cc2cc(OC(F)(F)F)cc(COc3ccc(CCC(=O)O)c4c3CCC4)c2o1]

a) (2-Methyl-5-(trifluoromethoxy)benzofuran-7-yl)methanol

The title compound was prepared according to the procedure as described in Example 89 substituting propyne for but-1-yne.

b) 3-(7-{[2-Methyl-5-(trifluoromethoxy)-1-benzofuran-7-yl]methoxy}-2,3-dihydro-1H-inden-4-yl)propanoic acid The title compound was prepared by reacting (2-methyl-5-(trifluoromethoxy)benzofuran-7-yl)methanol and ethyl 3-(7-hydroxy-2,3-dihydro-1H-inden-4-yl)propanoate (prepared as described in U.S. Pat. Appl. Publ., 20110313003, 22 Dec. 2011), according to the procedure as described in Example 87.

$^1$H NMR (CHLOROFORM-d) δ: 7.27 (s, 1H), 7.23 (s, 1H), 6.96 (d, J=8.6 Hz, 1H), 6.75 (d, J=8.1 Hz, 1H), 6.41 (d, J=1.0 Hz, 1H), 5.34 (s, 2H), 2.96 (t, J=7.3 Hz, 2H), 2.86-2.93 (m, 4H), 2.59-2.68 (m, 2H), 2.48 (s, 3H), 2.11 (quin, J=7.5 Hz, 2H). Mass spectrum (ESI, m/z): Calculated for $C_{23}H_{21}F_3O_5$, 435.1 (M+H). found 435.0.

Example 104

3-{4-[(5-Chloro-2-propyl-1-benzofuran-7-yl)methoxy]-2,3-difluorophenyl}propanoic acid

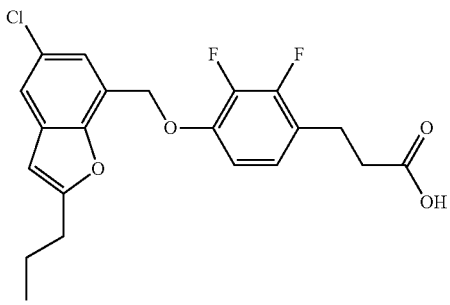 [SMILES: CCCc1cc2cc(Cl)cc(COc3ccc(CCC(=O)O)c(F)c3F)c2o1]

The title compound was prepared by reacting (5-chloro-2-propylbenzofuran-7-yl)methanol (prepared as described in Example 94 step b) and ethyl 3-(2,3-difluoro-4-hydroxyphenyl)propanoate (prepared as described in Example 86 step b) according to the procedure as described in Example 87.

$^1$H NMR (CHLOROFORM-d) δ: 7.41 (d, J=2.0 Hz, 1H), 7.30 (d, J=2.0 Hz, 1H), 6.81-6.89 (m, 1H), 6.71-6.80 (m, 1H), 6.36 (s, 1H), 5.36 (s, 2H), 2.90-3.00 (m, 2H), 2.74 (t, J=7.6 Hz, 2H), 2.63-2.71 (m, 2H), 1.69-1.85 (m, 2H), 1.01 (t, J=7.3 Hz, 3H). Mass spectrum (ESI, m/z): Calculated for $C_{21}H_{19}ClF_2O_4$, 431.1 (M+Na). found 431.0.

Example 105

3-{4-[(2,3-Dimethyl-1-benzofuran-4-yl)methoxy]-2,3-dimethylphenyl}propanoic acid

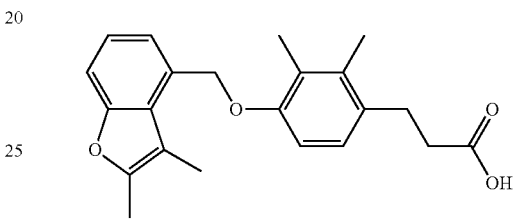

The title compound was prepared according to the procedure as described in Example 86 substituting ethyl 3-(2,3-dimethyl-4-hydroxyphenyl)propanoate for ethyl 3-(2,3-difluoro-4-hydroxyphenyl)propanoate.

$^1$H NMR (CHLOROFORM-d) δ: 7.36 (d, J=7.1 Hz, 1H), 7.13-7.24 (m, 2H), 7.00 (d, J=8.1 Hz, 1H), 6.82 (d, J=8.1 Hz, 1H), 5.26 (s, 2H), 2.92-3.00 (m, 2H), 2.57-2.67 (m, 2H), 2.38 (s, 3H), 2.25 (s, 3H), 2.23 (s, 3H), 2.16 (s, 3H).

Example 106

3-(4-{[4,6-Difluoro-2-methyl-5-(trifluoromethoxy)-1-benzofuran-7-yl]methoxy}-2,3-dimethylphenyl)propanoic acid

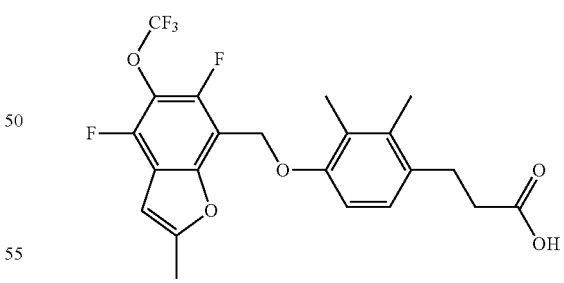

a) 3,5-Difluoro-4-(trifluoromethoxy)phenol

To a solution of 5-bromo-1,3-difluoro-2-(trifluoromethoxy)benzene (20 g, 72.2 mmol) in diethyl ether (200 mL) under an atmosphere of argon at −78° C. was slowly added a solution of n-BuLi (1.6M hexane, 49.6 mL). The resulting residue was stirred for 30 minutes and then added via cannula to a solution of trimethylborate (9.04 mL, 79.4 mmol) in diethyl ether (100 mL) at −70° C. After the addition was complete, the temperature was allowed to rise to room temperature then recooled to −10° C. Glacial acetic acid (14.2 mL) was added followed by a solution of 30% aqueous hydrogen peroxide (20 mL) in water (20 mL) while maintaining the solution at 0° C. The resulting solution was allowed to warm to room temperature while stirring for an additional 40 min. Saturated aqueous ammonium chloride solution was added (200 mL) followed by tetrahydrofuran (100 mL), and the organic layer was separated, washed with sat NaHCO$_3$, water (300 mL), and brine (100 mL), dried with magnesium sulfate, and filtered. The solvent was removed under vacuum and the residue was purified by silica gel column chromatography to yield 3,5-difluoro-4-(trifluoromethoxy)phenol.

b) 1,3-Difluoro-5-methoxy-2-(trifluoromethoxy)benzene

A mixture of 3,5-difluoro-4-(trifluoromethoxy)phenol (10 g, 46.71 mmol), potassium carbonate (19.37 g, 140.13 mmol), and methyl iodide (8.72 mL, 140.13 mmol), in 28 mL of acetone was refluxed under Ar atmosphere for 18 h. The solution was cooled to room temperature and filtered to remove solids. The filtrate was evaporated under vacuum and the residue purified by silica gel column chromatography to yield 1,3-difluoro-5-methoxy-2-(trifluoromethoxy)benzene.

c) 3-(4-{[4,6-Difluoro-2-methyl-5-(trifluoromethoxy)-1-benzofuran-7-yl]methoxy}-2,3-dimethylphenyl)propanoic acid The title compound was prepared according to the procedure as described in Example 89 substituting 1,3-difluoro-5-methoxy-2-(trifluoromethoxy)benzene for 1-methoxy-4-(trifluoromethoxy)benzene in step (a).
$^1$H NMR (CHLOROFORM-d) δ: 7.02 (d, J=8.6 Hz, 1H), 6.89 (d, J=8.1 Hz, 1H), 6.51 (s, 1H), 5.27 (s, 2H), 2.85-3.01 (m, 2H), 2.55-2.68 (m, 2H), 2.46 (s, 3H), 2.22 (s, 3H), 2.13 (s, 3H). Mass spectrum (ESI, m/z): Calculated for C$_{22}$H$_{19}$F$_5$O$_5$, 481.1 (M+Na). found 481.0.

Example 107

3-(2,3-Difluoro-4-{[6-fluoro-4-methoxy-2-methyl-5-(trifluoromethoxy)-1-benzofuran-7-yl]methoxy}phenyl)propanoic acid

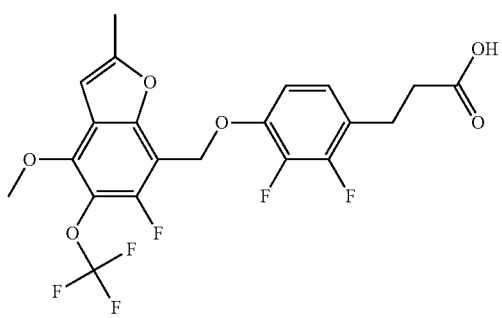 [SMILES: COc1c(OC(F)(F)F)c(F)c(COc2ccc(CCC(=O)O)c(F)c2F)c2oc(C)cc12]

To a solution of ethyl 3-(4-((4,6-difluoro-2-methyl-5-(trifluoromethoxy)benzofuran-7-yl)methoxy)-2,3-difluorophenyl)propanoate (304 mg, 0.62 mmol, prepared as described in Example 108) in a mixture of THF/MeOH was added NaOH (25 mg, 0.62 mmol) and the resulting mixture stirred at room temperature for 18 h. To the resulting mixture was then added 6N HCl until a precipitate formed, which was collected by filtration and purified by silica gel chromatography to yield 3-(2,3-difluoro-4-{[6-fluoro-4-methoxy-2-methyl-5-(trifluoromethoxy)-1-benzofuran-7-yl]methoxy}phenyl)propanoic acid.
$^1$H NMR (CHLOROFORM-d) δ: 6.78-6.97 (m, 2H), 6.56 (d, J=1.0 Hz, 1H), 5.34 (s, 2H), 4.13 (s, 3H), 2.95 (t, J=7.6 Hz, 2H), 2.61-2.76 (m, 2H), 2.44 (s, 3H). Mass spectrum (ESI, m/z): Calculated for C$_{21}$H$_{16}$F$_6$O$_6$, 501.1 (M+Na). found 501.0.

Example 108

3-(4-{[4,6-Difluoro-2-methyl-5-(trifluoromethoxy)-1-benzofuran-7-yl]methoxy}-2,3-difluorophenyl)propanoic acid

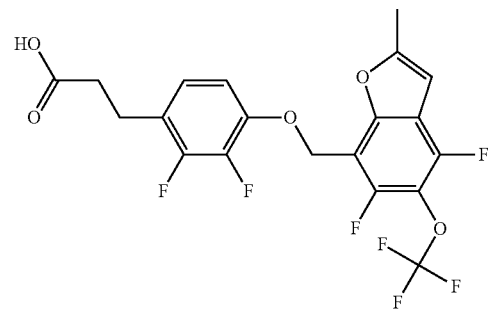 [SMILES: Cc1cc2c(F)c(OC(F)(F)F)c(F)c(COc3ccc(CCC(=O)O)c(F)c3F)c2o1]

The title compound was prepared according to the procedure as described in Example 106 substituting ethyl 3-(2,3-difluoro-4-hydroxyphenyl)propanoate (prepared as described in Example 86) for ethyl 3-(4-hydroxy-2,3-dimethylphenyl)propanoate.
$^1$H NMR (CHLOROFORM-d) δ: 6.79-6.95 (m, 2H), 6.51 (d, J=1.0 Hz, 1H), 5.36 (s, 2H), 2.89-3.02 (m, 2H), 2.61-2.71 (m, 2H), 2.47 (s, 3H). Mass spectrum (ESI, m/z): Calculated for C$_{20}$H$_{13}$F$_7$O$_5$, 489.0 (M+Na). found 489.0.

Example 109

3-{4-[(6-Chloro-2,3-dimethyl-1-benzofuran-4-yl)methoxy]-2,3-dimethylphenyl}propanoic acid

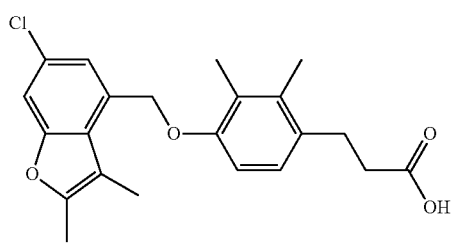 [SMILES: Cc1oc2cc(Cl)cc(COc3ccc(CCC(=O)O)c(C)c3C)c2c1C]

a) Methyl 3-chloro-5-hydroxybenzoate

3-Chloro-5-hydroxybenzoic acid (2 g, 11.6 mmol) was dissolved in MeOH and cooled in an ice bath. Hydrogen chloride gas was bubbled into the solution for 10 min and the flask was capped and the solution was allowed to warm to room temperature and stirred for 18 h. The resulting residue was concentrated under vacuum and the residue was purified by silica gel chromatography to yield methyl 3-chloro-5-hydroxybenzoate.

b) 3-Oxobutan-2-yl 3-chloro-5-((3-oxobutan-2-yl)oxy)benzoate

A mixture of methyl 3-chloro-5-hydroxybenzoate (2 g, 10.72 mmol), 3-chloro-2-butanone (2.28 g, 21.44 mmol), potassium carbonate (4.44 g, 32.15 mmol), and potassium iodide (0.48 g, 2.89 mmol) in acetone (20 mL) was stirred at reflux for 16 h. After cooling to room temperature water and diethyl ether were added, the layers were separated and the aq. layer was extracted with diethyl ether. The combined organic layers were washed with NaOH solution (1.0 M) and water, dried over $Na_2SO_4$ and concentrated in vacuo to 3-oxobutan-2-yl 3-chloro-5-((3-oxobutan-2-yl)oxy)benzoate.

c) 3-Oxobutan-2-yl 6-chloro-2,3-dimethylbenzofuran-4-carboxylate 3-oxobutan-2-yl 3-chloro-5-((3-oxobutan-2-yl)oxy)benzoate (0.24 g, 0.78 mmol) was added in portions to sulfuric acid (0.1 mL) at 30° C. and then stirred for 2 h. The resulting residue was cooled to room temperature and poured on to ice. The resulting aqueoud mixture was extracted with EtOAc. The EtOAc fraction was washed with 1N NaOH, water and saturated NaCl. The EtOAc fraction was dried over $Na_2SO_4$ and evaporated and the resulting residue was purified by silica gel chromatography to yield 3-oxobutan-2-yl 6-chloro-2,3-dimethylbenzofuran-4-carboxylate.

d) (6-Chloro-2,3-dimethylbenzofuran-4-yl)methanol

To a solution of 3-oxobutan-2-yl 6-chloro-2,3-dimethylbenzofuran-4-carboxylate (0.15 g, 0.51 mmol) in DCM (1.3 mL) at −78° C. was added a 1M DCM solution of DIBAL (4.07 mlm 4.07 mmol). After 45 min the solution was allowed to reach room temperature and poured into sat NaCl and stirred for 2 hr. The resulting mixture was filtered through CELITE and washed with EtOAc. The combined organic layers were washed with brine, dried over $Na_2SO_4$ and concentrated in vacuo. The resulting residue was purified by silica gel chromatography to (6-chloro-2,3-dimethylbenzofuran-4-yl)methanol.

e) 3-{4-[(6-Chloro-2,3-dimethyl-1-benzofuran-4-yl)methoxy]-2,3-dimethylphenyl}propanoic acid The title compound was prepared by reacting (6-chloro-2,3-dimethylbenzofuran-4-yl)methanol according to the procedure as described Example 83.

$^1$H NMR (CHLOROFORM-d) δ: 7.35 (d, J=2.0 Hz, 1H), 7.24 (d, J=2.0 Hz, 1H), 7.00 (d, J=8.6 Hz, 1H), 6.77 (d, J=8.6 Hz, 1H), 5.21 (s, 2H), 2.92-2.99 (m, 2H), 2.58-2.66 (m, 2H), 2.36 (s, 3H), 2.24 (s, 3H), 2.22 (s, 3H), 2.17 (s, 3H). Mass spectrum (ESI, m/z): Calculated for $C_{22}H_{23}ClO_4$, 409.1 (M+Na). found 409.0.

Example 110

3-{4-[(6-Chloro-2-methyl-1-benzofuran-4-yl)methoxy]-2,3-dimethylphenyl}propanoic acid

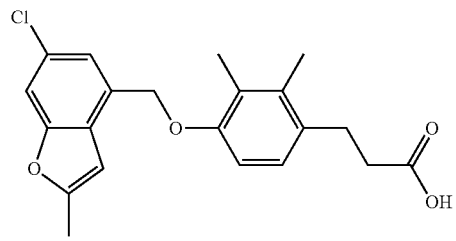 [SMILES: Cc1cc2c(COc3ccc(CCC(=O)O)c(C)c3C)cc(Cl)cc2o1]

a) (6-Chloro-2-methylbenzofuran-4-yl)methanol

The title compound was prepared according to the procedure as described in Example 87 substituting methyl 3-chloro-5-hydroxybenzoate for methyl 3-hydroxybenzoate.

b) 3-{4-[(6-Chloro-2-methyl-1-benzofuran-4-yl)methoxy]-2,3-dimethylphenyl}propanoic acid The title compound was prepared by reacting (6-chloro-2-methylbenzofuran-4-yl)methanol according to procedure in Example 83.

$^1$H NMR (CHLOROFORM-d) δ: 7.38 (s, 1H), 7.26 (s, 2H), 6.97 (d, J=8.1 Hz, 1H), 6.74 (d, J=8.6 Hz, 1H), 6.46 (s, 1H), 5.15 (s, 2H), 2.94 (t, J=8.1 Hz, 2H), 2.53-2.67 (m, 2H), 2.45 (s, 3H), 2.24 (s, 3H), 2.22 (s, 3H)

Example 111

3-{4-[(5-Chloro-2-methyl-1,3-benzoxazol-7-yl)methoxy]-2,3-dimethylphenyl}propanoic acid

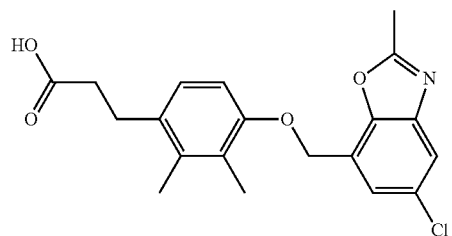 [SMILES: Cc1nc2cc(Cl)cc(COc3ccc(CCC(=O)O)c(C)c3C)c2o1]

a) Methyl 5-chloro-2-hydroxy-3-nitrobenzoate

To a solution of methyl 5-chloro-2-hydroxybenzoate (5 g, 26.8 mmol) in sulfuric acid (40 mL) cooled in an ice bath was added dropwise a mixture of nitric acid (4.6 mL) in sulfuric acid (5 mL). The resulting residue was allowed to warm to room temp and stirred for 5 hr and poured on to ice. The resulting solid that was formed was collected by filtration, washed with water and dried under high vacuum to yield methyl 5-chloro-2-hydroxy-3-nitrobenzoate.

b) Methyl 3-amino-5-chloro-2-hydroxybenzoate

To a solution of methyl 5-chloro-2-hydroxy-3-nitrobenzoate (2 g, 8.6 mmol) in methanol (60 mL) and acetic acid (60 mL) was added iron powder (9.6 g, 171.5) and the mixture was heated at reflux for 1 h. After cooling to room temperature, the resulting mixture was filtered through a pad of CELITE, the solid was washed with EtOAc (3×) and the filtrate was evaporated. The black residue was taken up with EtOAc, washed with water, saturated Na$_2$CO$_3$ and dried over Na$_2$SO$_4$. The EtOAc was evaporated to yield methyl 3-amino-5-chloro-2-hydroxybenzoate.

c) Methyl 5-chloro-2-methylbenzo[d]oxazole-7-carboxylate

A solution of methyl 3-amino-5-chloro-2-hydroxybenzoate (1.32 g, 6.53 mmol), triethylorthoacetate (4 mL, 21.2 mmol), and p-toluenesulfonic acid (40 mg, 0.21 mmol) was heated at 100° C. for 18 hours. The resulting mixture was concentrated in vacuo and the resulting residue purified by flash column chromatography on silica gel with 30% EtOAc/heptane to yield methyl 5-chloro-2-methylbenzo[d]oxazole-7-carboxylate.

d) 3-{4-[(5-Chloro-2-methyl-1,3-benzoxazol-7-yl)methoxy]-2,3-dimethylphenyl}propanoic acid The title compound was prepared by reacting methyl 5-chloro-2-methylbenzo[d]oxazole-7-carboxylate according to the procedure as described in Example 83.
$^1$H NMR (DMSO-d$_6$) δ: 12.14 (br. s., 1H), 7.77 (s, 1H), 7.49 (s, 1H), 6.90-7.00 (m, 1H), 6.87 (d, J=8.6 Hz, 1H), 5.30 (s, 2H), 2.72-2.84 (m, 3H), 2.64 (s, 3H), 2.40 (t, J=7.6 Hz, 3H), 2.15 (s, 4H), 2.13 (s, 3H).

Example 112

3-(4-{[5-Chloro-2-(2,2-difluoroethyl)-1-benzofuran-7-yl]methoxy}-2,3-dimethylphenyl)propanoic acid

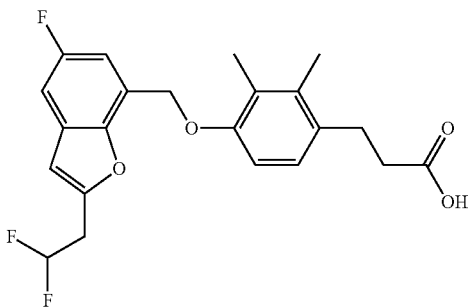 [SMILES: Cc1c(CCC(=O)O)ccc(OCc2cc(F)cc3cc(CC(F)F)oc23)c1C]

a) Methyl 5-chloro-2-(2-hydroxyethyl)benzofuran-7-carboxylate

The title compound was prepared from methyl 5-chloro-2-hydroxy-3-iodobenzoate (prepared as described in Example 94 step (a)) and but-3-yn-1-ol (prepared as described in Example 1, step (a)).

b) Methyl 5-chloro-2-(2-oxoethyl)benzofuran-7-carboxylate

To a solution of methyl 5-chloro-2-(2-hydroxyethyl)benzofuran-7-carboxylate (0.80 g, 3.14 mmol) in DCM (2 mL) was added Dess-Martin periodinane (1.60 g, 3.77 mmol) and the mixture stirred for 4 hr at room temperature. The resulting residue was purified by preparative TLC to yield methyl 5-chloro-2-(2-oxoethyl)benzofuran-7-carboxylate.

c) Methyl 5-chloro-2-(2,2-difluoroethyl)benzofuran-7-carboxylate

To a solution of methyl 5-chloro-2-(2-oxoethyl)benzofuran-7-carboxylate (0.50 g, 1.98 mmol) in DCM (3 mL) was added bis(2-methoxyethyl)aminosulfur trifluoride (1.10 mL, 5.94 mmol) and the mixture was stirred for 18 hr. The resulting mixture was purified by silica gel column chromatography (0-20% EtOAc/heptane) to yield methyl 5-chloro-2-(2,2-difluoroethyl)benzofuran-7-carboxylate.

d) (5-Chloro-2-(2,2-difluoroethyl)benzofuran-7-yl)methanol

The title compound was prepared by DIBAL reduction of methyl 5-chloro-2-(2,2-difluoroethyl)benzofuran-7-carboxylate according to the procedure as described in Example 86 step (c).

e) 3-(4-{[5-Chloro-2-(2,2-difluoroethyl)-1-benzofuran-7-yl]methoxy}-2,3-dimethylphenyl)propanoic acid The title compound was prepared by reacting (5-chloro-2-(2,2-difluoroethyl)benzofuran-7-yl)methanol according to the procedure as described in Example 83.
$^1$H NMR (MeOH) δ: 7.49 (d, J=2.0 Hz, 1H), 7.39 (d, J=2.0 Hz, 1H), 6.99 (d, J=8.6 Hz, 1H), 6.82 (d, J=8.1 Hz, 1H), 6.68 (s, 1H), 6.16 (tt, J=56.0, 4.4 Hz, 1H), 5.30 (s, 2H), 3.36-3.46 (m, 2H), 2.86-2.99 (m, 2H), 2.49-2.59 (m, 2H), 2.26 (s, 3H), 2.24 (s, 3H).

Example 113

3-(4-{[2-(2-Hydroxyethyl)-5-(trifluoromethoxy)-1-benzofuran-7-yl]methoxy}-2,3-dimethylphenyl)propanoic acid

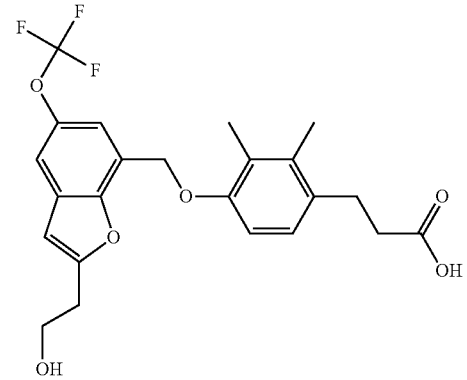 [SMILES: Cc1c(CCC(=O)O)ccc(OCc2cc(OC(F)(F)F)cc3cc(CCO)oc23)c1C]

a) 2-(2-Hydroxyethyl)-5-(trifluoromethoxy)benzofuran-7-carbaldehyde 2-(2-Hydroxyethyl)-5-(trifluoromethoxy)benzofuran-7-carbaldehyde was prepared from 2-hydroxy-3-iodo-5-(trifluoromethoxy)benzaldehyde (prepared as described in Example 89 step (c)) and but-3-yn-1-ol (prepared as described in Example 1 step a)).

b) 2-(2-((Tetrahydro-2H-pyran-2-yl)oxy)ethyl)-5-(trifluoromethoxy)benzofuran-7-carbaldehyde To an ice-cooled solution of 2-(2-hydroxyethyl)-5-(trifluoromethoxy)benzofuran-7-carbaldehyde (1.45 g, 5.29 mmol) in DCM (25 mL) was added dihydropyran (2.42 mL, 26.4 mmol) and p-toluenesulfonic acid monohydrate (9.1 mg, 0.053 mmol) and the mixture was stirred at 0° C. for 10 min and at room temperature for 1.25 h. The resulting residue was partitioned between diethyl ether and a solution made up of saturated brine (40 mL), saturated sodium bicarbonate (40 mL), and water (80 mL). The organic phase was washed twice with saturated brine, dried (MgSO$_4$-K$_2$CO$_3$), and evaporated in vacuo to yield 2-(2-((tetrahydro-2H-pyran-2-yl)oxy)ethyl)-5-(trifluoromethoxy)benzofuran-7-carbaldehyde.

c) (2-(2-((Tetrahydro-2H-pyran-2-yl)oxy)ethyl)-5-(trifluoromethoxy)benzofuran-7-yl)methanol The title compound was prepared by NaBH$_4$ reduction of 2-(2-((tetrahydro-2H-pyran-2-yl)oxy)ethyl)-5-(trifluoromethoxy)benzofuran-7-carbaldehyde according to the procedure as described in Example 88 step (b).

d) Ethyl 3-(2,3-dimethyl-4-((2-(2-((tetrahydro-2H-pyran-2-yl)oxy)ethyl)-5-(trifluoromethoxy)benzofuran-7-yl)methoxy)phenyl)propanoate The title compound was prepared by reacting (2-(2-((tetrahydro-2H-pyran-2-yl)oxy)ethyl)-5-(trifluoromethoxy)benzofuran-7-yl)methanol according to Mitsonobu coupling according to procedure as described in Example 83 step (d).

e) Ethyl 3-(4-((2-(2-hydroxyethyl)-5-(trifluoromethoxy)benzofuran-7-yl)methoxy)-2,3-dimethylphenyl)propanoate To a solution of ethyl 3-(2,3-dimethyl-4-((2-(2-((tetrahydro-2H-pyran-2-yl)oxy)ethyl)-5-(trifluoromethoxy)benzofuran-7-yl)methoxy)phenyl)propanoate (1.6 g, 2.83 mmol) in ethanol (30 mL) was added pyridinium p-toluenesulfonate (0.30 g, 1.19 mmol) and the resulting solution stirred at 55° C. for 2.5 hr. The ethanol was removed under vacuum and the residue was poured in to a solution of 10% citric acid and extracted with EtOAc. The EtOAc was removed under vacuum and the residue purified by silica gel column chromatography to yield ethyl 3-(4-((2-(2-hydroxyethyl)-5-(trifluoromethoxy)benzofuran-7-yl)methoxy)-2,3-dimethylphenyl)propanoate.

f) 3-(4-{[2-(2-Hydroxyethyl)-5-(trifluoromethoxy)-1-benzofuran-7-yl]methoxy}-2,3-dimethylphenyl)propanoic acid The title compound was prepared by reacting ethyl 3-(4-((2-(2-hydroxyethyl)-5-(trifluoromethoxy)benzofuran-7-yl)methoxy)-2,3-dimethylphenyl)propanoate according to the procedure as described in Example 1.

$^1$H NMR (MeOH) δ: 7.33 (s, 1H), 7.26 (s, 1H), 7.00 (d, J=8.6 Hz, 1H), 6.83 (d, J=8.6 Hz, 1H), 6.59 (s, 1H), 5.33 (s, 2H), 3.95 (t, J=6.6 Hz, 2H), 3.05 (t, J=6.8 Hz, 2H), 2.90-2.98 (m, 2H), 2.50-2.57 (m, 2H), 2.26 (s, 3H), 2.24 (s, 3H). Mass spectrum (ESI, m/z): Calculated for C$_{23}$H$_{23}$F$_3$O$_6$, 453.1 (M+H). found 453.0.

Example 114

3-{4-[(6-Chloro-2-methyl-1,3-benzoxazol-4-yl)methoxy]-2,3-dimethylphenyl}propanoic acid

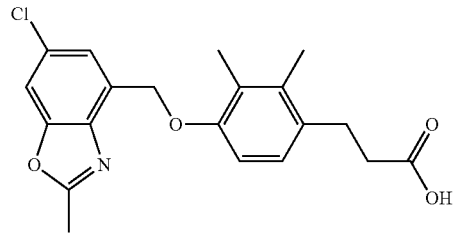

a) 2-Amino-3-bromo-5-chlorophenol

To a solution of 2-bromo-4-chloro-6-methoxyaniline (5 g, 21.14 mmol) dissolved in DCM at −78° C. was added boron tribromide (6.01 mL, 63.42 mmol) dropwise. The resulting solution was allowed to warm to room temperature and stirred for 18 hr. The reaction was quenched by slowly adding ice and the resulting mixture was evaporated under vacuum to remove DCM and diluted with water. The aqueous solution was neutralized by adding NaOH and the solid that formed was collected by filtration, washed with water, and dried under vacuum to yield 2-amino-3-bromo-5-chlorophenol b) 4-Bromo-6-chloro-2-methyl benzo[d]oxazole

A solution of methyl 2-amino-3-bromo-5-chlorophenol (4.65 g, 20.90 mmol), triethylorthoacetate (20 mL, 105.83 mmol), and p-toluenesulfonic acid (200 mg, 1.05 mmol) was heated at 100° C. for 18 hours. The reaction was concentrated in vacuo and the resulting residue was purified by flash column chromatography on silica gel with 30% EtOAc/heptane to yield 4-bromo-6-chloro-2-methylbenzo[d]oxazole.

c) 3-{4-[(6-Chloro-2-methyl-1,3-benzoxazol-4-yl)methoxy]-2,3-dimethylphenyl}propanoic acid The title compound was prepared according to the procedure as described in Example 118 step (d) substituting 4-bromo-6-chloro-2-methylbenzo[d]oxazole for 4-bromo-2-methyl-6-(trifluoromethoxy)benzo[d]thiazole.

$^1$H NMR (MeOD) δ: 7.46-7.55 (m, 2H), 6.98 (d, J=8.3 Hz, 1H), 6.78 (d, J=8.3 Hz, 1H), 5.38 (s, 2H), 2.87-2.98 (m, 2H), 2.68 (s, 3H), 2.48-2.58 (m, 2H), 2.27 (s, 3H), 2.26 (s, 3H). Mass spectrum (ESI, m/z): Calculated for C$_{20}$H$_{20}$ClNO$_4$, 374 (M+H). found 374.

Example 115

3-(4-{[2-(2,2-Difluoroethyl)-5-(trifluoromethoxy)-1-benzofuran-7-yl]methoxy}-2,3-dimethylphenyl)propanoic acid

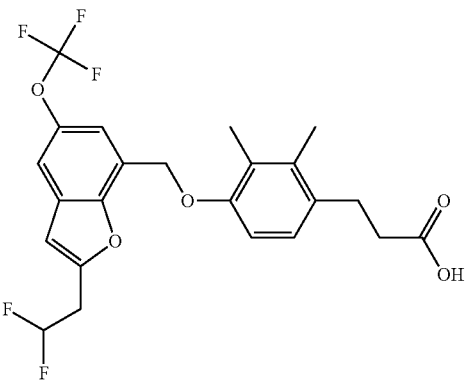 [SMILES: Cc1c(CCC(=O)O)ccc(OCc2cc(OC(F)(F)F)cc3cc(CC(F)F)oc23)c1C]

The title compound was prepared according to the procedure as described in Example 95 substituting ethyl 3-(4-((2-(2-hydroxyethyl)-5-(trifluoromethoxy)benzofuran-7-yl)methoxy)-2,3-dimethylphenyl)propanoate (prepared as described in Example 113 step (e)) for 3-(4-((5-fluoro-2-(hydroxymethyl)benzofuran-7-yl)methoxy)-2,3-dimethylphenyl)propanoate in step (b).

$^1$H NMR (CHLOROFORM-d) δ: 7.36 (s, 1H), 7.33 (s, 1H), 7.00 (d, J=8.6 Hz, 1H), 6.80 (d, J=8.1 Hz, 1H), 6.68 (s, 1H), 6.12 (tt, J=55.9, 4.5 Hz, 1H), 5.31 (s, 2H), 3.37 (td, J=15.9, 4.5 Hz, 2H), 2.89-3.00 (m, 2H), 2.57-2.65 (m, 2H), 2.25 (s, 3H), 2.24 (s, 3H). Mass spectrum (ESI, m/z): Calculated for $C_{23}H_{21}F_5O_5$, 495 (M+Na). found 495.

Example 116

3-(4-{[2-(2-Fluoroethenyl)-5-(trifluoromethoxy)-1-benzofuran-7-yl]methoxy}-2,3-dimethylphenyl)propanoic acid (mixture of E/Z)

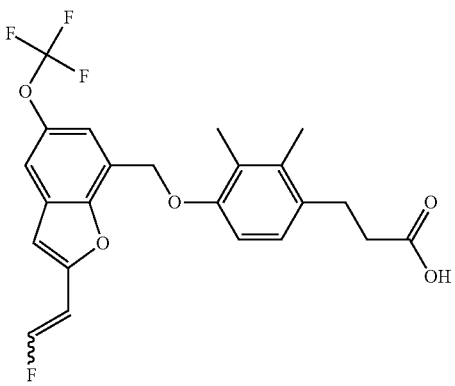 [SMILES: Cc1c(CCC(=O)O)ccc(OCc2cc(OC(F)(F)F)cc3cc(C=CF)oc23)c1C]

a) Ethyl 3-(4-((2-(2,2-difluoroethyl)-5-(trifluoromethoxy)benzofuran-7-yl)methoxy)-2,3-dimethylphenyl)propanoate The title compound was prepared according to the procedure as described in Example 95 substituting ethyl 3-(4-((2-(2-hydroxyethyl)-5-(trifluoromethoxy)benzofuran-7-yl)methoxy)-2,3-dimethylphenyl)propanoate (prepared as described in Example 113) for 3-(4-((5-fluoro-2-(hydroxymethyl)benzofuran-7-yl)methoxy)-2,3-dimethylphenyl)propanoate in step (b).

b) 3-(4-{[2-(2-Fluoroethenyl)-5-(trifluoromethoxy)-1-benzofuran-7-yl]methoxy}-2,3-dimethylphenyl)propanoic acid (mixture of E/Z)

A solution of ethyl 3-(4-((2-(2,2-difluoroethyl)-5-(trifluoromethoxy)benzofuran-7-yl)methoxy)-2,3-dimethylphenyl)propanoate (50 mg, 0.10 mmol) in THF/MeOH was cooled in an ice bath and treated with NaOH (4 mg, 0.10 mmol) and stirred for 3 h. To the resulting mixture was then added HCl (6N) was added to bring the pH to ~5 and the resulting precipitate collected and purified by reverse phase HPLC to yield 3-(4-{[2-(2-Fluoroethenyl)-5-(trifluoromethoxy)-1-benzofuran-7-yl]methoxy}-2,3-dimethylphenyl)propanoic acid (mixture of E/Z). Mass spectrum (ESI, m/z): Calculated for $C_{20}H_{20}F_4O_5$, 475 (M+Na). found 475.

Example 117

3-{4-[(6-Chloro-2-methyl-1,3-benzothiazol-4-yl)methoxy]-2,3-dimethylphenyl}propanoic acid

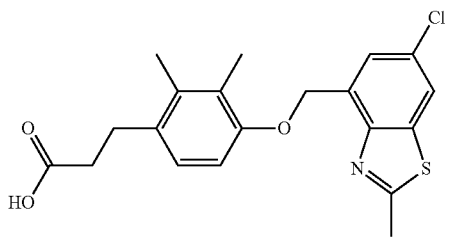 [SMILES: Cc1nc2c(COc3ccc(CCC(=O)O)c(C)c3C)cc(Cl)cc2s1]

The title compound was prepared according to the procedure as described in Example 118 substituting 4-chloro-2,6-dibromoaniline for 2,6-dibromo-4-(trifluoromethoxy)aniline in step (a).

$^1$H NMR (MeOD) δ: 7.81 (d, J=2.0 Hz, 1H), 7.62 (d, J=1.3 Hz, 1H), 6.98 (d, J=8.6 Hz, 1H), 6.81 (d, J=8.6 Hz, 1H), 5.54 (s, 2H), 2.90-2.96 (m, 2H), 2.87 (s, 3H), 2.50-2.57 (m, 2H), 2.30 (s, 3H), 2.27 (s, 3H). Mass spectrum (ESI, m/z): Calculated for $C_{20}H_{20}ClNO_3S$, 390 (M+H). found 390.

Example 118

3-(2,3-Dimethyl-4-{[2-methyl-6-(trifluoromethoxy)-1,3-benzothiazol-4-yl]methoxy}phenyl)propanoic acid

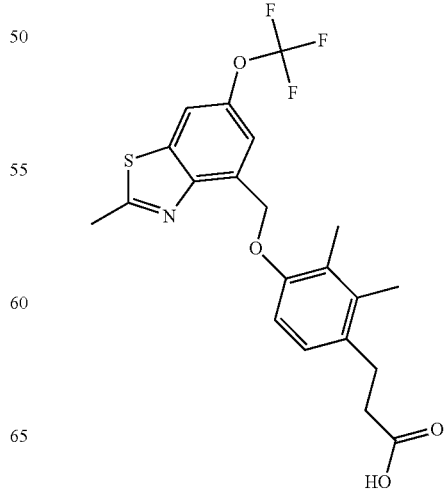

a) N-(2,6-dibromo-4-(trifluoromethoxy)phenyl)acetamide

To a solution of 2,6-dibromo-4-(trifluoromethoxy)aniline (5.0 g, 14.9 mmol) in acetic acid (10 mL) was added acetic anhydride (2.1 mL, 22.5 mmol) and the mixture stirred for 48 hrs at 90° C. The resulting residue was cooled to room temperature, poured into ice water and the resulting precipitate collected by filtration, washed with water and dried under vacuum to yield N-(2,6-dibromo-4-(trifluoromethoxy)phenyl)acetamide.

b) N-(2,6-dibromo-4-(trifluoromethoxy)phenyl)ethanethioamide

To a solution of N-(2,6-dibromo-4-(trifluoromethoxy)phenyl)acetamide (5.5 g, 14.6 mmol) in toluene (90 mL) was added Lawesson's reagent (3.0 g, 7.3 mmol) and the mixture heated to reflux for 2.5 hrs. The resulting residue was concentrated and the resulting residue was purified by silica gel chromatography to yield N-(2,6-dibromo-4-(trifluoromethoxy)phenyl)ethanethioamide.

c) 4-Bromo-2-methyl-6-(trifluoromethoxy)benzo[d]thiazole

To a solution of N-(2,6-dibromo-4-(trifluoromethoxy)phenyl)ethanethioamide (2.6 g, 6.7 mmol) in DME (10 mL) was added copper(I)iodide (66 mg, 0.35 mmol), 3,4,7,8-tetramethyl-1,10-phenanthroline (165 mg, 0.70 mmol), and cesium carbonate (3.3 g, 10.1 mmol) and the mixture was stirred at 81° C. for 20 hrs. The resulting residue was filtered through CELITE and concentrated, and the residue was purified by silica gel chromatography to yield 4-bromo-2-methyl-6-(trifluoromethoxy)benzo[d]thiazole.

d) 2-Methyl-6-(trifluoromethoxy)benzo[d]thiazole-4-carboxylic acid

To a suspension of 4-bromo-2-methyl-6-(trifluoromethoxy)benzo[d]thiazole (1.85 g, 5.93 mmol), potassium carbonate (3.85 g, 27.83 mmol), Pd(OAc)$_2$ (133 mg, 0.59 mmol), and 1,10-bis(diphenylphosphino)ferrocene (0.70 g, 1.24 mmol) in DMF (13 mL) was bubbled in gaseous CO for 15 min. The resulting residue was heated to 80° C. for 18 h with a balloon of CO. The resulting mixture was cooled and partitioned between saturated aqueous NaHCO$_3$ and EtOAc, and filtered. The aqueous layer was separated, acidified with 10% citric acid and extracted with EtOAc. The EtOAc layer was dried over Na$_2$SO$_4$ and evaporated to yield 2-methyl-6-(trifluoromethoxy)benzo[d]thiazole-4-carboxylic acid, which was used in the next step without further purification.

e) Methyl 2-methyl-6-(trifluoromethoxy)benzo[d]thiazole-4-carboxylate

Thionyl chloride (1.31 mL, 18.10 mmol) was added dropwise to methano (5 mL) at −5° C. and the mixture stirred at 0° C. for 15 minutes. 2-Methyl-6-(trifluoromethoxy)benzo[d]thiazole-4-carboxylic acid (1.40 g, 5.05 mmol) was introduced at the same temperature and the mixture was stirred for 15 minutes, then kept at 70° C. overnight. The resulting residue was concentrated and then ethyl acetate and ice-water were added to the residue and the pH was adjusted to pH 7.5 by addition of saturated sodium bicarbonate solution. The product was extracted with ethyl acetate and the extracts were washed with water, dried over sodium sulfate, concentrated and purified by silica gel column chromatography to yield methyl 2-methyl-6-(trifluoromethoxy)benzo[d]thiazole-4-carboxylate.

f) 3-(2,3-Dimethyl-4-{[2-methyl-6-(trifluoromethoxy)-1,3-benzothiazol-4-yl]methoxy}phenyl)propanoic acid The title compound was prepared by reacting methyl 2-methyl-6-(trifluoromethoxy)benzo[d]thiazole-4-carboxylate according to the procedure as described in Example 83.

$^1$H NMR (MeOH) δ: 7.70 (s, 1H), 7.57 (s, 1H), 6.99 (d, J=8.1 Hz, 1H), 6.83 (d, J=8.6 Hz, 1H), 5.57 (s, 2H), 2.90-2.97 (m, 2H), 2.89 (s, 3H), 2.49-2.57 (m, 2H), 2.30 (s, 3H), 2.27 (s, 3H). Mass spectrum (ESI, m/z): Calculated for C$_{21}$H$_{20}$F$_3$NO$_4$S, 439.1 (M+H). found 440.0.

Example 119

3-(5-Bromo-4-{[3-bromo-2-methyl-5-(trifluoromethoxy)-1-benzofuran-7-yl]methoxy}-2,3-dimethylphenyl)propanoic acid

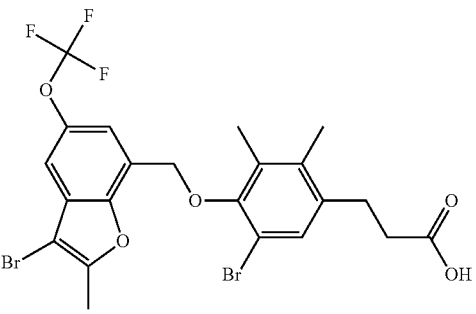 [SMILES: Cc1oc2c(COc3c(Br)cc(CCC(=O)O)c(C)c3C)cc(OC(F)(F)F)cc2c1Br]

a) Ethyl 3-(5-bromo-4-((3-bromo-2-methyl-5-(trifluoromethoxy)benzofuran-7-yl)methoxy)-2,3-dimethylphenyl)propanoate To a mixture of ethyl 3-(2,3-dimethyl-4-((2-methyl-5-(trifluoromethoxy)benzofuran-7-yl)methoxy)phenyl)propanoate (0.25 g, 0.55 mmol, prepared as described in Example 99) and sodium acetate (0.05 g, 0.61 mmol) in acetic acid (1.3 mL) cooled in an ice bath was added bromine (0.06 mL, 1.11 mmol) dropwise. After the mixture was stirred for 30 min the resulting solution was concentrated under reduced pressure, the resulting oil was taken up in ethyl acetate, washed successively with aqueous 5% NaHSO$_3$, water, and dried over anhydrous magnesium sulfate. The filtrate was concentrated, and the residue was purified by column chromatography to yield ethyl 3-(5-bromo-4-((3-bromo-2-methyl-5-(trifluoromethoxy)benzofuran-7-yl)methoxy)-2,3-dimethylphenyl)propanoate.

b) 3-(5-Bromo-4-{[3-bromo-2-methyl-5-(trifluoromethoxy)-1-benzofuran-7-yl]methoxy}-2,3-dimethylphenyl)propanoic acid The title compound was prepared by reacting ethyl 3-(5-bromo-4-((3-bromo-2-methyl-5-(trifluoromethoxy)benzofuran-7-yl)methoxy)-2,3-dimethylphenyl)propanoate according to the procedure as described in Example 1.

$^1$H NMR (CHLOROFORM-d) δ: 7.42 (s, 1H), 7.27-7.30 (m, 2H), 5.16 (s, 2H), 2.89-2.99 (m, 2H), 2.62 (t, J=7.8 Hz, 2H), 2.49 (s, 3H), 2.23 (s, 3H), 2.18 (s, 3H). Mass spectrum (ESI, m/z): Calculated for $C_{22}H_{19}Br_2F_3O_5$, 601/603 (M+Na). found 601/603.

Biological Example 1

Human GPR120 DiscoveRx PathHunter Beta-Arrestin Assay

Assay Principle:

The binding of an agonist (medium/long chain fatty acids or small molecule agonists) to the G-protein-coupled receptor GPR120 activates phospholipase C, leading to release of intracellular $Ca^{+2}$ through the generation of inositol 1,4,5-trisphosphate (InsP3 or IP3). GPR120 activation can also trigger intracellular signaling via recruitment of β-Arrestin. In the present method, agonist-induced activation of the human GPR120 receptor is monitored through the use of PathHunter CHO-K1 GPR120 β-Arrestin Cell Line engineered by DiscoveRx, as detailed below. The cell lines are designed to co-express both the ProLink/Enzyme Donor (PK)-tagged GPCR and the Enzyme Activator (EA)-tagged β-Arrestin fusion proteins. Upon GPR120 receptor stimulation/activation, the EA-tagged β-Arrestin portion is translocated to the tagged receptor, where the two enzyme fragments are brought within close proximity. Under these conditions, these fragments can interact and form an active Beta-gal enzyme complex through Enzyme Fragment Complementation (EFC). This active Beta-gal complex can enzymatically hydrolyse the substrate to produce a detectable light signal; therefore, activation as a function of agonist concentration can be expressed as an $EC_{50}$ value to determine relative compound activities. This in vitro assay therefore serves to assess compound agonist activity of the GPR120.

Procedure β-arrestin A:

In Procedure β-arrestin A, the cell used were PathHunter CHO-K1 GPR120 β-Arrestin Cell Line, expressing the long form of human GPR120 (Genbank accession number NM_181745), with 3000 cells per well.

Procedure β-arrestin B:

In Procedure β-arrestin B the cells used were PathHunter CHO-K1 GPR120S β-Arrestin Cell Line, expressing the short form of the GPR120 receptor (Accession #NM_181745), with 5000 cells/well.

Assay Procedure:

The selected CHO-K1 GPR120 β-Arrestin cells were cultured in Ham's F12 media supplemented with 10% fetal bovine serum (FBS), 1% Glutamine, 1×p/s, 800 μg/ml G418 and 300 μg/ml Hygromycin B (for selection). Cell stocks were maintained and grown in a sub-confluent state using standard cell culture procedures. The day before the experiment, the cells were harvested with non-enzymatic cell dissociation buffer and re-suspended in complete growth media at the desired concentration. A Corning 384-plate was then seeded with the proper number of cells in a volume of 25 μL, per well. The seeded plates were incubated overnight at 37° C.

On the day of the experiment, the Assay Buffer containing (a) HBSS with $Ca^{++}$ and $Mg^{++}$, (b) 20 mM HEPES, and (c) 0.1% BSA stabilizer (pH 7.4) was prepared. The growth medium was gently removed from the cell plates and 20 μL of Assay Buffer added to each well. The plate was then incubated at 37° C. for 60 mins. Test compounds were serially diluted in Assay Buffer to desired concentrations (more particularly, to one or more of the following μM concentrations: 25 μM, 12.5 μM, 6.25 μM, 3.125 μM, 1.562 μM, 0.781 μM, 0.391 μM, 0.195 μM, 0.098 μM, 0.049 μM, 0.024 μM, 0.012 μM). Five μl of compound dilution was then added to each well and the plate incubated at 37° C. for 90 mins. The detection reagents were prepared according to the manufacture's instruction. Twelve μL of the detection reagents were added to each well and the plate incubated at room temperature for 60 mins.

The plates were read on an EnVision instrument, using Protocol name: Luminescence, Plate type: 384 Costar, Measurement height: 3 mm, Measurement time: 1 s, Aperture: 384 Plate aperture. The % activity relative to the positive control was calculated using the following equation:

$$\% \text{ Activity} = \frac{Count_{compound} - Count_{vehicle}}{Count_{postivite\ control} - Count_{vehicle}} \times 100\%$$

The % Activity values were plotted versus the concentration of test compound and fitted to a sigmoidal dose-response curve with a Hill slope=1 (fixed value) using nonlinear regression with GraphPad Prism 5.0 to calculate the $EC_{50}$ values. The Fitting Equation was: Y=Bottom+(Top−Bottom)/(1+10^((LogEC$_{50}$−X)*HillSlope)), where X is the log of the concentration and Y is the response.

Biological Example 2

In Vitro Assay

Human GPR120 in Calcium Flux Assay

Assay Principle

This in vitro assay serves to assess test compound agonist activity against the short splice variant (SVS with Accession number NM_001195755.1 confirmed by sequencing data) of the GPR120 receptor. The Human Short splice variant #2 (NM_001195755.1) is missing an in-frame coding exon compared to variant 1 (the Human Long splice variant NM_181745.3), resulting in a shorter isoform (GPR120-S) lacking a 16 aa protein segment compared to isoform GPR120-L. The assay platform utilizes HEK-293 cells stably transfected to express the Human GPR120 short form. These cells are first loaded with the $Ca^{+2}$ sensitive dye, Fluo-4 NW. Upon stimulation, intracellular released $Ca^{+2}$ can bind to the dye and alter its fluorescence intensity. This increase in fluorescence signal, and thus the flux in intracellular $[Ca^{+2}]$, is detected and quantitated by fluorescence imaging using a FLIPR reader. The effect of the agonist is measured as a function of concentration and used to calculate an $EC_{50}$ based upon a response curve.

Procedure Calcium A:

In this procedure 2500 cells/well were employed.

Procedure Calcium B:

In this procedure 4200 cells/well were employed.

Assay Procedure:

A Human GPR120 clone (Genbank accession number NM_001195755.1) was placed into the pcDNA3.1 mammalian expression vector carrying the neomycin resistance gene. A stable mammalian cell was generated by placing the above clone into a HEK293 background. Clonal cells responding to long chain fatty acids had expression levels of GPR120 confirmed by RT-qPCR. Human HEK-GPR120 cells were cultured in Dulbecco's Modified Eagle's Medium (DMEM)/F12 medium supplemented with 10% fetal bovine serum (FBS), 1% L-Glutamine and 1% penicillin/streptomycin and 0.5 mg/ml G-418. Cells were split 2 times a week to keep the cells in the log-phase growth.

In preparation for the assay, HEK cells stably transfected with Human GPR120 (2.5K cells per well in 25 uL growth medium) were seeded into 384-well plates and then incubated overnight (37° C., 5% $CO_2$). The next day, the media was changed to 20 μl assay buffer and the cell starved for 1 h at 37° C. The dye loading solution (2× dye) was prepared using 10 ml assay buffer, 100 μl of 250 mM probenecid, 1 bottle of Component A, and 20 μl of dye in DMSO. Twenty μl of the 2× dye loading buffer was then added to each well. The plates were incubated at 37° C. for 30 min, then at room temperature for an additional 15 minutes, before performing the assay on FLIPR.

Test compounds were prepared in assay buffer (2 μl of test compound+198 μl assay buffer, final DMSO in assay plate is 0.2%) at the desired concentration, more particularly at 100 μM, 50 μM, 25 μM, 12.5 μM, 6.25 μM, 3.125 μM, 1.562 μM, 0.781 μM, 0.391 μM, 0.195 μM, 0.098 μM, 0.049 μM, 0.024 μM and 0.012 μM.

The assay was performed on a FLIPR plate reader using the following parameters. Baseline was read for 10 seconds at 1 sec intervals. The program was set to transfer 10 μL of ligand from compound plate to cell plate after baseline reading. Aspiration was executed at: 10 μl/sec speed, 4.6 μl height; Dispensing was executed at: 30 μl/sec speed, 45 μl height. After compound addition, each well was read for 300 sec, with measurements collected at 1 sec intervals.

The kinetic data from the FLIPR was based upon a 5 minute window for data collection. The fluorescence of each sample well was used for individual calculations of a normalized RFU value, which was defined as maximum response minus the minimum response. The normalized fluorescence reading (RFU) was calculated as follows:

$$RFU = F\max - F\min$$

The data were fitted to a sigmoidal dose-response curve with a variable Hill slope (<2) using nonlinear regression with GraphPad Prism 5.0 to calculate the $EC_{50}$ values. The Fitting Equation was: Y=Bottom+(Top−Bottom)/(1+10^((LogEC_{50}−X)*HillSlope)), where X is the log of the concentration and Y is the response.

Representative compounds of formula (I) were tested according to procedure as described in Biological Example 1 and 2, above, with results as listed in Table 6 below.

TABLE 6

| | GPR120 $EC_{50}$ (μM) | | | |
|---|---|---|---|---|
| ID No | B-arrestin A $EC_{50}$ (μM) | B-arrestin B $EC_{50}$ (μM) | Calcium A $EC_{50}$ (μM) | Calcium B $EC_{50}$ (μM) |
| 1 | >19.9986 | | | |
| 2 | 0.374 | | 0.051 | |
| 3 | 0.327 | | 0.058 | |
| 4 | 5.206 | | 0.279 | |
| 5 | 0.949 | | 1.241 | |
| 6 | >19.9986 | | | |
| 7 | 0.108 | | 0.124 | |
| 8 | 0.613 | | 0.297 | |
| 9 | | | 2.750 | |
| 10 | | | 0.424 | |
| 11 | 0.283 | 0.094 | 0.023 | |
| 12 | 0.151 | 0.070 | 0.039 | |
| 13 | 0.302 | | | |
| 14 | | | 1.315 | |
| 15 | | | 4.754 | |
| 17 | 0.455 | | 0.345 | |
| 18 | 1.666 | | 0.653 | |
| 19 | | | 1.681 | |
| 20 | | | 5.286 | |
| 21 | 0.458 | | 0.159 | |
| 22 | 0.797 | | 0.166 | |
| 23 | 0.470 | | 0.339 | |
| 29 | 0.616 | | 0.107 | |
| 30 | | | 0.759 | |
| 31 | 0.232 | | 0.044 | |
| 32 | 2.907 | | 0.277 | |
| 33 | | | 1.107 | |
| 34 | | | 1.015 | |
| 35 | 0.190 | | 0.040 | |
| 36 | 0.085 | 0.069 | 0.010 | 0.012 |
| 37 | 0.271 | | 0.043 | |
| 38 | | | 0.028 | |
| 40 | 0.107 | | 0.034 | |
| 41 | 0.626 | | 0.291 | |
| 44 | 0.230 | | 0.027 | |
| 45 | 0.095 | | 0.024 | |
| 47 | 0.197 | | 0.022 | |
| 49 | 0.507 | | 0.237 | |
| 50 | 0.496 | | 0.059 | |
| 51 | | | 0.392 | |
| 52 | 0.374 | | 0.029 | |
| 53 | | | 0.673 | |
| 54 | 0.429 | 0.150 | 0.036 | |
| 55 | 0.073 | | 0.028 | |
| 57 | 0.077 | | 0.017 | |
| 58 | 0.410 | | 0.087 | |
| 59 | 0.146 | | 0.093 | |
| 60 | 0.706 | | 0.162 | |
| 61 | 0.190 | | 0.024 | |
| 62 | 0.274 | | 0.067 | |
| 63 | 0.231 | | 0.067 | |
| 64 | 0.271 | | 0.056 | |
| 65 | 0.240 | | 0.096 | |
| 66 | 1.412 | | 0.077 | |
| 67 | 0.221 | | 0.093 | |
| 69 | 0.223 | | 0.045 | |
| 70 | 2.499 | 1.291 | 0.162 | |
| 71 | 0.045 | | 0.064 | |
| 75 | 0.394 | | 0.182 | |
| 76 | 0.144 | | 0.020 | |
| 77 | 0.176 | | 0.028 | |
| 78 | 0.121 | | 0.020 | |
| 79 | 2.225 | | | |
| 80 | 0.249 | | 0.151 | |
| 81 | 0.817 | | 0.136 | |
| 82 | 0.851 | | 0.153 | |
| 83 | 0.440 | | 0.051 | |
| 84 | 0.434 | | 0.131 | |
| 85 | 0.238 | | 0.015 | |
| 86 | 0.460 | | 0.207 | |
| 87 | 0.409 | | 0.079 | |
| 88 | 0.594 | | 0.147 | |
| 89 | 0.119 | | 0.017 | |
| 90 | 0.532 | | 0.113 | |
| 91 | 0.629 | | 1.915 | |
| 92 | | | 0.417 | |
| 93 | 0.536 | | 1.598 | |
| 94 | | | 0.274 | |
| 95 | | | 0.134 | |
| 96 | 0.148 | | 0.030 | |
| 97 | 0.169 | | 0.020 | |
| 98 | 0.154 | | 0.018 | |
| 99 | | | >5.00034 | |
| 100 | | | >5.00034 | |
| 101 | | | 3.200 | |
| 102 | | | >5.00034 | |
| 103 | | | 2.998 | |
| 104 | | 1.549 | 1.883 | 0.499 |
| 105 | | 0.402 | 0.204 | 0.091 |
| 106 | 0.882 | | | 0.184 |
| 107 | 3.917 | | 1.012 | |

TABLE 6-continued

| | GPR120 EC$_{50}$ (µM) | | | |
|---|---|---|---|---|
| ID No | B-arrestin A EC$_{50}$ (µM) | B-arrestin B EC$_{50}$ (µM) | Calcium A EC$_{50}$ (µM) | Calcium B EC$_{50}$ (µM) |
| 108 | | | | 2.737 |
| 109 | | 0.191 | | 0.038 |
| 110 | | 3.309 | | 0.949 |
| 111 | | 0.299 | | 0.107 |
| 112 | | 0.110 | 0.121 | |
| 115 | | 0.772 | 0.468 | |
| 117 | | 0.681 | 0.422 | |
| 118 | | 0.237 | 0.065 | |
| 119 | | 1.439 | | |
| 120 | | | 1.543 | |
| 121 | | 1.188 | 0.382 | |
| 123 | | | 1.415 | |

Biological Example 3

In Vivo Assay

GPR120 DIO Mice OGTT Screening 18-22 week old, C57Bl6 mice on a high fat diet (60% HFD) for 12-16 weeks (ave. body weight ~37-41 g) were fasted for 6 hr, with removal of food occurring at 7 am on the morning of the study. The animals were sorted into treatment groups the day before the study by body weight. Animals outside the bounds of ~30-50 g were left out of the study. The animals had been handled and shammed a total of 5-8 days (1-3 days immediately prior to the study). Glucose (in 1 ml syringes) was drawn up the morning of the study. Test compounds were kept spinning and were only drawn into 1 ml syringes prior to study commencement. Animals were bled via tail snip to determine basal glucose levels prior to dosing of treatments. An Ascensia BREEZE Blood Glucose Monitoring System by Bayer was used for determining glucose levels.

Animals were moved into the testing room at ~9-11 am, to yield them time to acclimate. The bleeds and dosing started at approximately 1 pm in 30-second intervals per animal. All groups were dosed 30 minutes prior to glucose administration at a dose volume of 10 ml/kg (the dose volume was calculated separately for each individual animal). Test compounds were administered at one or more of the following dosages: 0.1 mg/kg, 0.3 mg/kg, 1 mg/kg, 3 mg/kg, 10 mg/kg and 30 mg/kg.

Thirty minutes after the first dose (with test compound) animals were bled again for a second baseline, or T=0, and immediately dosed with glucose (20% solution; TEKNOVA, 250 ml sterile bottle w/catalogue number G0525) via a PO injection. The exact dose volume for glucose was also calculated separately for each individual animal.

Blood glucose was measured at 15, 30, 45, 60, and 90 minutes post-glucose administration via the snipped tail. If an animal reached a value of "HI", the upper limit of the glucometer (600 mg/dl) was substituted as the blood glucose value and the study was analyzed as normal with no exclusions. If 50% or more of any treatment group reaches a "HI" value at least once, the study was considered invalid and repeated. Glucose values were typed into an EXCEL spreadsheet where they were used to calculate glucose AUC and delta AUC post-compound and post-glucose. The glucose excursion curves and the different versions of the AUC's were graphed in GraphPad Prism 5.

Statistical Methods:

Note: All statistics completed in this study were completed using the statistical software package GraphPad Prism 5. Standard procedures for analyzing data sets from screening GPR120 compounds in DIO mouse OGTT's were as listed here below. In addition to the statistics that were run using GraphPad Prism 5, Microsoft Excel was used to calculate the percent changes in AUC from vehicle groups as detailed below.

Change from −30 to 0 BSLN Glucose, Raw Glucose AUC −30 to 90 min, Delta Glucose AUC −30 to 90 min, Raw Glucose AUC 0 to 90 min, Delta Glucose AUC 0 to 90 min were analyzed using Column Statistics Analysis, with mean values used to calculate % change from the vehicle mean group, as well as mean, SEM and/or % change from vehicle, where appropriate; and using One-Way ANOVA w/a Tukey Post-Test (Comparing All Pairs of Columns) with each treatment group examined to see if it was statistically significant compared to vehicle (*=P<0.05, =P<0.01, *=P<0.001).

Representative compounds of the present invention were tested according to the procedure as described in Biological Example 2, with results as listed in Table 7, below.

TABLE 7

| | GPR120 DIO OGTT Results |
|---|---|
| ID No. | DIO Lowering Glucose AUC (−30 to 90) @10 mg/kg |
| 11 | −0.39 |
| 12 | −0.70 |
| 31 | −0.67 |
| 37 | 0.03 |
| 44 | 0.07 |
| 52 | 0.03 |
| 55 | −0.41 |
| 75 | −31% |
| 85 | −37% |
| 98 | −0.33 |

Biological Example 4

In Vivo Assays

A: GPR120 C57bl6 Mouse IPGTT

Male, C57bl/6J Mice were ordered in at 8 weeks of age from Jackson Labs. Individual mice weighed anywhere in the range of 25-30 grams on study day. The mice were fasted, with removal of food occurring at 7 am on the morning of the study. Animals were moved into the room at 10:00 am, to give them time to acclimate. Glucose (insulin syringes) was drawn up either the night before or the morning of the study. Glucose was dosed (IP) at 1.5 g/kg at 7.5 ml/kg (20% glucose straight TEKNOVA, 250 ml sterile bottle w/catalogue number G0525). Test compounds were kept spinning and were only drawn into the syringes prior to study commencement. Animals were bled via tail snip to determine basal glucose levels prior to dosing of treatments. An Ascensia BREEZE Blood Glucose Monitoring System by Bayer (using unique 10-test disks) was used for determining glucose levels. The bleeds started at approximately 12:45 pm and dosing started, at 1-minute intervals, immediately after. All groups were dosed 30 minutes prior to glucose administration at a dose volume of 10 ml/kg (the dose volume was calculated separately for each individual animal). Thirty minutes after the first dose animals were bled again for a second baseline, or T=0, and immediately dosed with glucose via an i.p. injection. The exact dose volume for glucose was also calculated separately for each individual animal. Glucose measurements were taken at −30 min prior to compound dose, at t=0 (immediately prior to glucose dose), and at 15, 30, 45, 60, 90 min post glucose dose.

Glucose values were entered into an Excel sheet and graphed in GraphPad Prism. The following were calculated from Prism: Change from −30 to 0 BSLN Glucose, Raw Glucose AUC −30 to 90 min, Delta Glucose AUC −30 to 90 min, Raw Glucose AUC 0 to 90 min, Delta Glucose AUC 0 to 90 min.

B: C57bl6 mouse OGTT:

The assay design is the same as that described above for the C57bl6 mouse IPGTT. The difference is that glucose was dosed PO at 3 g/kg, 7.5 ml/kg of 40% glucose.

Representative compounds of the present invention were tested according to the procedures as described in Biological Example 3, above with results as listed in Table 8, below. In the results presented below, the designation "nd" indicates that no numbers were reported (results were not different from vehicle). Where a compound was tested more than once, each result is listed individually.

TABLE 8

GPR120 C57bl6 Mouse IPGTT and OGTT Results

| | C57 IPGTT | | | | C57 OGTT |
|---|---|---|---|---|---|
| ID no. | 1 mg/kg | 3 mg/kg | 10 mg/kg | 30 mg/kg | 30 mg/kg |
| 2 | | | | −50 | |
| 2 | | | | −54 | |
| 2 | | | | −64 | −53 |
| 2 | | | | −27 | −52 |
| 2 | | | | −67 | −40 |
| 2 | | | | −57 | |
| 2 | | | | −32 | |
| 2 | | | | | −34 |
| 3 | | | | | −35 |
| 4 | | | | | nd |
| 11 | | | | −39 | |
| 12 | | | | −66 | |
| 13 | | | | −38 | |
| 22 | | | nd | | |
| 27 | | | | −42 | |
| 28 | | | | −45 | |
| 29 | | | nd | | |
| 35 | | | | −47 | |
| 35 | | −15 | −28 | −42 | |
| 36 | | | | −54 | |
| 40 | | | | −41 | |
| 44 | | | | nd | |
| 45 | | | | −15 | |
| 47 | | | | −27 | |
| 55 | | −14 | | | |
| 55 | | | | −10 | |
| 57 | | | | −25 | |
| 58 | | | | −20 | |
| 63 | | | | nd | |
| 71 | | | | −35 | |
| 71 | nd | | −12 | −23 | |
| 78 | | | | −21 | |
| 87 | | −13 | | | |
| 88 | | −6 | | | |
| 89 | | −11 | | | |

The C57bl6 Mouse IPGTT and OGTT dose response was measured for representative compounds of the present invention, with results as listed in Table 9, below.

TABLE 9

| | C57bl6 Mouse IPGTT and OGTT dose response | | | |
|---|---|---|---|---|
| ID No. | 1 mg/kg | 3 mg/kg | 10 mg/kg | 30 mg/kg |
| | Dose Responses C57 IPGTT | | | |
| 2 | −3% | −20% | −27% | −53% |
| 36 | | −7% | −36% | −46% |
| 40 | −28% | 13% | −34% | |
| | Dose Responses C57 OGTT | | | |
| 2 | | −29% | −31% | −51% |
| 3 | | −15% | −24% | −35% |
| 11 | | −30% | −38% | −43% |
| 12 | | 6% | −26% | −30% |
| 13 | | | | −43% |
| 13 | | −16% | −16% | −63% |

Formulation Example 1

Prophetic Example

Solid, Oral Dosage Form

As a specific embodiment of an oral composition, 100 mg of the Compound #85, prepared as in Example 53 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound selected from the group consisting of
   3-{4-[(5-Chloro-2-ethyl-1-benzofuran-7-yl)methoxy]-2,3-dimethylphenyl}propanoic acid;
   3-(2,3-Dimethyl-4-{[2-methyl-5-(trifluoromethoxy)-1-benzofuran-7-yl]methoxy}phenyl)propanoic acid;
   3-(7-{[2-Methyl-5-(trifluoromethoxy)-1-benzofuran-7-yl]methoxy}-2,3-dihydro-1H-inden-4-yl)propanoic acid;
   3-{4-[(5-Chloro-2-methyl-1-benzofuran-7-yl)methoxy]-2,3-dimethylphenyl}propanoic acid;
   3-{4-[(5-Chloro-2,6-dimethyl-1-benzofuran-7-yl)methoxy]-2,3-dimethylphenyl}propanoic acid;
   3-(4-{[2-(2-Fluoroethenyl)-5-(trifluoromethoxy)-1-benzofuran-7-yl]methoxy}-2,3-dimethylphenyl)propanoic acid;
   3-{4-[(6-Chloro-2-methyl-1,3-benzothiazol-4-yl)methoxy]-2,3-dimethylphenyl}propanoic acid;
   and pharmaceutically acceptable salts thereof.
2. A pharmaceutical composition comprising a pharmaceutically acceptable carrier and a compound of claim 1.
3. A pharmaceutical composition made by mixing a compound of claim 1 and a pharmaceutically acceptable carrier.

* * * * *